(12) United States Patent
Hiscox et al.

(10) Patent No.: US 11,161,846 B2
(45) Date of Patent: Nov. 2, 2021

(54) SUBSTITUTED PYRAZOLO[4,3-B]PYRIDINES AND THEIR USE AS GLUN2B RECEPTOR MODULATORS

(71) Applicant: JANSSEN PHARMACEUTICA NV, Beerse (BE)

(72) Inventors: Afton Hiscox, Toronto (CA); Brice Stenne, La Jolla, CA (US); Christine Gelin, San Diego, CA (US); Andrew Samant, San Diego, CA (US); Jessica Wall, San Diego, CA (US); Michael A. Letavic, San Diego, CA (US); Curt Dvorak, Poway, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/899,836

(22) Filed: Jun. 12, 2020

(65) Prior Publication Data
US 2020/0392130 A1   Dec. 17, 2020

Related U.S. Application Data

(60) Provisional application No. 62/861,674, filed on Jun. 14, 2019.

(51) Int. Cl.
*C07D 471/04*   (2006.01)

(52) U.S. Cl.
CPC ................... *C07D 471/04* (2013.01)

(58) Field of Classification Search
CPC .................................................. C07D 471/04
See application file for complete search history.

(56) References Cited

U.S. PATENT DOCUMENTS

| | | |
|---|---|---|
| 7,622,486 B2 | 11/2009 | Pal et al. |
| 8,765,784 B2 | 7/2014 | Arrington et al. |
| 8,785,438 B2 | 7/2014 | Ohtsuka et al. |
| 8,877,772 B2 | 11/2014 | Gelbard et al. |
| 9,434,743 B2 | 9/2016 | Cheruvallath et al. |
| 9,963,447 B2 | 5/2018 | Chrovian et al. |
| 9,981,950 B2 | 5/2018 | Schindler et al. |
| 10,071,988 B2 | 9/2018 | Chen et al. |
| 10,155,727 B2 | 12/2018 | Schindler et al. |
| 10,233,173 B2 | 3/2019 | Chen et al. |
| 10,323,021 B2 | 6/2019 | Schindler et al. |
| 10,377,753 B2 | 8/2019 | Chrovian et al. |
| 10,617,676 B2 | 4/2020 | Chrovian et al. |
| 2007/0275965 A1 | 11/2007 | Thomas et al. |
| 2008/0300239 A1 | 12/2008 | Adams et al. |
| 2011/0130384 A1 | 6/2011 | Setoh et al. |
| 2014/0275011 A1 | 9/2014 | Mastracchio et al. |
| 2015/0210681 A1 | 7/2015 | Bourque et al. |
| 2016/0024087 A1 | 1/2016 | Gelbard et al. |
| 2018/0125826 A1 | 5/2018 | Chrovian et al. |
| 2018/0208595 A1 | 7/2018 | Chrovian et al. |
| 2018/0282305 A1 | 10/2018 | Schindler et al. |
| 2018/0334451 A1 | 11/2018 | Chen et al. |
| 2019/0135791 A1 | 5/2019 | Chen et al. |
| 2019/0308950 A1 | 10/2019 | Ziff et al. |
| 2020/0392113 A1 | 12/2020 | Dvorak et al. |
| 2020/0392154 A1 | 12/2020 | Gelin et al. |
| 2020/0392155 A1 | 12/2020 | Gelin |
| 2021/0017168 A1 | 1/2021 | Hiscox et al. |
| 2021/0017169 A1 | 1/2021 | Hiscox et al. |

FOREIGN PATENT DOCUMENTS

| | | |
|---|---|---|
| CN | 110294756 A | 10/2019 |
| EP | 928789 A1 | 7/1999 |
| EP | 2194045 A1 | 6/2010 |
| JP | 2012-188363 A | 4/2012 |
| WO | 1995028400 A1 | 10/1995 |
| WO | 2002060877 A1 | 8/2002 |
| WO | 2003082868 A1 | 10/2003 |
| WO | 2003097637 A1 | 11/2003 |
| WO | 2005080379 A1 | 9/2005 |
| WO | 2008145616 A1 | 12/2008 |
| WO | 2009004430 A1 | 1/2009 |
| WO | 2009058261 A1 | 5/2009 |
| WO | 2009118187 A1 | 10/2009 |
| WO | 2009/157196 A1 | 12/2009 |
| WO | 2010043396 A1 | 4/2010 |
| WO | 2010108187 A1 | 9/2010 |
| WO | 2011140202 A2 | 11/2011 |
| WO | 2013060029 A1 | 5/2013 |
| WO | 2013130855 A1 | 9/2013 |
| WO | 2014124651 A1 | 8/2014 |
| WO | 2014145051 A1 | 9/2014 |
| WO | 2015002754 A2 | 1/2015 |

(Continued)

OTHER PUBLICATIONS

Vippagunta et al. (2001).*
U.S. Appl. No. 16/899,829, filed Jun. 14, 2019.*
International Search Report and Written Opinion of the International Searching Authority for International Application No. PCT/EP2020/066391, dated Jul. 29, 2020.
International Search Report and Written Opinion of the International Searching Authority for International Application No. PCT/US2015/045412, dated Nov. 10, 2015.
International Search Report and Written Opinion of the International Searching Authority for International Application No. PCT/US2015/045413, dated Nov. 27, 2015.
International Search Report and Written Opinion of the International Searching Authority for International Application No. PCT/US2016/041339 dated Sep. 27, 2016.

(Continued)

*Primary Examiner* — Paul V Ward

(74) *Attorney, Agent, or Firm* — Biospark Intellectual Property Law

(57) ABSTRACT

Substituted pyrazolo[4,3-b]pyridines as GluN2B receptor ligands. Such compounds may be used in GluN2B receptor modulation and in pharmaceutical compositions and methods for the treatment of disease states, disorders, and conditions mediated by GluN2B receptor activity.

26 Claims, No Drawings

(56) References Cited

FOREIGN PATENT DOCUMENTS

| WO | 2015017502 A1 | 2/2015 |
|---|---|---|
| WO | 2016025917 A1 | 2/2016 |
| WO | 2016081649 A1 | 5/2016 |
| WO | 2016/150971 A1 | 9/2016 |
| WO | 2017/007938 | 1/2017 |
| WO | 2018/067786 | 4/2018 |
| WO | 2018/231745 A1 | 12/2018 |
| WO | 2020/249785 A1 | 12/2020 |
| WO | 2020/249791 A1 | 12/2020 |
| WO | 2020/249792 A1 | 12/2020 |
| WO | 2020/249796 A1 | 12/2020 |
| WO | 2020/249799 A1 | 12/2020 |
| WO | 2020/249802 A1 | 12/2020 |

OTHER PUBLICATIONS

International Search Report and Written Opinion of the International Searching Authority for International Application No. PCT/US2017/017093, dated Apr. 7, 2017.
International Search Report and Written Opinion of the International Searching Authority issued in connection with PCT/US2017/055278, dated Mar. 9, 2018.
International Search Report and Written Opinion of the International Searching Authority for International Application No. PCT/IB2019/052731, dated Nov. 1, 2019.
Addy, et al., Single-Dc3e Administration of MK-0657, an N112B-Selective NMDA Antagonist, Does Not Result in Clinically Meaningful Improvement in Motor Function in Patients 127ith Moderate Parkinson's Disease, Journal of Clinical Pharmacology, 2009, pp. 856-864, vol. 49.
Andreas Straube., Pharmacology of vertigo/nystagmus/oscillopsia, Current Opinion in Neurology, 2005, pp. 11-14, vol. 18 Issue 1.
Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 Issue 2.
Bagshawe, Kenneth D., 1995, "Antibody-Directed Enzyme prodrug Therapy : A Review," Drug Development Research, 34:220-230.
Berberich, et al., The role of NMDAR subtypes and charge transfer during hippocampal LTP induction, Neuropharmacology, 2007, pp. 77-86, vol. 52 Issue 1.
Berge, et al., Pharmaceutical Salts, Journal of Pharmaceutical Sciences, 1977, pp. 1-19, vol. 66, No. 1.
Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.
Bodor, Nicholas, 1984, "Novel Approaches to the Design of Safer Drugs: Soft Drugs and Site-Specific Chemical Delivery Systems," Advances in Drug Research, 13:256-331.
Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.
Buonarati, et al., Role of sulfation and acetylation in the activation of 2-hydroxyamino-1-methyl-6-phenylimidazo[4,5-b]pyridine to intermediates which bind DNA, Mutation Research, Jun. 21, 1990, pp. 185-190, vol. 245.
Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.
Chrovian, et al., "1H-Pyrrolo[3,2-b]pyridine GluN2B-Selective Negative Allosteric Modulators", ACS Med. Chem. Lett, 2019, vol. 10, pp. 261-266.
Chemical Abstract Service (CAS), Database Registry [Online], Database Registry [Online], STN Sep. 18, 2012, pp. 1-1, Database Accession No. 1394745_67_5.

Collingridge, et al., "A nomenclature for ligand-gated ion channels" Neuropharmacology, 2009, vol. 56, pp. 2-5.
Cull-Candy, et al., NMDA receptor subunits: diversity, development and disease, Current Opinion in Neurobiology, 2001, pp. 327-335, vol. 11 Issue 3.
Dalmau, et al., Anti-NMDA-receptor encephalitis: case series and analysis of the eff ects of antibodies, Lancet Neurol, Dec. 2008, pp. 1091-1098, vol. 7 Issue 12.
Dorval, et al., Association of the glutamate receptor subunit gene GRIN2B with attention-deficit/hyperactivity disorder, Genes, Brain and Behavior, 2007, pp. 444452, vol. 6 Issue 5.
Duty, Susan, 2012, "Targeting Glutamate Receptors to Tackle the Pathogenesis, Clinical Symptoms and Levodopa-lnduced Dyskinesia Associated with Parkinson's Disease," Cns Drugs, 26(12):1017-1032.
Farjam, et al., Inhibition of NR2B-Containing N-methyl-D-Aspartate Receptors (Nm DARs) in Experimental Autoimmune Encephalomyelitis, a Model of Multiple Sclerosis, Iranian Journal of Pharmaceutical Research, 2014, pp. 695-705, vol. 13 Issue 2.
Fleisher, et al., Improved oral drug delivery: solubility limitations overcome by the use of prodrugs, Advanced Drug Delivery Reviews, 1996, pp. 115-130, vol. 19.
Fuller, et al., Differential expression of the Nmda NR2B receptor subunit in motoneuron populations susceptible and resistant to amyotrophic lateral sclerosis, Neuroscience Letters, 26-Jan-2006, pp. 157-161, vol. 399 Issue (1-2).
Glenn D. Considine, Van Nostrand's Encyclopedia of Chemistry Encyclopedia of Chemistry, 2005, pp. 261, Chapter 5.
Grasselli, et al., Abnormal Nmda receptor function exacerbates experimental autoimmune encephalomyelitis, British Journal of Pharmacology, 2013, pp. 502517, vol. 168 Issue 2.
Grimwood, et al., NR2B-containing Nm Da receptors are upregulated in temporal cortex in schizophrenia, NeuroReport, 25-Feb-1999, pp. 461-465, vol. 10 Issue 3.
Guitton, et al., Blockade of Cochlear Nmda Receptors Prevents Long-Term Tinnitus during a Brief Consolidation Window after Acoustic Trauma, Neural Plasticity, 12-Dec-2007, pp. 1-11, Article Id 80904.
Haller, et al., NR2B subunit-specific Nm Da antagonist Ro25-6981 inhibits the expression of conditioned fear: a comparison with the Nmda antagonist Mk-801 and fluoxetine, Behavioural Pharmacology, 2011, pp. 113-121, vol. 22 Issue 2.
Hanson, et al., Altered GluN2B Nmda receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Houston, et al., "Methods for Predicting In Vivo Pharmacokinetics Using Data from In Vitro Assays" Current Drug Metabolism, 2008, vol. 9, pp. 940-951.
Ito, et al., A Medium-term rat liver bioassay for rapid in vivo detection of carcinogenic potential of chemicals, Cancer Sci, 2003, pp. 3-8, vol. 94 Issue 1.
Jozsef Nagy, The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kamalesh B. Ruppa et al., Chapter 7: NMDA Antagonists of GluN2B Subtype and Modulators of GluN2A, GluN2C, and GluN2D Subtypes—Recent Results and Developments, Annual Reports in Medicinal Chemistry, Jan. 1, 2012, pp. 89-103, vol. 47.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.

(56) References Cited

OTHER PUBLICATIONS

Layton, et al., Discovery of 5-aryl-1,3-dihydro-2H-imidazo[4,5-b]pyridin-2-ones as positive allosteric modulators of metabotropic glutamate subtype-2(mGlu2) receptors with efficacy in a preclinical model of psychosis, Bioorganic & Medicinal Chemistry Letters, Feb. 15, 2016, pp. 1260-1264, vol. 26.
Leaderbrand, et al., Co-activation of NR2A and NR2B subunits induces resistance to fear extinction, Neurobiol Learn Mem, 2013, pp. 35-40, vol. 113.
Leaver, et al., Neuroprotective Effects of a Selective N-Methyl-d-Aspartate NR2B Receptor Antagonist in the 6-Hydroxydopamine Rat Model of Parkinson's Disease, Clinical and Experimental Pharmacology and Physiology, May 27, 2008, pp. 1388-1394, vol. 35 Issue 11.
Leyva, et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.
Li, et al., Enhanced Striatal NR2B-Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B-Containing NMDA Receptors, The Journal of Neuroscience, May 4, 2011, pp. 6627-6638, vol. 31 Issue 18.
Lima-Ojeda, et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Martucci, et al., N-methyl-d-aspartate receptor NR2B subunit gene GRIN2B in schizophrenia and bipolar disorder: Polymorphisms and mRNA levels, Schizophrenia Research, Mar. 20, 2006, pp. 214-221, vol. 84 Issue (2-3).
Massey, et al., Differential Roles of NR2A and NR2B-Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B-containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp. 12-19, vol. 100 Issue (1-2).
Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.
Orgogozo, et al., Efficacy and Safety of Memantine in Patients With Mild to Moderate Vascular Dementia a Randomized, Placebo-Controlled Trial (MMM 300), Stroke, 2002, pp. 1834-1839, vol. 33.
Paoletti, et al., NMDA receptor subunit diversity: impact on receptor properties, synaptic plasticity and disease, Nature Reviews | Neuroscience, 2013, pp. 383-400, vol. 14 Issue 6.
Park et al. "Metabolism of Fluorine-containing drugs", Annu. Rev. Pharmacol. Toxicol. 2001. vol. 41, pp. 443-470, entire document.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.
Porsolt, et al., Behavioural Despair in Mice: A Primary Screening Test for Antidepressants, Arch int Pharmacodyn, 1977, pp. 327-336, vol. 229.
Preskorn, et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology, Dec. 2008, pp. 631-637, vol. 28 Issue 6.
PubChem-CID-90046926, Create Date: Feb. 13, 2015 (Feb. 13, 2015), entire document.
Remington, Remington Pharmaceutical Sciences., Pharmaceutical Sciences., 1985, pp. 1418, vol. 76.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Shan, et al., Prodrug Strategies Based on Intramolecular Cyclization Reactions, Journal of Pharmaceutical Sciences, Jul. 1997, pp. 765-767, vol. 86 Issue 7.
Shen, et al., Heroin relapse requires long-term potentiation-like plasticity mediated by NMDA2b-containing receptors, PNAS, Nov. 29, 2011, pp. 19407-19412, vol. 108 Issue 48.
Starck, et al., Drug therapy for acquired pendular nystagmus in multiple sclerosis, J Neurol, 1997, pp. 9-16, vol. 244 Issue 1.
Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.
STN Registry database entry for CAS RN 1394745-67-5, entered STN Sep. 18, 2012, Accessed Sep. 8, 2017.
STN Registry database entry for CAS RN 1493474-46-6, 1491341-24-2, 1479235-62-5, and 1477636-42-2, Accessed Apr. 10, 2019.
Tang, et al., 2005, "Disturbed Ca2+ signaling and apoptosis of medium spiny neurons in Huntington's disease," PNAS, 102(7):2602-2607.
Tang, et al., Genetic enchancement of learning and memory in mice, Nature, Sep. 2, 1999, pp. 63-69, vol. 401 Issue 6748.
Traynelis, et al., Glutamate Receptor Ion Channels: Structure, Regulation, and Function, Pharmacol Rev, 2010, pp. 405-496, vol. 62 Issue 3.
Wang, et al., Targeting the NMDA receptor subunit NR2B for treating or preventing age-related memory decline, Expert Opin. Ther. Targets, 2014, pp. 1121-1130, vol. 18 Issue 10.
Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.
Weickert, et al., Molecular evidence of N-methyl-D-aspartate receptor hypofunction in schizophrenia, Molecular Psychiatry, 2013, pp. 1185-1192, vol. 18.
Won, et al., Autistic-like social behaviour in Shank2-mutant mice improved by restoringNMDA receptor function, Nature, Jun. 14, 2012, pp. 261-265, vol. 486.
Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.
Youssif, S. "Recent trends in the chemistry of pyridine N-oxides" ARKIVOC, 2001, pp. 242-268.
Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.
Zarate, et al., A Randomized Trail of an N-methyl_D-aspartate Antagonist in Treatment-Resistant Major Depression, Arch Gen Psychiatry, 2006, pp. 856-864, vol. 63.

(56) References Cited

OTHER PUBLICATIONS

International Search Report and Written Opinion of the International Searching Authority for International Application No. PCT/EP2020/066400, dated Jul. 28, 2020.
International Search Report and Written Opinion of the International Searching Authority for International Application No. PCT/EP2020/066396, dated Jul. 29, 2020.
International Search Report and Written Opinion of the International Searching Authority for International Application No. PCT/EP2020/066392, dated Sep. 21, 2020.
International Search Report and Written Opinion of the International Searching Authority for International Application No. PCT/EP2020/066384, dated Jul. 28, 2020.
International Search Report and Written Opinion of the International Searching Authority for International Application No. PCT/EP2020/066405, dated Jul. 29, 2020.
Iadarola et al., 2015 Therapeutic Advances in Chronic Disease, vol. 6 (3), p. 97-114.
Machado-Vieira et al., 2017, "New Targets for Rapid Antidepressant Action" Prog. Neurobiol. 152-21-37.
Sun et al., 2020, "Synthesis and preliminary evaluation of novel C-labled GluN2B-selective NMDA receptor negative allosteric modulators" Acta Pharmacologica Sinica, 0:1-8.

\* cited by examiner ns and Trial. 2004; 3(4):219-60;

SUBSTITUTED PYRAZOLO[4,3-B]PYRIDINES AND THEIR USE AS GLUN2B RECEPTOR MODULATORS

CROSS-REFERENCE TO RELATED APPLICATIONS

This application claims the priority benefit of U.S. provisional application No. 62/861,674, filed Jun. 14, 2019, the contents of which are incorporated herein in their entireties by reference thereto.

FIELD OF THE INVENTION

The present invention is related to compounds having GluN2B modulating properties, pharmaceutical compositions comprising these compounds, chemical processes for preparing these compounds and their use in the treatment of diseases associated with GluN2B receptor activity in animals, in particular humans.

BACKGROUND OF THE INVENTION

Glutamate is one of the major excitatory neurotransmitters that is widely spread in the brain.

First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., Pharmacol Rev. 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., Neuropharmacology 2007; 52(1):77-86) and long-term depression (LTD) (Massey, P V et al., J Neurosci. 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., Nat Rev Neurosci. 2013; 14(6):383-400; Watanabe M et al., J Comp Neurol. 1993; 338(3):377-90) and are implicated in learning, memory processing, mood, attention, emotion and pain perception (Cull-Candy S et al., Curr Opin Neurobiol. 2001; 11(3):327-35).

Compounds that modulate GluN2B-containing NMDA receptor function can be useful in treatment of many neurological and psychiatric disorders including but not limited to bipolar disorder (Martucci L et al., Schizophrenia Res, 2006; 84(2-3):214-21), major depressive disorder (Miller O H et al., eLife. 2014; 3:e03581; Li N et al., Biol Psychiatry. 2011; 69(8):754-61), treatment-resistant depression (Preskorn S H et al. J Clin Psychopharmacol. 2008; 28(6): 631-7) and ther mood disorders (including schizophrenia (Grimwood S et al., Neuroreport. 1999; 10(3):461-5; Weickert C S et al. Molecular Psychiatry (2013) 18, 1185-1192), ante- and postpartum depression, seasonal affective disorder and the like), Alzheimer's disease (Hanson J E et al., Neurobiol Dis. 2015; 74:254-62; Li S et al., J Neurosci. 2011; 31(18):6627-38) and other dementias (Orgogozo J M et al. Stroke 2002, 33: 1834-1839), Parkinson's disease (Duty S, CNS Drugs. 2012; 26(12):1017-32; Steece-Collier K et al., Exp Neurol. 2000; 163(1):239-43; Leaver K R et al. Clin Exp Pharmacol Physiol. 2008; 35(11):1388-94), Huntington's chorea (Tang T S et al., Proc Natl Acad Sci USA. 2005; 102(7):2602-7; Li L et al., J Neuro physiol. 2004; 92(5):2738-46), multiple sclerosis (Grasselli G et al., Br J Pharmacol. 2013; 168(2):502-17; Farjam M et al., Iran J Pharm Res. 2014; 13(2):695-705), cognitive impairment (Wang D et al. 2014, Expert Opin Ther Targets Expert Opin Ther Targets. 2014; 18(10):1121-30), head injury (Bullock M R et al., Ann N Y Acad Sci. 1999; 890:51-8), spinal cord injury, stroke (Yang Y et al., J Neurosurg. 2003; 98(2):397-403), epilepsy (Naspolini A P et al., Epilepsy Res. 2012 June; 100(1-2):12-9), movement disorders (e.g. dyskinesias) (Morissette M et al., Mov Disord. 2006; 21(1):9-17), various neurodegenerative diseases (e.g. amyotrophic lateral sclerosis (Fuller P I et al., Neurosci Lett. 2006; 399(1-2):157-61) or neurodegeneration associated with bacterial or chronic infections), glaucoma (Naskar R et al. Semin Ophthalmol. 1999 September; 14(3):152-8), pain (e.g. chronic, cancer, post-operative and neuropathic pain (Wu L J and Zhuo M, Neurotherapeutics. 2009; 6(4):693-702), diabetic neuropathy, migraine (Peeters M et al., J Pharmacol Exp Ther. 2007; 321(2):564-72), cerebral ischemia (Yuan H et al., Neuron. 2015; 85(6):1305-18), encephalitis (Dalmau J. et al., Lancet Neurol. 2008; 7(12):1091-8.), autism and autism spectrum disorders (Won H. et al., Nature. 2012; 486(7402):261-5), memory and learning disorders (Tang, Y. P. et al., Nature. 1999; 401(6748):63-9), obsessive compulsive disorder (Arnold P D et al., Psychiatry Res. 2009; 172(2):136-9.), attention deficit hyperactivity disorder (ADHD) (Dorval K M et al., Genes Brain Behav. 2007; 6(5):444-52), PTSD (Haller J et al. Behav Pharmacol. 2011; 22(2):113-21; Leaderbrand K et al. Neurobiol Learn Mem. 2014; 113:35-40), tinnitus (Guitton M J, and Dudai Y, Neural Plast. 2007; 80904; Hu S S et al. 2016; 273(2): 325-332), sleep disorders (like narcolepsy or excessive daytime sleepiness, patent WO 2009058261 A1), vertigo and nystagmus (Straube A. et al., Curr Opin Neurol. 2005; 18(1):11-4; Starck M et al. J Neurol. 1997 January; 244(1):9-16), anxiety autoimmunological disorders like neuropsychiatric systemic lupus erythematosus (Kowal C et al. Proc. Natl. Acad. Sci. U.S.A. 2006; 103, 19854-19859) and addictive illnesses (e.g. alcohol addiction, drug addiction) (Nagy J, 2004, Curr Drug Targets CNS Neurol Disord 2004; 3(3):169-79.; Shen H et al., *Proc Natl Acad Sci USA*. 2011; 108(48):19407-12).

In view of the clinical importance of GluN2B, the identification of compounds that modulate GluN2B receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

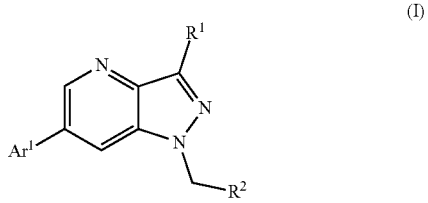

(I)

wherein
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo, and $C_{1-6}$alkyl;
$R^2$ is selected from the group consisting of:
(e)

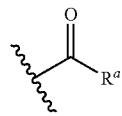

$R^a$ wherein R is selected from the group consisting of: $C_{1-6}$alkyl; $C_{3-6}$cycloalkyl; thienyl; pyridyl; pyridyl substituted with one or two F members; pyrazinyl;

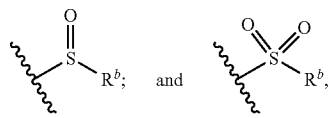

wherein $R^b$ is $C_{1-6}$alkyl;
(f) $C_{1-6}$alkyl substituted with one, two, or three members each independently selected from the group consisting of: OH, halo, $OC_{1-6}$alkyl, (=N—OH), (=N—$OCH_3$), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl;

and pharmaceutically acceptable salts, stereoisomers, isotopic variants, N-oxides, or solvates of compounds of Formula (I).

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as the pharmaceutically acceptable salts.

In a further aspect, the invention relates to pharmaceutical compositions for treating a disease, disorder, or medical condition mediated by GluN2B receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as GluN2B receptor modulators. Thus, the invention is directed to a method for modulating GluN2B receptor activity, including when such receptor is in a subject, comprising exposing GluN2B receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by GluN2B receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I),

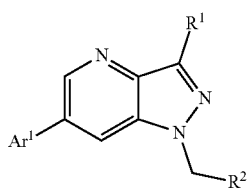

(I)

wherein
R$^1$ is H, halo, or CH$_3$;
Ar$^1$ is selected from the group consisting of:
(a) phenyl;
(b) phenyl substituted with one member selected from the group consisting of: halo, C$_{1-6}$alkyl, C$_{1-6}$perhaloalkyl, and OC$_{1-6}$perhaloalkyl;
(c) phenyl substituted with two or three members each independently selected from the group consisting of: halo, C$_{1-6}$alkyl, C$_{1-6}$perhaloalkyl, and OC$_{1-6}$perhaloalkyl; and
(d) thienyl substituted with one member selected from the group consisting of: halo, and C$_{1-6}$alkyl;
R$^2$ is selected from the group consisting of:
(e)

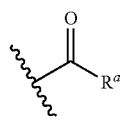

R$^a$ wherein R is selected from the group consisting of: C$_{1-6}$alkyl; C$_{3-6}$cycloalkyl; thienyl; pyridyl; pyridyl substituted with one or two F members; pyrazinyl;

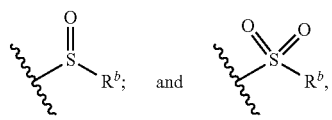

wherein R is C$_{1-6}$alkyl;
(f) C$_{1-6}$alkyl substituted with one, two, or three members each independently selected from the group consisting of: OH, halo, OC$_{1-6}$alkyl, (=N—OH), (=N—OCH$_3$), and cyclopropyl; and
(g) oxetanyl; oxetanyl substituted with C$_{1-6}$alkyl; tetrahydrofuranyl; oxazolidinone; oxazolidinone substituted with C$_{1-4}$alkyl, or cyclopropyl; and pyrrolidinone substituted with C$_{1-4}$alkyl;
and pharmaceutically acceptable salts, stereoisomers, isotopic variants, N-oxides, or solvates thereof.

An additional embodiment of the invention is a compound of Formula (I) wherein R$^1$ is H.
An additional embodiment of the invention is a compound of Formula (I) wherein R$^1$ is F.
An additional embodiment of the invention is a compound of Formula (I) wherein R$^1$ is CH$_3$.
An additional embodiment of the invention is a compound of Formula (I) wherein Ar$^1$ is phenyl.
An additional embodiment of the invention is a compound of Formula (I) wherein Ar$^1$ is phenyl substituted with one member selected from the group consisting of: F, CH$_3$, CF$_2$H, CF$_2$CH$_3$, CF$_3$, and OCF$_3$.
An additional embodiment of the invention is a compound of Formula (I) wherein Ar$^1$ is selected from the group consisting of:

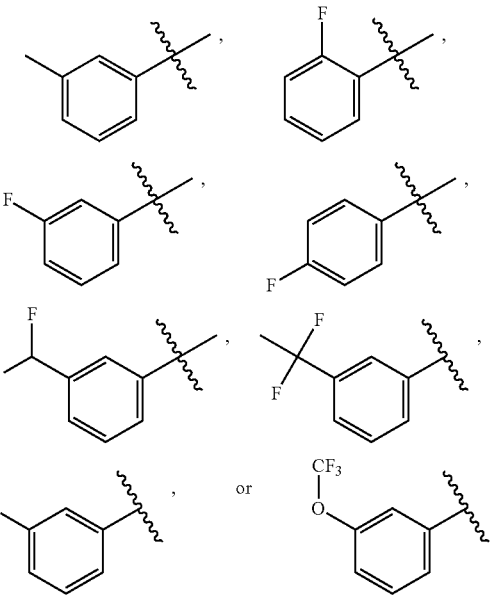

An additional embodiment of the invention is a compound of Formula (I) wherein Ar$^1$ is phenyl substituted with two members each independently selected from the group consisting of: F, Cl, CH$_3$, CF$_2$H, CF$_3$, CF$_2$CH$_3$, and OCF$_2$H.
An additional embodiment of the invention is a compound of Formula (I) wherein Ar$^1$ is selected from the group consisting of:

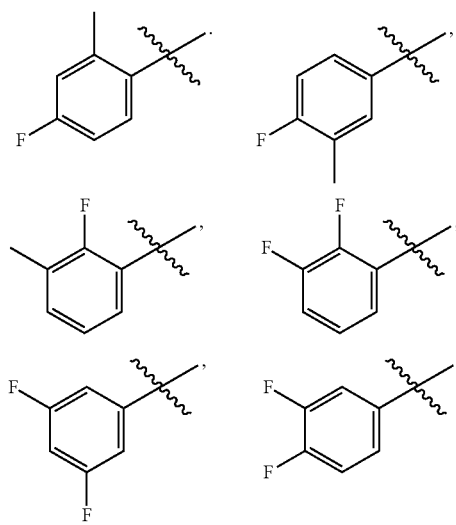

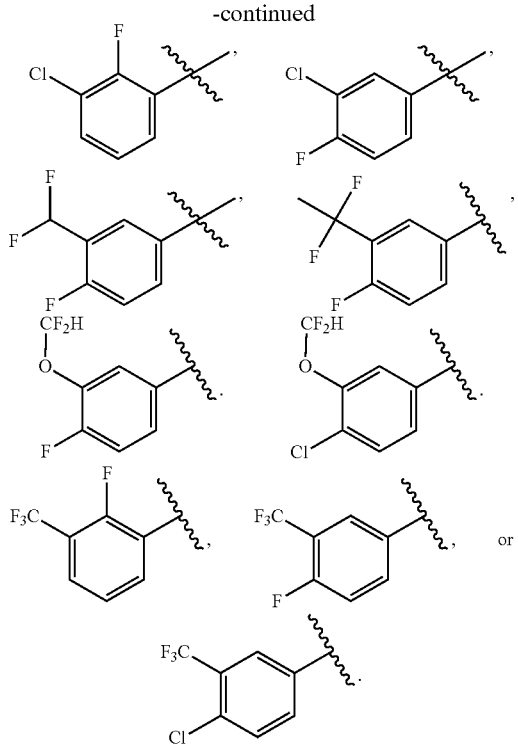

An additional embodiment of the invention is a compound of Formula (I) wherein Ar¹ is phenyl substituted with three members each independently selected from the group consisting of: F and CH₃.

An additional embodiment of the invention is a compound of Formula (I) wherein Ar¹ is

An additional embodiment of the invention is a compound of Formula (I) wherein Ar¹ is thienyl is substituted with Cl or CH₃.

An additional embodiment of the invention is a compound of Formula (I) wherein Ar¹ is

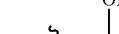

An additional embodiment of the invention is a compound of Formula (I) wherein R² is

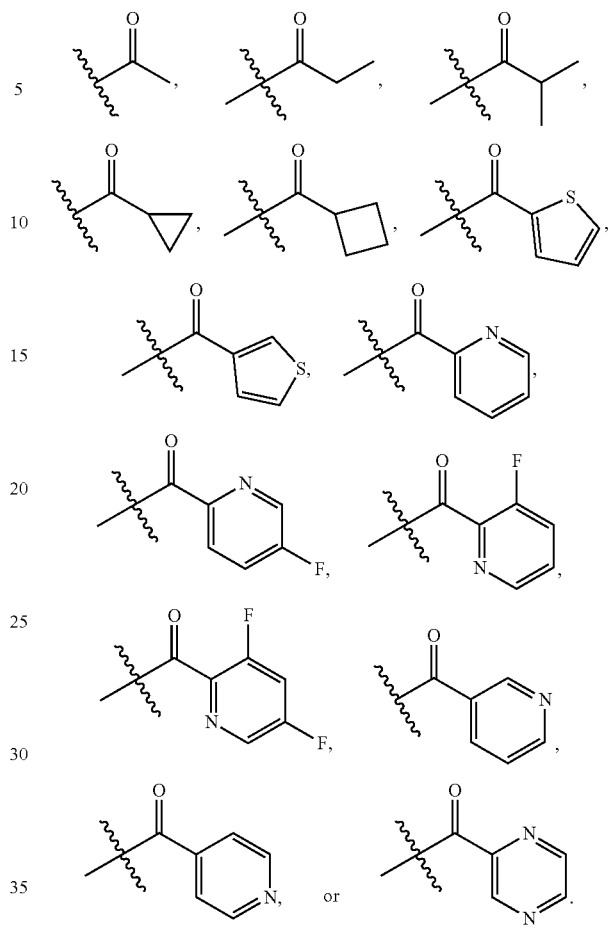

An additional embodiment of the invention is a compound of Formula (I) wherein R² is

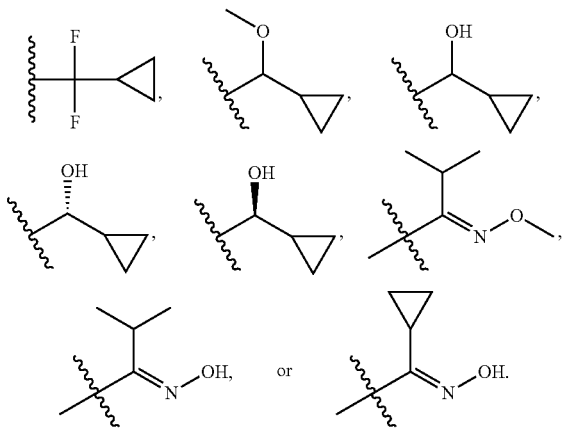

An additional embodiment of the invention is a compound of Formula (I) wherein R² is

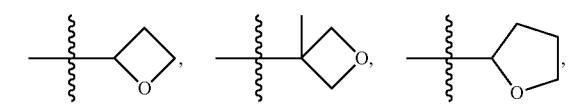
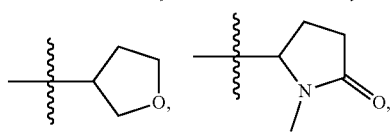
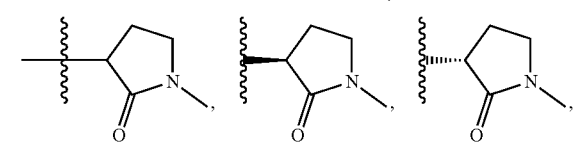
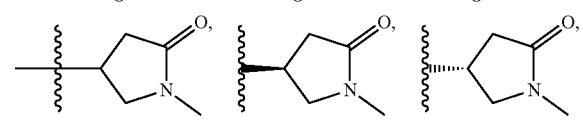
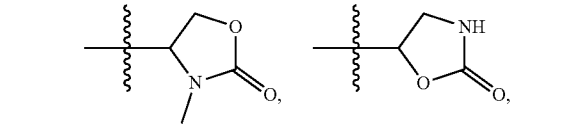
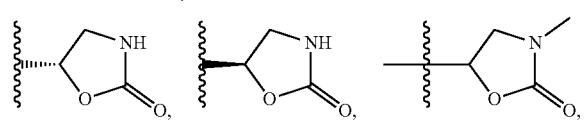
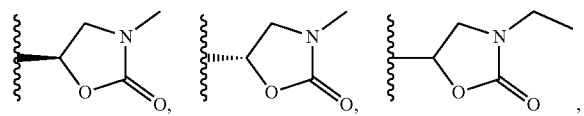
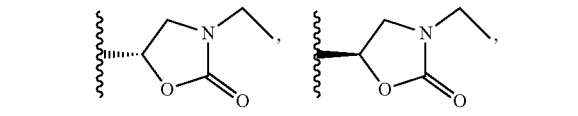
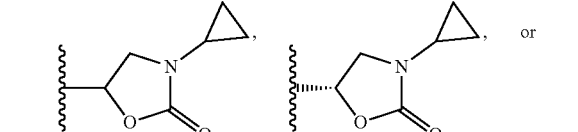

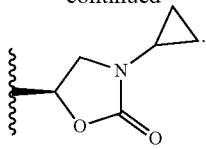

An additional embodiment of the invention is a compound of Formula (I) having the Formula (IA):

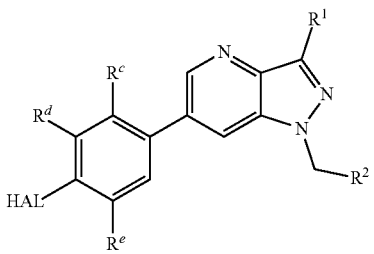

(IA)

wherein
HAL is F or Cl;
R¹ is H, F, or CH₃;
R² is selected from the group consisting of:
(a) (S=O)CH₂CH₃; (SO₂)CH₂CH₃; or

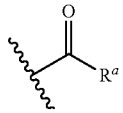

wherein $R^a$ is selected from the group consisting of: CH₃, CH₂CH₃, CH(CH₃)₂, cyclopropyl, cyclobutyl,

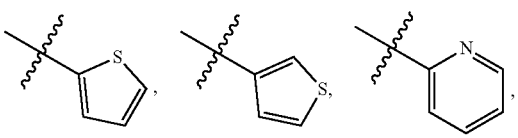
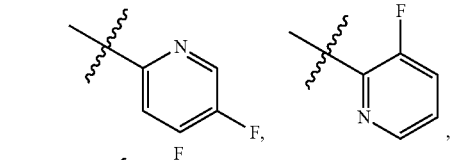
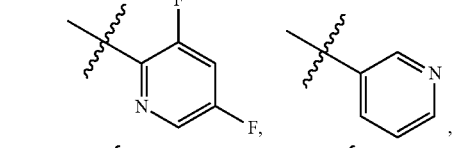
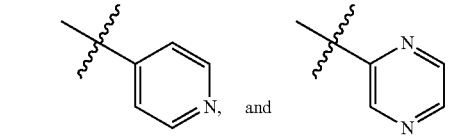

(b) CH₂OCH₃, CH(OH)(CH₂CH₃), CH(OH)CH(CH₃)₂, CF₂CH₂CH₃, CF₂(cyclopropyl), CH(OCH₃)(cyclopropyl), CH(OH)(cyclopropyl), or

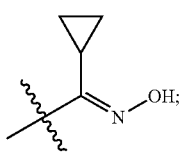 [SMILES: */C(=N/O)C1CC1]

and

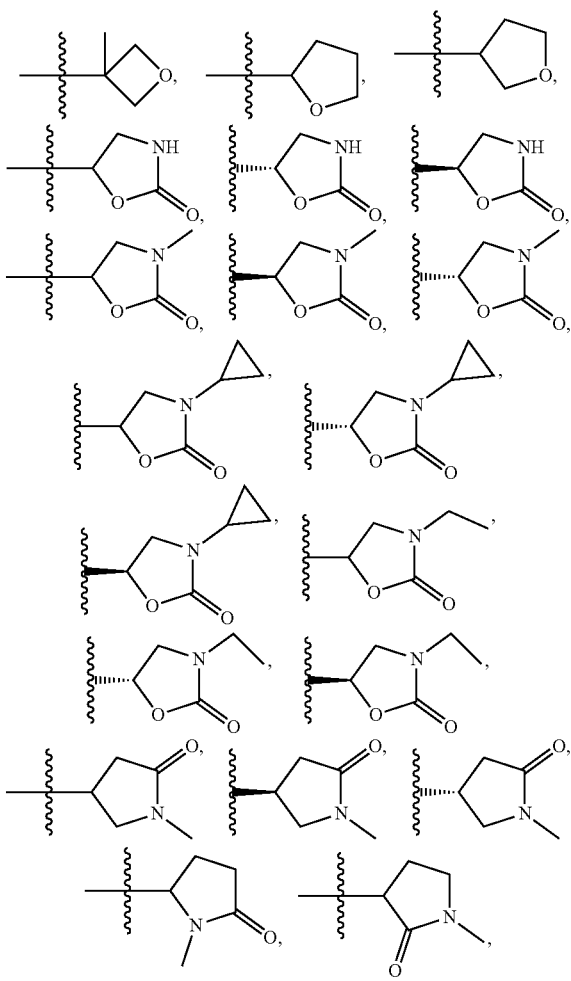

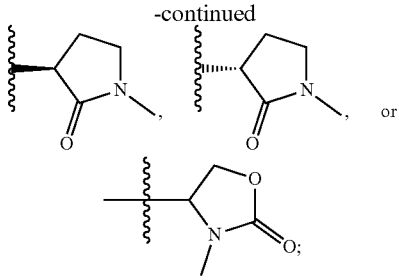

$R^c$ is H, F or $CH_3$;
$R^d$ is selected from the group consisting of: H, F, Cl, $CH_3$, $CF_2H$, $CF_2CH_3$, $CF_3$, and $OCF_2H$; and
$R^e$ is H or F; wherein when $R^e$ is F, $R^c$ is H.

An additional embodiment of the invention is a compound of Formula (I) having the Formula (IA), wherein HAL is F; $R^1$ is H; $R^c$ is H; and $R^e$ is H.

An additional embodiment of the invention is a compound of Formula (I) having the Formula (IB)

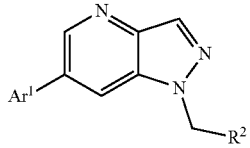

(IB)

wherein
$Ar^1$ is selected from the group consisting of:
(a) phenyl, 3-methylphenyl, 2-fluorophenyl, 3-fluorophenyl, 3-(difluoromethyl)phenyl, 3-(1,1-difluoroethyl)phenyl, 3-(trifluoromethyl)phenyl, 3-(trifluoromethoxy)phenyl, 5-methyl-2-thienyl, or 5-chloro-2-thienyl; and
(b) 2-fluoro-3-methyl-phenyl, 2,3-difluorophenyl, 3,5-difluorophenyl, 3-chloro-2-fluoro-phenyl, 2-fluoro-3-(trifluoromethyl)phenyl, 4-chloro-3-(difluoromethoxy)phenyl, or 4-chloro-3-(trifluoromethyl)phenyl; and $R^2$ is selected from the group consisting of: $(S=O)CH_2CH_3$, $(C=O)CH_2CH_3$, $(C=O)CH(CH_3)_2$, and $(C=O)$cyclopropyl.

A further embodiment of the current invention is a compound as shown below in Table 1.

| Ex # | Compound Name |
|---|---|
| 1 | 1-[6-(3,5-Difluorophenyl)pyrazol[4,3-b]pyridin-1-yl]butan-2-one |
| 2 | 3-Methyl-1-[6-[3-(trifluoromethyl)phenyl]pyrazolo[4,3-b]pyridin-1-yl]butan-2-one; |
| 3 | (RS)-3-Methyl-1-[6-[3-(trifluoromethyl)phenyl]pyrazolo[4,3-b]pyridin-1-yl]butan-2-ol; |
| 4 | 1-[6-[3-(Difluoromethyl)-4-fluoro-phenyl]pyrazolo[4,3-b]pyridin-1-yl]butan-2-one; |
| 5 | (RS)-1-[6-[3-(Difluoromethyl)-4-fluoro-phenyl]pyrazolo[4,3-b]pyridin-1-yl]butan-2-ol; |
| 6 | (E/Z)-3-Methyl-1-[6-[3-(trifluoromethyl)phenyl]pyrazolo[4,3-b]pyridin-1-yl]butan-2-one oxime; |
| 7 | 1-[6-(4-Fluoro-3-methyl-phenyl)pyrazolo[4,3-b]pyridin-1-yl]-3-methyl-butan-2-one; |
| 8 | (RS)-1-[6-(4-Fluoro-3-methyl-phenyl)pyrazolo[4,3-b]pyridin-1-yl]-3-methyl-butan-2-ol; |
| 9 | 1-Cyclopropyl-2-[6-(3,4,5-trifluorophenyl)pyrazolo[4,3-b]pyridin-1-yl]ethanone; |

-continued

| Ex # | Compound Name |
|---|---|
| 10 | (RS)-1-Cyclopropyl-2-[6-(3,4,5-trifluorophenyl)pyrazolo[4,3-b]pyridin-1-yl]ethanol; |
| 11 | (RS)-1-(2-Cyclopropyl-2-methoxy-ethyl)-6-(3,4,5-trifluorophenyl)pyrazolo[4,3-b]pyridine; |
| 12 | (RS)-6-[3-(Difluoromethoxy)-4-fluoro-phenyl]-1-(ethylsulfinylmethyl)pyrazolo[4,3-b]pyridine; |
| 13 | 6-[3-(Difluoromethoxy)-4-fluoro-phenyl]-1-(ethylsulfonylmethyl)pyrazolo[4,3-b]pyridine; |
| 14 | 2-[6-[3-(Difluoromethyl)-4-fluoro-phenyl]pyrazolo[4,3-b]pyridin-1-yl]-1-(2-pyridyl)ethanone; |
| 15 | 2-(6-(3-(Difluoromethyl)-4-fluorophenyl)-1H-pyrazolo[4,3-b]pyridin-1-yl)-1-(5-fluoropyridin-2-yl)ethan-1-one; |
| 16 | 2-(6-(3-(Difluoromethyl)-4-fluorophenyl)-1H-pyrazolo[4,3-b]pyridin-1-yl)-1-(pyridin-3-yl)ethan-1-one; |
| 17 | (RS)-1-(Oxetan-2-ylmethyl)-6-[3-(trifluoromethyl)phenyl]pyrazolo[4,3-b]pyridine; |
| 18 | (RS)-6-[3-(Difluoromethyl)-4-fluoro-phenyl]-1-(tetrahydrofuran-2-ylmethyl)pyrazolo[4,3-b]pyridine; |
| 19 | (RS)-4-[[6-[3-(Difluoromethoxy)-4-fluoro-phenyl]pyrazolo[4,3-b]pyridin-1-yl]methyl]-1-methyl-pyrrolidin-2-one; |
| 20 | (RS)-5-[[6-[3-(Difluoromethyl)-4-fluoro-phenyl]pyrazolo[4,3-b]pyridin-1-yl]methyl]oxazolidin-2-one; |
| 21 | (S)-5-[[6-[3-(Difluoromethyl)-4-fluoro-phenyl]pyrazolo[4,3-b]pyridin-1-yl]methyl]oxazolidin-2-one; |
| 22 | (R)-5-[[6-[3-(Difluoromethyl)-4-fluoro-phenyl]pyrazolo[4,3-b]pyridin-1-yl]methyl]oxazolidin-2-one; |
| 23 | 1-[6-[3-(Difluoromethyl)-4-fluoro-phenyl]pyrazolo[4,3-b]pyridin-1-yl]propan-2-one; |
| 24 | 1-[6-(4-Fluoro-3-methyl-phenyl)pyrazolo[4,3-b]pyridin-1-yl]propan-2-one; |
| 25 | 1-[6-[3-(Difluoromethoxy)-4-fluoro-phenyl]pyrazolo[4,3-b]pyridin-1-yl]propan-2-one; |
| 26 | 1-[6-[4-Chloro-3-(difluoromethoxy)phenyl]pyrazolo[4,3-b]pyridin-1-yl]propan-2-one; |
| 27 | 1-[6-(5-Chloro-2-thienyl)pyrazolo[4,3-b]pyridin-1-yl]butan-2-one; |
| 28 | 1-[6-(4-Fluorophenyl)pyrazolo[4,3-b]pyridin-1-yl]butan-2-one; |
| 29 | 1-[6-(3-Fluorophenyl)pyrazolo[4,3-b]pyridin-1-yl]butan-2-one; |
| 30 | 1-[6-[3-(Difluoromethyl)phenyl]pyrazolo[4,3-b]pyridin-1-yl]butan-2-one; |
| 31 | 1-[6-[3-(1,1-Difluoroethyl)phenyl]pyrazolo[4,3-b]pyridin-1-yl]butan-2-one; |
| 32 | 1-[6-(4-Fluoro-3-methyl-phenyl)pyrazolo[4,3-b]pyridin-1-yl]butan-2-one; |
| 33 | 1-[6-(2,3-Difluorophenyl)pyrazolo[4,3-b]pyridin-1-yl]butan-2-one; |
| 34 | 1-[6-(3,4-Difluorophenyl)pyrazolo[4,3-b]pyridin-1-yl]butan-2-one; |
| 35 | 1-[6-(3,4-Difluorophenyl)-3-fluoro-pyrazolo[4,3-b]pyridin-1-yl]butan-2-one; |
| 36 | 1-(6-(3-(Difluoromethyl)-4-fluorophenyl)-3-methyl-1H-pyrazolo[4,3-b]pyridin-1-yl)butan-2-one; |
| 37 | 1-[6-[3-(1,1-Difluoroethyl)-4-fluoro-phenyl]pyrazolo[4,3-b]pyridin-1-yl]butan-2-one; |
| 38 | 1-[6-[2-Fluoro-3-(trifluoromethyl)phenyl]pyrazolo[4,3-b]pyridin-1-yl]butan-2-one; |
| 39 | 1-[6-[4-Fluoro-3-(trifluoromethyl)phenyl]pyrazolo[4,3-b]pyridin-1-yl]butan-2-one; |
| 40 | 1-[6-[3-(Difluoromethoxy)-4-fluoro-phenyl]pyrazolo[4,3-b]pyridin-1-yl]butan-2-one; |
| 41 | 1-[6-[4-Chloro-3-(difluoromethoxy)phenyl]pyrazolo[4,3-b]pyridin-1-yl]butan-2-one; |
| 42 | 1-[6-(3,4,5-Trifluorophenyl)pyrazolo[4,3-b]pyridin-1-yl]butan-2-one; |
| 43 | 1-[6-(2,3,4-Trifluorophenyl)pyrazolo[4,3-b]pyridin-1-yl]butan-2-one; |
| 44 | 3-Methyl-1-(6-phenylpyrazolo[4,3-b]pyridin-1-yl)butan-2-one; |
| 45 | 1-[6-(4-Fluorophenyl)pyrazolo[4,3-b]pyridin-1-yl]-3-methyl-butan-2-one; |
| 46 | 1-[6-(3-Fluorophenyl)pyrazolo[4,3-b]pyridin-1-yl]-3-methyl-butan-2-one; |
| 47 | 1-[6-[3-(Difluoromethyl)phenyl]pyrazolo[4,3-b]pyridin-1-yl]-3-methyl-butan-2-one; |
| 48 | 1-[6-(2,3-Difluorophenyl)pyrazolo[4,3-b]pyridin-1-yl]-3-methyl-butan-2-one; |
| 49 | 1-[6-(3,4-Difluorophenyl)pyrazolo[4,3-b]pyridin-1-yl]-3-methyl-butan-2-one; |
| 50 | 1-[6-[2-Fluoro-3-(trifluoromethyl)phenyl]pyrazolo[4,3-b]pyridin-1-yl]-3-methyl-butan-2-one; |
| 51 | 1-[6-[4-Fluoro-3-(trifluoromethyl)phenyl]pyrazolo[4,3-b]pyridin-1-yl]-3-methyl-butan-2-one; |
| 52 | 1-[6-(4-Fluoro-2-methyl-phenyl)pyrazolo[4,3-b]pyridin-1-yl]-3-methyl-butan-2-one; |
| 53 | 3-Methyl-1-[6-(3,4,5-trifluorophenyl)pyrazolo[4,3-b]pyridin-1-yl]butan-2-one; |
| 54 | 3-Methyl-1-[6-(2,3,4-trifluorophenyl)pyrazolo[4,3-b]pyridin-1-yl]butan-2-one; |

| Ex # | Compound Name |
|---|---|
| 55 | 2-[6-(5-Chloro-2-thienyl)pyrazolo[4,3-b]pyridin-1-yl]-1-cyclopropyl-ethanone; |
| 56 | 1-Cyclopropyl-2-[6-(5-methyl-2-thienyl)pyrazolo[4,3-b]pyridin-1-yl]ethanone; |
| 57 | 1-Cyclopropyl-2-[6-(3-fluorophenyl)pyrazolo[4,3-b]pyridin-1-yl]ethanone; |
| 58 | 1-Cyclopropyl-2-[6-(2-fluorophenyl)pyrazolo[4,3-b]pyridin-1-yl]ethanone; |
| 59 | 1-Cyclopropyl-2-[6-(4-fluorophenyl)pyrazolo[4,3-b]pyridin-1-yl]ethanone; |
| 60 | 1-Cyclopropyl-2-[6-(m-tolyl)pyrazolo[4,3-b]pyridin-1-yl]ethanone; |
| 61 | 1-Cyclopropyl-2-[6-[3-(difluoromethyl)phenyl]pyrazolo[4,3-b]pyridin-1-yl]ethanone; |
| 62 | 1-Cyclopropyl-2-[6-[3-(trifluoromethyl)phenyl]pyrazolo[4,3-b]pyridin-1-yl]ethanone; |
| 63 | 1-Cyclopropyl-2-[6-[3-(trifluoromethoxy)phenyl]pyrazolo[4,3-b]pyridin-1-yl]ethanone; |
| 64 | 1-Cyclopropyl-2-[6-(2,3-difluorophenyl)pyrazolo[4,3-b]pyridin-1-yl]ethanone; |
| 65 | 1-Cyclopropyl-2-[6-(3,4-difluorophenyl)pyrazolo[4,3-b]pyridin-1-yl]ethanone; |
| 66 | 1-Cyclopropyl-2-[6-(3,5-difluorophenyl)pyrazolo[4,3-b]pyridin-1-yl]ethanone; |
| 67 | 2-[6-(3-Chloro-2-fluoro-phenyl)pyrazolo[4,3-b]pyridin-1-yl]-1-cyclopropyl-ethanone; |
| 68 | 2-[6-[3-Chloro-4-fluoro-phenyl)pyrazolo[4,3-b]pyridin-1-yl]-1-cyclopropyl-ethanone; |
| 69 | 1-Cyclopropyl-2-[6-(4-fluoro-3-methyl-phenyl)pyrazolo[4,3-b]pyridin-1-yl]ethanone; |
| 70 | 1-Cyclobutyl-2-[6-(4-fluoro-3-methyl-phenyl)pyrazolo[4,3-b]pyridin-1-yl]ethanone; |
| 71 | 1-Cyclopropyl-2-[6-(2-fluoro-3-methyl-phenyl)pyrazolo[4,3-b]pyridin-1-yl]ethanone; |
| 72 | 1-Cyclopropyl-2-[6-(4-fluoro-2-methyl-phenyl)pyrazolo[4,3-b]pyridin-1-yl]ethanone; |
| 73 | 1-Cyclopropyl-2-[6-[2-fluoro-3-(trifluoromethyl)phenyl]pyrazolo[4,3-b]pyridin-1-yl]ethanone; |
| 74 | 1-Cyclopropyl-2-[6-[4-fluoro-3-(trifluoromethyl)phenyl]pyrazolo[4,3-b]pyridin-1-yl]ethanone; |
| 75 | 2-[6-[4-Chloro-3-(trifluoromethyl)phenyl]pyrazolo[4,3-b]pyridin-1-yl]-1-cyclopropyl-ethanone; |
| 76 | 1-Cyclopropyl-2-[6-[3-(difluoromethyl)-4-fluoro-phenyl]pyrazolo[4,3-b]pyridin-1-yl]ethanone; |
| 77 | 1-Cyclopropyl-2-[6-[3-(difluoromethoxy)-4-fluoro-phenyl]pyrazolo[4,3-b]pyridin-1-yl]ethanone; |
| 78 | 1-Cyclopropyl-2-[6-(4-fluoro-2,3-dimethyl-phenyl)pyrazolo[4,3-b]pyridin-1-yl]ethanone; |
| 79 | 1-Cyclopropyl-2-[6-(2,3,4-trifluorophenyl)pyrazolo[4,3-b]pyridin-1-yl]ethanone; |
| 80 | (RS)-1-(Ethylsulfinylmethyl)-6-(3-fluorophenyl)pyrazolo[4,3-b]pyridine; |
| 81 | (RS)-1-(Ethylsulfinylmethyl)-6-[3-(trifluoromethyl)phenyl]pyrazolo[4,3-b]pyridine; |
| 82 | (RS) 6-(3,4-Difluorophenyl)-1-(ethylsulfinylmethyl)pyrazolo[4,3-b]pyridine; |
| 83 | (RS)-6-(3-(Difluoromethyl)-4-fluorophenyl)-1-((ethylsulfinyl)methyl)-1H-pyrazolo[4,3-b]pyridine; |
| 84 | (S*)-6-(3-(Difluoromethyl)-4-fluorophenyl)-1-((ethylsulfinyl)methyl)-1H-pyrazolo[4,3-b]pyridine; |
| 85 | (R*)-6-(3-(Difluoromethyl)-4-fluorophenyl)-1-((ethylsulfinyl)methyl)-1H-pyrazolo[4,3-b]pyridine; |
| 86 | (RS)-1-(Ethylsulfinylmethyl)-6-[2-fluoro-3-(trifluoromethyl)phenyl]pyrazolo[4,3-b]pyridine; |
| 87 | (RS)-6-[4-Chloro-3-(difluoromethoxy)phenyl]-1-(ethylsulfinylmethyl)pyrazolo[4,3-b]pyridine; |
| 88 | (RS)-1-(Ethylsulfinylmethyl)-6-(3,4,5-trifluorophenyl)pyrazolo[4,3-b]pyridine; |
| 89 | 6-(4-Fluoro-3-methyl-phenyl)-1-(2-methoxyethyl)pyrazolo[4,3-b]pyridine; |
| 90 | (RS)-4-Methoxy-1-[6-[3-(trifluoromethyl)phenyl]pyrazolo[4,3-b]pyridin-1-yl]butan-2-ol; |
| 91 | (RS)-1-[6-(3,4-Difluorophenyl)pyrazolo[4,3-b]pyridin-1-yl]butan-2-ol; |
| 92 | (RS)-1-[6-[3-(Difluoromethoxy)-4-fluoro-phenyl]pyrazolo[4,3-b]pyridin-1-yl]butan-2-ol; |
| 93 | (RS)-1-[6-[4-Chloro-3-(difluoromethoxy)phenyl]pyrazolo[4,3-b]pyridin-1-yl]butan-2-ol; |
| 94 | (RS)-1-[6-(3,4-Difluorophenyl)-3-fluoro-pyrazolo[4,3-b]pyridin-1-yl]butan-2-ol; |
| 95 | (RS)-1-[6-[3-(1,1-Difluoroethyl)phenyl]pyrazolo[4,3-b]pyridin-1-yl]butan-2-ol; |

-continued

| Ex # | Compound Name |
|---|---|
| 96 | (RS)-3-Methyl-1-(6-phenylpyrazolo[4,3-b]pyridin-1-yl)butan-2-ol; |
| 97 | (RS)-3-Methyl-1-[6-(3,4,5-trifluorophenyl)pyrazolo[4,3-b]pyridin-1-yl]butan-2-ol; |
| 98 | 1-(2,2-Difluorobutyl)-6-[3-(difluoromethyl)-4-fluoro-phenyl]pyrazolo[4,3-b]pyridine; |
| 99 | 1-(2,2-Difluorobutyl)-6-[3-(difluoromethoxy)-4-fluoro-phenyl]pyrazolo[4,3-b]pyridine; |
| 100 | (RS)-1-Cyclopropyl-2-[6-[3-(trifluoromethyl)phenyl]pyrazolo[4,3-b]pyridin-1-yl]ethanol; |
| 101 | (RS)-1-Cyclopropyl-2-[6-(4-fluoro-3-methyl-phenyl)pyrazolo[4,3-b]pyridin-1-yl]ethanol; |
| 102 | (R)-1-Cyclopropyl-2-[6-(4-fluoro-3-methyl-phenyl)pyrazolo[4,3-b]pyridin-1-yl]ethanol; |
| 103 | (S)-1-Cyclopropyl-2-[6-(4-fluoro-3-methyl-phenyl)pyrazolo[4,3-b]pyridin-1-yl]ethanol; |
| 104 | (RS)-1-Cyclopropyl-2-(6-(3-(difluoromethyl)-4-fluorophenyl)-1H-pyrazolo[4,3-b]pyridin-1-yl)ethan-1-ol; |
| 105 | (E/Z)-N-Methoxy-3-methyl-1-[6-[3-(trifluoromethyl)phenyl]pyrazolo[4,3-b]pyridin-1-yl]butan-2-imine; |
| 106 | (E/Z)-1-Cyclopropyl-2-[6-[3-(trifluoromethyl)phenyl]pyrazolo[4,3-b]pyridin-1-yl]ethanone oxime; |
| 107 | (E/Z)-1-Cyclopropyl-2-[6-[3-(difluoromethyl)-4-fluoro-phenyl]pyrazolo[4,3-b]pyridin-1-yl]ethanone oxime; |
| 108 | 1-(2-Cyclopropyl-2,2-difluoro-ethyl)-6-[3-(difluoromethyl)-4-fluoro-phenyl]pyrazolo[4,3-b]pyridine; |
| 109 | 1-(2-Cyclopropyl-2,2-difluoro-ethyl)-6-[3-(difluoromethoxy)-4-fluoro-phenyl]pyrazolo[4,3-b]pyridine; |
| 110 | 6-[3-(Difluoromethyl)-4-fluoro-phenyl]-1-[(3-methyloxetan-3-yl)methyl]pyrazolo[4,3-b]pyridine; |
| 111 | (RS)-1-(Tetrahydrofuran-2-ylmethyl)-6-[3-(trifluoromethyl)phenyl]pyrazolo[4,3-b]pyridine; |
| 112 | (RS)-6-[3-(Difluoromethoxy)-4-fluoro-phenyl]-1-(tetrahydrofuran-2-ylmethyl)pyrazolo[4,3-b]pyridine; |
| 113 | (RS)-6-[3-(Difluoromethyl)-4-fluoro-phenyl]-1-(tetrahydrofuran-3-ylmethyl)pyrazolo[4,3-b]pyridine; |
| 114 | (RS)-5-((6-(3-(Difluoromethoxy)-4-fluorophenyl)-1H-pyrazolo[4,3-b]pyridin-1-yl)methyl)-1-methylpyrrolidin-2-one; |
| 115 | (RS)-5-[[6-[3-(Difluoromethyl)-4-fluoro-phenyl]pyrazolo[4,3-b]pyridin-1-yl]methyl]-1-methyl-pyrrolidin-2-one; |
| 116 | (RS)-3-[[6-[3-(Difluoromethyl)-4-fluoro-phenyl]pyrazolo[4,3-b]pyridin-1-yl]methyl]-1-methyl-pyrrolidin-2-one; |
| 117 | (S)-3-[[6-[3-(Difluoromethyl)-4-fluoro-phenyl]pyrazolo[4,3-b]pyridin-1-yl]methyl]-1-methyl-pyrrolidin-2-one; |
| 118 | (R)-3-[[6-[3-(Difluoromethyl)-4-fluoro-phenyl]pyrazolo[4,3-b]pyridin-1-yl]methyl]-1-methyl-pyrrolidin-2-one; |
| 119 | (RS)-3-((6-(3-(Difluoromethoxy)-4-fluorophenyl)-1H-pyrazolo[4,3-b]pyridin-1-yl)methyl)-1-methylpyrrolidin-2-one; |
| 120 | (RS)-4-[[6-[3-(Difluoromethyl)-4-fluoro-phenyl]pyrazolo[4,3-b]pyridin-1-yl]methyl]-1-methyl-pyrrolidin-2-one; |
| 121 | (S)-4-[[6-[3-(Difluoromethyl)-4-fluoro-phenyl]pyrazolo[4,3-b]pyridin-1-yl]methyl]-1-methyl-pyrrolidin-2-one; |
| 122 | (R)-4-[[6-[3-(Difluoromethyl)-4-fluoro-phenyl]pyrazolo[4,3-b]pyridin-1-yl]methyl]-1-methyl-pyrrolidin-2-one; |
| 123 | (RS)-4-((6-(3-(difluoromethoxy)-4-fluorophenyl)-1H-pyrazolo[4,3-b]pyridin-1-yl)methyl)-3-methyloxazolidin-2-one; |
| 124 | (RS)-4-[[6-[3-(Difluoromethyl)-4-fluoro-phenyl]pyrazolo[4,3-b]pyridin-1-yl]methyl]-3-methyl-oxazolidin-2-one; |
| 125 | (RS)-5-[[6-[3-(Difluoromethoxy)-4-fluoro-phenyl]pyrazolo[4,3-b]pyridin-1-yl]methyl]oxazolidin-2-one; |
| 126 | (RS)-5-[[6-[4-Chloro-3-(difluoromethoxy)phenyl]pyrazolo[4,3-b]pyridin-1-yl]methyl]oxazolidin-2-one; |
| 127 | (RS)-5-[[6-[3-(1,1-Difluoroethyl)-4-fluoro-phenyl]pyrazolo[4,3-b]pyridin-1-yl]methyl]oxazolidin-2-one; |
| 128 | (RS)-5-((6-(3-(Difluoromethoxy)-4-fluorophenyl)-1H-pyrazolo[4,3-b]pyridin-1-yl)methyl)-3-methyloxazolidin-2-one; |
| 129 | (5R)-5-[[6-[3-(Difluoromethyl)-4-fluoro-phenyl]pyrazolo[4,3-b]pyridin-1-yl]methyl]-3-methyl-oxazolidin-2-one; |
| 130 | (5S)-5-[[6-[3-(Difluoromethyl)-4-fluoro-phenyl]pyrazolo[4,3-b]pyridin-1-yl]methyl]-3-methyl-oxazolidin-2-one; |
| 131 | (RS)-5-[[6-[3-(Difluoromethyl)-4-fluoro-phenyl]pyrazolo[4,3-b]pyridin-1-yl]methyl]-3-ethyl-oxazolidin-2-one; |
| 132 | (S)-5-[[6-[3-(Difluoromethyl)-4-fluoro-phenyl]pyrazolo[4,3-b]pyridin-1-yl]methyl]-3-ethyl-oxazolidin-2-one; |
| 133 | (R)-5-[[6-[3-(Difluoromethyl)-4-fluoro-phenyl]pyrazolo[4,3-b]pyridin-1-yl]methyl]-3-ethyl-oxazolidin-2-one; |
| 134 | (RS)-3-Cyclopropyl-5-[[6-[3-(difluoromethyl)-4-fluoro-phenyl]pyrazolo[4,3-b]pyridin-1-yl]methyl]oxazolidin-2-one; |

-continued

| Ex # | Compound Name |
|------|---------------|
| 135 | (S)-3-Cyclopropyl-5-[[6-[3-(difluoromethyl)-4-fluoro-phenyl]pyrazolo[4,3-b]pyridin-1-yl]methyl]oxazolidin-2-one; |
| 136 | (R)-3-Cyclopropyl-5-[[6-[3-(difluoromethyl)-4-fluoro-phenyl]pyrazolo[4,3-b]pyridin-1-yl]methyl]oxazolidin-2-one; |
| 137 | 2-[6-[3-(Difluoromethyl)-4-fluoro-phenyl]pyrazolo[4,3-b]pyridin-1-yl]-1-(2-thienyl)ethanone; |
| 138 | 2-[6-[3-(Difluoromethyl)-4-fluoro-phenyl]pyrazolo[4,3-b]pyridin-1-yl]-1-(3-thienyl)ethanone; |
| 139 | 2-[6-[3-(Difluoromethyl)-4-fluoro-phenyl]pyrazolo[4,3-b]pyridin-1-yl]-1-(4-pyridyl)ethanone; |
| 140 | 2-(6-(3-(Difluoromethyl)-4-fluorophenyl)-1H-pyrazolo[4,3-b]pyridin-1-yl)-1-(3-fluoropyridin-2-yl)ethan-1-one; |
| 141 | 2-(6-(3-(Difluoromethyl)-4-fluorophenyl)-1H-pyrazolo[4,3-b]pyridin-1-yl)-1-(3,5-difluoropyridin-2-yl)ethan-1-one; and |
| 142 | 2-(6-(3-(Difluoromethyl)-4-fluorophenyl)-1H-pyrazolo[4,3-b]pyridin-1-yl)-1-(pyrazin-2-yl)ethan-1-one; | and pharmaceutically acceptable salts, N-oxides, or solvates thereof.

A further embodiment of the current invention is a compound selected from the group consisting of:
1-[6-[3-(Difluoromethyl)-4-fluoro-phenyl]pyrazolo[4,3-b]pyridin-1l-yl]butan-2-one;
1-[6-[3-(Difluoromethyl)-4-fluoro-phenyl]pyrazolo[4,3-b]pyridin-1l-yl]propan-2-one;
1-[6-(3,4-Difluorophenyl)pyrazolo[4,3-b]pyridin-1l-yl]butan-2-one;
1-(6-(3-(Difluoromethyl)-4-fluorophenyl)-3-methyl-1H-pyrazolo[4,3-b]pyridin-1-yl)butan-2-one;
1-[6-[3-(Difluoromethoxy)-4-fluoro-phenyl]pyrazolo[4,3-b]pyridin-1l-yl]butan-2-one;
1-Cyclopropyl-2-[6-(4-fluorophenyl)pyrazolo[4,3-b]pyridin-1l-yl]ethanone;
1-Cyclopropyl-2-[6-[3-(difluoromethyl)-4-fluoro-phenyl]pyrazolo[4,3-b]pyridin-1-yl]ethanone;
(RS)-6-(3-(Difluoromethyl)-4-fluorophenyl)-1-((ethylsulfinyl)methyl)-1H-pyrazolo[4,3-b]pyridine;
(S*)-6-(3-(Difluoromethyl)-4-fluorophenyl)-1-((ethylsulfinyl)methyl)-1H-pyrazolo[4,3-b]pyridine; and
(5R)-5-[[6-[3-(Difluoromethyl)-4-fluoro-phenyl]pyrazolo[4,3-b]pyridin-1-yl]methyl]-3-methyl-oxazolidin-2-one;
and pharmaceutically acceptable salts, solvates, stereoisomers, isotopic variants, or N-oxides thereof.

An additional embodiment of the invention is a pharmaceutical composition comprising:
(A) an effective amount of at least one compound selected from compounds of Formula (I):

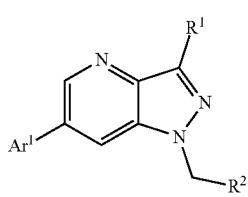

(I)

wherein
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo, and $C_{1-6}$alkyl;
$R^2$ is selected from the group consisting of:
(e)

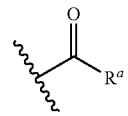

$R^a$ wherein R is selected from the group consisting of: $C_{1-6}$alkyl; $C_{3-6}$cycloalkyl; thienyl; pyridyl; pyridyl substituted with one or two F members; pyrazinyl;

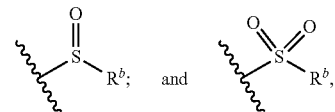

wherein R is $C_{1-6}$alkyl;
(f) $C_{1-6}$alkyl substituted with one, two, or three members each independently selected from the group consisting of OH, halo, $OC_{1-6}$alkyl, (=N—OH), (=N—$OCH_3$), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl;
and pharmaceutically acceptable salts, stereoisomers, isotopic variants, N-oxides or solvates of compounds of Formula (I);
and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

Also within the scope of the invention are enantiomers and diastereomers of the compounds of Formula (I) (as well as Formulas (IA), and (IB)). Also within the scope of the invention are the pharmaceutically acceptable salts, N-oxides or solvates of the compounds of Formula (I) (as well as Formulas (IA), and (IB)). Also within the scope of the invention are the pharmaceutically acceptable prodrugs of compounds of Formula (I) (as well as Formulas (IA), and (IB)), and pharmaceutically active metabolites of the compounds of Formula (I) (as well as Formulas (IA), and (IB)).

Also within the scope of the invention are isotopic variations of compounds of Formula (I) (as well as Formulas (IA), and (IB)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), and (IB)). Also within the scope of the invention are the pharmaceutically acceptable prodrugs of the isotopic variations of the compounds of Formula (I) (as well as Formulas (IA), and (IB)), and pharmaceutically active metabolites of the isotopic variations of the compounds of Formula (I) (as well as Formulas (IA), and (IB)).

An additional embodiment of the invention is a method of treating a subject suffering from or diagnosed with a disease, disorder, or medical condition mediated by GluN2B receptor activity, comprising administering to a subject in need of such treatment an effective amount of at least one compound selected from compounds of Formula (I):

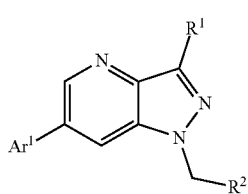

(I)

wherein
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo, and $C_{1-6}$alkyl;
$R^2$ is selected from the group consisting of:
(e)

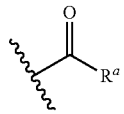

wherein $R^a$ is selected from the group consisting of: $C_{1-6}$alkyl; $C_{3-6}$cycloalkyl; thienyl; pyridyl; pyridyl substituted with one or two F members; pyrazinyl

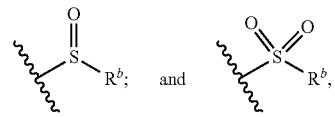

wherein $R^b$ is $C_{1-6}$alkyl;
(f) $C_{1-6}$alkyl substituted with one, two, or three members each independently selected from the group consisting of: OH, halo, $OC_{1-6}$alkyl, (=N—OH), (=N—$OCH_3$), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl;
and pharmaceutically acceptable salts, stereoisomers, isotopic variants, N-oxides, or solvates thereof, to a subject in need thereof.

An additional embodiment of the invention is a method of treating a subject suffering from or diagnosed with a disease, disorder, or medical condition mediated by GluN2B receptor activity, comprising administering to a subject in need of such treatment an effective amount of at least one compound selected from compounds of Formula (I) (as well as Formulas (IA), and (IB)), enantiomers and diastereomers of the compounds of Formula (I), isotopic variations of the compounds of Formula (I), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorders with postpartum onset, depressive disorders with psychotic symptoms; persistent mood disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include but are not limited to mental and behavioral disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present invention include, but are not limited to Parkinson's disease; second Parkinsonism, such as post encephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include but are not limited to dystonia including but not limited to focal dystonia, multiple-focal or segmental dystonia, torsion dystonia, hemispheric, generalised and tardive dystonia (induced by psychopharmacological drugs). Focal dystonia includes cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "thienyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

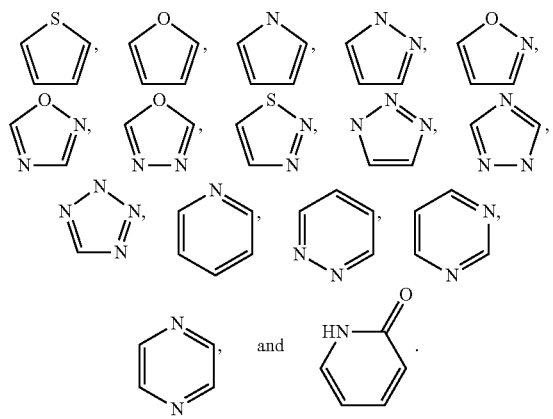

Those skilled in the art will recognize that the species of heteroaryl, cycloalkyl, aryl and heterocycloalkyl groups listed or illustrated above are not exhaustive, and that additional species within the scope of these defined terms may also be selected.

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

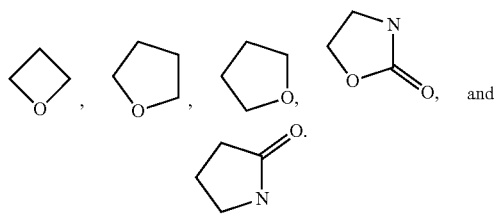

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

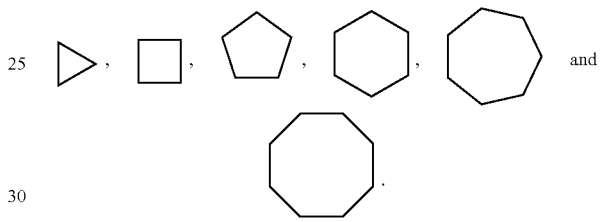

The term "halo" represents chloro, fluoro, bromo or iodo.

The term "perhaloalkyl" or "haloalkyl" refers to a straight- or branched-chain alkyl group having from 1 to 6 carbon atoms in the chain optionally substituting hydrogens with halogens. The term "$C_{1-4}$haloalkyl" as used here refers to a straight- or branched-chain alkyl group having from 1 to 4 carbon atoms in the chain, optionally substituting hydrogens with halogens. The term "$C_{1-6}$haloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

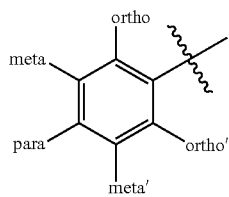

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

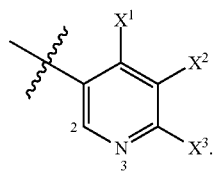

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of 7 electrons and an atom (usually H).

For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬▬ and ▬◀ are used as meaning the same spatial arrangement in chemical structures shown herein. Analogously, the symbols ⦀⦀⦀⦀ and ·····⦀⦀⦀ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (IA), and (IB)), or pharmaceutically acceptable salts of compounds of Formula (I) (as well as Formulas (IA), and (IB)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), and (IB)) or pharmaceutically acceptable salts of compounds of Formula (I) (as well as Formulas (IA), and (IB)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example deuterium (i.e., D or $^2$H); or tritium (i.e., T or $^3$H)), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $Ar^1$, $R^2$, $R^a$, $R^b$, $R^e$, $R^d$, $R^e$, HAL, and X, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $Ar^1$, $R^2$, $R^a$, $R^b$, $R^c$, $R^d$, $R^e$, HAL, and X, and any other generic substituent symbol used herein.

The nomenclature "$C_{i\text{-}j}$" with j>i, when applied herein to a class of substituents, is meant to refer to embodiments of this invention for which each and every one of the number of carbon members, from i to j including i and j, is independently realized. By way of example, the term $C_{1\text{-}4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n\text{-}m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), and (IB)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), and (IB)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002.

Examples of pharmaceutically acceptable salts are those that are pharmacologically effective and suitable for contact with the tissues of patients without undue toxicity, irritation, or allergic response. A compound of Formula (I) (as well as Formulas (IA), and (IB)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), and (IB)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), and (IB)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (IA), and (IB)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), and (IB)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), and (IB)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), and (IB)), which may also be used in the methods of the invention. A "pharmaceutically active metabolite" means a pharmacologically active product of metabolism in the body of a compound of Formula (I) (as well as Formulas (IA), and (IB)) as applicable, or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, Drug DevRes. 1995, 34, 220-230; Bodor, AdvDrug Res. 1984, 13, 224-331; Bundgaard, *Design of Prodrugs* (Elsevier Press, 1985); and Larsen, *Design and Application of Prodrugs, Drug Design andDevelopment* (Krogsgaard-Larsen, et al., eds., Harwood Academic Publishers, 1991).

The compounds of Formula (I) (as well as Formulas (IA), and (IB)) and their pharmaceutically acceptable salts, pharmaceutically acceptable prodrugs, and pharmaceutically active metabolites of the present invention are useful as modulators of the GluN2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the GluN2B receptor expression or activity, and "activators" are compounds that increase, activate, facilitate, sensitize, or up-regulate GluN2B receptor expression or activity.

The term "treat", "treatment" or "treating", as used herein, is intended to refer to administration of an active agent or composition of the invention to a subject for the purpose of affecting a therapeutic or prophylactic benefit through modulation of GluN2B receptor activity.

Treating includes reversing, ameliorating, alleviating, inhibiting the progress of, lessening the severity of, or preventing a disease, disorder, or condition, or one or more symptoms of such disease, disorder or condition mediated through modulation of GluN2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by GluN2B receptor activity, such as: bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder; anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalization-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as post encephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal) (partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures; epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases; glaucoma and other neuropathies; dementias, vascular dementia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by GluN2B activity, such as another GluN2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following

TABLE 2

| Term | Acronym |
| --- | --- |
| Aqueous | aq |
| Atmosphere | atm |
| tert-Butylcarbamoyl | Boc |
| Broad | br |
| Diatomaceous Earth | Celite ® |
| Electrospray ionization | ESI |
| Normal-phase silica gel chromatography | FCC |
| GluNR2B * | GluN$_{2B}$, NMDA-R2B, NR2B, hNR3 |
| Grams | g |
| Hours | h |
| High-pressure liquid chromatography | HPLC |
| Hertz | Hz |
| Isopropyl alcohol | iPrOH, IPA |
| Liquid chromatography and mass spectrometry | LCMS |
| Molar | M |
| Mass to charge ratio | m/z |
| Milligrams | mg |
| Minute | min |
| Milliliter | mL |
| Microliter | μL |
| Millimoles | mmol |
| Mass spectrometry | MS |
| Normal | N |
| Nuclear magnetic resonance | NMR |
| Parts per million | ppm |
| Precipitate | ppt |
| Polytetrafluoroethylene | PTFE |
| Retention time | R$_t$ |
| Room temperature | rt |
| Saturated | sat |
| Supercritical Fluid Chromatography | SFC |
| Temperature | T |
| Thin layer chromatography | TLC |
| Volume in milliliters of solvent per gram of substrate | V, or volumes |

* (Collinridge, G. L, et al, *Neuropharmacology*, 2009, 56, 2-5)

PREPARATIVE EXAMPLES

Exemplary compounds useful in methods of the invention will now be described by reference to the illustrative synthetic schemes for their general preparation below and the specific examples to follow.

SCHEME 1

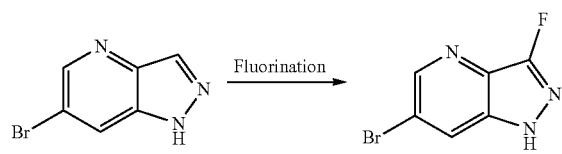

According to SCHEME 1, commercially available or synthetically accessible 6-bromo-1H-pyrrolo[3,2-b]pyridine is fluorinated with an electrophilic halogen source under conditions known to one skilled in the art. For example, 6-bromo-1H-pyrrolo[3,2-b]pyridine is fluorinated using a reagent such as N-fluoro-N'-(chloromethyl)triethylenediamine bis(tetrafluoroborate) (Selectfluor®) and the like; in a suitable solvent such as acetonitrile (ACN), dichloromethane (DCM), and the like, at a temperature of 90° C., to provide 6-Bromo-3-fluoro-1H-pyrazolo[4,3-b]pyridine.

SCHEME 2

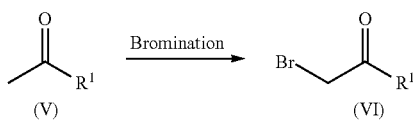

According to SCHEME 2, a compound of formula (V), where R$^1$ is cyclobutyl, pyrizinyl, pyridyl, pyridyl substituted with one or two F members is brominated using a reagent such as Br$_2$, HBr, pyridinium tribromide, phenyltrimehtylammonium tribromide, and the like; in a suitable solvent such as methanol (MeOH), tetrahydrofuran (THF), acetic acid (AcOH), and the like; at temperatures ranging from 0° C. to 60° C.; to provide a compound of formula (VI).

SCHEME 3

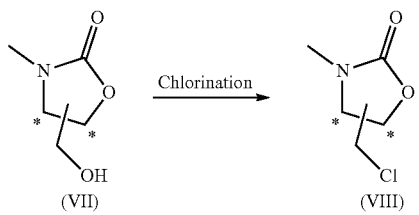

According to SCHEME 3, a compound of formula (VII) where the hydroxymethyl group is attached at either of the carbon atoms as indicated with (*), is chlorinated using a reagent such as SOCl$_2$, and the like; an amine base such as pyridine; in a solvent such as DCM, and the like; at a temperature of 90° C.; to afford a compound of formula (VIII).

SCHEME 4

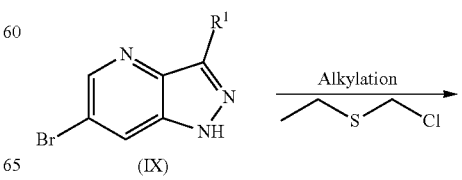

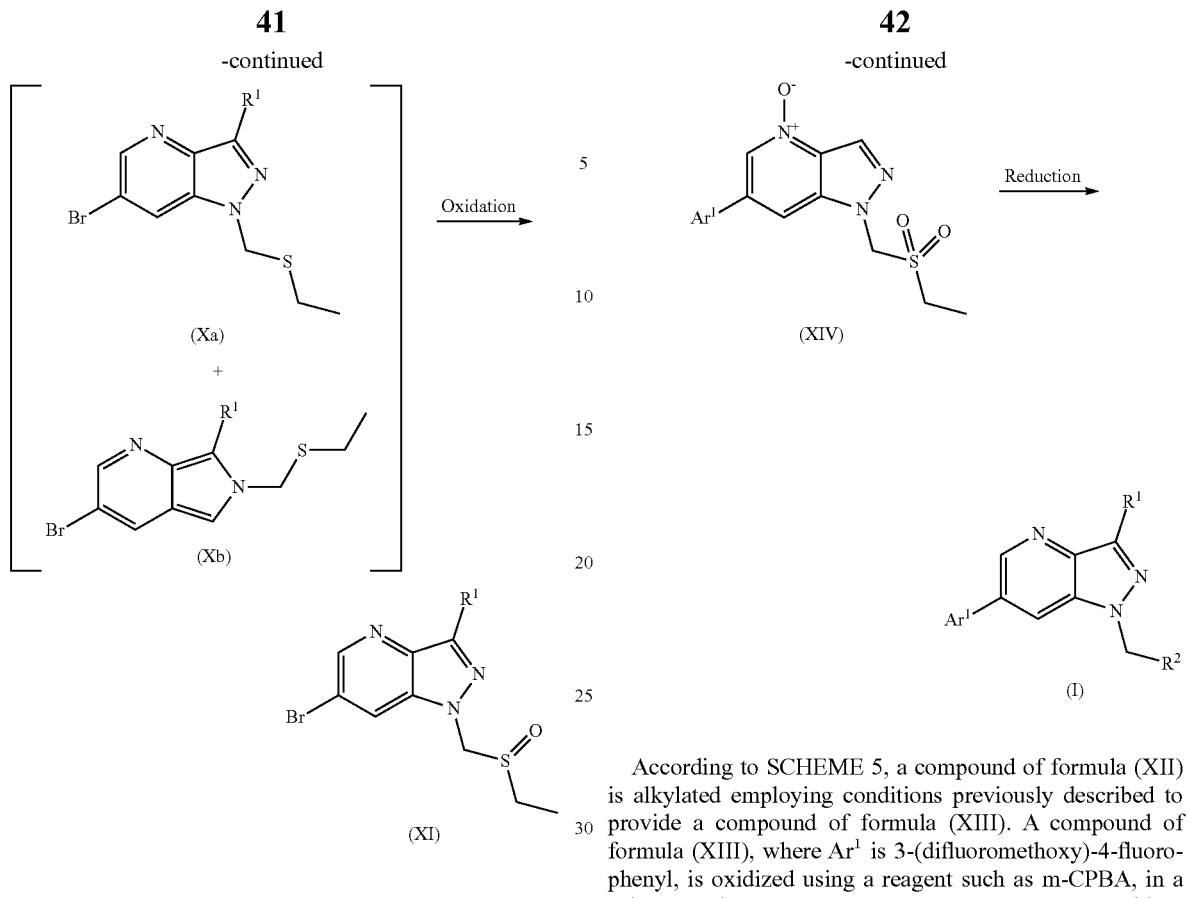

According to SCHEME 4, a compound of formula (IX) where R¹ is H, is alkylated with (chloromethyl)(ethyl)sulfane, a base such as Cs$_2$CO$_3$, and the like; in a solvent such as DMF, and the like, at room temperature, for a period of 20 hours, to provide 6-bromo-1-(ethylsulfanylmethyl)pyrazolo[4,3-b]pyridine and 6-bromo-2-(ethylsulfanylmethyl)pyrazolo[4,3-b]pyridine. 6-Bromo-1-(ethylsulfanylmethyl)pyrazolo[4,3-b]pyridine is oxidized using a reagent such as meta-chloroperoxybenzoic acid (m-CPBA), and the like, in a suitable solvent such as DCM, and the like; at a temperature of 0° C.; to provide a 6-bromo-1-(ethylsulfinylmethyl)pyrazolo[4,3-b]pyridine.

SCHEME 5

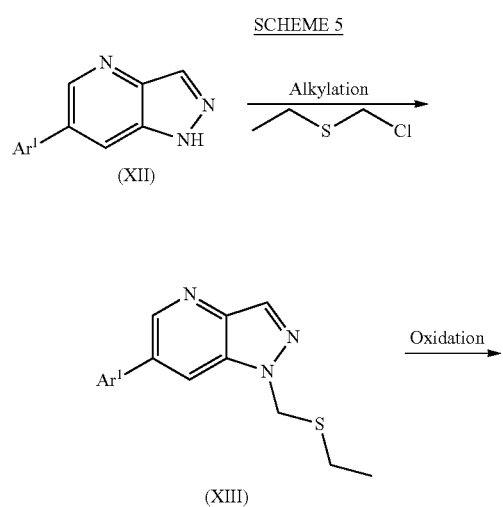

According to SCHEME 5, a compound of formula (XII) is alkylated employing conditions previously described to provide a compound of formula (XIII). A compound of formula (XIII), where Ar¹ is 3-(difluoromethoxy)-4-fluorophenyl, is oxidized using a reagent such as m-CPBA, in a solvent such as DCM, at room temperature, to provide a compound of formula (XIV). A compound of formula (XIV), where Ar¹ is 3-(difluoromethoxy)-4-fluorophenyl, is reduced using a reagent such as Pd/C (10%), in a solvent such as EtOH, EtOAc, or a mixture thereof, at room temperature, to provide a compound of Formula (I).

SCHEME 6

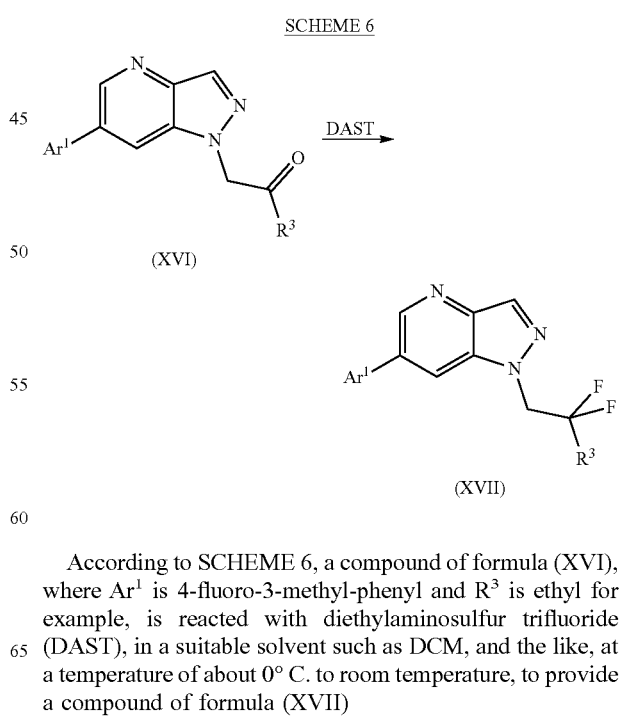

According to SCHEME 6, a compound of formula (XVI), where Ar¹ is 4-fluoro-3-methyl-phenyl and R³ is ethyl for example, is reacted with diethylaminosulfur trifluoride (DAST), in a suitable solvent such as DCM, and the like, at a temperature of about 0° C. to room temperature, to provide a compound of formula (XVII)

SCHEME 7

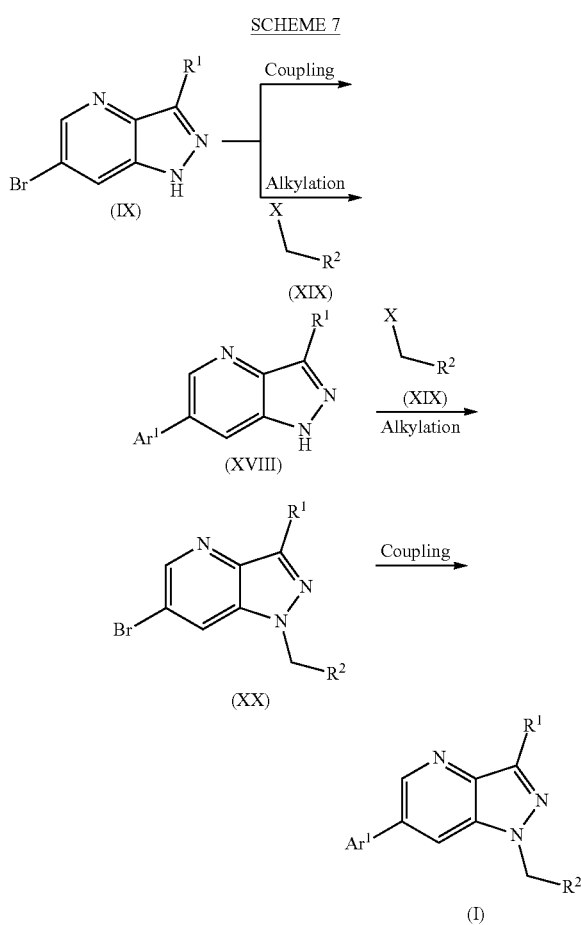

According to SCHEME 7, a compound of Formula (I) is prepared in two steps from a compound of formula (IX). In a first step, a compound of formula (IX), where $R^1$ is H, or $CH_3$, is reacted in a metal mediated cross coupling reaction to provide a compound of formula (XVIII), where $Ar^1$ is a phenyl optionally substituted with one, two, or three members each independently selected from halo, $C_{1-6}$alkyl, $C_{1-6}$perhaloalkyl, and $OC_{1-6}$perhaloalkyl. For example, a compound of formula (IX), where $R^1$ is H, or $CH_3$, is reacted with a commercially available or synthetically accessible suitably substituted aryl boronic acid, boronate ester, and the like; in the presence of a palladium catalyst such as bis(triphenylphosphine)palladium(II)chloride ($PdCl_2(PPh_3)_2$), bis(diphenylphosphino)ferrocene]dichloropalladium(II) complex with dichloromethane ($PdCl_2(dppf)$.DCM), [1,1'-bis(diphenylphosphino)ferrocene]dichloropalladium(II) ($PdCl_2(dppf)$), tetrakis(triphenylphosphine)palladium(0) ($Pd(PPh_3)_4$), 2-dicyclohexylphosphino-2',6'-diisopropoxy-1,1'-biphenyl)[2-(2'-amino-1,1'-biphenyl)]palladium(II) methanesulfonate (RuPhos-Pd-G3), and the like; a base such as $Na_2CO_3$, $Cs_2CO_3$, and the like; in a suitable solvent such as ACN, water, 1,4-dioxane, or a mixture thereof; at a temperature ranging from 70° C.-120° C.; for a period ranging from 2 h to 48 h, using conventional or microwave heating, to provide a compound of formula (XVIII).

In a second step, a compound of formula (XVIII), where $R^1$ is H or $CH_3$, and $Ar^1$ is a phenyl optionally substituted with one, two, or three members each independently selected from halo, $C_{1-6}$alkyl, $C_{1-6}$perhaloalkyl, and $OC_{1-6}$perhaloalkyl, is alkylated with a compound of formula (XIX), where X is Br or Cl, and $R^2$ is as described in claim 1; using a base such as N-ethyldiisopropylamine (DIEA, DIPEA), $Cs_2CO_3$, $NaHCO_3$, NaH, and the like; an additive such as KI; in a solvent such as dimethylformamide (DMF), tetrahydrofuran (THF), acetonitrile (ACN), and the like; at a temperature ranging from 0° C. to 80° C.; for a period of up to 76 h; to provide a compound of Formula (I).

In an alternate method, a compound of Formula (I) is prepared in two steps from a compound of formula (IX). In a first step, a compound of formula (IX) where $R^1$ is H, or F, is alkylated employing conditions previously described with an alkyl agent of formula (XIX), where X is Br or Cl, and $R^2$ is as described in claim 1, to provide a compound of formula (XX). In a second step, coupling with a suitably substituted phenyl or thienyl boronic acid or ester, employing conditions previously described, provides a compound of Formula (I).

A compound of Formula (I), where $R^2$ is (C=O)$C_{1-6}$alkyl, is reduced with a reducing agent such as $NaBH_4$, and the like; in a suitable solvent such as MeOH, THF, or a mixture thereof, at a temperature ranging from 0° C. to rt; to provide a compound of Formula (I), where $R^2$ is CH(OH)$C_{1-6}$alkyl.

A compound of Formula (I), where $R^2$ is (C=O)$C_{1-6}$alkyl, is reacted with a nucleophile such as hydroxylamine hydrochloride, o-methylhydroxylamine hydrochloride, and the like; using a base such as $Cs_2CO_3$, triethylamine, $NaHCO_3$, and the like; in a solvent such as MeOH, EtOH, $H_2O$, or a mixture thereof, to provide a compound of Formula (I), where $R^2$ is C(=N—OH)$C_{1-6}$alkyl, or C(=N—OCH_3)$C_{1-6}$alkyl.

A compound of Formula (I), where $R^2$ is (C=O)$C_{1-6}$alkyl, is fluorinated under conditions known to one skilled in the art, for example, reaction with a fluorinated reagent such as DAST, bis(2-methoxyethyl)aminosulfur trifluoride (Deoxo-Fluor®), and the like; in a solvent such as DCM, THF, and the like; at a temperature ranging from 0° C. to rt; to provide a compound of Formula (I), where $R^2$ is C($F_2$)$C_{1-6}$alkyl.

A compound of Formula (I), where $R^2$ is CH(OH)$C_{1-6}$alkyl, is fluorinated under conditions known to one skilled in the art, for example, reaction with a fluorinated reagent such as DAST, Deoxo-Fluor®, and the like; in a solvent such as DCM, THF, and the like; at a temperature ranging from 0° C. to rt; to provide a compound of Formula (I), where $R^2$ is CH(F)$C_{1-6}$alkyl.

A compound of Formula (I), where $R^2$ is CH(OH)$C_{1-6}$alkyl is methylated with iodomethane; using a base such as NaH, and the like; in a suitable solvent such as DMF, and the like; to provide a compound of Formula (I), where $R^2$ is CH(OCH_3)$C_{1-6}$alkyl.

A compound of Formula (I), where $R^2$ is oxetanyl, is treated with an Agilent Bond Elut strong cation exchange (SCX) cartridge to provide a compound of Formula (I), where $R^2$ is CH(OH)$CH_2CH_2OCH_3$.

Compounds of Formula (I) may be converted to their corresponding salts using methods known to one of ordinary skill in the art. For example, an amine of Formula (I) is treated with trifluoroacetic acid, HCl, or citric acid in a solvent such as diethyl ether ($Et_2O$), $CH_2Cl_2$, THF, MeOH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

Examples

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16″ PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min. or METHOD B. A Shimadzu LC-8A Series HPLC with an Inertsil ODS-3 column (3 m, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min. or METHOD C. A Shimadzu LC-8A Series HPLC with an XBridge C18 OBD column (5 m, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min. or METHOD D. A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min. or METHOD E. A Wufeng LC100 equipped with a manual Rheodyne 3725i sampler with a Gemini-NX C18 column (5 μM, 30×100 mm), and a mobile phase of 20-100% ACN:8 mM $(NH_4)HCO_3$ (9:1) in 10 mM aqueous $(NH_4)HCO_3$ over 16 min, with a flow rate of 40 mL/min. or METHOD F. A Wufeng LC100 equipped with a manual Rheodyne 3725i sampler with a Gemini-NX C18 column (5 μM, 30×100 mm), and a mobile phase of 50-100% ACN:8 mM $(NH_4)HCO_3$ (9:1) in 10 mM aqueous $(NH_4)HCO_3$ over 8 min, with a flow rate of 30 mL/min. or METHOD G. A Wufeng LC100 equipped with a manual Rheodyne 3725i sampler with a Gemini-NX C18 column (5 μM, 30×100 mm), and a mobile phase of 30-100% ACN:8 mM $(NH_4)HCO_3$ (9:1) in 10 mM aqueous $(NH_4)HCO_3$ over 5 min, with a flow rate of 30 mL/min. or METHOD H. An HPLC equipped with an XBridge C18 OBD column (5 μM, 30×100 or 50×150 mm), and a mobile phase of 46-64% ACN:8 mM $(NH_4)HCO_3$ (9:1) in 10 mM aqueous $(NH_4)HCO_3$.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, Mass.) or OEMetaChem V1.4.0.4 (Open Eye).

Compounds designated as R* or S* are enantiopure compounds where the absolute configuration was not determined.

Intermediate 1: 6-Bromo-3-fluoro-1H-pyrazolo[4,3-b]pyridine

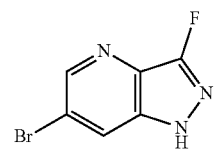 [SMILES: Fc1n[nH]c2cc(Br)cnc12]

To a solution of 6-bromo-1H-pyrazolo[4,3-b]pyridine (2.5 g, 12.6 mmol) in acetonitrile (62.5 mL) was added N-fluoro-N-(chloromethyl)triethylenediamine bis(tetrafluoroborate) (6.7 g, 18.9 mmol) and the reaction mixture was stirred at 90° C. for 22 h. The reaction mixture was poured into water (120 mL) and was diluted with ethyl acetate (EA or EtOAc) (80 mL). The layers were separated, and the aqueous layer was extracted with EtOAc (2×60 mL). The combined organic layers were dried over MgSO$_4$, filtered and evaporated. Purification (METHOD E) afforded the title compound (641 mg, 2.97 mmol, 23%) as a brown powder. MS (ESI): mass calcd. for $C_6H_3BrFN_3$; 214.9 m/z found, 216.0 [M+H]$^+$.

Intermediate 2: 6-(4-Fluoro-3-methylphenyl)-1H-pyrazolo[4,3-b]pyridine

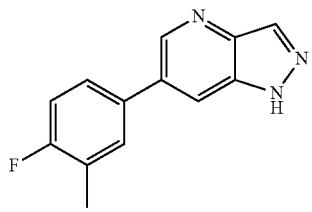 [SMILES: Cc1cc(-c2cnc3cn[nH]c3c2)ccc1F]

6-Bromo-1H-pyrazolo[4,3-B]pyridine (1 g, 5.05 mmol), 4-fluoro-3-methylphenylboronic acid (1.17 g, 7.58 mmol), Cs$_2$CO$_3$ (3.29 g, 10.1 mmol), PdCl$_2$(dppf).DCM (258.66 mg, 0.353 mmol), and 1,4-dioxane (46.6 mL), were combined and heated, with stirring, to 70° C. After two hours the reaction was removed from the heat and allowed to cool to rt. It was then loaded on to a column for purification (FCC, SiO$_2$, 0-70% EtOAc in hexanes) to afford the title compound (210 mg, 18.3%). MS (ESI): mass calcd for $C_{13}H_{10}FN_3$, 227.1; m/z found, 228.1 [M+H]$^+$.

Intermediate 3: 6-(3-(Difluoromethyl)-4-fluorophenyl)-1H-pyrazolo[4,3-b]pyridine

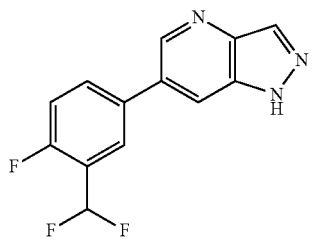 [SMILES: Fc1ccc(-c2cnc3cn[nH]c3c2)cc1C(F)F]

A mixture of 6-bromo-1H-pyrazolo[4,3-b]pyridine (1.40 g, 7.07 mmol), 2-[3-(difluoromethyl)-4-fluoro-phenyl]-4,4,5,5-tetramethyl-1,3,2-dioxaborolane (2.31 g, 8.49 mmol), [1,1'-bis(diphenylphosphino)ferrocene]dichloropalladium (II) (0.673 g, 0.92 mmol) and Na$_2$CO$_3$ (2.25 g, 21.2 mmol) in degassed acetonitrile (24.4 mL) and water (3.76 mL) was stirred at 120° C. for 4 h under microwave irradiation. The reaction mixture was poured into water (30 mL) and the mixture was extracted with EtOAc (3×30 mL). The combined organic layers were dried over Na$_2$SO$_4$, filtered and evaporated. Purification (FCC, SiO$_2$, 10 to 50% n-heptane/EtOAc) afforded a solid that was triturated with Et$_2$O (4 mL) to afford the title compound (1.41 g, 5.36 mmol, 76%) as an off-white powder. MS (ESI): mass calcd. for $C_{13}HF_3N_3$, 263.1; m/z found, 264.2 [M+H]$^+$. $^1$H NMR (300 MHz, DMSO-d$_6$) δ 13.48 (br s, 1H), 8.84 (d, J=2.0 Hz, 1H), 8.41-8.30 (m, 1H), 8.30-8.20 (m, 1H), 8.13-7.99 (m, 2H), 7.60-7.49 (m, 1H), 7.27 (t, J=54.1 Hz, 1H).

Intermediate 4: 6-(3-(Difluoromethoxy)-4-fluorophenyl)-1H-pyrazolo[4,3-b]pyridine

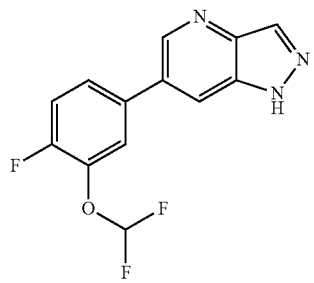 [SMILES: Fc1ccc(-c2cnc3cn[nH]c3c2)cc1OC(F)F]

The title compound was prepared in a manner analogous to Intermediate 3 using 2-(3-(difluoromethoxy)-4-fluorophenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{13}H_8F_3N_3O$, 279.0; m/z found, 280.2 [M+H]$^+$.

Intermediate 5: 6-(4-Chloro-3-(difluoromethoxy)phenyl)-1H-pyrazolo[4,3-b]pyridine

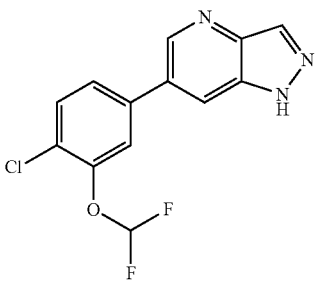 [SMILES: FC(F)Oc1cc(-c2cnc3cn[nH]c3c2)ccc1Cl]

The title compound was prepared in a manner analogous to Intermediate 3 using 2-(3-(difluoromethoxy)-4-chlorophenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{13}H_8ClF_2N_3O$, 295.0; m/z found, 296.0 [M+H]$^+$.

Intermediate 6: 6-(3-(1,1-Difluoroethyl)-4-fluorophenyl)-1H-pyrazolo[4,3-b]pyridine

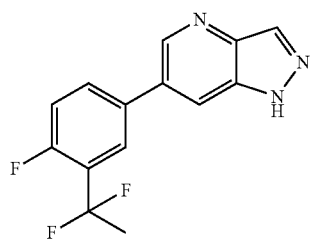 [SMILES: CC(F)(F)c1cc(-c2cnc3cn[nH]c3c2)ccc1F]

The title compound was prepared in a manner analogous to Intermediate 3 using 2-(3-(1,1-difluoroethyl)-4-fluorophenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{14}H_{10}F_3N_3$, 277.1; m/z found, 278.1 [M+H]$^+$.

Intermediate 7: 6-(3-(1,1-Difluoroethyl)phenyl)-1H-pyrazolo[4,3-b]pyridine

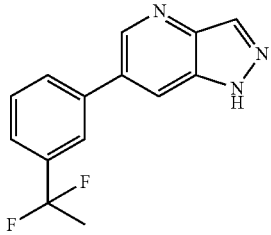 [SMILES: CC(F)(F)c1cccc(-c2cnc3cn[nH]c3c2)c1]

The title compound was prepared in a manner analogous to Intermediate 3 using 2-(3-(1,1-difluoroethyl)phenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{14}H_{11}F_2N_3$, 259.1; m/z found, 260.1 [M+H]$^+$.

Intermediate 8: 6-(3-(Trifluoromethyl)phenyl)-1H-pyrazolo[4,3-b]pyridine

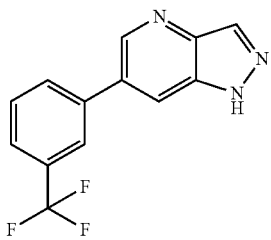 [SMILES: FC(F)(F)c1cccc(-c2cnc3cn[nH]c3c2)c1]

A suspension of 6-bromo-1H-pyrazolo[4,3-B]pyridine (5.0 g, 25.25 mmol), 3-trifluoromethylphenylboronic acid (5.755 g, 30.3 mmol), Pd(PPh$_3$)$_4$ (1.459 g, 1.262 mmol) and Na$_2$CO$_3$ (2 M in H$_2$O, 32.468 mL, 64.935 mmol) in 1,4-dioxane (96.9 mL) was stirred at 120° C. for 48 h. The mixture was cooled to rt, diluted with EtOAc, and washed with H$_2$O (×2). The organic layer was dried over Na$_2$SO$_4$ and concentrated under reduced pressure. Purification (FCC, SiO$_2$, 0-50% EtOAc in heptane), followed by trituration with Et$_2$O, afforded the title compound (2.1 g, 32%). MS (ESI): mass calcd. for $C_{13}HF_3N_3$, 263.1; m/z found, 264.1 [M+H]$^+$.

Intermediate 9: 6-(4-Fluorophenyl)-1H-pyrazolo[4,3-b]pyridine

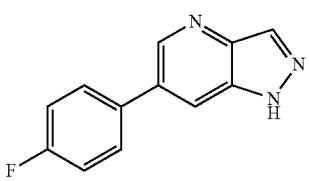 [SMILES: Fc1ccc(-c2cnc3cn[nH]c3c2)cc1]

The title compound was prepared in a manner analogous to Intermediate 2 using 4-fluorophenylboronic acid instead of 4-fluoro-3-methylphenylboronic acid. MS (ESI): mass calcd. for $C_{13}H_8F_3N_3$, 213.1; m/z found, 214.0 [M+H]$^+$.

Intermediate 10: 6-(3-(Difluoromethyl)-4-fluorophenyl)-3-methyl-1H-pyrazolo[4,3-b]pyridine

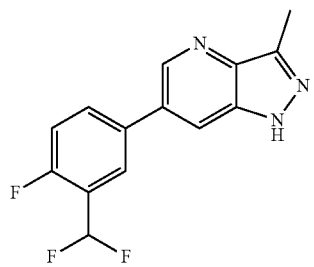 [SMILES: Cc1n[nH]c2cc(-c3ccc(F)c(C(F)F)c3)cnc12]

The title compound was prepared in a manner analogous to Intermediate 3, using 6-bromo-3-methyl-1H-pyrazolo[4,3-b]pyridine instead of 6-bromo-1H-pyrazolo[4,3-b]pyridine. MS (ESI): mass calcd. for $C_{14}H_{10}F_3N_3$, 277.1; m/z found, 278.1 [M+H]$^+$.

Intermediate 11: 1-(6-Bromo-1H-pyrazolo[4,3-b]pyridin-1-yl)butan-2-one

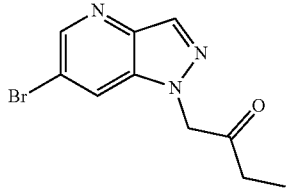

Under an atmosphere of nitrogen was added 6-bromo-1H-pyrazolo[4,3-B]pyridine (500 mg, 2.53 mmol) to a suspension of NaH (60% dispersion in mineral oil, 141.39 mg, 3.54 mmol) in DMF (21.7 mL) at rt. After 10 min, 1-bromo-2-butanone (0.373 mL, 3.54 mmol) was added, and the reaction mixture was left to stir at rt overnight. The reaction was quenched with a small amount of H$_2$O, then adsorbed onto silica gel and purified (FCC, SiO$_2$, 0-100% EtOAc in hexanes) to afford the title compound (265 mg, 39%). MS (ESI): mass calcd. for $C_{10}H_{10}BrN_3O$, 267.0; m/z found, 268.0 [M+H]$^+$.

Intermediate 12: 1-(6-Bromo-1H-pyrazolo[4,3-b]pyridin-1-yl)propan-2-one

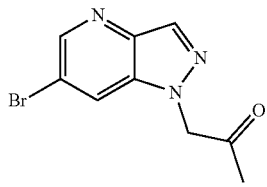

The title compound was prepared in a manner analogous to Intermediate 11 using chloroacetone instead of 1-bromo-2-butanone. MS (ESI): mass calcd. for $C_9HBrN_3O$, 253.0; m/z found, 254.0 $[M+H]^+$.

Intermediate 13: 1-(6-Bromo-1H-pyrazolo[4,3-b]pyridin-1-yl)-3-methylbutan-2-one

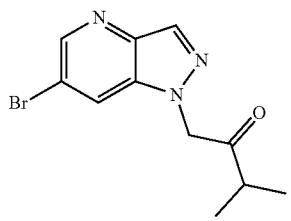 [SMILES: CC(C)C(=O)Cn1ncc2ncc(Br)cc21]

The title compound was prepared in a manner analogous to Intermediate 11 using 1-bromo-3-methyl-2-butanone instead of 1-bromo-2-butanone. MS (ESI): mass calcd. for $C_{11}H_{12}BrN_3O$, 282.1; m/z found 283 $[M+H]^+$.

Intermediate 14: 2-(6-Bromo-1H-pyrazolo[4,3-b]pyridin-1-yl)-1-cyclopropylethan-1-one

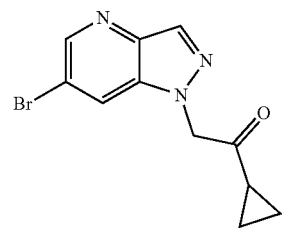 [SMILES: O=C(Cn1ncc2ncc(Br)cc21)C1CC1]

The title compound was prepared in a manner analogous to Intermediate 11 using 2-bromo-1-cyclopropylethanone instead of 1-bromo-2-butanone. MS (ESI): mass calcd. for $C_{11}H_{10}BrN_3O$, 280.1; m/z found 282 $[M+H]^+$.

Intermediate 15: 1-(6-Bromo-3-fluoro-1H-pyrazolo[4,3-b]pyridin-1-yl)butan-2-one

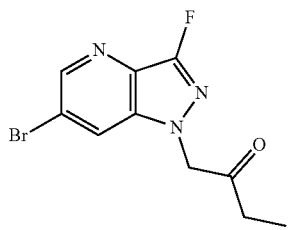 [SMILES: CCC(=O)Cn1nc(F)c2ncc(Br)cc21]

The title compound was prepared in a manner analogous to Intermediate 11 using 6-bromo-3-fluoro-1H-pyrazolo[4,3-b]pyridine (Intermediate 1) instead of 6-bromo-1H-pyrazolo[4,3-b]pyridine. MS (ESI): mass calcd. for $C_{10}H_9BrFN_3O$, 284.9; m/z found, 286.1 $[M+H]^+$.

Intermediate 16: 6-Bromo-1-((ethylsulfinyl)methyl)-1H-pyrazolo[4,3-b]pyridine

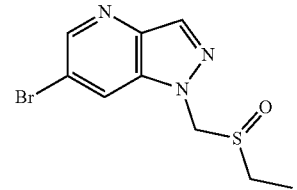

Step A. 6-Bromo-1-(ethylsulfanylmethyl)pyrazolo[4,3-b]pyridine

A mixture of 6-bromo-1H-pyrazolo[4,3-b]pyridine (600 mg, 3.03 mmol), (chloromethyl)(ethyl)sulfane (369 mg, 3.34 mmol) and $Cs_2CO_3$ (1.48 g, 4.54 mmol) in dry DMF (12 mL) was stirred at room temperature for 20 h. The reaction mixture was poured into water (15 mL) and extracted with EtOAc (3×10 mL). The combined organic layers were dried over $Na_2SO_4$, filtered and evaporated. Purification (FCC, $SiO_2$, 0 to 10% hexanes/EtOAc) afforded the title compound (431 mg, 1.584 mmol, 52%) as a pale yellow oil. MS (ESI): mass calcd. for $C_9H_{10}BrN_3S$, 270.9; m/z found, 272.0 $[M+H]^+$. The reaction also provided 6-bromo-2-(ethylsulfanylmethyl)pyrazolo[4,3-b]pyridine (240 mg, 0.882 mmol, 29%) as a pale yellow powder. MS (ESI): mass calcd. for $C_9H_{10}BrN_3S$, 270.9; m/z found, 272.0 $[M+H]^+$.

Step B. 6-Bromo-1-(ethylsulfinylmethyl)pyrazolo[4,3-b]pyridine

To a solution of 6-bromo-1-(ethylsulfanylmethyl)pyrazolo[4,3-b]pyridine (421 mg, 1.55 mmol) from Step A in DCM (12.9 mL) was added 3-chloroperbenzoic acid (248 mg, 1.11 mmol) at 0° C. The reaction mixture was stirred at 0° C. for 1 h, then at room temperature for 46 h. The reaction mixture was diluted with DCM (12 mL) and washed with 10% $Na_2CO_3$ (1×15 mL). The aqueous layer was extracted with DCM (2×15 mL) and the combined organic layers were dried over $Na_2SO_4$, filtered and evaporated. Purification (FCC, $SiO_2$, 0 to 5% MeOH in DCM) afforded the title compound (290 mg, 1.01 mmol, 91%) as a white powder. MS (ESI): mass calcd. for $C_9H_{10}BrN_3OS$, 286.9; m/z found, 288.0 $[M+H]^+$.

Intermediate 17: 2-Bromo-1-cyclobutylethan-1-one

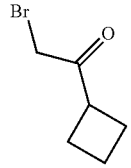

To cyclobutyl methyl ketone (1.0 g, 10.189 mmol) stirring in MeOH (10 mL) at 0° C. was added bromine (1.6 g, 10.012 mmol). The reaction mixture was allowed to stir and slowly warm to rt as the ice bath melted. After 2 hours, water was added to the reaction mixture and it was stirred for an additional 30 min. Water (50 mL) was added, and the aqueous layer was extracted with ether (2×50 mL). The organic layer was dried, filtered, and concentrated under reduced pressure to afford the title compound (376 mg, 21%). $^1$H NMR (300 MHz, CDCl$_3$) δ 3.89 (s, 2H), 3.70-3.53 (m, 1H), 2.37-2.16 (m, 4H), 2.12-1.97 (m, 1H), 1.95-1.80 (m, 1H).

Intermediate 18:
(R)-5-(Chloromethyl)-3-methyloxazolidin-2-one

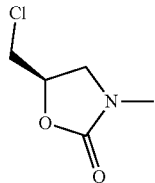

To (R)-5-(hydroxymethyl)-3-methyloxazolidin-2-one (518.2 mg, 3.952 mmol) stirring in DCE (20 mL) in a round bottom flask at rt was added SOCl$_2$ (1.5 mL, 20.677 mmol) followed by pyridine (1.6 mL, 19.863 mmol). The reaction was connected to a reflux apparatus and stirred at 90° C. for 1 h. The reaction mixture was then cooled to rt, then cooled to 0° C. and quenched by the dropwise addition of a saturated aqueous solution of NaHCO$_3$ until pH 7 was reached. The layers were separated and the organic layer was washed with saturated aqueous solutions of NaHCO$_3$ (×3), NH$_4$C$_1$ (×3), then CuSO$_4$ (×2). The organic layer was then dried (Na$_2$SO$_4$) and concentrated under reduced pressure to afford the title compound as a yellow oil (172.2 mg, 29%). $^1$H NMR (500 MHz, CDCl$_3$) δ 4.70 (dddd, J=8.7, 7.0, 5.7, 4.1 Hz, 1H), 3.78-3.59 (m, 3H), 3.46 (dd, J=9.0, 5.7 Hz, 1H), 2.90 (s, 3H).

Intermediate 19:
(S)-5-(Chloromethyl)-3-methyloxazolidin-2-one

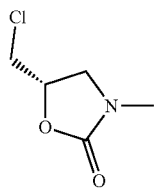

The title compound was prepared in a manner analogous to Intermediate 18 using (S)-5-(hydroxymethyl)-3-methyl-oxazolidin-2-one instead of (R)-5-(hydroxymethyl)-3-methyloxazolidin-2-one. $^1$H NMR (500 MHz, CDCl$_3$) δ 4.70 (dddd, J=8.7, 7.0, 5.7, 4.1 Hz, 1H), 3.78-3.59 (m, 3H), 3.46 (dd, J=9.0, 5.7 Hz, 1H), 2.90 (s, 3H).

Intermediate 20:
(RS)-4-(Chloromethyl)-3-methyloxazolidin-2-one

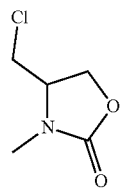

The title compound was prepared in a manner analogous to Intermediate 18 using (RS)-4-(hydroxymethyl)-3-methyl-1,3-oxazolidin-2-one instead of (R)-5-(hydroxymethyl)-3-methyloxazolidin-2-one. $^1$H NMR (500 MHz, CDCl$_3$) δ 4.48-4.33 (m, 1H), 4.20 (dd, J=9.1, 5.4 Hz, 1H), 4.05-3.89 (m, 1H), 3.70-3.56 (m, 2H), 2.91 (s, 3H).

Intermediate 21:
2-Bromo-1-(pyridin-2-yl)ethan-1-one

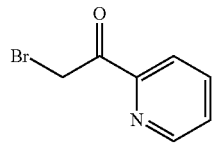

To a solution of 2-acetylpyridine (500 mg, 4.13 mmol) in acetic acid (AcOH) (6.25 mL, 109 mmol) was added pyridinium tribromide (1.32 g, 4.13 mmol) and the reaction mixture was stirred at 50° C. for 17 h. The precipitate was collected and was washed with Et$_2$O (4×5 mL) to give the title compound (941 mg, 3.35 mmol, 81%) as an off-white powder. MS (ESI): mass calcd. for C$_7$H$_6$BrNO; 198.9 m/z found, 200.1 [M+H]$^+$.

Intermediate 22:
2-Bromo-1-(pyridin-4-yl)ethan-1-one

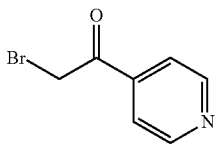

The title compound was prepared in a manner analogous to Intermediate 21 using 1-(pyridin-4-yl)ethan-1-one instead of 2-acetylpyridine. MS (ESI): mass calcd. for C$_7$H$_6$BrNO; 198.9 m/z found, 200.1 [M+H]$^+$.

Intermediate 23:
2-Bromo-1-(3,5-difluoropyridin-2-yl)ethan-1-one

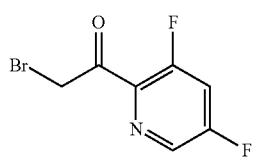 [SMILES: O=C(CBr)c1ncc(F)cc1F]

To a solution of phenyltrimethylammonium tribromide (420 mg, 1.12 mmol) in THF (3.5 mL) was added a solution of 1-(3,5-difluoropyridin-2-yl)ethanone (160 mg, 1.02 mmol) in THF (1.5 mL) and the reaction mixture was stirred at 60° C. for 1 h. The mixture was filtered and the solids washed with THF (5×5 mL). The combined filtrates were concentrated. Purification (FCC, SiO$_2$, 0 to 100% n-heptane/DCM) afforded the title compound (142 mg, 0.651 mmol, 64%) as a pale yellow oil. No mass found in MS.

Intermediate 24:
2-Bromo-1-(3-fluoropyridin-2-yl)ethan-1-one

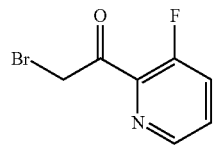 [SMILES: O=C(CBr)c1ncccc1F]

The title compound was prepared in a manner analogous to Intermediate 23 using 1-(3-fluoropyridin-2-yl)ethan-1-one instead of 1-(3,5-difluoropyridin-2-yl)ethanone. Material used without further purification. No mass found in MS.

Intermediate 25:
2-Bromo-1-(pyrazin-2-yl)ethan-1-one

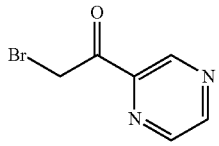

The title compound was prepared in a manner analogous to Intermediate 23 using 1-(pyrazin-2-yl)ethan-1-one instead of 1-(3,5-difluoropyridin-2-yl)ethanone. Material used without further purification. No mass found in MS.

Intermediate 26:
2-Bromo-1-(pyrimidin-2-yl)ethan-1-one

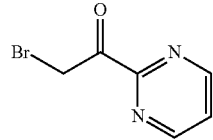

The title compound was prepared in a manner analogous to Intermediate 23 using 1-(pyrimidin-2-yl)ethan-1-one instead of 1-(3,5-difluoropyridin-2-yl)ethanone. Material used without further purification. No mass found in MS.

Intermediate 27:
2-Bromo-1-(pyridin-3-yl)ethan-1-one

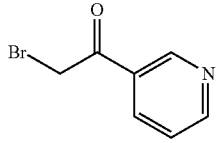

To a solution of 3-acetylpyridine (500 mg, 4.128 mmol) and HBr (33 wt % in acetic acid, 1.25 mL, 7.238 mmol) in acetic acid (1.25 mL) was added pyridinium tribromide (1.45 g, 4.534 mmol) and the reaction mixture was stirred at rt for 30 min. Diethyl ether (8 mL) was added to the reaction, and the mixture was cooled to 0° C. The precipitate was collected and washed with diethyl ether (5×5 mL) to afford the title compound as an off-white powder (1.921 g, 165%). MS (ESI): mass calcd. for $C_7H_6BrNO$; 198.9 m/z found, 200.1 $[M+H]^+$.

Intermediate 28:
2-Bromo-1-(5-fluoropyridin-2-yl)ethan-1-one

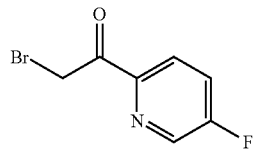 [SMILES: O=C(CBr)c1ccc(F)cn1]

The title compound was prepared in a manner analogous to Intermediate 23 using 1-(5-fluoropyridin-2-yl)ethanone instead of 1-(3,5-difluoropyridin-2-yl)ethanone. No mass found in MS.

Intermediate 29: 2-(3-(Difluoromethyl)-4-fluorophenyl)-4,4,5,5-tetramethyl-1,3,2-dioxaborolane

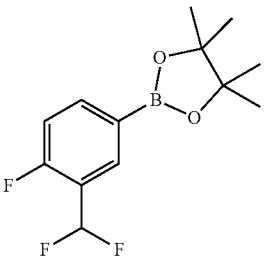 [SMILES: CC1(C)OB(c2ccc(F)c(C(F)F)c2)OC1(C)C]

A solution of 4-bromo-2-(difluoromethyl)-1-fluorobenzene (20 g, 88.9 mmol), bis(pinacolato)diboron (24.8 g, 97.8 mmol), potassium acetate (26.2 g, 267 mmol), and [1,1'-bis(diphenylphosphino)ferrocene]-dichloropalladium(II) (3.12 g, 4.44 mmol) in 1,4-dioxane (400 mL) was purged with $N_2$, and the reaction mixture was stirred at 90° C. overnight. Upon completion, the reaction mixture was cooled to room temperature, filtered through Celite®, and rinsed with EtOAc. The filtrate was washed with water and brine. The combined organics were dried with $Na_2SO_4$, filtered and concentrated to yield a clear oil (22.1 g, 81.0 mmol, 91%), which solidified upon standing. $^1$H NMR (400 MHz, Chloroform-d) δ 8.12-8.00 (m, 1H), 7.96-7.85 (m, 1H), 7.17-7.06 (m, 1H), 6.88 (t, J=54.9 Hz, 1H), 1.35 (s, 12H). MS (ESI): mass calcd. for $C_{13}H_{16}BF_3O_2$, 272.1; m/z found, 273.0 $[M+H]^+$.

Intermediate 30: 2-(3-(1,1-Difluoroethyl)-4-fluorophenyl)-4,4,5,5-tetramethyl-1,3,2-dioxaborolane

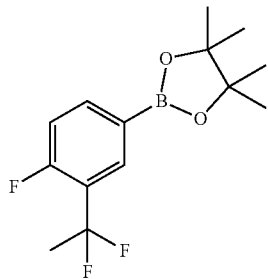 [SMILES: CC(F)(F)c1cc(B2OC(C)(C)C(C)(C)O2)ccc1F]

Step A:
4-Bromo-2-(1,1-difluoroethyl)-1-fluorobenzene

In a round bottom flask, a mixture of 1-(5-bromo-2-fluorophenyl)-1-ethanone (2.5 g, 11.5 mmol, 1 equiv) and DAST (1.9 mL, 14.4 mmol, 1.25 equiv) was heated at 60° C. for 16 h. Then a sat. aq. solution of NaHCO$_3$ was slowly added at 0° C. and the mixture was extracted with DCM. The organic layers were combined, dried over MgSO$_4$, filtered, and partially concentrated (product is volatile). Purification (FCC, SiO$_2$, 100% DCM) afforded the title compound (3 g, 7.5 mmol, purity 60%, 65%) as a brown oil. $^1$H NMR (300 MHz, CDCl$_3$) δ 7.73-7.61 (m, 1H), 7.60-7.48 (m, 1H), 7.02 (t, J=9.4 Hz, 1H), 1.98 (t, J=18.6 Hz, 3H).

Step B: 2-(3-(1,1-Difluoroethyl)-4-fluorophenyl)-4,4,5,5-tetramethyl-1,3,2-dioxaborolane In a round bottom flask, bis(pinacolato)diboron (2.87 g, 11.3 mmol, 1.5 equiv), potassium acetate (2.22 g, 22.6 mmol, 3 equiv), and [1,1'-bis(diphenylphosphino)ferrocene]-dichloropalladium(II) (615 mg, 0.75 mmol, 0.1 equiv) were added to a solution of 4-bromo-2-(1,1-difluoroethyl)-1-fluorobenzene (3 g, 7.5 mmol, 1 equiv) in dry 1,4-dioxane (40 mL). The reaction mixture was purged with nitrogen and stirred at 90° C. for 16 h. Then, a sat. aq. solution of NaHCO$_3$ was added and the mixture was extracted with EtOAc. The combined organics were dried with MgSO$_4$, filtered and concentrated to afford the title compound as a brown oil (2.15 g, 7.53 mmol), which was used in the next step without further purification. MS (ESI): mass calcd. for C$_{14}$H$_{18}$BF$_3$O$_2$, 286.1; m/z found, 287.1 [M+H]$^+$.

Intermediate 31: 2-(3-(Difluoromethyl)phenyl)-4,4,5,5-tetramethyl-1,3,2-dioxaborolane

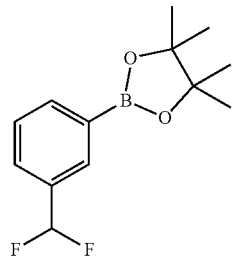 [SMILES: CC1(C)OB(c2cccc(C(F)F)c2)OC1(C)C]

The title compound was prepared in a manner analogous to Intermediate 29 using 1-bromo-3-(difluoromethyl)benzene instead of 4-bromo-2-(difluoromethyl)-1-fluorobenzene. No mass observed.

Intermediate 32: 2-(3-(1,1-Difluoroethyl)phenyl)-4,4,5,5-tetramethyl-1,3,2-dioxaborolane

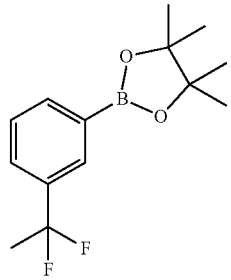 [SMILES: CC(F)(F)c1cccc(B2OC(C)(C)C(C)(C)O2)c1]

The title compound was prepared in a manner analogous to Intermediate 29 using 1-bromo-3-(1,1-difluoroethyl)benzene instead of 4-bromo-2-(difluoromethyl)-1-fluorobenzene. No mass observed.

Intermediate 33: 2-(3-(Difluoromethoxy)-4-fluorophenyl)-4,4,5,5-tetramethyl-1,3,2-dioxaborolane

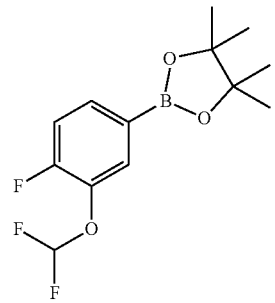 [SMILES: CC1(C)OB(c2ccc(F)c(OC(F)F)c2)OC1(C)C]

The title compound was prepared in a manner analogous to Intermediate 29 using 4-bromo-2-(difluoromethoxy)-1-fluorobenzene instead of 4-bromo-2-(difluoromethyl)-1-fluorobenzene. MS (ESI): mass calcd. for C$_{13}$H$_{16}$BF$_3$O$_3$, 288.1; m/z found, 289.0 [M+H]$^+$.

Intermediate 34: 2-(4-Chloro-3-(difluoromethoxy)phenyl)-4,4,5,5-tetramethyl-1,3,2-dioxaborolane

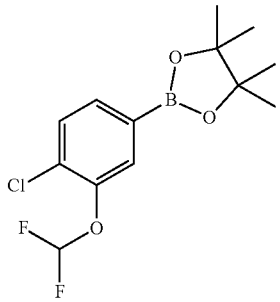 [SMILES: CC1(C)OB(c2ccc(Cl)c(OC(F)F)c2)OC1(C)C]

The title compound was prepared in a manner analogous to Intermediate 29 using 4-bromo-1-chloro-2-(difluoromethoxy)benzene instead of 4-bromo-2-(difluoromethyl)-1-fluorobenzene. 1H NMR (500 MHz, CDCl$_3$) δ 7.62-7.56 (m, 2H), 7.44 (d, J=7.9 Hz, 1H), 6.56 (t, J=73.6 Hz, 1H), 1.34 (s, 12H).

Example 1: 1-[6-(3,5-Difluorophenyl)pyrazolo[4,3-b]pyridin-1-yl]butan-2-one

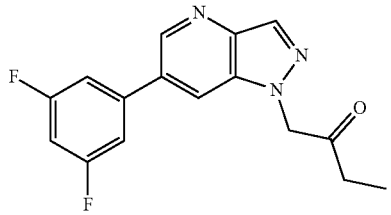 [SMILES: CCC(=O)Cn1ncc2ncc(-c3cc(F)cc(F)c3)cc21]

1-(6-Bromo-1H-pyrazolo[4,3-b]pyridin-1-yl)butan-2-one (Intermediate 11, 30 mg, 0.112 mmol), 3,5-difluorophenylboronic acid (21.2 mg, 0.134 mmol), Cs$_2$CO$_3$ (109 mg, 0.336 mmol), Pd(dppf)C$_{12}$·DCM (8.2 mg, 0.0112 mmol), and 1,4-dioxane (1 mL) were combined and heated, with stirring, to 90° C. overnight. After cooling to rt, the crude material was loaded directly onto a column and purified (FCC, SiO$_2$, 0-100% EtOAc in hexanes) to afford the title compound (37.4 mg, 111%). MS (ESI): mass calcd. for C$_{16}$H$_{13}$F$_2$N$_3$O, 301.1; m/z found, 302.0 [M+H]$^+$.

Example 2: 3-Methyl-1-[6-[3-(trifluoromethyl)phenyl]pyrazolo[4,3-b]pyridin-1-yl]butan-2-one

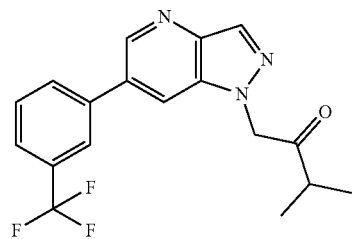 [SMILES: CC(C)C(=O)Cn1ncc2ncc(-c3cccc(C(F)(F)F)c3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 3-trifluoromethyl-phenylboronic acid instead of 3,5-difluorophenylboronic acid. MS (ESI): mass calcd. for C$_{18}$H$_{16}$F$_3$N$_3$O, 347.1; m/z found, 348.0 [M+H]$^+$. 1H NMR (400 MHz, DMSO) δ 8.94 (d, J=2.0 Hz, 1H), 8.47-8.43 (m, 1H), 8.40-8.38 (m, 1H), 8.16-8.10 (m, 2H), 7.85-7.75 (m, 2H), 5.67 (s, 2H), 2.89-2.77 (m, 1H), 1.13 (m, 6H).

Example 3: (RS)-3-Methyl-1-[6-[3-(trifluoromethyl)phenyl]pyrazolo[4,3-b]pyridin-1-yl]butan-2-ol

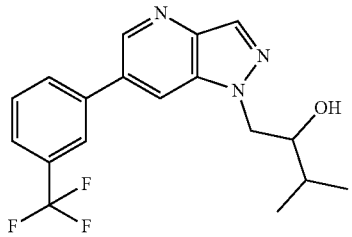 [SMILES: CC(C)C(O)Cn1ncc2ncc(-c3cccc(C(F)(F)F)c3)cc21]

To 3-methyl-1-[6-[3-(trifluoromethyl)phenyl]pyrazolo[4,3-b]pyridin-1-yl]butan-2-one (Example 2, 50 mg, 0.144 mmol) stirring in THF (1.885 mL) and MeOH (1.885 mL) at 0° C. was added NaBH$_4$ (10.89 mg, 0.288 mmol). The reaction mixture was stirred at this temperature for 30 min, then warmed to rt. The reaction mixture was concentrated under reduced pressure and taken up in EtOAc. The organic layer was washed with water, dried, and concentrated under reduced pressure to afford the title compound (34.6 mg, 69%). MS (ESI): mass calcd. for C$_{18}$H$_{18}$F$_3$N$_3$O, 349.1; m/z found, 350.0 [M+H]$^+$. 1H NMR (500 MHz, DMSO-d$_6$) δ 8.89 (d, J=1.9 Hz, 1H), 8.52-8.50 (m, 1H), 8.34-8.33 (m, 1H), 8.17-8.13 (m, 2H), 7.84-7.77 (m, 2H), 4.79 (d, J=6.0 Hz, 1H), 4.50-4.46 (m, 2H), 3.69 (p, J=5.8 Hz, 1H), 1.68-1.59 (m, 1H), 0.97 (d, J=6.9 Hz, 3H), 0.94 (d, J=6.7 Hz, 3H).

Example 4: 1-[6-[3-(Difluoromethyl)-4-fluoro-phenyl]pyrazolo[4,3-b]pyridin-1-yl]butan-2-one

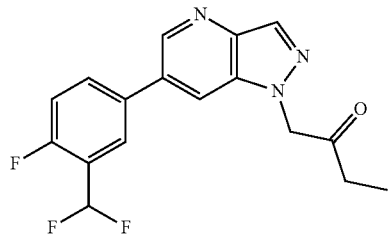 [SMILES: CCC(=O)Cn1ncc2ncc(-c3ccc(F)c(C(F)F)c3)cc21]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-B]pyridine, and 1-bromo-2-butanone instead of (chloromethyl)(ethyl)sulfane. MS (ESI): mass calcd. for C$_{17}$H$_{14}$F$_3$N$_3$O, 333.1; m/z found, 334.1 [M+H]$^+$. 1H NMR (500 MHz, DMSO-d$_6$) δ 8.88 (d, J=2.0 Hz, 1H), 8.44-8.41 (m, 1H), 8.38-8.36 (m, 1H), 8.08-8.01 (m, 1H), 7.61-7.53 (m, 1H), 7.29 (t, J=54.2 Hz, 1H), 5.54 (s, 2H), 2.57 (q, J=7.3 Hz, 2H), 0.98 (t, J=7.3 Hz, 3H).

Example 5: (RS)-1-[6-[3-(Difluoromethyl)-4-fluoro-phenyl]pyrazolo[4,3-b]pyridin-1-yl]butan-2-ol

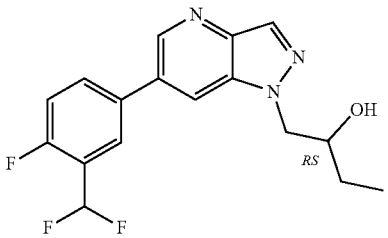 [SMILES: CCC(O)Cn1ncc2ncc(-c3ccc(F)c(C(F)F)c3)cc21]

To a solution of 1-[6-[3-(difluoromethyl)-4-fluoro-phenyl]pyrazolo[4,3-b]pyridin-1-yl]butan-2-one (Example 4, 45 mg, 0.135 mmol) in methanol (1.5 mL) was added sodium borohydride (13 mg, 0.344 mmol) at 0° C. The reaction mixture was warmed to room temperature and stirred for 1 h. Water (5 mL) was added and the mixture was extracted with EtOAc (2×5 mL). The combined organics were dried over $Na_2SO_4$, filtered and evaporated. Purification (FCC, $SiO_2$, 0 to 5% MeOH in DCM) afforded the title compound (35 mg, 0.104 mmol, 77%) as a white powder. MS (ESI): mass calcd. for $C_{17}H_{16}F_3N_3O$, 335.1; m/z found, 336.1 $[M+H]^+$. $^1H$ NMR (300 MHz, DMSO-$d_6$) δ 8.84 (d, J=1.9 Hz, 1H), 8.51-8.40 (m, 1H), 8.38-8.26 (m, 1H), 8.16-8.00 (m, 2H), 7.64-7.52 (m, 1H), 7.30 (t, J=54.1 Hz, 1H), 4.85 (d, J=5.6 Hz, 1H), 4.44 (d, J=5.7 Hz, 2H), 3.92-3.76 (m, 1H), 1.57-1.26 (m, 2H), 0.93 (t, J=7.4 Hz, 3H).

Example 6: (E/Z)-3-Methyl-1-[6-[3-(trifluoromethyl)phenyl]pyrazolo[4,3-b]pyridin-1-yl]butan-2-one oxime

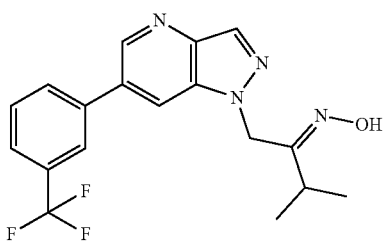 [SMILES: CC(C)/C(Cn1ncc2ncc(-c3cccc(C(F)(F)F)c3)cc21)=N\O]

To 3-methyl-1-[6-[3-(trifluoromethyl)phenyl]pyrazolo[4,3-b]pyridin-1-yl]butan-2-one (Example 2, 20 mg, 0.0576 mmol) stirring in MeOH (2 mL) was added an aqueous solution of hydroxylamine hydrochloride (8.0 mg, 0.115 mmol) and $NaHCO_3$ (9.8 mg, 0.115 mmol) in 0.5 mL $H_2O$. The reaction was stirred at rt overnight. The reaction was then diluted with $H_2O$ and extracted with EtOAc. The organic layer was dried and concentrated under reduced pressure to afford the title compound (20.1 mg, 96%). MS (ESI): mass calcd. for $CH_{17}F_3N_4O$, 362.1; m/z found, 363.0 $[M+H]^+$.

Example 7: 1-[6-(4-Fluoro-3-methyl-phenyl)pyrazolo[4,3-b]pyridin-1-yl]-3-methyl-butan-2-one

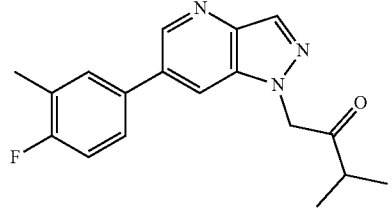 [SMILES: Cc1cc(-c2cnc3cnn(CC(=O)C(C)C)c3c2)ccc1F]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 4-fluoro-3-methylphenylboronic acid instead of 3,5-difluorophenylboronic acid. MS (ESI): mass calcd. for $C_{18}H_{18}FN_3O$, 311.1; m/z found, 312.1 $[M+H]^+$. $^1H$ NMR (400 MHz, DMSO) δ 8.85 (d, J=1.9 Hz, 1H), 8.35-8.33 (m, 1H), 8.32-8.30 (m, 1H), 7.76-7.71 (m, 1H), 7.67-7.62 (m, 1H), 7.35-7.27 (m, 1H), 5.65 (s, 2H), 2.89-2.77 (m, 1H), 2.36-2.32 (m, 3H), 1.12 (d, J=6.9 Hz, 6H).

Example 8: (RS)-1-[6-(4-Fluoro-3-methyl-phenyl)pyrazolo[4,3-b]pyridin-1-yl]-3-methyl-butan-2-ol

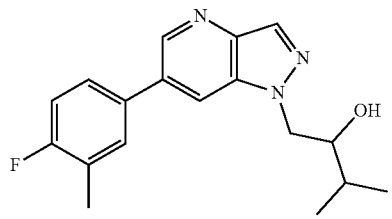 [SMILES: Cc1cc(-c2cnc3cnn(CC(O)C(C)C)c3c2)ccc1F]

The title compound was prepared in a manner analogous to Example 3 using 1-[6-(4-fluoro-3-methyl-phenyl)pyrazolo[4,3-b]pyridin-1-yl]-3-methyl-butan-2-one (Example 7) instead of 3-methyl-1-[6-[3-(trifluoromethyl)phenyl]pyrazolo[4,3-b]pyridin-1-yl]butan-2-one. MS (ESI): mass calcd. for $C_{18}H_{20}FN_3O$, 313.2; m/z found, 314.1 $[M+H]^+$. $^1H$ NMR (500 MHz, DMSO) δ 8.80 (d, J=1.9 Hz, 1H), 8.36-8.34 (m, 1H), 8.30-8.28 (m, 1H), 7.78-7.75 (m, 1H), 7.69-7.64 (m, 1H), 7.34-7.29 (m, 1H), 4.79 (d, J=5.9 Hz, 1H), 4.48-4.42 (m, 2H), 3.71-3.65 (m, 1H), 2.36-2.33 (m, 3H), 1.68-1.58 (m, 1H), 0.97 (d, J=6.8 Hz, 3H), 0.94 (d, J=6.8 Hz, 3H).

Example 9: 1-Cyclopropyl-2-[6-(3,4,5-trifluorophenyl)pyrazolo[4,3-b]pyridin-1-yl]ethanone

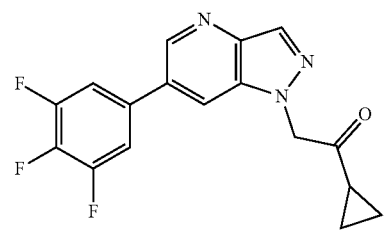 [SMILES: O=C(Cn1ncc2ncc(-c3cc(F)c(F)c(F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3,4,5-trifluorophenylboronic acid instead of 3,5-difluorophenylboronic acid. MS (ESI): mass calcd. for $C_{17}H_{12}F_3N_3O$, 331.1; m/z found, 332.0 [M+H]$^+$. $^1$H NMR (500 MHz, DMSO-$d_6$) δ 8.94 (d, J=2.0 Hz, 1H), 8.54-8.51 (m, 1H), 8.39-8.37 (m, 1H), 7.92-7.85 (m, 2H), 5.69 (s, 2H), 2.16-2.09 (m, 1H), 1.04-0.92 (m, 4H).

Example 10: (R/S)-1-Cyclopropyl-2-[6-(3,4,5-trifluorophenyl)pyrazolo[4,3-b]pyridin-1-yl]ethanol

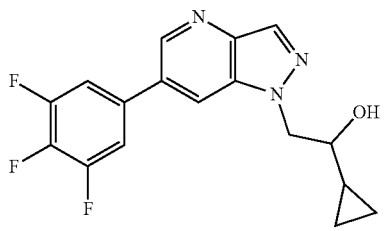 [SMILES: OC(Cn1ncc2ncc(-c3cc(F)c(F)c(F)c3)cc21)C1CC1]

The title compound was prepared in a manner analogous to Example 3 using 1-cyclopropyl-2-[6-(3,4,5-trifluorophenyl)pyrazolo[4,3-b]pyridin-1-yl]ethanone (Example 9) instead of 3-methyl-1-[6-[3-(trifluoromethyl)phenyl]pyrazolo[4,3-b]pyridin-1-yl]butan-2-one. MS (ESI): mass calcd. for $C_{17}H_{14}F_3N_3O$, 333.1; m/z found, 334.0 [M+H]$^+$.

Example 11: (R/S)-1-(2-Cyclopropyl-2-methoxyethyl)-6-(3,4,5-trifluorophenyl)pyrazolo[4,3-b]pyridine

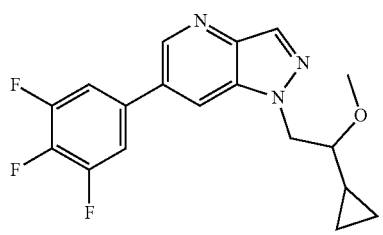 [SMILES: COC(Cn1ncc2ncc(-c3cc(F)c(F)c(F)c3)cc21)C1CC1]

To (RS)-1-cyclopropyl-2-[6-(3,4,5-trifluorophenyl)pyrazolo[4,3-b]pyridin-1-yl]ethanol (Example 10, 15 mg, 0.045 mmol) stirring in DMF (0.86 mL) at rt was added NaH (60% dispersion in mineral oil, 3.6 mg, 0.09 mmol). The mixture was stirred at rt for 10 min, then iodomethane (0.00336 mL) was added, and the reaction mixture was stirred at rt for 3 h. The reaction was quenched with H$_2$O, then evaporated under reduced pressure. The residue was dissolved in MeOH and purified by prep HPLC (METHOD A) to afford the title compound (2.4 mg, 15%). MS (ESI): mass calcd. for $C_{18}H_{16}F_3N_3O$, 347.1; m/z found, 347.9 [M+H]$^+$. $^1$H NMR (400 MHz, DMSO) δ 8.90 (d, J=2.0 Hz, 1H), 8.58-8.53 (m, 1H), 8.36-8.32 (m, 1H), 7.96-7.87 (m, 2H), 4.70-4.55 (m, 2H), 3.19 (s, 3H), 3.10-3.03 (m, 1H), 0.86-0.74 (m, 1H), 0.57-0.46 (m, 1H), 0.43-0.34 (m, 1H), 0.27-0.18 (m, 1H), −0.08-0.16 (m, 1H).

Example 12: (RS)-6-[3-(Difluoromethoxy)-4-fluorophenyl]-1-(ethylsulfinylmethyl)pyrazolo[4,3-b]pyridine

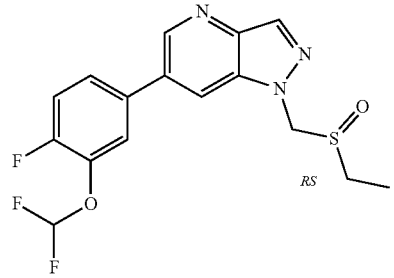 [SMILES: CCS(=O)Cn1ncc2ncc(-c3ccc(F)c(OC(F)F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 2-(3-(difluoromethoxy)-4-fluorophenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane. MS (ESI): mass calcd. for $C_{16}H_{14}F_3N_3O_2S$, 369.1; m/z found, 370.1 [M+H]$^+$. $^1$H NMR (500 MHz, DMSO-$d_6$) δ 8.92 (d, J=2.0 Hz, 1H), 8.58 (dd, J=2.0, 1.0 Hz, 1H), 8.50 (d, J=0.9 Hz, 1H), 7.82 (dd, J=7.5, 2.3 Hz, 1H), 7.78-7.72 (m, 1H), 7.62 (dd, J=10.5, 8.6 Hz, 1H), 7.38 (t, J=73.2 Hz, 1H), 5.92 (d, J=13.7 Hz, 1H), 5.76 (d, J=13.7 Hz, 1H), 2.98-2.89 (m, 1H), 2.84-2.76 (m, 1H), 1.25 (t, J=7.5 Hz, 3H).

Example 13: 6-[3-(Difluoromethoxy)-4-fluoro-phenyl]-1-(ethylsulfonylmethyl)pyrazolo[4,3-b]pyridine

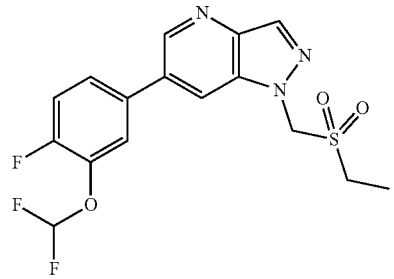 [SMILES: CCS(=O)(=O)Cn1ncc2ncc(-c3ccc(F)c(OC(F)F)c3)cc21]

Step A: 6-(3-(Difluoromethoxy)-4-fluorophenyl)-1-((ethylsulfonyl)methyl)-1H-pyrazolo[4,3-b]pyridine 4-oxide m-CPBA (6.8 mg, 0.03 mmol) was added to a solution of (RS)-6-[3-(difluoromethoxy)-4-fluoro-phenyl]-1-(ethylsulfinylmethyl)pyrazolo[4,3-b]pyridine (Example 12, 8.63 mg, 0.02 mmol) in DCM (2 mL) at room temperature. After 16 hours, the reaction mixture was quenched with saturated aqueous NaHCO$_3$ (10 mL). The mixture was extracted with DCM (3×150 mL). The combined organic layers were dried (MgSO$_4$), filtered and concentrated under vacuum to provide the title compound. MS (ESI): mass calcd. for $C_{16}H_{14}F_3N_3O_4S$, 401.1; m/z found, 402.1 [M+H]$^+$.

Step B: 6-[3-(Difluoromethoxy)-4-fluoro-phenyl]-1-(ethylsulfonylmethyl)pyrazolo[4,3-b]pyridine A mixture of 6-(3-(difluoromethoxy)-4-fluorophenyl)-1-((ethylsulfonyl)methyl)-1H-pyrazolo[4,3-b]pyridine 4-oxide (9.4 mg, 0.02 mmol) from Step A and Pd/C (10 wt. %, 1.2 mg, 0.001 mmol) in EtOH (2.0 mL) and EtOAc (2.0 mL) was stirred at room temperature under a nitrogen atmosphere. After 16 hours, the reaction mixture was filtered. The filtrate was purified (HPLC, METHOD D) to provide the title compound (3.7 mg, 41%). MS (ESI): mass calcd. for $C_{16}H_{14}F_3N_3O_3S$, 385.1; m/z found, 386.1 $[M+H]^+$. $^1H$ NMR (500 MHz, DMSO-$d_6$) δ 8.97 (d, J=2.0 Hz, 1H), 8.69-8.67 (m, 1H), 8.57-8.55 (m, 1H), 7.85-7.82 (m, 1H), 7.79-7.75 (m, 1H), 7.63 (dd, J=10.5, 8.6 Hz, 1H), 7.39 (t, J=73.1 Hz, 1H), 6.20 (s, 2H), 3.16 (q, J=7.4 Hz, 2H), 1.26 (t, J=7.5 Hz, 3H).

Example 14: 2-[6-[3-(Difluoromethyl)-4-fluoro-phenyl]pyrazolo[4,3-b]pyridin-1-yl]-1-(2-pyridyl)ethanone

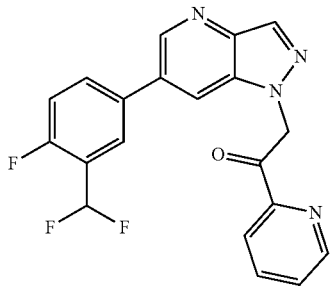 [SMILES: O=C(Cn1ncc2ncc(-c3ccc(F)c(C(F)F)c3)cc21)c1ccccn1]

To a solution of 6-[3-(difluoromethyl)-4-fluoro-phenyl]-1H-pyrazolo[4,3-b]pyridine (Intermediate 3, 100 mg, 0.380 mmol) in acetonitrile (2 mL) was added $Cs_2CO_3$ (371 mg, 1.14 mmol) and the reaction mixture was stirred at room temperature for 30 min. To the reaction mixture was added 2-bromo-1-(2-pyridyl)ethanone hydrobromide (Intermediate 21, 140 mg, 0.498 mmol) and the reaction mixture was stirred at room temperature for 22 h. The mixture was then diluted with water (8 mL) and extracted with EtOAc (3×8 mL). The combined organics were dried over $Na_2SO_4$, filtered and evaporated. Purification (FCC, $SiO_2$, 0 to 5% DCM/MeOH) afforded a solid that was recrystallized from ethanol (3 mL) to give the title compound (44 mg, 0.115 mmol, 30%) as an off-white powder. MS (ESI): mass calcd. for $C_{20}H_{13}F_3N_4O$, 382.1; m/z found, 383.1 $[M+H]^+$. $^1H$ NMR (500 MHz, DMSO-$d_6$) δ 8.92 (d, J=1.9 Hz, 1H), 8.88-8.85 (m, 1H), 8.60-8.56 (m, 1H), 8.43-8.40 (m, 1H), 8.09 (td, J=7.7, 1.8 Hz, 1H), 8.07-8.03 (m, 2H), 8.02-7.97 (m, 1H), 7.81-7.76 (m, 1H), 7.57-7.51 (m, 1H), 7.27 (t, J=54.1 Hz, 1H), 6.33 (s, 2H).

Example 15: 2-(6-(3-(Difluoromethyl)-4-fluorophenyl)-1H-pyrazolo[4,3-b]pyridin-1-yl)-1-(5-fluoropyridin-2-yl)ethan-1-one

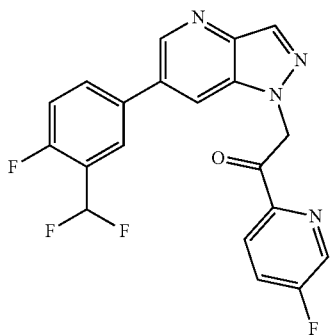 [SMILES: O=C(Cn1ncc2ncc(-c3ccc(F)c(C(F)F)c3)cc21)c1ccc(F)cn1]

A mixture of 6-[3-(difluoromethyl)-4-fluoro-phenyl]-1H-pyrazolo[4,3-b]pyridine (Intermediate 3, 150 mg, 0.57 mmol) and $NaHCO_3$ (105 mg, 1.25 mmol) in DMF (2.9 mL) was stirred at rt for 30 min. To the reaction mixture was added 2-bromo-1-(5-fluoropyridin-2-yl)ethan-1-one (Intermediate 28, 149 mg, 0.683 mmol) in DMF (1 mL) and the reaction mixture was stirred at rt for 3 h. Additional $NaHCO_3$ (105 mg, 1.25 mmol) and a solution of 2-bromo-1-(5-fluoropyridin-2-yl)ethan-1-one (Intermediate 28, 149 mg, 0.683 mmol) in DMF (1 mL) was added and the reaction mixture was stirred at rt for 17 h. The reaction was evaporated under reduced pressure, and the residue was purified (FCC, $SiO_2$, dichloromethane:methanol (100/0 to 98/2), then re-purified by n-hexane/ethyl acetate (4/1 to ½)). The product was re-purified by prep HPLC (METHOD E) and triturated with diethyl ether (4 mL) to afford the title compound. MS (ESI): mass calcd. for $C_{20}H_{12}F_4N_4O$, 400.1; m/z found, 401.1 $[M+H]^+$. $^1H$ NMR (500 MHz, DMSO-$d_6$) δ 8.95-8.90 (m, 1H), 8.90-8.85 (m, 1H), 8.59-8.55 (m, 1H), 8.44-8.39 (m, 1H), 8.11 (dd, J=8.8, 4.6 Hz, 1H), 8.08-8.03 (m, 2H), 8.00 (td, J=8.7, 2.6 Hz, 1H), 7.58-7.51 (m, 1H), 7.27 (t, J=54.1 Hz, 1H), 6.30 (s, 2H).

Example 16: 2-(6-(3-(Difluoromethyl)-4-fluorophenyl)-1H-pyrazolo[4,3-b]pyridin-1-yl)-1-(pyridin-3-yl)ethan-1-one

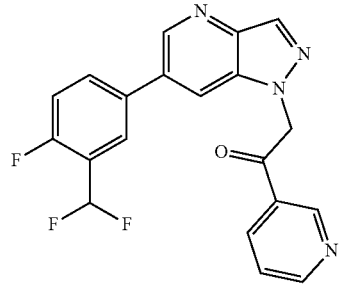 [SMILES: O=C(Cn1ncc2ncc(-c3ccc(F)c(C(F)F)c3)cc21)c1cccnc1]

To a solution of 6-[3-(difluoromethyl)-4-fluoro-phenyl]-1H-pyrazolo[4,3-b]pyridine (Intermediate 3, 150 mg, 0.57 mmol) and DIPEA (300 μL, 1.722 mmol) in DMF (3.9 mL) was added 2-bromo-1-(pyridin-3-yl)ethan-1-one HBr salt (Intermediate 27, 192 mg, 0.683 mmol) and the reaction mixture was stirred at rt for 1 h. Over the next 75 h, 6 additional portions of DIPEA (300 μL, 1.722 mmol) for a total of 2.1 mL (12.06 mmol) and 2-bromo-1-(pyridine-3-yl)ethan-1-one HBr salt (192 mg, 0.683 mmol) for a total of 1.34 g (4.78 mmol) were added. The reaction mixture was poured into water (20 mL), then extracted with ethyl acetate (3×20 mL). The combined organic layers were dried ($Na_2SO_4$), filtered, and evaporated. The residue was purified (FCC, $SiO_2$, n-hexane/ethyl acetate/methanol (2:1:0 to 0:1:0 to 0:20:1) to afford the title compound. MS (ESI): mass calcd. for $C_{20}H_{13}F_3N_4O$, 382.1; m/z found, 383.1 $[M+H]^+$. $^1H$ NMR (500 MHz, DMSO-$d_6$) δ 9.33-9.26 (m, 1H), 8.92 (d, J=2.0 Hz, 1H), 8.89 (dd, J=4.9, 1.7 Hz, 1H), 8.56-8.51 (m, 1H), 8.46-8.39 (m, 2H), 8.09-7.98 (m, 2H), 7.66 (dd, J=7.9, 4.8 Hz, 1H), 7.59-7.50 (m, 1H), 7.27 (t, J=54.1 Hz, 1H), 6.34 (s, 2H).

Example 17: (RS)-1-(Oxetan-2-ylmethyl)-6-[3-(trifluoromethyl)phenyl]pyrazolo[4,3-b]pyridine

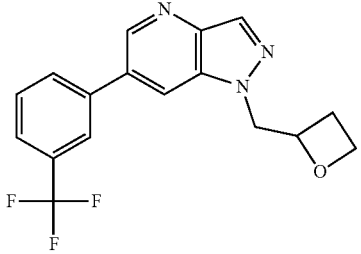 [SMILES: FC(F)(F)c1cccc(-c2cnc3cnn(CC4CCO4)c3c2)c1]

To a suspension of NaH (60% dispersion in mineral oil, 28.9 mg, 0.723 mmol) in DMF (5.4 mL) at rt under an atmosphere of $N_2$ was added 6-(3-(trifluoromethyl)phenyl)-1H-pyrazolo[4,3-b]pyridine (Intermediate 8, 136 mg, 0.517 mmol). After 10 minutes, 2-(bromomethyl)oxetane (0.0697 mL, 0.723 mmol) was added and the reaction mixture was heated to 75° C. Upon completion the reaction mixture was cooled to rt and water (20 mL) was added. The mixture was extracted using EtOAc (3×30 mL) and the combined organic layers were dried over $MgSO_4$, filtered and concentrated under vacuum. Purification by prep HPLC (METHOD A) afforded the title compound and (RS)-4-methoxy-1-[6-[3-(trifluoromethyl)phenyl]pyrazolo[4,3-b]pyridin-1-yl]butan-2-ol. MS (ESI): mass calcd. for $C_{17}H_{14}F_3N_3O$, 333.1; m/z found, 334.2 [M+H]$^+$. $^1$H NMR (400 MHz, CDCl$_3$) δ 8.82 (d, J=1.9 Hz, 1H), 8.33-8.31 (m, 1H), 8.12-8.09 (m, 1H), 7.91-7.88 (m, 1H), 7.86-7.82 (m, 1H), 7.72-7.61 (m, 2H), 5.31-5.24 (m, 1H), 4.71-4.67 (m, 2H), 4.61-4.54 (m, 1H), 4.19-4.13 (m, 1H), 2.80-2.70 (m, 1H), 2.60-2.50 (m, 1H).

Example 18: (RS)-6-[3-(Difluoromethyl)-4-fluoro-phenyl]-1-(tetrahydrofuran-2-ylmethyl)pyrazolo[4,3-b]pyridine

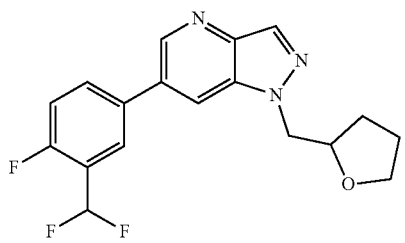 [SMILES: Fc1ccc(-c2cnc3cnn(CC4CCCO4)c3c2)cc1C(F)F]

A mixture of 6-[3-(difluoromethyl)-4-fluoro-phenyl]-1H-pyrazolo[4,3-b]pyridine (Intermediate 3, 150 mg, 0.570 mmol), 2-(chloromethyl)oxolane (76 mg, 0.63 mmol), $Cs_2CO_3$ (279 mg, 0.856 mmol) and potassium iodide (19 mg, 0.114 mmol) in dry DMF (3 mL) was stirred at 80° C. for 20 h. The reaction mixture was poured into water (5 mL) and extracted with EtOAc (3×5 mL).

The combined organics were dried over $Na_2SO_4$, filtered and evaporated. The residue was purified by preparative HPLC (METHOD F) to afford the title compound (42 mg, 0.121 mmol, 21%) as a brown oil. MS (ESI): mass calcd. for $C_{18}H_{16}F_3N_3O$, 347.1; m/z found, 348.1 [M+H]$^+$. $^1$H NMR (300 MHz, DMSO-d$_6$) δ 8.85 (d, J=1.9 Hz, 1H), 8.54-8.46 (m, 1H), 8.33 (s, 1H), 8.13-7.99 (m, 2H), 7.63-7.52 (m, 1H), 7.30 (t, J=54.1 Hz, 1H), 4.57 (d, J=5.6 Hz, 2H), 4.36-4.24 (m, 1H), 3.73-3.62 (m, 1H), 3.63-3.52 (m, 1H), 2.02-1.87 (m, 1H), 1.84-1.59 (m, 3H).

Example 19: (RS)-4-[[6-[3-(Difluoromethoxy)-4-fluoro-phenyl]pyrazolo[4,3-b]pyridin-1-yl]methyl]-1-methyl-pyrrolidin-2-one

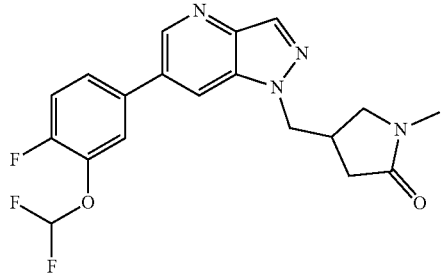

A mixture of 6-[3-(difluoromethoxy)-4-fluoro-phenyl]-1H-pyrazolo[4,3-b]pyridine (Intermediate 4, 60 mg, 0.215 mmol), 4-(chloromethyl)-1-methyl-pyrrolidin-2-one (35 mg, 0.237 mmol) and $Cs_2CO_3$ (420 mg, 1.29 mmol) in dry DMF (1.2 mL) was stirred at room temperature for 2 h, then at 60° C. for 11 h. The reaction mixture was then cooled, and diluted with water (5 mL), and extracted with EtOAc (2×). The combined organics were dried over $Na_2SO_4$, filtered and evaporated. Purification (FCC, $SiO_2$, 5 to 10% DCM/MeOH) afforded the title compound (17 mg, 0.044 mmol, 20%) as an off-white powder after triturating the solid with diethyl ether. MS (ESI): mass calcd. for $C_{19}H_{17}F_3N_4O_2$, 390.1; m/z found, 391.1 [M+H]$^+$. $^1$H NMR (500 MHz, DMSO-d$_6$) δ 8.89 (d, J=1.9 Hz, 1H), 8.61-8.54 (m, 1H), 8.39-8.32 (m, 1H), 7.87 (dd, J=7.6, 2.3 Hz, 1H), 7.83-7.77 (m, 1H), 7.60 (dd, J=10.5, 8.6 Hz, 1H), 7.38 (t, J=73.2 Hz, 1H), 4.57 (d, J=7.4 Hz, 2H), 3.35 (dd, J=9.9, 8.0 Hz, 1H), 3.20 (dd, J=9.9, 5.6 Hz, 1H), 3.06-2.96 (m, 1H), 2.68 (s, 3H), 2.34 (dd, J=16.7, 8.8 Hz, 1H), 2.14 (dd, J=16.7, 6.6 Hz, 1H).

Example 20: (RS)-5-[[6-[3-(Difluoromethyl)-4-fluoro-phenyl]pyrazolo[4,3-b]pyridin-1-yl]methyl]oxazolidin-2-one

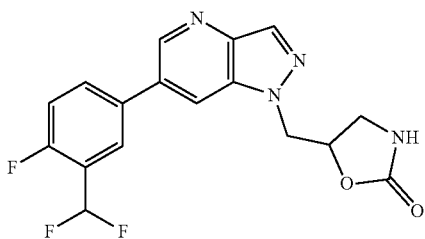 [SMILES: O=C1NCC(Cn2ncc3ncc(-c4ccc(F)c(C(F)F)c4)cc32)O1]

To a suspension of sodium hydride (60% in mineral oil, 18 mg, 0.45 mmol) in dry DMF (1 mL) was added a solution of 6-[3-(difluoromethyl)-4-fluoro-phenyl]-1H-pyrazolo[4,3-b]pyridine (Intermediate 3, 100 mg, 0.38 mmol) in dry DMF (500 μL) at 0° C. and the reaction was stirred at 0° C. for 30 min. To the reaction mixture was added a solution of 5-chloromethyl-2-oxazolidinone (77 mg, 0.568 mmol) in dry DMF (500 μL) and the reaction mixture was stirred at 80° C. for 18 h under argon. The reaction mixture was poured into water (10 mL) and extracted with EtOAc (3×5 mL). The combined organics were dried over MgSO$_4$, filtered and evaporated. Purification (FCC, SiO$_2$, 0 to 5% CHCl$_3$/MeOH) afforded the title compound (46 mg, 0.127 mmol, 33%) as a white powder. MS (ESI): mass calcd. for C$_{17}$H$_{13}$F$_3$N$_4$O$_2$, 362.1; m/z found, 363.1 [M+H]$^+$. $^1$H NMR (500 MHz, DMSO-d$_6$) δ 8.88 (d, J=1.9 Hz, 1H), 8.55-8.52 (m, 1H), 8.39 (d, J=0.9 Hz, 1H), 8.12-8.04 (m, 2H), 7.61-7.55 (m, 1H), 7.52-7.47 (m, 1H), 7.29 (t, J=54.2 Hz, 1H), 5.09-5.00 (m, 1H), 4.84 (dd, J=15.0, 6.4 Hz, 1H), 4.79 (dd, J=15.1, 4.5 Hz, 1H), 3.66-3.60 (m, 1H), 3.38-3.33 (m, 1H).

Example 21: (S)-5-[[6-[3-(Difluoromethyl)-4-fluoro-phenyl]pyrazolo[4,3-b]pyridin-1-yl]methyl]oxazolidin-2-one

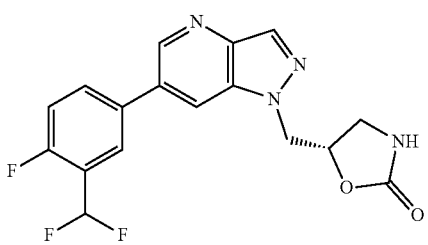 [SMILES: O=C1NC[C@@H](Cn2ncc3ncc(-c4ccc(F)c(C(F)F)c4)cc32)O1]

The title compound was prepared by the separation of (RS)-5-[[6-[3-(difluoromethyl)-4-fluoro-phenyl]pyrazolo[4,3-b]pyridin-1-yl]methyl]oxazolidin-2-one (Example 20) using chiral SFC (Stationary phase: Chiralpak IA, 5 um 250×21 mm, Mobile phase: 20% methanol, 80% CO$_2$). MS (ESI): mass calcd. for C$_{17}$H$_{13}$F$_3$N$_4$O$_2$, 362.1; m/z found, 363.1 [M+H]$^+$.

Example 22: (R)-5-[[6-[3-(Difluoromethyl)-4-fluoro-phenyl]pyrazolo[4,3-b]pyridin-1-yl]methyl]oxazolidin-2-one

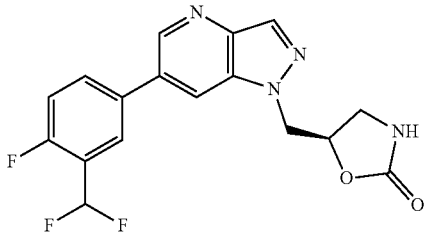 [SMILES: O=C1NC[C@H](Cn2ncc3ncc(-c4ccc(F)c(C(F)F)c4)cc32)O1]

The title compound was prepared by the separation of (RS)-5-[[6-[3-(difluoromethyl)-4-fluoro-phenyl]pyrazolo[4,3-b]pyridin-1-yl]methyl]oxazolidin-2-one (Example 20) using chiral SFC (Stationary phase: Chiralpak IA, 5um 250×21 mm, Mobile phase: 20% methanol, 80% CO$_2$). MS (ESI): mass calcd. for C$_{17}$H$_{13}$F$_3$N$_4$O$_2$, 362.1; m/z found, 363.1 [M+H]$^+$.

Example 23: 1-[6-[3-(Difluoromethyl)-4-fluoro-phenyl]pyrazolo[4,3-b]pyridin-1-yl]propan-2-one

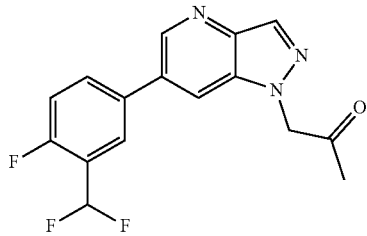 [SMILES: CC(=O)Cn1ncc2ncc(-c3ccc(F)c(C(F)F)c3)cc21]

The title compound was prepared in a manner analogous to Intermediate 16, Step A using 6-(3-(difluoromethyl)-4-fluorophenyl)-1H-pyrazolo[4,3-b]pyridine (Intermediate 3) instead of 6-bromo-1H-pyrazolo[4,3-b]pyridine, and chloropropane-2-one instead of (chloromethyl)(ethyl)sulfane. MS (ESI): mass calcd. for C$_{16}$H$_{12}$F$_3$N$_3$O, 319.1; m/z found, 320.1 [M+H]$^+$. $^1$H NMR (500 MHz, DMSO-d$_6$) δ 8.89 (d, J=1.9 Hz, 1H), 8.44-8.43 (m, 1H), 8.37 (d, J=1.0 Hz, 1H), 8.08-8.00 (m, 2H), 7.62-7.53 (m, 1H), 7.30 (t, J=54.1 Hz, 1H), 5.55 (s, 2H), 2.21 (s, 3H).

Example 24: 1-[6-(4-Fluoro-3-methyl-phenyl)pyrazolo[4,3-b]pyridin-1-yl]propan-2-one

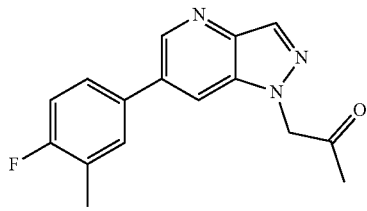 [SMILES: CC(=O)Cn1ncc2ncc(-c3ccc(F)c(C)c3)cc21]

The title compound was prepared in a manner analogous to Intermediate 3, using 1-(6-bromo-1H-pyrazolo[4,3-b]pyridin-1-yl)propan-2-one (Intermediate 12) instead of 6-bromo-1H-pyrazolo[4,3-B]pyridine, and 4-fluoro-3-methylphenylboronic acid instead of 2-[3-(difluoromethyl)-4-fluoro-phenyl]-4,4,5,5-tetramethyl-1,3,2-dioxaborolane. MS (ESI): mass calcd. for C$_{16}$H$_{14}$FN$_3$O, 283.1; m/z found, 284.2 [M+H]$^+$. $^1$H NMR (500 MHz, DMSO-d$_6$) δ 8.86-8.78 (m, 1H), 8.37-8.28 (m, 2H), 7.77-7.67 (m, 1H), 7.67-7.59 (m, 1H), 7.28 (t, J=9.1 Hz, 1H), 5.51 (s, 2H), 2.38-2.25 (m, 3H), 2.18 (s, 3H).

Example 25: 1-[6-[3-(Difluoromethoxy)-4-fluoro-phenyl]pyrazolo[4,3-b]pyridin-1-yl]propan-2-one

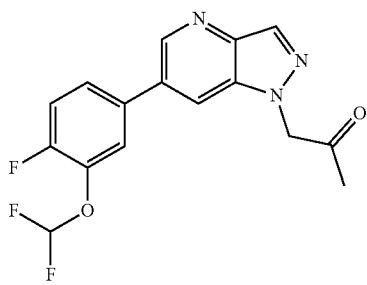 [SMILES: CC(=O)Cn1ncc2ncc(-c3ccc(F)c(OC(F)F)c3)cc21]

The title compound was prepared in a manner analogous to Intermediate 3, using 1-(6-bromo-1H-pyrazolo[4,3-b]pyridin-1-yl)propan-2-one (Intermediate 12) instead of 6-bromo-1H-pyrazolo[4,3-B]pyridine, and 2-(3-(difluoromethoxy)-4-fluorophenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{16}H_{12}F_3N_3O_2$, 335.1; m/z found, 336.1 [M+H]$^+$. $^1$H NMR (500 MHz, DMSO-d$_6$) δ 8.94-8.83 (m, 1H), 8.43-8.38 (m, 1H), 8.39-8.35 (m, 1H), 7.87-7.79 (m, 1H), 7.78-7.70 (m, 1H), 7.63-7.56 (m, 1H), 7.37 (t, J=73.2 Hz, 1H), 5.55 (s, 2H), 2.21 (s, 3H).

Example 26: 1-[6-[4-Chloro-3-(difluoromethoxy)phenyl]pyrazolo[4,3-b]pyridin-1-yl]propan-2-one

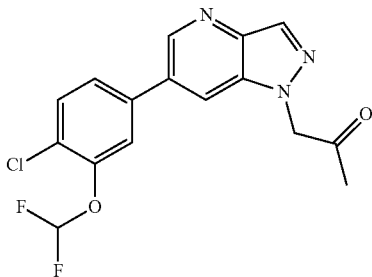 [SMILES: CC(=O)Cn1ncc2ncc(-c3ccc(Cl)c(OC(F)F)c3)cc21]

The title compound was prepared in a manner analogous to Intermediate 3, using 1-(6-bromo-1H-pyrazolo[4,3-b]pyridin-1-yl)propan-2-one (Intermediate 12) instead of 6-bromo-1H-pyrazolo[4,3-B]pyridine, and 2-(3-(difluoromethoxy)-4-chlorophenyl)-4,4,5,5-tetramethyl-1,3,2-dioxaborolane instead of 2-[3-(difluoromethyl)-4-fluoro-phenyl]-4,4,5,5-tetramethyl-1,3,2-dioxaborolane. MS (ESI): mass calcd. for $C_{16}H_{12}ClF_2N_3O_2$, 351.1; m/z found, 352.1 [M+H]$^+$. $^1$H NMR (300 MHz, DMSO-d$_6$) δ 8.92 (d, J=1.9 Hz, 1H), 8.46-8.41 (m, 1H), 8.41-8.35 (m, 1H), 7.83-7.79 (m, 1H), 7.77 (d, J=8.6 Hz, 1H), 7.72 (dd, J=8.4, 2.0 Hz, 1H), 7.43 (t, J=73.2 Hz, 1H), 5.56 (s, 2H), 2.21 (s, 3H).

Example 27: 1-[6-(5-Chloro-2-thienyl)pyrazolo[4,3-b]pyridin-1-yl]butan-2-one

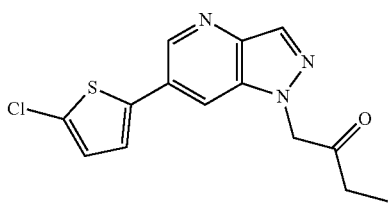 [SMILES: CCC(=O)Cn1ncc2ncc(-c3ccc(Cl)s3)cc21]

The title compound was prepared in a manner analogous to Example 1 using 5-chlorothiophene-2-boronic acid instead of 3,5-difluorophenylboronic acid. MS (ESI): mass calcd. for $C_{14}H_{12}ClN_3S$, 305.0; m/z found, 306.0 [M+H]$^+$. $^1$H NMR (400 MHz, DMSO-d$_6$) δ 8.86 (d, J=1.8 Hz, 1H), 8.35-8.33 (m, 1H), 8.30-8.28 (m, 1H), 7.59 (d, J=4.0 Hz, 1H), 7.25 (d, J=4.0 Hz, 1H), 5.52 (s, 2H), 2.58 (q, J=7.3 Hz, 2H), 0.98 (t, J=7.3 Hz, 3H).

Example 28: 1-[6-(4-Fluorophenyl)pyrazolo[4,3-b]pyridin-1-yl]butan-2-one

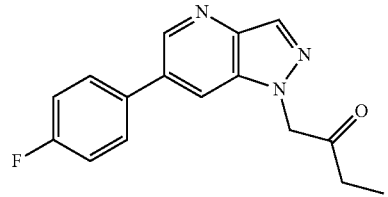 [SMILES: CCC(=O)Cn1ncc2ncc(-c3ccc(F)cc3)cc21]

The title compound was prepared in a manner analogous to Example 1 using 4-fluorophenylboronic acid instead of 3,5-difluorophenylboronic acid. MS (ESI): mass calcd. for $C_{16}H_{14}FN_3O$, 283.1; m/z found, 284.0 [M+H]$^+$. $^1$H NMR (400 MHz, DMSO-d$_6$) δ 8.85 (d, J=1.9 Hz, 1H), 8.36-8.34 (m, 2H), 7.88-7.81 (m, 2H), 7.42-7.34 (m, 2H), 5.53 (s, 2H), 2.57 (q, J=7.3 Hz, 2H), 0.97 (t, J=7.2 Hz, 3H).

Example 29: 1-[6-(3-Fluorophenyl)pyrazolo[4,3-b]pyridin-1-yl]butan-2-one

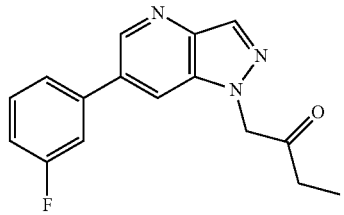 [SMILES: CCC(=O)Cn1ncc2ncc(-c3cccc(F)c3)cc21]

The title compound was prepared in a manner analogous to Example 1 using 3-fluorophenylboronic acid instead of 3,5-difluorophenylboronic acid. MS (ESI): mass calcd. for $C_{16}H_{14}FN_3O$, 283.1; m/z found, 284.1 [M+H]$^+$. $^1$H NMR (400 MHz, DMSO-d$_6$) δ 8.91 (d, J=1.9 Hz, 1H), 8.44-8.42 (m, 1H), 8.38-8.35 (m, 1H), 7.72-7.65 (m, 2H), 7.62-7.55 (m, 1H), 7.32-7.25 (m, 1H), 5.54 (s, 2H), 2.57 (q, J=7.3 Hz, 2H), 0.98 (t, J=7.3 Hz, 3H).

Example 30: 1-[6-[3-(Difluoromethyl)phenyl]pyrazolo[4,3-b]pyridin-1-yl]butan-2-one

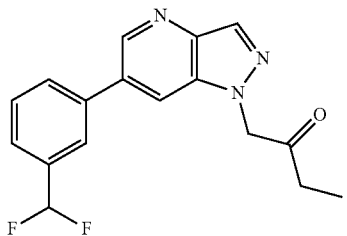 [SMILES: CCC(=O)Cn1ncc2ncc(-c3cccc(C(F)F)c3)cc21]

The title compound was prepared in a manner analogous to Example 1 using 3-difluoromethyl-phenylboronic acid instead of 3,5-difluorophenylboronic acid. MS (ESI): mass calcd. for $C_{17}H_{15}F_2N_3O$, 315.1; m/z found, 316.0 [M+H]$^+$. $^1$H NMR (500 MHz, DMSO-d$_6$) δ 8.90 (d, J=1.9 Hz, 1H), 8.44-8.42 (m, 1H), 8.38-8.36 (m, 1H), 8.01-7.97 (m, 2H), 7.73-7.64 (m, 2H), 7.13 (t, J=55.8 Hz, 1H), 5.55 (s, 2H), 2.57 (q, J=7.3 Hz, 2H), 0.98 (t, J=7.3 Hz, 3H).

Example 31: 1-[6-[3-(1,1-Difluoroethyl)phenyl]pyrazolo[4,3-b]pyridin-1-yl]butan-2-one

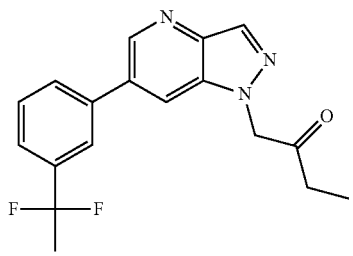 [SMILES: CCC(=O)Cn1ncc2ncc(-c3cccc(C(C)(F)F)c3)cc21]

The title compound was prepared in a manner analogous to Intermediate 11, using 6-(3-(1,1-difluoroethyl)phenyl)-1H-pyrazolo[4,3-b]pyridine (Intermediate 7) instead of bromo-1H-pyrazolo[4,3-B]pyridine. MS (ESI): mass calcd. for $C_{18}H_{17}F_2N_3O$, 329.1; m/z found, 330.2 [M+H]$^+$. $^1$H NMR (500 MHz, DMSO-$d_6$) δ 8.91 (d, J=2.0 Hz, 1H), 8.44-8.40 (m, 1H), 8.39-8.36 (m, 1H), 7.96-7.91 (m, 2H), 7.69-7.62 (m, 2H), 5.55 (s, 2H), 2.57 (q, J=7.3 Hz, 2H), 2.06 (t, J=18.9 Hz, 3H), 0.98 (t, J=7.3 Hz, 3H).

Example 32: 1-[6-(4-Fluoro-3-methyl-phenyl)pyrazolo[4,3-b]pyridin-1-yl]butan-2-one Trifluoroacetate Salt

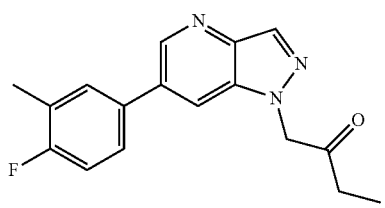 [SMILES: CCC(=O)Cn1ncc2ncc(-c3ccc(F)c(C)c3)cc21]

The title compound was prepared in a manner analogous to Intermediate 11, using 6-(4-fluoro-3-methylphenyl)-1H-pyrazolo[4,3-b]pyridine (Intermediate 2) instead of 6-bromo-1H-pyrazolo[4,3-B]pyridine. MS (ESI): mass calcd. for $C_{17}H_{16}FN_3O$, 297.1; m/z found, 299.1 [M+H]$^+$. $^1$H NMR (500 MHz, MeOD) δ 8.87-8.84 (m, 1H), 8.34-8.32 (m, 1H), 8.31-8.29 (m, 1H), 7.68-7.63 (m, 1H), 7.61-7.55 (m, 1H), 7.22-7.16 (m, 1H), 5.50 (s, 2H), 2.63 (q, J=7.4 Hz, 2H), 2.38-2.36 (m, 3H), 1.09 (t, J=7.3 Hz, 3H).

Example 33: 1-[6-(2,3-Difluorophenyl)pyrazolo[4,3-b]pyridin-1-yl]butan-2-one

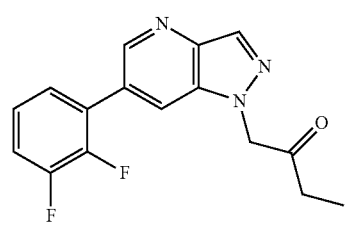 [SMILES: CCC(=O)Cn1ncc2ncc(-c3cccc(F)c3F)cc21]

The title compound was prepared in a manner analogous to Example 1 using 2,3-difluorophenylboronic acid instead of 3,5-difluorophenylboronic acid. MS (ESI): mass calcd. for $C_{16}H_{13}F_2N_3O$, 301.1; m/z found, 302.0 [M+H]$^+$. $^1$H NMR (500 MHz, DMSO-$d_6$) δ 8.73 (t, J=1.9 Hz, 1H), 8.40 (d, J=1.0 Hz, 1H), 8.34-8.33 (m, 1H), 7.58-7.51 (m, 1H), 7.50-7.45 (m, 1H), 7.41-7.36 (m, 1H), 5.55 (s, 2H), 2.57 (q, J=7.3 Hz, 2H), 0.97 (t, J=7.3 Hz, 3H).

Example 34: 1-[6-(3,4-Difluorophenyl)pyrazolo[4,3-b]pyridin-1-yl]butan-2-one

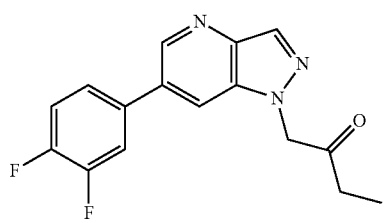 [SMILES: CCC(=O)Cn1ncc2ncc(-c3ccc(F)c(F)c3)cc21]

The title compound was prepared in a manner analogous to Example 1 using 3,4-difluorophenylboronic acid instead of 3,5-difluorophenylboronic acid. MS (ESI): mass calcd. for $C_{16}H_{13}F_2N_3O$, 301.1; m/z found, 302.0 [M+H]$^+$. $^1$H NMR (500 MHz, DMSO-$d_6$) δ 8.90 (d, J=2.0 Hz, 1H), 8.43-8.41 (m, 1H), 8.36 (d, J=1.0 Hz, 1H), 7.98-7.92 (m, 1H), 7.72-7.67 (m, 1H), 7.66-7.58 (m, 1H), 5.53 (s, 2H), 2.57 (q, J=7.3 Hz, 2H), 0.98 (t, J=7.3 Hz, 3H).

Example 35: 1-[6-(3,4-Difluorophenyl)-3-fluoropyrazolo[4,3-b]pyridin-1-yl]butan-2-one

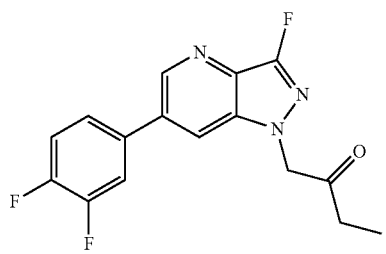 [SMILES: CCC(=O)Cn1nc(F)c2ncc(-c3ccc(F)c(F)c3)cc21]

The title compound was prepared in a manner analogous to Intermediate 3, using 1-(6-bromo-3-fluoro-1H-pyrazolo[4,3-b]pyridin-1-yl)butan-2-one (Intermediate 15) instead of 6-bromo-3-methyl-1H-pyrazolo[4,3-b]pyridine, and 3,4-difluorophenylboronic acid instead of 2-(3-(difluoromethyl)-4-fluorophenyl)-4,4,5,5-tetramethyl-1,3,2-dioxaborolane. MS (ESI): mass calcd. for $C_{16}H_{12}F_3N_3O$, 319.1; m/z found, 320.3 [M+H]$^+$. $^1$H NMR (500 MHz, DMSO-$d_6$) δ 8.94 (d, J=1.8 Hz, 1H), 8.47-8.41 (m, 1H), 8.00-7.92 (m, 1H), 7.73-7.68 (m, 1H), 7.64 (dt, J=10.5, 8.5 Hz, 1H), 5.42 (s, 2H), 2.57 (q, J=7.3 Hz, 2H), 0.98 (t, J=7.3 Hz, 3H).

Example 36: 1-(6-(3-(Difluoromethyl)-4-fluorophenyl)-3-methyl-1H-pyrazolo[4,3-b]pyridin-1-yl)butan-2-one

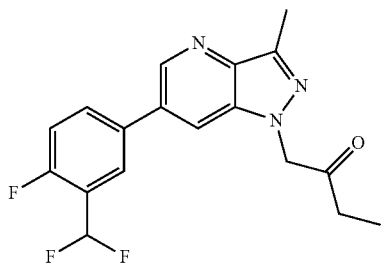 [SMILES: CCC(=O)Cn1nc(C)c2ncc(-c3ccc(F)c(C(F)F)c3)cc21]

The title compound was prepared in a manner analogous to Intermediate 11, using 6-(3-(difluoromethyl)-4-fluorophenyl)-3-methyl-1H-pyrazolo[4,3-b]pyridine (Intermediate 10) instead of 6-bromo-1H-pyrazolo[4,3-B]pyridine. MS (ESI): mass calcd. for $C_{18}H_{16}F_3N_3O$, 347.1; m/z found, 348.1 [M+H]$^+$. $^1$H NMR (400 MHz, CDCl$_3$) δ 8.75 (d, J=1.9 Hz, 1H), 7.83 (d, J=6.5 Hz, 1H), 7.76-7.68 (m, 1H), 7.64 (d, J=1.9 Hz, 1H), 7.26 (s, 1H), 6.98 (t, J=54.9 Hz, 1H), 5.14 (s, 2H), 2.71 (s, 3H), 2.47 (q, J=7.3 Hz, 2H), 1.09 (t, J=7.3 Hz, 3H).

Example 37: 1-[6-[3-(1,1-Difluoroethyl)-4-fluorophenyl]pyrazolo[4,3-b]pyridin-1-yl]butan-2-one

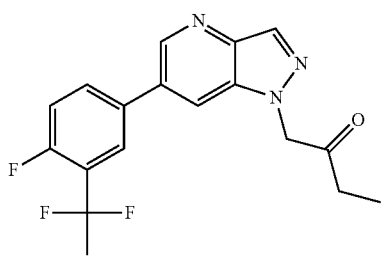 [SMILES: CCC(=O)Cn1ncc2ncc(-c3ccc(F)c(C(C)(F)F)c3)cc21]

The title compound was prepared in a manner analogous to Intermediate 11, using 6-(3-(1,1-difluoroethyl)-4-fluorophenyl)-1H-pyrazolo[4,3-b]pyridine (Intermediate 6) instead of 6-bromo-1H-pyrazolo[4,3-B]pyridine. MS (ESI): mass calcd. for $C_{18}H_{16}F_3N_3O$, 347.1; m/z found, 348.1 [M+H]$^+$. $^1$H NMR (500 MHz, DMSO-d$_6$) δ 8.89 (d, J=1.9 Hz, 1H), 8.43-8.39 (m, 1H), 8.38-8.36 (m, 1H), 8.02-7.96 (m, 1H), 7.92 (dd, J=7.1, 2.4 Hz, 1H), 7.55 (dd, J=11.0, 8.6 Hz, 1H), 5.55 (s, 2H), 2.57 (q, J=7.3 Hz, 2H), 2.09 (t, J=19.1 Hz, 3H), 0.97 (t, J=7.3 Hz, 3H).

Example 38: 1-[6-[2-Fluoro-3-(trifluoromethyl)phenyl]pyrazolo[4,3-b]pyridin-1-yl]butan-2-one

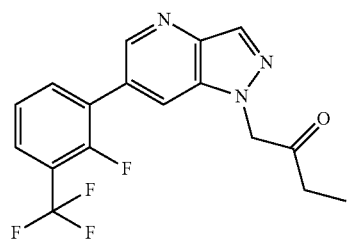 [SMILES: CCC(=O)Cn1ncc2ncc(-c3cccc(C(F)(F)F)c3F)cc21]

The title compound was prepared in a manner analogous to Example 1 using (2-fluoro-3-(trifluoromethyl)phenyl)boronic acid instead of 3,5-difluorophenylboronic acid. MS (ESI): mass calcd. for $C_{17}H_{13}F_4N_3O$, 351.1; m/z found, 352.0 [M+H]$^+$. $^1$H NMR (400 MHz, DMSO-d$_6$) δ 8.73 (t, J=1.8 Hz, 1H), 8.42-8.40 (m, 1H), 8.38-8.36 (m, 1H), 8.03-7.97 (m, 1H), 7.93-7.86 (m, 1H), 7.59 (t, J=7.8 Hz, 1H), 5.56 (s, 2H), 2.57 (q, J=7.3 Hz, 2H), 0.97 (t, J=7.3 Hz, 3H).

Example 39: 1-[6-[4-Fluoro-3-(trifluoromethyl)phenyl]pyrazolo[4,3-b]pyridin-1-yl]butan-2-one

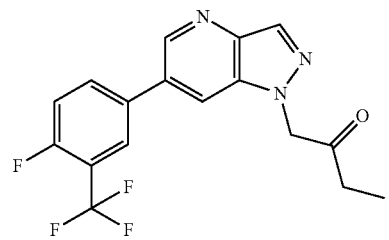 [SMILES: CCC(=O)Cn1ncc2ncc(-c3ccc(F)c(C(F)(F)F)c3)cc21]

The title compound was prepared in a manner analogous to Example 1 using (4-fluoro-3-(trifluoromethyl)phenyl)boronic acid instead of 3,5-difluorophenylboronic acid. MS (ESI): mass calcd. for $C_{17}H_{13}F_4N_3O$, 351.1; m/z found, 352.0 [M+H]$^+$. $^1$H NMR (400 MHz, DMSO-d$_6$) δ 8.92 (d, J=2.0 Hz, 1H), 8.48-8.45 (m, 1H), 8.40-8.38 (m, 1H), 8.23-8.13 (m, 2H), 7.75-7.67 (m, 1H), 5.54 (s, 2H), 2.57 (q, J=7.3 Hz, 2H), 0.98 (t, J=7.3 Hz, 3H).

Example 40: 1-[6-[3-(Difluoromethoxy)-4-fluorophenyl]pyrazolo[4,3-b]pyridin-1-yl]butan-2-one

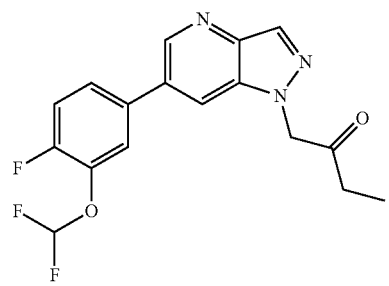 [SMILES: CCC(=O)Cn1ncc2ncc(-c3ccc(F)c(OC(F)F)c3)cc21]

The title compound was prepared in a manner analogous to Intermediate 11, using 6-(3-(difluoromethoxy)-4-fluorophenyl)-1H-pyrazolo[4,3-b]pyridine (Intermediate 4) instead of 6-bromo-1H-pyrazolo[4,3-B]pyridine. MS (ESI): mass calcd. for $C_{17}H_{14}F_3N_3O_2$, 349.1; m/z found, 350.2 [M+H]$^+$. $^1$H NMR (500 MHz, DMSO-d$_6$) δ 8.88 (d, J=2.0 Hz, 1H), 8.41-8.38 (m, 1H), 8.38-8.35 (m, 1H), 7.82 (dd, J=7.7, 2.2 Hz, 1H), 7.77-7.71 (m, 1H), 7.59 (dd, J=10.5, 8.6 Hz, 1H), 7.36 (t, J=73.2 Hz, 1H), 5.53 (s, 2H), 2.56 (q, J=7.3 Hz, 2H), 0.98 (t, J=7.3 Hz, 3H).

Example 41: 1-[6-[4-Chloro-3-(difluoromethoxy) phenyl]pyrazolo[4,3-b]pyridin-1-yl]butan-2-one

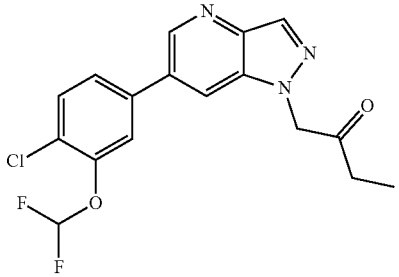 [SMILES: CCC(=O)Cn1ncc2ncc(-c3ccc(Cl)c(OC(F)F)c3)cc21]

The title compound was prepared in a manner analogous to Intermediate 11, using 6-(4-chloro-3-(difluoromethoxy) phenyl)-1H-pyrazolo[4,3-b]pyridine (Intermediate 5) instead of 6-bromo-1H-pyrazolo[4,3-B]pyridine. MS (ESI): mass calcd. for $C_{17}H_{14}ClF_2N_3O_2$, 365.1; m/z found, 366.1 [M+H]$^+$. $^1$H NMR (300 MHz, DMSO-d$_6$) δ 8.92 (d, J=1.9 Hz, 1H), 8.46-8.41 (m, 1H), 8.41-8.36 (m, 1H), 7.84-7.76 (m, 2H), 7.72 (dd, J=8.4, 1.9 Hz, 1H), 7.44 (t, J=73.2 Hz, 1H), 5.55 (s, 2H), 2.57 (q, J=7.5 Hz, 2H), 0.98 (t, J=7.2 Hz, 3H).

Example 42: 1-[6-(3,4,5-Trifluorophenyl)pyrazolo[4,3-b]pyridin-1-yl]butan-2-one

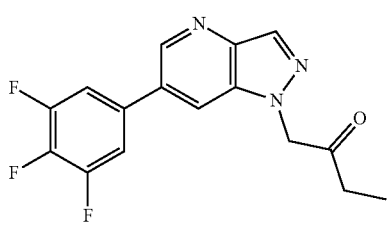 [SMILES: CCC(=O)Cn1ncc2ncc(-c3cc(F)c(F)c(F)c3)cc21]

The title compound was prepared in a manner analogous to Example 1 using 3,4,5-trifluorophenylboronic acid instead of 3,5-difluorophenylboronic acid. MS (ESI): mass calcd. for $C_{16}H_{12}F_3N_3O$, 319.1; m/z found, 320.0 [M+H]$^+$. $^1$H NMR (500 MHz, DMSO-d$_6$) δ 8.94 (d, J=2.0 Hz, 1H), 8.48-8.46 (m, 1H), 8.38 (d, J=1.0 Hz, 1H), 7.91-7.84 (m, 2H), 5.53 (s, 2H), 2.58 (q, J=7.3 Hz, 2H), 0.98 (t, J=7.3 Hz, 3H).

Example 43: 1-[6-(2,3,4-Trifluorophenyl)pyrazolo[4,3-b]pyridin-1-yl]butan-2-one

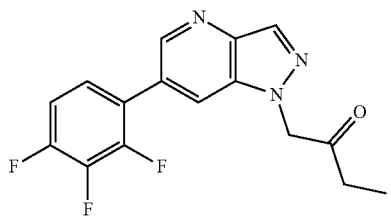 [SMILES: CCC(=O)Cn1ncc2ncc(-c3ccc(F)c(F)c3F)cc21]

The title compound was prepared in a manner analogous to Example 1 using 2,3,4-trifluorophenylboronic acid instead of 3,5-difluorophenylboronic acid. MS (ESI): mass calcd. for $C_{16}H_{12}F_3N_3O$, 319.1; m/z found, 320.0 [M+H]$^+$.

Example 44: 3-Methyl-1-(6-phenylpyrazolo[4,3-b]pyridin-1-yl)butan-2-one

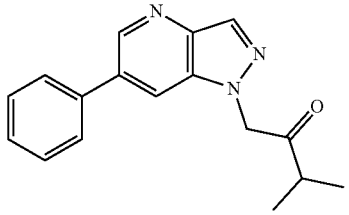 [SMILES: CC(C)C(=O)Cn1ncc2ncc(-c3ccccc3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and phenylboronic acid instead of 3,5-difluorophenylboronic acid. MS (ESI): mass calcd. for $C_{17}H_{17}N_3O$, 279.1; m/z found, 280.1 [M+H]$^+$. $^1$H NMR (400 MHz, DMSO) δ 8.87 (d, J=1.9 Hz, 1H), 8.35-8.32 (m, 2H), 7.83-7.77 (m, 2H), 7.58-7.52 (m, 2H), 7.49-7.43 (m, 1H), 5.65 (s, 2H), 2.89-2.78 (m, 1H), 1.13 (d, J=6.9 Hz, 6H).

Example 45: 1-[6-(4-Fluorophenyl)pyrazolo[4,3-b]pyridin-1-yl]-3-methyl-butan-2-one

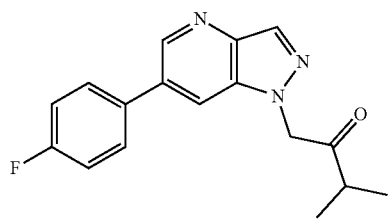 [SMILES: CC(C)C(=O)Cn1ncc2ncc(-c3ccc(F)cc3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 4-fluorophenylboronic acid instead of 3,5-difluorophenylboronic acid. MS (ESI): mass calcd. for $C_{17}H_{16}FN_3O$, 297.1; m/z found, 298.0 [M+H]$^+$. $^1$H NMR (400 MHz, DMSO-d$_6$) δ 8.86 (d, J=1.9 Hz, 1H), 8.36-8.31 (m, 2H), 7.88-7.81 (m, 2H), 7.43-7.35 (m, 2H), 5.65 (s, 2H), 2.89-2.77 (m, 1H), 1.13 (d, J=6.9 Hz, 6H).

Example 46: 1-[6-(3-Fluorophenyl)pyrazolo[4,3-b]pyridin-1-yl]-3-methyl-butan-2-one

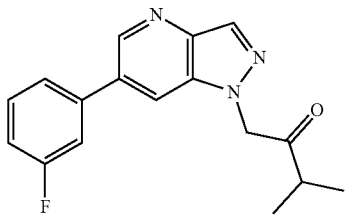 [SMILES: CC(C)C(=O)Cn1ncc2ncc(-c3cccc(F)c3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 3-fluorophenylboronic acid instead of 3,5-difluorophenylboronic acid. MS (ESI): mass calcd. for C$_{17}$H$_{16}$FN$_3$O, 297.1; m/z found, 298.1 [M+H]$^+$.

Example 47: 1-[6-[3-(Difluoromethyl)phenyl]pyrazolo[4,3-b]pyridin-1-yl]-3-methyl-butan-2-one

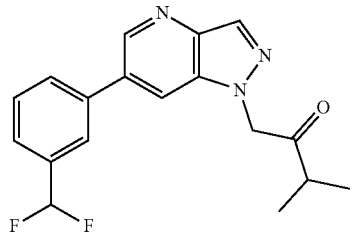 [SMILES: CC(C)C(=O)Cn1ncc2ncc(-c3cccc(C(F)F)c3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and (3-(difluoromethyl)phenyl)boronic acid instead of 3,5-difluorophenylboronic acid. MS (ESI): mass calcd. for C$_{18}$H$_{17}$F$_2$N$_3$O, 329.1; m/z found, 330.1 [M+H]$^+$.

Example 48: 1-[6-(2,3-Difluorophenyl)pyrazolo[4,3-b]pyridin-1-yl]-3-methyl-butan-2-one

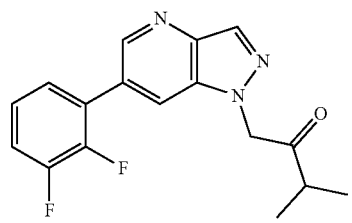 [SMILES: CC(C)C(=O)Cn1ncc2ncc(-c3cccc(F)c3F)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 2,3-difluorophenylboronic acid instead of 3,5-difluorophenylboronic acid. MS (ESI): mass calcd. for C$_{17}$H$_{15}$F$_2$N$_3$O, 315.1; m/z found, 316.0 [M+H]$^+$.

Example 49: 1-[6-(3,4-Difluorophenyl)pyrazolo[4,3-b]pyridin-1-yl]-3-methyl-butan-2-one

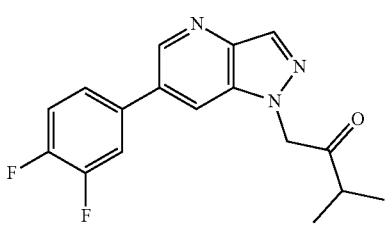 [SMILES: CC(C)C(=O)Cn1ncc2ncc(-c3ccc(F)c(F)c3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 3,4-difluorophenylboronic acid instead of 3,5-difluorophenylboronic acid. MS (ESI): mass calcd. for C$_{17}$H$_{15}$F$_2$N$_3$O, 315.1; m/z found, 316.0 [M+H]$^+$.

Example 50: 1-[6-[2-Fluoro-3-(trifluoromethyl)phenyl]pyrazolo[4,3-b]pyridin-1-yl]-3-methyl-butan-2-one

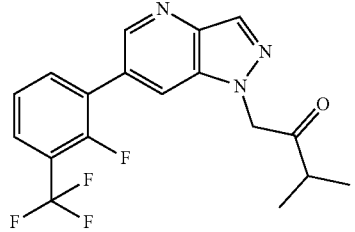 [SMILES: CC(C)C(=O)Cn1ncc2ncc(-c3cccc(C(F)(F)F)c3F)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and (2-fluoro-3-(trifluoromethyl)phenyl)boronic acid instead of 3,5-difluorophenylboronic acid. MS (ESI): mass calcd. for C$_{18}$H$_{15}$F$_4$N$_3$O, 365.1; m/z found, 366.0 [M+H]$^+$. $^1$H NMR (400 MHz, DMSO-d$_6$) δ 8.73 (t, J=1.8 Hz, 1H), 8.43-8.39 (m, 1H), 8.37-8.33 (m, 1H), 8.03-7.97 (m, 1H), 7.93-7.87 (m, 1H), 7.63-7.56 (m, 1H), 5.67 (s, 2H), 2.87-2.77 (m, 1H), 1.12 (d, J=6.9 Hz, 6H).

Example 51: 1-[6-[4-Fluoro-3-(trifluoromethyl)phenyl]pyrazolo[4,3-b]pyridin-1-yl]-3-methyl-butan-2-one

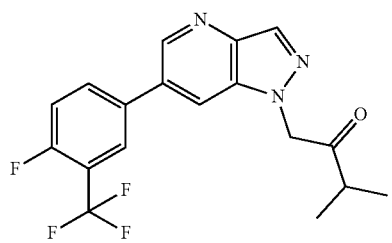 [SMILES: CC(C)C(=O)Cn1ncc2ncc(-c3ccc(F)c(C(F)(F)F)c3)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and (4-fluoro-3-(trifluoromethyl)phenyl)boronic acid instead of 3,5-difluorophenylboronic acid. MS (ESI): mass calcd. for C$_{18}$H$_{15}$F$_4$N$_3$O, 365.1; m/z found, 366.0 [M+H]$^+$. $^1$H NMR (400 MHz, DMSO-d$_6$) δ 8.92 (d, J=2.0 Hz, 1H), 8.45-8.41 (m, 1H), 8.40-8.37 (m, 1H), 8.21-8.12 (m, 2H), 7.76-7.67 (m, 1H), 5.65 (s, 2H), 2.88-2.78 (m, 1H), 1.13 (d, J=6.9 Hz, 6H).

Example 52: 1-[6-(4-Fluoro-2-methyl-phenyl)pyrazolo[4,3-b]pyridin-1-yl]-3-methyl-butan-2-one

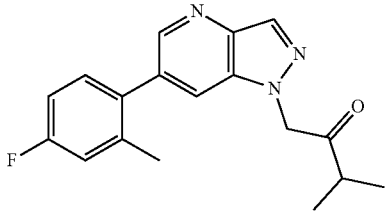 [SMILES: Cc1cc(F)ccc1-c1cnc2cnn(CC(=O)C(C)C)c2c1]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 4-fluoro-2-methylphenylboronic acid instead of 3,5-difluorophenylboronic acid. MS (ESI): mass calcd. for $C_{18}H_{18}FN_3O$, 311.1; m/z found, 312.1 [M+H]$^+$. $^1$H NMR (400 MHz, DMSO) δ 8.51 (d, J=1.8 Hz, 1H), 8.39-8.33 (m, 1H), 8.08-8.02 (m, 1H), 7.39-7.32 (m, 1H), 7.29-7.21 (m, 1H), 7.20-7.12 (m, 1H), 5.62 (s, 2H), 2.86-2.74 (m, 1H), 2.26 (s, 3H), 1.10 (d, J=7.0 Hz, 6H).

Example 53: 3-Methyl-1-[6-(3,4,5-trifluorophenyl)pyrazolo[4,3-b]pyridin-1-yl]butan-2-one

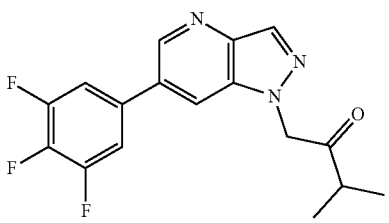 [SMILES: CC(C)C(=O)Cn1ncc2ncc(-c3cc(F)c(F)c(F)c3)cc21]

The title compound was prepared in a manner analogous to Example 1 using 1-(6-bromo-1H-pyrazolo[4,3-b]pyridin-1-yl)-3-methylbutan-2-one (intermediate 13) instead of 1-(6-bromo-1H-pyrazolo[4,3-b]pyridin-1-yl)butan-2-one (Intermediate 11), and 3,4,5-trifluorophenylboronic acid instead of 3,5-difluorophenylboronic acid. MS (ESI): mass calcd. for $C_{17}H_{14}F_3N_3O$, 333.1; m/z found, 334.0 [M+H]$^+$. $^1$H NMR (400 MHz, DMSO-d$_6$) δ 8.93 (d, J=2.0 Hz, 1H), 8.46-8.44 (m, 1H), 8.39-8.37 (m, 1H), 7.92-7.82 (m, 2H), 5.64 (s, 2H), 2.90-2.79 (m, 1H), 1.13 (d, J=6.9 Hz, 6H).

Example 54: 3-Methyl-1-[6-(2,3,4-trifluorophenyl)pyrazolo[4,3-b]pyridin-1-yl]butan-2-one

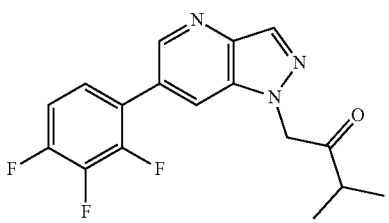 [SMILES: CC(C)C(=O)Cn1ncc2ncc(-c3ccc(F)c(F)c3F)cc21]

The title compound was prepared in a manner analogous to Example 1 using 1-(6-bromo-1H-pyrazolo[4,3-b]pyridin-1-yl)-3-methylbutan-2-one (Intermediate 13) instead of 1-(6-bromo-1H-pyrazolo[4,3-b]pyridin-1-yl)butan-2-one (Intermediate 11), and 2,3,4-trifluorophenylboronic acid instead of 3,5-difluorophenylboronic acid. MS (ESI): mass calcd. for $C_{17}H_{14}F_3N_3O$, 333.1; m/z found, 334.1 [M+H]$^+$. $^1$H NMR (400 MHz, DMSO-d$_6$) δ 8.71 (t, J=1.9 Hz, 1H), 8.40 (d, J=1.0 Hz, 1H), 8.31-8.28 (m, 1H), 7.57-7.48 (m, 2H), 5.66 (s, 2H), 2.88-2.77 (m, 1H), 1.12 (d, J=7.0 Hz, 6H).

Example 55: 2-[6-(5-Chloro-2-thienyl)pyrazolo[4,3-b]pyridin-1-yl]-1-cyclopropyl-ethanone

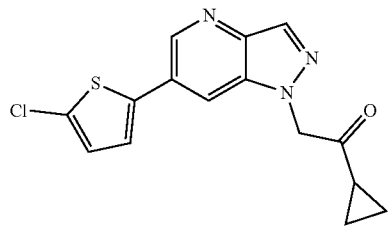 [SMILES: O=C(Cn1ncc2ncc(-c3ccc(Cl)s3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 2-(5-chlorothiophen-2-yl)-4,4,5,5-tetramethyl-1,3,2-dioxaborolane instead of 3,5-difluorophenylboronic acid. MS (ESI): mass calcd. for $C_{15}H_{12}ClN_3S$, 317.0; m/z found, 317.9 [M+H]$^+$. $^1$H NMR (500 MHz, DMSO-d$_6$) δ 8.86 (d, J=1.9 Hz, 1H), 8.36-8.31 (m, 2H), 7.61 (d, J=4.0 Hz, 1H), 7.26 (d, J=3.9 Hz, 1H), 5.69 (s, 2H), 2.15-2.07 (m, 1H), 1.05-0.91 (m, 4H).

Example 56: 1-Cyclopropyl-2-[6-(5-methyl-2-thienyl)pyrazolo[4,3-b]pyridin-1-yl]ethanone

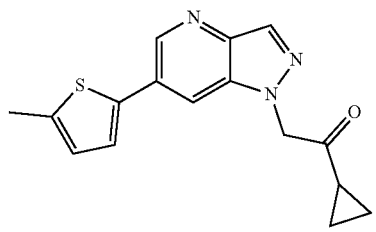 [SMILES: Cc1ccc(-c2cnc3cnn(CC(=O)C4CC4)c3c2)s1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 4,4,5,5-tetramethyl-2-(5-methylthiophen-2-yl)-1,3,2-dioxaborolane instead of 3,5-difluorophenylboronic acid. MS (ESI): mass calcd. for $C_{16}H_{15}N_3S$, 297.1; m/z found, 298.0 [M+H]$^+$. $^1$H NMR (500 MHz, DMSO-d$_6$) δ 8.83 (d, J=1.9 Hz, 1H), 8.30 (d, J=1.0 Hz, 1H), 8.24-8.22 (m, 1H), 7.51 (d, J=3.5 Hz, 1H), 6.92-6.89 (m, 1H), 5.68 (s, 2H), 2.14-2.07 (m, 1H), 1.04-0.90 (m, 4H).

Example 57: 1-Cyclopropyl-2-[6-(3-fluorophenyl)pyrazolo[4,3-b]pyridin-1-yl]ethanone

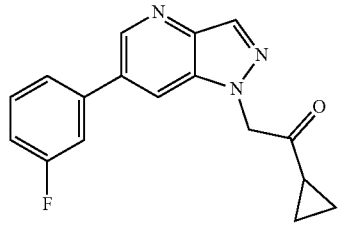

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3-fluorophenylboronic acid instead of 3,5-difluorophenylboronic acid. MS (ESI): mass calcd. for $C_{17}H_{14}FN_3O$, 295.1; m/z found, 296.0 [M+H]$^+$. $^1$H NMR (400 MHz, DMSO) δ 8.92 (d, J=2.0 Hz, 1H), 8.50-8.47 (m, 1H), 8.38-8.36 (m, 1H), 7.73-7.66 (m, 2H), 7.62-7.55 (m, 1H), 7.32-7.26 (m, 1H), 5.71 (s, 2H), 2.15-2.07 (m, 1H), 1.04-0.91 (m, 4H).

Example 58: 1-Cyclopropyl-2-[6-(2-fluorophenyl)pyrazolo[4,3-b]pyridin-1-yl]ethanone

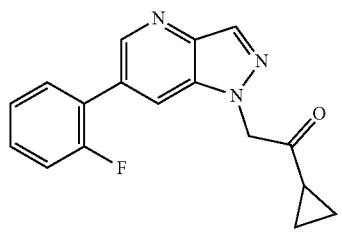 [SMILES: O=C(Cn1ncc2ncc(-c3ccccc3F)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 2-fluorophenylboronic acid instead of 3,5-difluorophenylboronic acid. MS (ESI): mass calcd. for $C_{17}H_{14}FN_3O$, 295.1; m/z found, 296.0 [M+H]$^+$. $^1$H NMR (500 MHz, DMSO) δ 8.71 (t, J=2.0 Hz, 1H), 8.38 (d, J=1.0 Hz, 1H), 8.31-8.29 (m, 1H), 7.68-7.63 (m, 1H), 7.54-7.49 (m, 1H), 7.43-7.36 (m, 2H), 5.72 (s, 2H), 2.13-2.07 (m, 1H), 1.02-0.90 (m, 4H).

Example 59: 1-Cyclopropyl-2-[6-(4-fluorophenyl)pyrazolo[4,3-b]pyridin-1-yl]ethanone

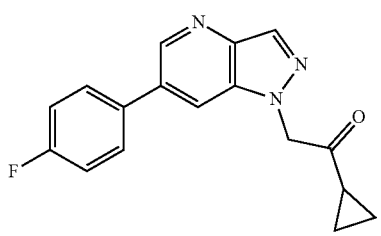 [SMILES: O=C(Cn1ncc2ncc(-c3ccc(F)cc3)cc21)C1CC1]

The title compound was prepared in a manner analogous to Intermediate 11, using 6-(4-fluorophenyl)-1H-pyrazolo[4,3-b]pyridine (Intermediate 9) instead of 6-bromo-1H-pyrazolo[4,3-B]pyridine, and 2-bromo-1-cyclopropylethanone instead of 1-bromo-2-butanone. MS (ESI): mass calcd. for $C_{17}H_{14}FN_3O$, 295.1; m/z found, 296.1 [M+H]$^+$. $^1$H NMR (500 MHz, DMSO-d$_6$) δ 8.85 (d, J=1.9 Hz, 1H), 8.39-8.37 (m, 1H), 8.35-8.34 (m, 1H), 7.88-7.83 (m, 2H), 7.41-7.35 (m, 2H), 5.70 (s, 2H), 2.14-2.07 (m, 1H), 1.02-0.91 (m, 4H).

Example 60: 1-Cyclopropyl-2-[6-(m-tolyl)pyrazolo[4,3-b]pyridin-1-yl]ethanone

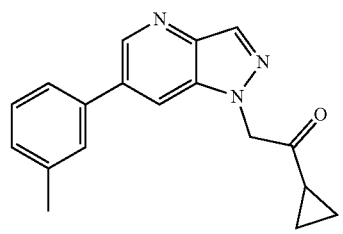 [SMILES: Cc1cccc(-c2cnc3cnn(CC(=O)C4CC4)c3c2)c1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3-methylphenylboronic acid instead of 3,5-difluorophenylboronic acid. MS (ESI): mass calcd. for $C_{18}H_{17}N_3O$, 291.1; m/z found, 292.1 [M+H]$^+$. $^1$H NMR (500 MHz, DMSO-d$_6$) δ 8.86 (d, J=1.9 Hz, 1H), 8.39-8.36 (m, 1H), 8.36-8.33 (m, 1H), 7.64-7.61 (m, 1H), 7.61-7.57 (m, 1H), 7.42 (t, J=7.6 Hz, 1H), 7.29-7.24 (m, 1H), 5.71 (s, 2H), 2.41 (s, 3H), 2.14-2.06 (m, 1H), 1.04-0.90 (m, 4H).

Example 61: 1-Cyclopropyl-2-[6-[3-(difluoromethyl)phenyl]pyrazolo[4,3-b]pyridin-1-yl]ethanone

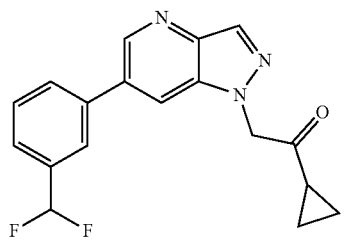 [SMILES: O=C(Cn1ncc2ncc(-c3cccc(C(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and (3-(difluoromethyl)phenyl)boronic acid instead of 3,5-difluorophenylboronic acid. MS (ESI): mass calcd. for $C_{18}H_{15}F_2N_3O$, 327.1; m/z found, 328.0 [M+H]$^+$. $^1$H NMR (400 MHz, DMSO) δ 8.90 (d, J=2.0 Hz, 1H), 8.49-8.46 (m, 1H), 8.39-8.36 (m, 1H), 8.03-7.96 (m, 2H), 7.73-7.63 (m, 2H), 7.13 (t, J=55.7 Hz, 1H), 5.73 (s, 2H), 2.15-2.07 (m, 1H), 1.04-0.91 (m, 4H).

Example 62: 1-Cyclopropyl-2-[6-[3-(trifluoromethyl)phenyl]pyrazolo[4,3-b]pyridin-1-yl]ethanone

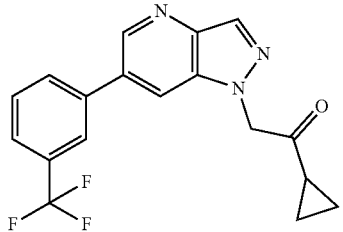 [SMILES: O=C(Cn1ncc2ncc(-c3cccc(C(F)(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3-(trifluoromethyl)phenylboronic acid instead of 3,5-difluorophenylboronic acid. MS (ESI): mass calcd. for $C_{18}H_{14}F_3N_3O$, 345.1; m/z found, 346.0 [M+H]$^+$. $^1$H NMR (500 MHz, DMSO) δ 9.05-8.86 (d, J=2.1 Hz, 1H), 8.60-8.47 (t, J=1.6 Hz, 1H), 8.44-8.32 (d, J=1.1 Hz, 1H), 8.21-8.07 (d, J=6.5 Hz, 2H), 7.91-7.69 (m, 2H), 5.84-5.57 (s, 2H), 2.19-1.99 (d, J=4.5 Hz, 1H), 1.13-0.78 (m, 6H).

Example 63: 1-Cyclopropyl-2-[6-[3-(trifluoromethoxy)phenyl]pyrazolo[4,3-b]pyridin-1-yl]ethanone

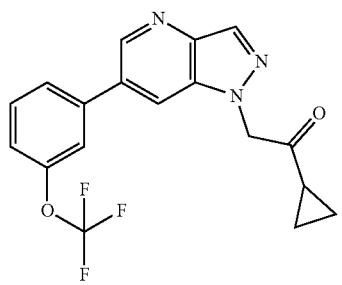 [SMILES: O=C(Cn1ncc2ncc(-c3cccc(OC(F)(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), 3-(trifluoromethoxy)phenylboronic acid instead of 3,5-difluorophenylboronic acid, and RuPhos Pd G3 instead of Pd(dppf)C$_{12}$.DCM. MS (ESI): mass calcd. for $C_{18}H_{14}F_3N_3O_2$, 361.1; m/z found, 362.1 [M+H]$^+$. $^1$H NMR (500 MHz, CDCl$_3$) δ 8.82 (d, J=1.9 Hz, 1H), 8.35 (d, J=1.0 Hz, 1H), 7.73 (dd, J=1.8, 1.0 Hz, 1H), 7.59-7.51 (m, 2H), 7.47 (d, J=2.7 Hz, 1H), 7.32-7.29 (m, 1H), 5.37 (s, 2H), 1.90 (tt, J=7.8, 4.5 Hz, 1H), 1.20-1.13 (m, 2H), 1.02-0.95 (m, 2H).

Example 64: 1-Cyclopropyl-2-[6-(2,3-difluorophenyl)pyrazolo[4,3-b]pyridin-1-yl]ethanone

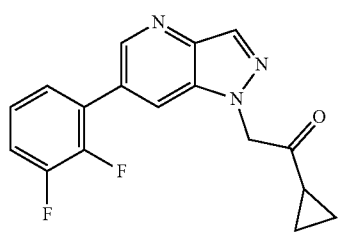 [SMILES: O=C(Cn1ncc2ncc(-c3cccc(F)c3F)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 2,3-difluorophenylboronic acid instead of 3,5-difluorophenylboronic acid. MS (ESI): mass calcd. for $C_{17}H_{13}F_2N_3O$, 313.1; m/z found, 313.9 [M+H]$^+$. $^1$H NMR (400 MHz, DMSO) δ 8.73 (t, J=1.9 Hz, 1H), 8.40 (d, J=1.0 Hz, 1H), 8.37-8.35 (m, 1H), 7.59-7.45 (m, 2H), 7.43-7.35 (m, 1H), 5.73 (s, 2H), 2.15-2.06 (m, 1H), 1.03-0.90 (m, 4H).

Example 65: 1-Cyclopropyl-2-[6-(3,4-difluorophenyl)pyrazolo[4,3-b]pyridin-1-yl]ethanone

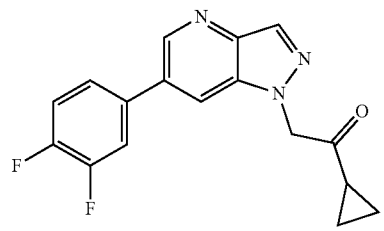 [SMILES: O=C(Cn1ncc2ncc(-c3ccc(F)c(F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3,4-difluorophenylboronic acid instead of 3,5-difluorophenylboronic acid. MS (ESI): mass calcd. for $C_{17}H_{13}F_2N_3O$, 313.1; m/z found, 314.0 [M+H]$^+$. $^1$H NMR (500 MHz, DMSO-d$_6$) δ 8.90 (d, J=1.9 Hz, 1H), 8.47-8.46 (m, 1H), 8.37 (d, J=0.9 Hz, 1H), 7.96 (ddd, J=12.2, 7.8, 2.3 Hz, 1H), 7.72-7.67 (m, 1H), 7.65-7.58 (m, 1H), 5.70 (s, 2H), 2.15-2.08 (m, 1H), 1.03-0.92 (m, 4H).

Example 66: 1-Cyclopropyl-2-[6-(3,5-difluorophenyl)pyrazolo[4,3-b]pyridin-1-yl]ethanone

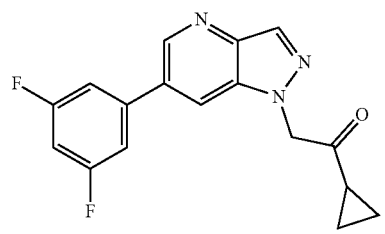 [SMILES: O=C(Cn1ncc2ncc(-c3cc(F)cc(F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11). MS (ESI): mass calcd. for $C_{17}H_{13}F_2N_3O$, 313.1; m/z found, 314.0 [M+H]$^+$. $^1$H NMR (400 MHz, DMSO) δ 8.95 (d, J=1.9 Hz, 1H), 8.56-8.54 (m, 1H), 8.39-8.37 (m, 1H), 7.69-7.60 (m, 2H), 7.38-7.29 (m, 1H), 5.70 (s, 2H), 2.17-2.08 (m, 1H), 1.04-0.91 (m, 4H).

Example 67: 2-[6-(3-Chloro-2-fluoro-phenyl)pyrazolo[4,3-b]pyridin-1-yl]-1-cyclopropyl-ethanone

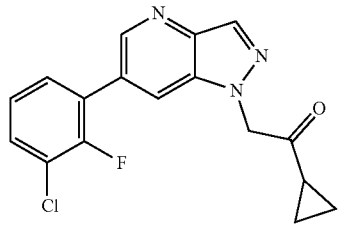 [SMILES: O=C(Cn1ncc2ncc(-c3cccc(Cl)c3F)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3-chloro-2-fluorophenylboronic acid instead of 3,5-difluorophenylboronic acid. MS (ESI): mass calcd. for $C_{17}H_{13}ClFN_3O$, 329.1; m/z found, 330.0 $[M+H]^+$.

Example 68: 2-[6-(3-Chloro-4-fluoro-phenyl)pyrazolo[4,3-b]pyridin-1-yl]-1-cyclopropyl-ethanone

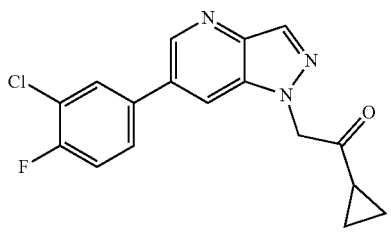 [SMILES: O=C(Cn1ncc2ncc(-c3ccc(F)c(Cl)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 3-chloro-4-fluorophenylboronic acid instead of 3,5-difluorophenylboronic acid. MS (ESI): mass calcd. for $C_{17}H_{13}ClFN_3O$, 329.1; m/z found, 330.0 $[M+H]^+$.

Example 69: 1-Cyclopropyl-2-[6-(4-fluoro-3-methyl-phenyl)pyrazolo[4,3-b]pyridin-1-yl]ethanone

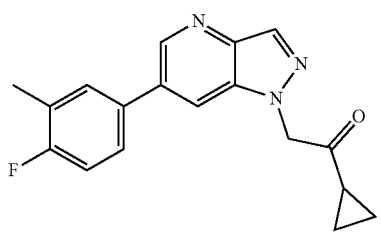 [SMILES: Cc1cc(-c2cnc3cnn(CC(=O)C4CC4)c3c2)ccc1F]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 4-fluoro-3-methylphenylboronic acid instead of 3,5-difluorophenylboronic acid. MS (ESI): mass calcd. for $C_{18}H_{16}FN_3O$, 309.1; m/z found, 310.0 $[M+H]^+$.
$^1$H NMR (400 MHz, DMSO-d$_6$) δ 8.85 (d, J=2.0 Hz, 1H), 8.39-8.36 (m, 1H), 8.35-8.33 (m, 1H), 7.78-7.73 (m, 1H), 7.69-7.63 (m, 1H), 7.34-7.27 (m, 1H), 5.70 (s, 2H), 2.37-2.31 (m, 3H), 2.14-2.06 (m, 1H), 1.03-0.90 (m, 4H).

Example 70: 1-Cyclobutyl-2-[6-(4-fluoro-3-methylphenyl)pyrazolo[4,3-b]pyridin-1-yl]ethanone

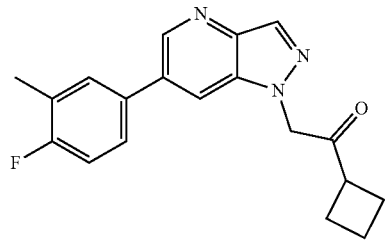 [SMILES: Cc1cc(-c2cnc3cnn(CC(=O)C4CCC4)c3c2)ccc1F]

The title compound was prepared in a manner analogous to Intermediate 16, Step A, using 6-(4-fluoro-3-methylphenyl)-1H-pyrazolo[4,3-b]pyridine (Intermediate 2) instead of 6-bromo-1H-pyrazolo[4,3-B]pyridine, and 2-bromo-1-cyclobutylethan-1-one (Intermediate 17) instead of (chloromethyl)(ethyl)sulfane. MS (ESI): mass calcd. for $C_{19}H_{18}FN_3O$, 323.1; m/z found, 324.0 $[M+H]^+$. $^1$H NMR (400 MHz, Methanol-d$_4$) δ 8.80 (br.s, 1H), 8.28-8.24 (m, 1H), 8.20-8.17 (m, 1H), 7.65-7.60 (m, 1H), 7.59-7.53 (m, 1H), 7.22-7.14 (m, 1H), 5.41 (s, 2H), 3.55-3.45 (m, 1H), 2.40-2.26 (m, 5H), 2.22-2.12 (m, 2H), 2.09-1.96 (m, 1H), 1.91-1.79 (m, 1H).

Example 71: 1-Cyclopropyl-2-[6-(2-fluoro-3-methyl-phenyl)pyrazolo[4,3-b]pyridin-1-yl]ethanone

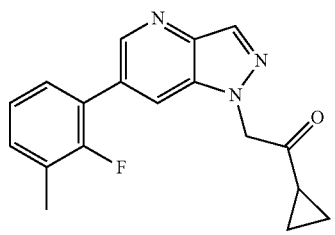 [SMILES: Cc1cccc(-c2cnc3cnn(CC(=O)C4CC4)c3c2)c1F]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 2-fluoro-3-methylphenylboronic acid instead of 3,5-difluorophenylboronic acid. MS (ESI): mass calcd. for $C_{18}H_{16}FN_3O$, 309.1; m/z found, 310.1 $[M+H]^+$.

Example 72: 1-Cyclopropyl-2-[6-(4-fluoro-2-methyl-phenyl)pyrazolo[4,3-b]pyridin-1-yl]ethanone

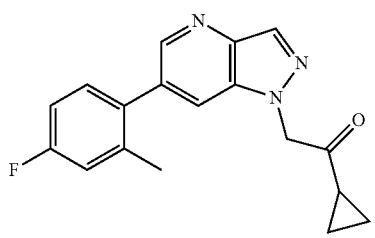 [SMILES: Cc1cc(F)ccc1-c1cnc2cnn(CC(=O)C3CC3)c2c1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 4-fluoro-2-methylphenylboronic acid instead of 3,5-difluorophenylboronic acid. MS (ESI): mass calcd. for $C_{18}H_{16}FN_3O$, 309.1; m/z found, 310.0 [M+H]$^+$. $^1$H NMR (400 MHz, DMSO) δ 8.51 (d, J=1.8 Hz, 1H), 8.37-8.36 (m, 1H), 8.11-8.08 (m, 1H), 7.38-7.33 (m, 1H), 7.27-7.22 (m, 1H), 7.19-7.13 (m, 1H), 5.68 (s, 2H), 2.27 (s, 3H), 2.12-2.03 (m, 1H), 1.04-0.87 (m, 4H).

Example 73: 1-Cyclopropyl-2-[6-[2-fluoro-3-(trifluoromethyl)phenyl]pyrazolo[4,3-b]pyridin-1-yl]ethanone

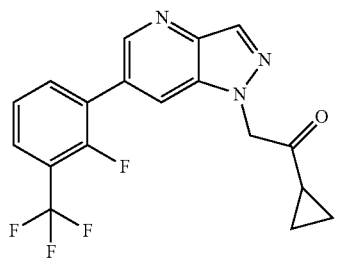 [SMILES: O=C(Cn1ncc2ncc(-c3cccc(C(F)(F)F)c3F)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and (2-fluoro-3-(trifluoromethyl)phenyl)boronic acid instead of 3,5-difluorophenylboronic acid. MS (ESI): mass calcd. for $C_{18}H_{13}F_4N_3O$, 363.1; m/z found, 363.9 [M+H]$^+$. $^1$H NMR (400 MHz, DMSO-d$_6$) δ 8.75-8.71 (m, 1H), 8.43-8.38 (m, 2H), 8.03-7.97 (m, 1H), 7.93-7.86 (m, 1H), 7.63-7.56 (m, 1H), 5.74 (s, 2H), 2.15-2.06 (m, 1H), 1.04-0.89 (m, 4H).

Example 74: 1-Cyclopropyl-2-[6-[4-fluoro-3-(trifluoromethyl)phenyl]pyrazolo[4,3-b]pyridin-1-yl]ethanone

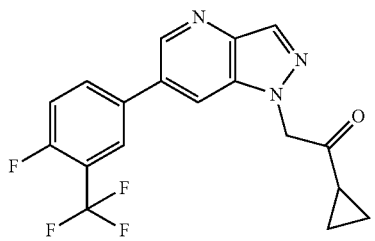 [SMILES: O=C(Cn1ncc2ncc(-c3ccc(F)c(C(F)(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), 4-fluoro-3-(trifluoromethyl)phenylboronic acid instead of 3,5-difluorophenylboronic acid, and RuPhos Pd G3 instead of Pd(dppf)C$_{12}$.DCM. MS (ESI): mass calcd. for $C_{18}H_{13}F_4N_3O$, 363.1; m/z found, 364.0 [M+H]$^+$. $^1$H NMR (500 MHz, CDCl$_3$) δ 8.79 (d, J=1.9 Hz, 1H), 8.35 (d, J=1.0 Hz, 1H), 7.86-7.82 (m, 1H), 7.82-7.77 (m, 1H), 7.70 (dd, J=1.9, 1.0 Hz, 1H), 7.40-7.35 (m, 1H), 5.39 (s, 2H), 1.92 (tt, J=7.7, 4.5 Hz, 1H), 1.19-1.14 (m, 2H), 1.02-0.97 (m, 2H).

Example 75: 2-[6-[4-Chloro-3-(trifluoromethyl)phenyl]pyrazolo[4,3-b]pyridin-1-yl]-1-cyclopropylethanone

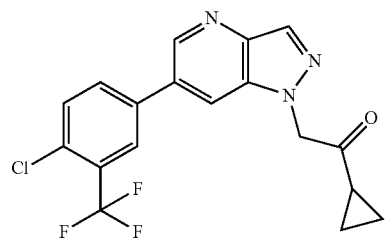 [SMILES: O=C(Cn1ncc2ncc(-c3ccc(Cl)c(C(F)(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), 4-chloro-3-(trifluoromethyl)phenylboronic acid instead of 3,5-difluorophenylboronic acid, and RuPhos Pd G3 instead of Pd(dppf)C$_{12}$.DCM. MS (ESI): mass calcd. for $C_{18}H_{13}ClF_3N_3O$, 379.1; m/z found, 380.0 [M+H]$^+$. $^1$H NMR (500 MHz, CDCl$_3$) δ 8.80 (d, J=1.9 Hz, 1H), 8.36 (d, J=1.0 Hz, 1H), 7.93 (d, J=2.2 Hz, 1H), 7.77-7.72 (m, 2H), 7.66 (d, J=8.4 Hz, 1H), 5.39 (s, 2H), 1.96-1.88 (m, 1H), 1.19-1.14 (m, 2H), 1.03-0.97 (m, 2H).

Example 76: 1-Cyclopropyl-2-[6-[3-(difluoromethyl)-4-fluoro-phenyl]pyrazolo[4,3-b]pyridin-1-yl]ethanone

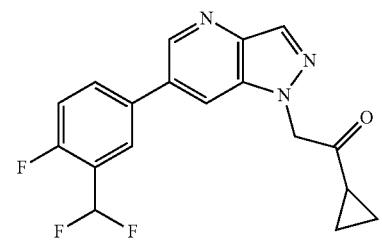 [SMILES: O=C(Cn1ncc2ncc(-c3ccc(F)c(C(F)F)c3)cc21)C1CC1]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 2-bromo-1-cyclopropylethanone instead of (chloromethyl)(ethyl)sulfane. MS (ESI): mass calcd. for $C_{18}H_{14}F_3N_3O$, 345.1; m/z found, 346.0 [M+H]$^+$. $^1$H NMR (500 MHz, CDCl$_3$) δ 8.80 (d, J=1.9 Hz, 1H), 8.35 (d, J=1.0 Hz, 1H), 7.86-7.82 (m, 1H), 7.75-7.70 (m, 2H), 7.31-7.27 (m, 1H), 6.98 (t, J=54.9 Hz, 1H), 5.38 (s, 2H), 1.91 (tt, J=7.8, 4.5 Hz, 1H), 1.19-1.14 (m, 2H), 1.02-0.97 (m, 2H).

Example 77: 1-Cyclopropyl-2-[6-[3-(difluoromethoxy)-4-fluoro-phenyl]pyrazolo[4,3-b]pyridin-1-yl]ethanone

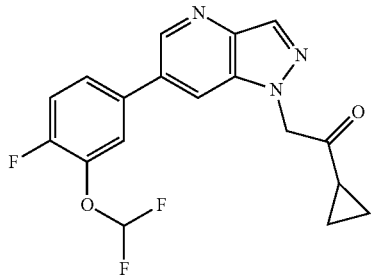 [SMILES: O=C(Cn1ncc2ncc(-c3ccc(F)c(OC(F)F)c3)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), 2-(3-(difluoromethoxy)-4-fluorophenyl)-4,4,5,5-tetramethyl-1,3,2-dioxaborolane instead of 3,5-difluorophenylboronic acid, and RuPhos Pd G3 instead of Pd(dppf)Cl$_2$.DCM. MS (ESI): mass calcd. for $C_{18}H_{14}F_3N_3O_2$, 361.1; m/z found, 362.1 [M+H]$^+$. $^1$H NMR (500 MHz, CDCl$_3$) δ 8.78 (d, J=1.9 Hz, 1H), 8.34 (d, J=1.0 Hz, 1H), 7.68 (dd, J=1.9, 1.0 Hz, 1H), 7.53-7.43 (m, 2H), 7.34-7.30 (m, 1H), 6.64 (t, J=73.2 Hz, 1H), 5.37 (s, 2H), 1.90 (tt, J=7.8, 4.5 Hz, 1H), 1.19-1.12 (m, 2H), 1.03-0.95 (m, 2H).

Example 78: 1-Cyclopropyl-2-[6-(4-fluoro-2,3-dimethyl-phenyl)pyrazolo[4,3-b]pyridin-1-yl]ethanone

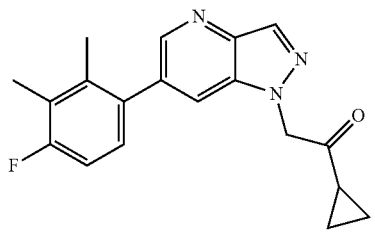 [SMILES: Cc1c(F)ccc(-c2cnc3cnn(CC(=O)C4CC4)c3c2)c1C]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11), and 4-fluoro-2,3-dimethylphenylboronic acid instead of 3,5-difluorophenylboronic acid. MS (ESI): mass calcd. for $C_{19}H_{18}FN_3O$, 323.1; m/z found, 324.0 [M+H]$^+$.

Example 79: 1-Cyclopropyl-2-[6-(2,3,4-trifluorophenyl)pyrazolo[4,3-b]pyridin-1-yl]ethanone

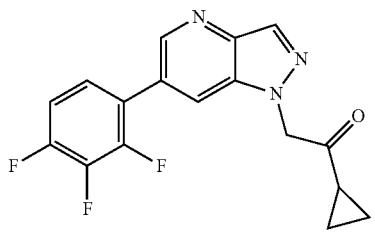 [SMILES: O=C(Cn1ncc2ncc(-c3ccc(F)c(F)c3F)cc21)C1CC1]

The title compound was prepared in a manner analogous to Example 1 using 2-(6-bromo-1H-pyrazolo[4,3-b]pyridin-1-yl)-1-cyclopropylethan-1-one (Intermediate 14) instead of 1-(6-bromo-1H-pyrazolo[4,3-b]pyridin-1-yl)butan-2-one (Intermediate 11) and 2,3,4-trifluorophenylboronic acid instead of 3,5-difluorophenylboronic acid. MS (ESI): mass calcd. for $C_{17}H_{12}F_3N_3O$, 331.1; m/z found, 331.9 [M+H]$^+$. $^1$H NMR (400 MHz, DMSO) δ 8.73-8.69 (m, 1H), 8.42-8.40 (m, 1H), 8.35 (s, 1H), 7.58-7.47 (m, 2H), 5.72 (s, 2H), 2.15-2.06 (m, 1H), 1.05-0.89 (m, 4H).

Example 80: (RS)-1-(Ethylsulfinylmethyl)-6-(3-fluorophenyl)pyrazolo[4,3-b]pyridine

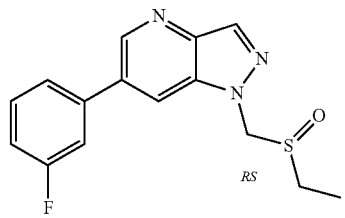 [SMILES: CCS(=O)Cn1ncc2ncc(-c3cccc(F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 3-fluorophenylboronic acid instead of 2-(3-(difluoromethyl)-4-fluorophenyl)-4,4,5,5-tetramethyl-1,3,2-dioxaborolane. MS (ESI): mass calcd. for $C_{15}H_{14}FN_3OS$, 303.1; m/z found, 304.1 [M+H]$^+$. $^1$H NMR (300 MHz, DMSO-d$_6$) δ 8.95 (d, J=1.9 Hz, 1H), 8.68-8.57 (m, 1H), 8.51 (s, 1H), 7.77-7.65 (m, 2H), 7.66-7.54 (m, 1H), 7.38-7.24 (m, 1H), 5.93 (d, J=13.7 Hz, 1H), 5.77 (d, J=13.6 Hz, 1H), 3.07-2.66 (m, 2H), 1.25 (t, J=7.5 Hz, 3H).

Example 81: (RS)-1-(Ethylsulfinylmethyl)-6-[3-(trifluoromethyl)phenyl]pyrazolo[4,3-b]pyridine

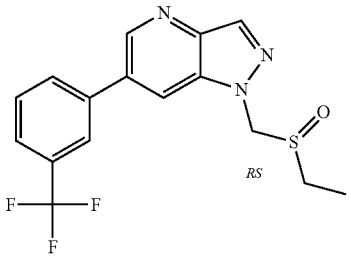 [SMILES: CCS(=O)Cn1ncc2ncc(-c3cccc(C(F)(F)F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 3-trifluoromethylphenylboronic acid instead of 2-(3-(difluoromethyl)-4-fluorophenyl)-4,4,5,5-tetramethyl-1,3,2-dioxaborolane. MS (ESI): mass calcd. for $C_{16}H_{14}F_3N_3S$, 353.1; m/z found, 354.1 [M+H]$^+$. $^1$H NMR (300 MHz, DMSO-d$_6$) δ 8.98 (d, J=1.9 Hz, 1H), 8.72-8.63 (m, 1H), 8.52 (s, 1H), 8.21-8.08 (m, 2H), 7.89-7.76 (m, 2H), 5.95 (d, J=13.7 Hz, 1H), 5.79 (d, J=13.7 Hz, 1H), 3.03-2.70 (m, 2H), 1.25 (t, J=7.5 Hz, 3H).

Example 82: (RS) 6-(3,4-Difluorophenyl)-1-(ethylsulfinylmethyl)pyrazolo[4,3-b]pyridine

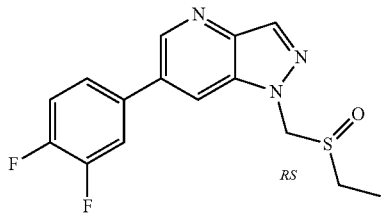 [SMILES: CCS(=O)Cn1ncc2ncc(-c3ccc(F)c(F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 3,4-difluorophenylboronic acid instead of 2-(3-(difluoromethyl)-4-fluorophenyl)-4,4,5,5-tetramethyl-1,3,2-dioxaborolane. MS (ESI): mass calcd. for $C_{15}H_{13}F_2N_3S$, 321.1; m/z found, 322.1 $[M+H]^+$. $^1H$ NMR (500 MHz, DMSO-$d_6$) δ 8.94 (d, J=2.0 Hz, 1H), 8.61 (dd, J=2.0, 1.0 Hz, 1H), 8.50 (d, J=1.0 Hz, 1H), 7.99-7.91 (m, 1H), 7.73-7.61 (m, 2H), 5.91 (d, J=13.7 Hz, 1H), 5.75 (d, J=13.7 Hz, 1H), 2.99-2.89 (m, 1H), 2.85-2.76 (m, 1H), 1.25 (t, J=7.5 Hz, 3H).

Example 83: (RS)-6-(3-(Difluoromethyl)-4-fluorophenyl)-1-((ethylsulfinyl)methyl)-1H-pyrazolo[4,3-b]pyridine

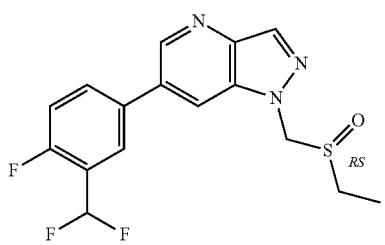 [SMILES: CCS(=O)Cn1ncc2ncc(-c3ccc(F)c(C(F)F)c3)cc21]

The title compound was prepared in a manner analogous to Intermediate 16, Steps A and B, using 6-(3-(difluoromethyl)-4-fluorophenyl)-1H-pyrazolo[4,3-b]pyridine (Intermediate 3) instead of 6-bromo-1H-pyrazolo[4,3-B]pyridine in Step A. MS (ESI): mass calcd. for $C_{16}H_{14}F_3N_3OS$, 353.1; m/z found, 354.1 $[M+H]^+$. $^1H$ NMR (500 MHz, DMSO-$d_6$) δ 8.92 (d, J=2.0 Hz, 1H), 8.61 (dd, J=2.0, 1.0 Hz, 1H), 8.51 (d, J=1.0 Hz, 1H), 8.10-8.01 (m, 2H), 7.64-7.56 (m, 1H), 7.31 (t, J=54.1 Hz, 1H), 5.93 (d, J=13.7 Hz, 1H), 5.77 (d, J=13.7 Hz, 1H), 2.99-2.89 (m, 1H), 2.85-2.76 (m, 1H), 1.25 (t, J=7.5 Hz, 3H).

Example 84: (S*)-6-(3-(Difluoromethyl)-4-fluorophenyl)-1-((ethylsulfinyl)methyl)-1H-pyrazolo[4,3-b]pyridine

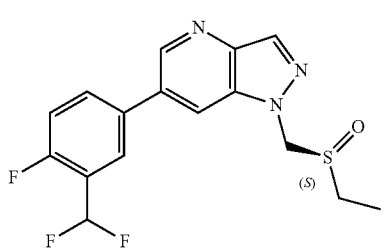

The title compound was prepared by the separation of Example 83 using chiral SFC (Stationary phase: CHIRALPAK IC 5 μm 250*30 mm, Mobile phase: 60% $CO_2$, 40% MeOH). MS (ESI): mass calcd. for $C_{16}H_{14}F_3N_3OS$, 353.1; m/z found, 354.1 $[M+H]^+$.

Example 85: (R*)-6-(3-(Difluoromethyl)-4-fluorophenyl)-1-((ethylsulfinyl)methyl)-1H-pyrazolo[4,3-b]pyridine

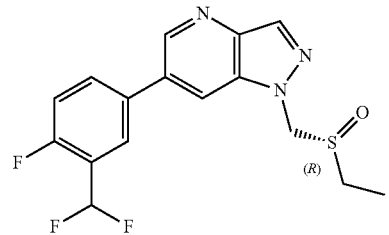

The title compound was prepared by the separation of Example 83 using chiral SFC (Stationary phase: CHIRALPAK IC 5 μm 250*30 mm, Mobile phase: 60% $CO_2$, 40% MeOH). MS (ESI): mass calcd. for $C_{16}H_{14}F_3N_3OS$, 353.1; m/z found, 354.1 $[M+H]^+$.

Example 86: (RS)-1-(Ethylsulfinylmethyl)-6-[2-fluoro-3-(trifluoromethyl)phenyl]pyrazolo[4,3-b]pyridine

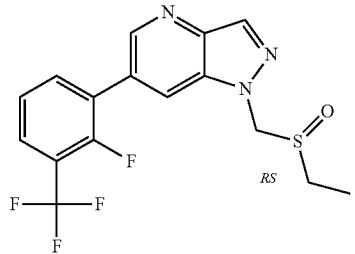 [SMILES: CCS(=O)Cn1ncc2ncc(-c3cccc(C(F)(F)F)c3F)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 2-fluoro-3-trifluoromethylphenylphenylboronic acid instead of 2-(3-(difluoromethyl)-4-fluorophenyl)-4,4,5,5-tetramethyl-1,3,2-dioxaborolane. MS (ESI): mass calcd. for $C_{16}H_{13}F_4N_3OS$, 371.1; m/z found, 372.1 $[M+H]^+$. $^1H$ NMR (300 MHz, DMSO-$d_6$) δ 8.84-8.71 (m, 1H), 8.64-8.46 (m, 2H), 8.06-7.96 (m, 1H), 7.96-7.87 (m, 1H), 7.61 (t, J=7.8 Hz, 1H), 5.95 (d, J=13.7 Hz, 1H), 5.78 (d, J=13.7 Hz, 1H), 3.02-2.86 (m, 1H), 2.87-2.72 (m, 1H), 1.24 (t, J=7.5 Hz, 3H).

Example 87: (RS)-6-[4-Chloro-3-(difluoromethoxy)phenyl]-1-(ethylsulfinylmethyl)pyrazolo[4,3-b]pyridine

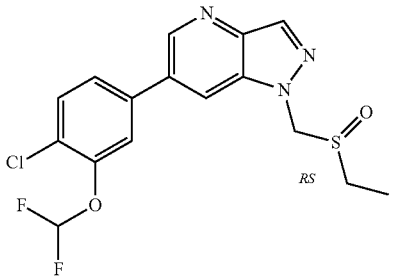 [SMILES: CCS(=O)Cn1ncc2ncc(-c3ccc(Cl)c(OC(F)F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 2-(3-(difluoromethoxy)-4-chlorophenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane. MS (ESI): mass calcd. for $C_{16}H_{14}ClF_2N_3O_2S$, 385.1; m/z found, 386.1 [M+H]$^+$. $^1$H NMR (300 MHz, DMSO-d$_6$) δ 8.95 (d, J=1.9 Hz, 1H), 8.66-8.57 (m, 1H), 8.57-8.48 (m, 1H), 7.86-7.77 (m, 2H), 7.73 (dd, J=8.4, 2.0 Hz, 1H), 7.45 (t, J=73.2 Hz, 1H), 5.94 (d, J=13.7 Hz, 1H), 5.77 (d, J=13.7 Hz, 1H), 3.04-2.72 (m, 2H), 1.25 (t, J=7.5 Hz, 3H).

Example 88: (RS)-1-(Ethylsulfinylmethyl)-6-(3,4,5-trifluorophenyl)pyrazolo[4,3-b]pyridine

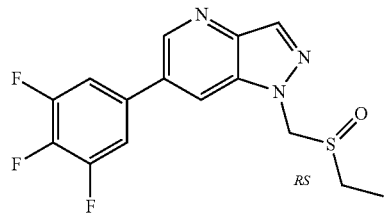 [SMILES: CCS(=O)Cn1ncc2ncc(-c3cc(F)c(F)c(F)c3)cc21]

The title compound was prepared in a manner analogous to Intermediate 3, using 6-bromo-1-((ethylsulfinyl)methyl)-1H-pyrazolo[4,3-b]pyridine (Intermediate 16) instead of 6-bromo-3-methyl-1H-pyrazolo[4,3-b]pyridine, and 3,4,5-trifluorophenylboronic acid instead of 2-(3-(difluoromethyl)-4-fluorophenyl)-4,4,5,5-tetramethyl-1,3,2-dioxaborolane. MS (ESI): mass calcd. for $C_{15}H_{12}F_3N_3S$, 339.1; m/z found, 340.1 [M+H]$^+$. $^1$H NMR (500 MHz, DMSO-d$_6$) δ 8.97 (d, J=2.0 Hz, 1H), 8.67 (dd, J=2.0, 1.0 Hz, 1H), 8.52 (d, J=1.0 Hz, 1H), 7.91-7.83 (m, 2H), 5.89 (d, J=13.6 Hz, 1H), 5.74 (d, J=13.7 Hz, 1H), 2.99-2.89 (m, 1H), 2.86-2.76 (m, 1H), 1.25 (t, J=7.5 Hz, 3H).

Example 89: 6-(4-Fluoro-3-methyl-phenyl)-1-(2-methoxyethyl)pyrazolo[4,3-b]pyridine Trifluoroacetate Salt

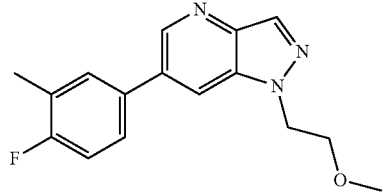 [SMILES: COCCn1ncc2ncc(-c3ccc(F)c(C)c3)cc21]

The title compound was prepared in a manner analogous to Intermediate 16, Step A, using 6-(4-fluoro-3-methylphenyl)-1H-pyrazolo[4,3-b]pyridine (Intermediate 2) instead of 6-bromo-1H-pyrazolo[4,3-B]pyridine, and 2-bromoethyl methyl ether instead of (chloromethyl)(ethyl)sulfane. MS (ESI): mass calcd. for $C_{16}H_{16}FN_3O$, 285.1; m/z found, 286.0 [M+H]$^+$.

Example 90: (RS)-4-Methoxy-1-[6-[3-(trifluoromethyl)phenyl]pyrazolo[4,3-b]pyridin-1-yl]butan-2-ol

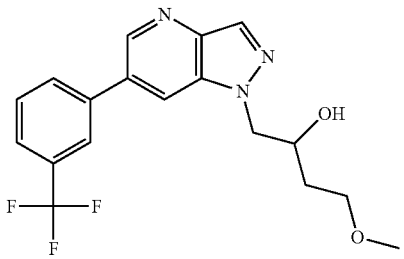 [SMILES: COCCC(O)Cn1ncc2ncc(-c3cccc(C(F)(F)F)c3)cc21]

The title compound was obtained from the treatment of Example 17 ((RS)-1-(oxetan-2-ylmethyl)-6-[3-(trifluoromethyl)phenyl]pyrazolo[4,3-b]pyridine) with Agilent Bond Elut SCX cartridge. MS (ESI): mass calcd. for $C_{18}H_{18}F_3N_3O_2$, 365.1; m/z found, 366.2 [M+H]$^+$. $^1$H NMR (400 MHz, DMSO-d$_6$) δ 8.90 (d, J=2.0 Hz, 1H), 8.54-8.51 (m, 1H), 8.34 (d, J=0.9 Hz, 1H), 8.18-8.13 (m, 2H), 7.85-7.76 (m, 2H), 4.92 (d, J=5.8 Hz, 1H), 4.50-4.46 (m, 2H), 4.08-3.98 (m, 1H), 3.47-3.40 (m, 2H), 3.20 (s, 3H), 1.74-1.64 (m, 1H), 1.62-1.52 (m, 1H).

Example 91: (RS)-1-[6-(3,4-Difluorophenyl)pyrazolo[4,3-b]pyridin-1-yl]butan-2-ol

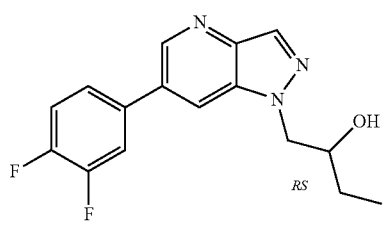 [SMILES: CCC(O)Cn1ncc2ncc(-c3ccc(F)c(F)c3)cc21]

The title compound was prepared in a manner analogous to Example 5 using 1-(6-(3,4-difluorophenyl)-1H-pyrazolo[4,3-b]pyridin-1-yl)butan-2-one (Example 34) instead of 1-[6-[3-(difluoromethyl)-4-fluoro-phenyl]pyrazolo[4,3-b]pyridin-1-yl]butan-2-one. MS (ESI): mass calcd. for $C_{16}H_{15}F_2N_3O$, 303.1; m/z found, 304.0 [M+H]$^+$. $^1$H NMR (500 MHz, CDCl$_3$) δ 8.67 (d, J=1.9 Hz, 1H), 8.17 (d, J=1.0 Hz, 1H), 7.91 (dd, J=1.9, 1.0 Hz, 1H), 7.50-7.42 (m, 1H), 7.41-7.35 (m, 1H), 7.35-7.29 (m, 1H), 4.52-4.45 (m, 1H), 4.34 (dd, J=14.2, 8.1 Hz, 1H), 4.17-4.10 (m, 1H), 3.23 (br s, 1H), 1.70-1.57 (m, 2H), 1.10 (t, J=7.4 Hz, 3H).

Example 92: (RS)-1-[6-[3-(Difluoromethoxy)-4-fluoro-phenyl]pyrazolo[4,3-b]pyridin-1-yl]butan-2-ol

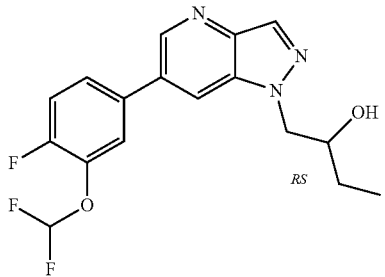 [SMILES: CCC(O)Cn1ncc2ncc(-c3ccc(F)c(OC(F)F)c3)cc21]

The title compound was prepared in a manner analogous to Example 5 using 1-(6-(3-(difluoromethoxy)-4-fluorophenyl)-1H-pyrazolo[4,3-b]pyridin-1-yl)butan-2-one (Example 40) instead of 1-[6-[3-(difluoromethyl)-4-fluoro-phenyl] pyrazolo[4,3-b]pyridin-1-yl]butan-2-one. MS (ESI): mass calcd. for $C_{17}H_{16}F_3N_3O_2$, 351.1; m/z found, 352.2 [M+H]$^+$. $^1$H NMR (500 MHz, CDCl$_3$) 8.75 (d, J=1.9 Hz, 1H), 8.28 (d, J=1.0 Hz, 1H), 7.91 (dd, J=1.9, 1.0 Hz, 1H), 7.54 (dd, J=7.3, 2.2 Hz, 1H), 7.52-7.48 (m, 1H), 7.37-7.31 (dd, J=9.9, 8.5 Hz, 1H), 6.82-6.51 (t, J=73.2 Hz, 1H), 4.53-4.48 (m, 1H), 4.40-4.33 (dd, J=14.1, 7.9 Hz, 1H), 4.17-4.10 (m, 1H), 2.89-2.78 (br s, 1H), 1.70-1.60 (m, 2H), 1.12-1.06 (t, J=7.5 Hz, 3H).

Example 93: (RS)-1-[6-[4-Chloro-3-(difluoromethoxy)phenyl]pyrazolo[4,3-b]pyridin-1-yl]butan-2-ol

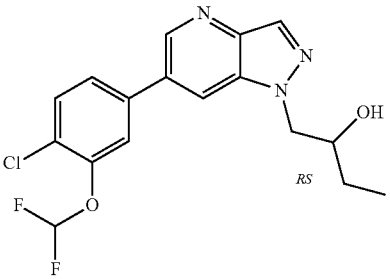 [SMILES: CCC(O)Cn1ncc2ncc(-c3ccc(Cl)c(OC(F)F)c3)cc21]

The title compound was prepared in a manner analogous to Example 5 using 1-[6-[4-chloro-3-(difluoromethoxy)phenyl]pyrazolo[4,3-b]pyridin-1-yl]butan-2-one (Example 41) instead of 1-[6-[3-(difluoromethyl)-4-fluoro-phenyl]pyrazolo[4,3-b]pyridin-1-yl]butan-2-one. MS (ESI): mass calcd. for $C_{17}H_{16}ClF_2N_3O_2$, 367.8; m/z found, 368.1 [M+H]$^+$. 1H NMR (500 MHz, CDCl$_3$) δ 8.72 (d, J=1.9 Hz, 1H), 8.24 (d, J=1.0 Hz, 1H), 7.93 (dd, J=1.9, 1.0 Hz, 1H), 7.62-7.58 (m, 1H), 7.54-7.52 (m, 1H), 7.50-7.46 (m, 1H), 6.65 (t, J=73.2 Hz, 1H), 4.53-4.48 (m, 1H), 4.36 (dd, J=14.2, 7.9 Hz, 1H), 4.17-4.10 (m, 1H), 3.01 (s, 1H), 1.71-1.57 (m, 2H), 1.10 (t, J=7.5 Hz, 3H).

Example 94: (RS)-1-[6-(3,4-Difluorophenyl)-3-fluoro-pyrazolo[4,3-b]pyridin-1-yl]butan-2-ol

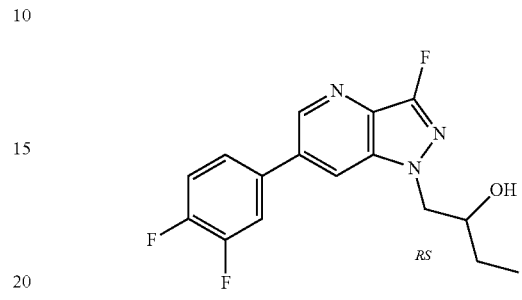

The title compound was prepared in a manner analogous to Example 5 using 1-[6-(3,4-difluorophenyl)-3-fluoro-pyrazolo[4,3-b]pyridin-1-yl]butan-2-one (Example 35) instead of 1-[6-[3-(difluoromethyl)-4-fluoro-phenyl]pyrazolo[4,3-b]pyridin-1-yl]butan-2-one. MS (ESI): mass calcd. for $C_{16}H_{14}F_3N_3O$, 321.1; m/z found, 322.0 [M+H]$^+$. 1H NMR (500 MHz, CDCl$_3$) δ 8.64 (d, J=1.8 Hz, 1H), 7.87-7.85 (m, 1H), 7.48-7.42 (m, 1H), 7.39-7.30 (m, 2H), 4.34-4.28 (m, 1H), 4.25-4.18 (m, 1H), 4.14-4.07 (m, 1H), 2.94 (d, J=4.2 Hz, 1H), 1.71-1.56 (m, 2H), 1.10 (t, J=7.5 Hz, 3H).

Example 95: (RS)-1-[6-[3-(1,1-Difluoroethyl)phenyl]pyrazolo[4,3-b]pyridin-1-yl]butan-2-ol

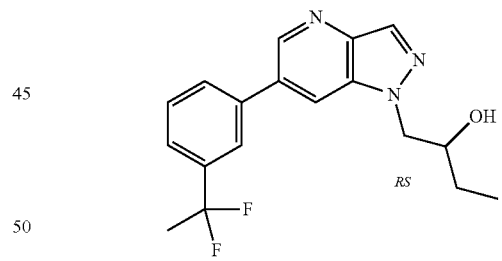

The title compound was prepared in a manner analogous to Example 5 using 1-[6-[3-(1,1-difluoroethyl)phenyl]pyrazolo[4,3-b]pyridin-1-yl]butan-2-one (Example 31) instead of 1-[6-[3-(difluoromethyl)-4-fluoro-phenyl]pyrazolo[4,3-b]pyridin-1-yl]butan-2-one. MS (ESI): mass calcd. for $C_{18}H_{19}F_2N_3O$, 331.1; m/z found, 332.1 [M+H]$^+$. 1H NMR (500 MHz, CDCl$_3$) δ 8.76 (d, J=1.9 Hz, 1H), 8.21 (d, J=1.0 Hz, 1H), 7.97-7.95 (m, 1H), 7.80-7.77 (m, 1H), 7.73-7.69 (m, 1H), 7.61-7.56 (m, 2H), 4.53-4.47 (m, 1H), 4.36 (dd, J=14.1, 8.0 Hz, 1H), 4.18-4.11 (m, 1H), 3.25-3.20 (m, 1H), 2.01 (t, J=18.2 Hz, 3H), 1.69-1.59 (m, 2H), 1.10 (t, J=7.5 Hz, 3H).

Example 96: (RS)-3-Methyl-1-(6-phenylpyrazolo[4,3-b]pyridin-1-yl)butan-2-ol

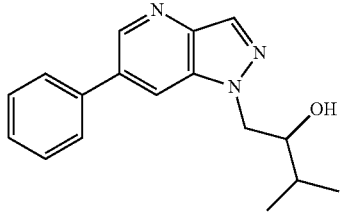 [SMILES: CC(C)C(O)Cn1ncc2ncc(-c3ccccc3)cc21]

The title compound was prepared in a manner analogous to Example 3 using 3-methyl-1-(6-phenylpyrazolo[4,3-b]pyridin-1-yl)butan-2-one (Example 44) instead of 3-methyl-1-[6-[3-(trifluoromethyl)phenyl]pyrazolo[4,3-b]pyridin-1-yl]butan-2-one. MS (ESI): mass calcd. for $C_{17}H_{19}N_3O$, 281.2; m/z found, 282.1 [M+H]$^+$. $^1$H NMR (400 MHz, DMSO) δ 8.83 (d, J=1.9 Hz, 1H), 8.39-8.36 (m, 1H), 8.30-8.29 (m, 1H), 7.85-7.79 (m, 2H), 7.58-7.52 (m, 2H), 7.49-7.43 (m, 1H), 4.79 (d, J=5.9 Hz, 1H), 4.49-4.40 (m, 2H), 3.73-3.63 (m, 1H), 1.70-1.57 (m, 1H), 0.97 (d, J=6.8 Hz, 3H), 0.94 (d, J=6.8 Hz, 3H).

Example 97: (RS)-3-Methyl-1-[6-(3,4,5-trifluorophenyl)pyrazolo[4,3-b]pyridin-1-yl]butan-2-ol

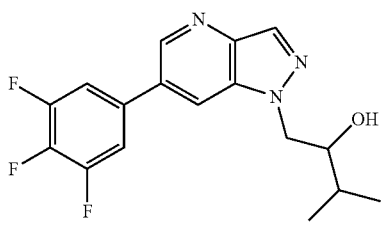 [SMILES: CC(C)C(O)Cn1ncc2ncc(-c3cc(F)c(F)c(F)c3)cc21]

The title compound was prepared in a manner analogous to Example 3 using 3-methyl-1-[6-(3,4,5-trifluorophenyl)pyrazolo[4,3-b]pyridin-1-yl]butan-2-one (Example 53) instead of 3-methyl-1-[6-[3-(trifluoromethyl)phenyl]pyrazolo[4,3-b]pyridin-1-yl]butan-2-one. MS (ESI): mass calcd. for $C_{17}H_{16}F_3N_3O$, 335.1; m/z found, 336.0 [M+H]$^+$. $^1$H NMR (400 MHz, DMSO) δ 8.88 (d, J=2.0 Hz, 1H), 8.51-8.48 (m, 1H), 8.34-8.30 (m, 1H), 7.95-7.86 (m, 2H), 4.75 (d, J=6.0 Hz, 1H), 4.49-4.42 (m, 2H), 3.74-3.65 (m, 1H), 1.70-1.57 (m, 1H), 0.97 (d, J=6.8 Hz, 3H), 0.95 (d, J=6.8 Hz, 3H).

Example 98: 1-(2,2-Difluorobutyl)-6-[3-(difluoromethyl)-4-fluoro-phenyl]pyrazolo[4,3-b]pyridine

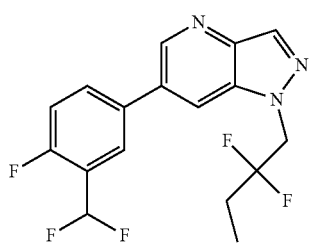 [SMILES: CCC(F)(F)Cn1ncc2ncc(-c3ccc(F)c(C(F)F)c3)cc21]

To 1-[6-[3-(difluoromethyl)-4-fluoro-phenyl]pyrazolo[4,3-b]pyridin-1-yl]butan-2-one (Example 4) (64.0 mg, 0.19 mmol) stirring in DCM (2 mL) at 0° C. was added DAST (0.101 mL, 0.76 mmol). The reaction was slowly warmed to rt. After 23 h, the reaction was washed with a saturated solution of NaHCO$_3$, then the organic layer was dried, filtered, and concentrated under reduced pressure. The residue was purified by silica gel chromatography (hexanes\EtOAc 25 to 50%) afford the title compound as a yellow oil. MS (ESI): mass calcd. for $C_{17}H_{14}F_5N_3$, 355.1; m/z found, 356.1 [M+H]$^+$. $^1$H NMR (300 MHz, DMSO-d$_6$) δ 8.91 (d, J=1.9 Hz, 1H), 8.59-8.49 (m, 1H), 8.44 (s, 1H), 8.13-8.00 (m, 2H), 7.64-7.53 (m, 1H), 7.31 (t, J=54.1 Hz, 1H), 5.08 (t, J=13.9 Hz, 2H), 2.06-1.82 (m, 2H), 1.01 (t, J=7.5 Hz, 3H).

Example 99: 1-(2,2-Difluorobutyl)-6-[3-(difluoromethoxy)-4-fluoro-phenyl]pyrazolo[4,3-b]pyridine

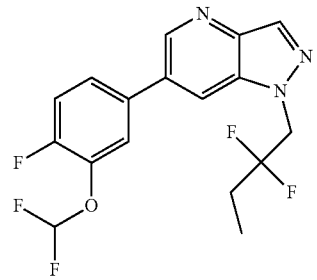 [SMILES: CCC(F)(F)Cn1ncc2ncc(-c3ccc(F)c(OC(F)F)c3)cc21]

The title compound was prepared in a manner analogous to Example 98 using 1-[6-[3-(difluoromethoxy)-4-fluorophenyl]pyrazolo[4,3-b]pyridin-1-yl]butan-2-one (Example 40) instead of 1-[6-[3-(difluoromethyl)-4-fluoro-phenyl]pyrazolo[4,3-b]pyridin-1-yl]butan-2-one. MS (ESI): mass calcd. for $C_{17}H_{14}F_5N_3O$, 371.1; m/z found, 372.1 [M+H]$^+$. $^1$H NMR (500 MHz, DMSO-d$_6$) δ 8.92-8.89 (m, 1H), 8.53-8.48 (m, 1H), 8.43 (s, 1H), 7.87-7.81 (m, 1H), 7.80-7.73 (m, 1H), 7.64-7.57 (m, 1H), 7.38 (t, J=73.2 Hz, 1H), 5.07 (t, J=13.8 Hz, 2H), 2.01-1.86 (m, 2H), 1.01 (t, J=7.5 Hz, 3H).

Example 100: (RS)-1-Cyclopropyl-2-[6-[3-(trifluoromethyl)phenyl]pyrazolo[4,3-b]pyridin-1-yl]ethanol

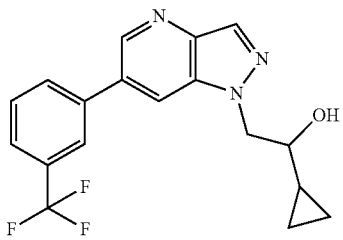 [SMILES: OC(Cn1ncc2ncc(-c3cccc(C(F)(F)F)c3)cc21)C1CC1]

The title compound was prepared in a manner analogous to Example 3 using 1-cyclopropyl-2-[6-[3-(trifluoromethyl)phenyl]pyrazolo[4,3-b]pyridin-1-yl]ethanone (Example 62) instead of 3-methyl-1-[6-[3-(trifluoromethyl)phenyl]pyrazolo[4,3-b]pyridin-1-yl]butan-2-one. MS (ESI): mass calcd. for $C_{18}H_{16}F_3N_3O$, 347.1; m/z found, 348.0 [M+H]$^+$. $^1$H NMR (500 MHz, DMSO-$d_6$) δ 8.90 (d, J=1.9 Hz, 1H), 8.58-8.55 (m, 1H), 8.32 (d, J=0.9 Hz, 1H), 8.19-8.14 (m, 2H), 7.85-7.75 (m, 2H), 4.94 (d, J=5.2 Hz, 1H), 4.58-4.54 (m, 2H), 3.41-3.32 (m, 1H), 0.92-0.81 (m, 1H), 0.39-0.31 (m, 1H), 0.31-0.21 (m, 2H), 0.06-0.03 (m, 1H).

Example 101: (RS)-1-Cyclopropyl-2-[6-(4-fluoro-3-methyl-phenyl)pyrazolo[4,3-b]pyridin-1-yl]ethanol

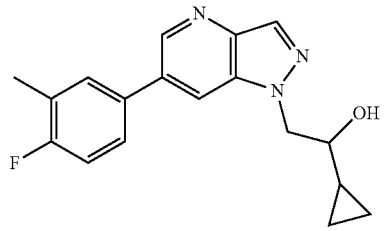 [SMILES: Cc1cc(-c2cnc3cnn(CC(O)C4CC4)c3c2)ccc1F]

The title compound was prepared in a manner analogous to Example 3 using 1-cyclopropyl-2-[6-(4-fluoro-3-methyl-phenyl)pyrazolo[4,3-b]pyridin-1-yl]ethanone (Example 69) instead of 3-methyl-1-[6-[3-(trifluoromethyl)phenyl]pyrazolo[4,3-b]pyridin-1-yl]butan-2-one. MS (ESI): mass calcd. for $C_{18}H_{18}FN_3O$, 311.1; m/z found, 312.1 [M+H]$^+$. $^1$H NMR (500 MHz, DMSO-$d_6$) δ 8.81 (d, J=1.9 Hz, 1H), 8.40-8.38 (m, 1H), 8.28 (d, J=0.9 Hz, 1H), 7.79-7.76 (m, 1H), 7.70-7.65 (m, 1H), 7.33-7.28 (m, 1H), 4.92 (d, J=5.2 Hz, 1H), 4.54-4.50 (m, 2H), 3.41-3.32 (m, 1H), 2.36-2.33 (m, 3H), 0.91-0.81 (m, 1H), 0.39-0.19 (m, 3H), 0.05-0.02 (m, 1H).

Example 102: (R)-1-Cyclopropyl-2-[6-(4-fluoro-3-methyl-phenyl)pyrazolo[4,3-b]pyridin-1-yl]ethanol

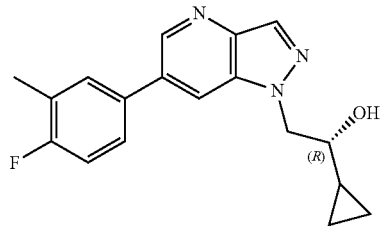

The title compound was prepared by the separation of Example 101 using chiral SFC (Stationary phase: CHIRALPAK IC 5 μm 250×20 mm, Mobile phase: 70% $CO_2$, 30% iPrOH). MS (ESI): mass calcd. for $C_{18}H_{18}FN_3O$, 311.1; m/z found, 312.1 [M+H]$^+$.

Example 103: (S)-1-Cyclopropyl-2-[6-(4-fluoro-3-methyl-phenyl)pyrazolo[4,3-b]pyridin-1-yl]ethanol

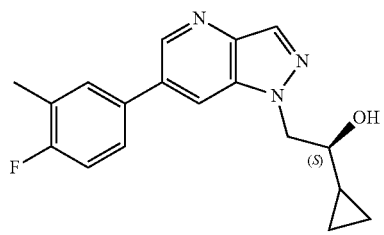

The title compound was prepared by the separation of Example 101 using chiral SFC (Stationary phase: CHIRALPAK IC 5 μm 250×20 mm, Mobile phase: 70% $CO_2$, 30% iPrOH). MS (ESI): mass calcd. for $C_{18}H_{18}FN_3O$, 311.1; m/z found, 312.1 [M+H]$^+$.

Example 104: (RS)-1-Cyclopropyl-2-(6-(3-(difluoromethyl)-4-fluorophenyl)-1H-pyrazolo[4,3-b]pyridin-1-yl)ethan-1-ol

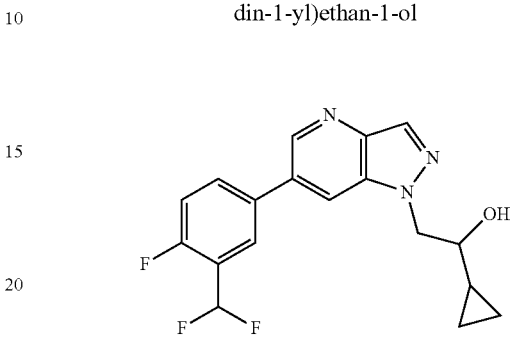

The title compound was prepared in a manner analogous to Example 5 using 1-cyclopropyl-2-[6-[3-(difluoromethyl)-4-fluoro-phenyl]pyrazolo[4,3-b]pyridin-1-yl]ethanone (Example 76) instead of 1-[6-[3-(difluoromethyl)-4-fluoro-phenyl]pyrazolo[4,3-b]pyridin-1-yl]butan-2-one. MS (ESI): mass calcd. for $C_{18}H_{16}F_3N_3O$, 347.1; m/z found, 348.1 [M+H]$^+$. $^1$H NMR (500 MHz, DMSO-$d_6$) δ 8.84 (d, J=2.0 Hz, 1H), 8.51-8.44 (m, 1H), 8.31 (d, J=1.0 Hz, 1H), 8.11-8.04 (m, 2H), 7.60-7.53 (m, 1H), 7.29 (t, J=54.1 Hz, 1H), 4.92 (d, J=5.1 Hz, 1H), 4.58-4.50 (m, 2H), 3.40-3.33 (m, 1H), 0.91-0.83 (m, 1H), 0.40-0.31 (m, 1H), 0.30-0.21 (m, 2H), 0.05-0.03 (m, 1H).

Example 105: (E/Z)-N-Methoxy-3-methyl-1-[6-[3-(trifluoromethyl)phenyl]pyrazolo[4,3-b]pyridin-1-yl]butan-2-imine

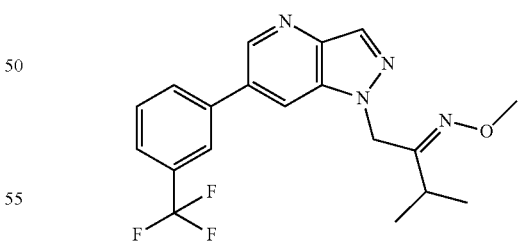

The title compound was prepared in a manner analogous to Example 6 using o-methylhydroxylamine hydrochloride instead of hydroxylamine hydrochloride, and EtOH as a solvent. (ESI): mass calcd. for $C_{19}H_{19}F_3N_4O$, 376.2; m/z found, 377.1 [M+H]$^+$.

Example 106: (E/Z)-1-Cyclopropyl-2-[6-[3-(trifluoromethyl)phenyl]pyrazolo[4,3-b]pyridin-1-yl]ethanone oxime

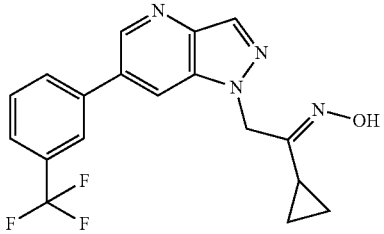 [SMILES: O/N=C(/Cn1ncc2ncc(-c3cccc(C(F)(F)F)c3)cc21)C1CC1]

The title compound was prepared in a manner analogous to Example 6 using 1-cyclopropyl-2-[6-[3-(trifluoromethyl)phenyl]pyrazolo[4,3-b]pyridin-1-yl]ethanone (Example 62) instead of 3-methyl-1-[6-[3-(trifluoromethyl)phenyl]pyrazolo[4,3-b]pyridin-1-yl]butan-2-one. MS (ESI): mass calcd. for $C_{18}H_{15}F_3N_4O$, 360.1; m/z found, 361.0 [M+H]$^+$.

Example 107: (E/Z)-1-Cyclopropyl-2-[6-[3-(difluoromethyl)-4-fluoro-phenyl]pyrazolo[4,3-b]pyridin-1-yl]ethanone Oxime

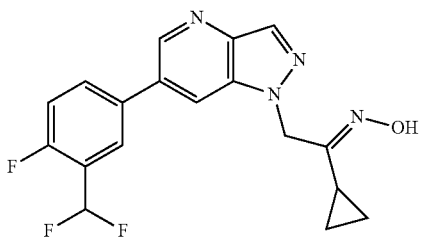 [SMILES: O/N=C(/Cn1ncc2ncc(-c3ccc(F)c(C(F)F)c3)cc21)C1CC1]

The title compound was prepared in a manner analogous to Example 6 using 1-cyclopropyl-2-[6-[3-(difluoromethyl)-4-fluoro-phenyl]pyrazolo[4,3-b]pyridin-1-yl]ethanone (Example 76) instead of 3-methyl-1-[6-[3-(trifluoromethyl)phenyl]pyrazolo[4,3-b]pyridin-1-yl]butan-2-one, and triethylamine instead of $Cs_2CO_3$. MS (ESI): mass calcd. for $C_{18}H_{15}F_3N_4O$, 360.1; m/z found, 361.0 [M+H]$^+$.

Example 108: 1-(2-Cyclopropyl-2,2-difluoro-ethyl)-6-[3-(difluoromethyl)-4-fluoro-phenyl]pyrazolo[4,3-b]pyridine

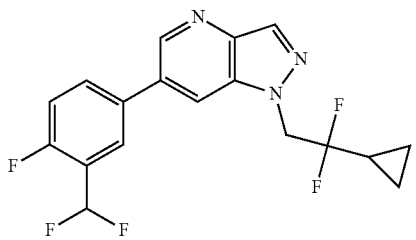 [SMILES: Fc1ccc(-c2cnc3cnn(CC(F)(F)C4CC4)c3c2)cc1C(F)F]

The title compound was prepared in a manner analogous to Example 98 using 1-cyclopropyl-2-[6-[3-(difluoromethyl)-4-fluoro-phenyl]pyrazolo[4,3-b]pyridin-1-yl]ethanone (Example 76) instead of 1-[6-[3-(difluoromethyl)-4-fluoro-phenyl]pyrazolo[4,3-b]pyridin-1-yl]butan-2-one. MS (ESI): mass calcd. for $C_{18}H_{14}F_5N_3$, 367.1; m/z found, 368.2 [M+H]$^+$. $^1$H NMR (500 MHz, DMSO-d$_6$) δ 8.91 (d, J=1.9 Hz, 1H), 8.59-8.55 (m, 1H), 8.42 (d, J=0.9 Hz, 1H), 8.10-8.03 (m, 2H), 7.62-7.53 (m, 1H), 7.30 (t, J=54.1 Hz, 1H), 5.14 (t, J=13.3 Hz, 2H), 1.52-1.39 (m, 1H), 0.54-0.47 (m, 2H), 0.47-0.41 (m, 2H).

Example 109: 1-(2-Cyclopropyl-2,2-difluoro-ethyl)-6-[3-(difluoromethoxy)-4-fluoro-phenyl]pyrazolo[4,3-b]pyridine

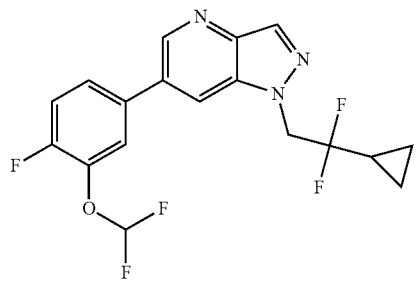 [SMILES: Fc1ccc(-c2cnc3cnn(CC(F)(F)C4CC4)c3c2)cc1OC(F)F]

A mixture of 1-cyclopropyl-2-[6-[3-(difluoromethoxy)-4-fluoro-phenyl]pyrazolo[4,3-b]pyridin-1-yl]ethenone (Example 77, 150 mg, 0.415 mmol) and Deoxo-Fluor® (50% in THF, 1.8 mL, 4.07 mmol, 2.26 M) was stirred at room temperature for 24 h, then at 80° C. for 2 h. The reaction was quenched with saturated sodium bicarbonate (11 mL) at 0° C. The layers were separated and the aqueous layer was extracted with EtOAc (3×5 mL). The combined organics were dried over MgSO$_4$, filtered and evaporated. The residue was purified by preparative HPLC (METHOD G) to afford the title compound (38 mg, 0.099 mmol, 24%) as a brown oil. MS (ESI): mass calcd. for $C_{18}H_{14}F_5N_3O$, 383.1; m/z found, 384.2 [M+H]$^+$. $^1$H NMR (500 MHz, DMSO-d$_6$) δ 8.91 (d, J=2.0 Hz, 1H), 8.56-8.52 (m, 1H), 8.42 (d, J=1.0 Hz, 1H), 7.84 (dd, J=7.6, 2.3 Hz, 1H), 7.80-7.73 (m, 1H), 7.61 (dd, J=10.5, 8.6 Hz, 1H), 7.38 (t, J=73.2 Hz, 1H), 5.13 (t, J=13.3 Hz, 2H), 1.52-1.38 (m, 1H), 0.54-0.46 (m, 2H), 0.47-0.40 (m, 2H).

Example 110: 6-[3-(Difluoromethyl)-4-fluoro-phenyl]-1-[(3-methyloxetan-3-yl)methyl]pyrazolo[4,3-b]pyridine

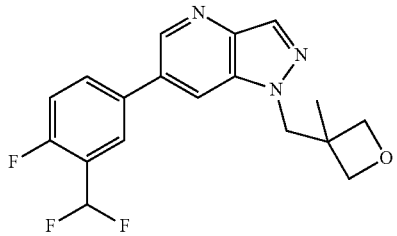 [SMILES: CC1(Cn2ncc3ncc(-c4ccc(F)c(C(F)F)c4)cc32)COC1]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-B]pyridine, and 3-(bromomethyl)-3-methyloxetane instead of (chloromethy- 1)(ethyl)sulfane, and THF instead of DMF. MS (ESI): mass calcd. for $C_{18}H_{16}F_3N_3O$, 347.1; m/z found, 348.0 [M+H]$^+$. $^1$H NMR (400 MHz, CDCl$_3$) δ 8.80 (d, J=2.0 Hz, 1H), 8.21 (d, J=0.9 Hz, 1H), 8.14 (dd, J=2.1, 0.9 Hz, 1H), 7.89-7.85 (m, 1H), 7.77-7.72 (m, 1H), 7.32-7.25 (m, 1H), 6.97 (t, J=54.9 Hz, 1H), 4.83 (d, J=6.2 Hz, 2H), 4.70 (s, 2H), 4.47 (d, J=6.2 Hz, 2H), 1.29 (s, 3H).

Example 111: (RS)-1-(Tetrahydrofuran-2-ylmethyl)-6-[3-(trifluoromethyl)phenyl]pyrazolo[4,3-b]pyridine hydrochloride Salt

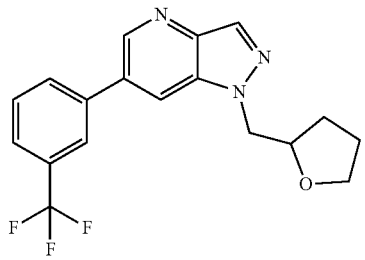 [SMILES: FC(F)(F)c1cccc(-c2cnc3cnn(CC4CCCO4)c3c2)c1]

The title compound was prepared in a manner analogous to Intermediate 16, Step A, using 6-(3-(trifluoromethyl)phenyl)-1H-pyrazolo[4,3-b]pyridine (Intermediate 8) instead of 6-bromo-1H-pyrazolo[4,3-b]pyridine, and 2-(chloromethyl)tetrahydrofuran instead of chloromethyl)(ethyl)sulfane. Heating was not required, and the hydrochloride salt was obtained upon treatment from 3N HCl in MeOH after purification by reversed phase HPLC (METHOD H). MS (ESI): mass calcd. for $C_{18}H_{16}F_3N_3O$, 347.1; m/z found, 348.3 [M+H]$^+$. $^1$H NMR (400 MHz, DMSO-d$_6$) δ 8.95 (d, J=1.85 Hz, 1H), 8.63 (dd, J=1.85, 0.92 Hz, 1H), 8.37 (d, J=0.92 Hz, 1H), 8.23-8.04 (m, 2H), 7.93-7.70 (m, 2H), 4.73-4.51 (m, 2H), 4.41-4.16 (m, 1H), 3.70-3.64 (m, 1H), 3.61-3.51 (m, 1H), 2.07-1.90 (m, 1H), 1.86-1.53 (m, 3H).

Example 112: (RS)-6-[3-(Difluoromethoxy)-4-fluoro-phenyl]-1-(tetrahydrofuran-2-ylmethyl)pyrazolo[4,3-b]pyridine

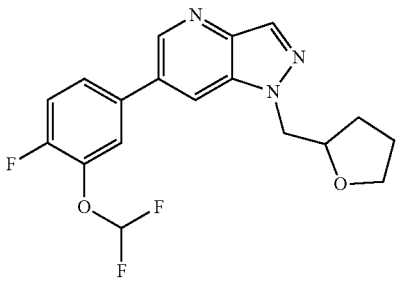 [SMILES: Fc1ccc(-c2cnc3cnn(CC4CCCO4)c3c2)cc1OC(F)F]

The title compound was prepared in a manner analogous to Example 18 using 6-(3-(difluoromethoxy)-4-fluorophenyl)-1H-pyrazolo[4,3-b]pyridine (Intermediate 4) instead of 6-[3-(difluoromethyl)-4-fluoro-phenyl]-1H-pyrazolo[4,3-b]pyridine. MS (ESI): mass calcd. for $C_{18}H_{16}F_3N_3O_2$, 363.1; m/z found, 364.1 [M+H]$^+$. $^1$H NMR (500 MHz, DMSO-d$_6$) δ 8.86 (d, J=2.0 Hz, 1H), 8.46 (dd, J=2.0, 1.0 Hz, 1H), 8.33 (d, J=0.9 Hz, 1H), 7.84 (dd, J=7.6, 2.3 Hz, 1H), 7.80-7.75 (m, 1H), 7.59 (dd, J=10.5, 8.6 Hz, 1H), 7.39 (t, J=73.2 Hz, 1H), 4.57 (d, J=5.6 Hz, 2H), 4.32-4.26 (m, 1H), 3.71-3.64 (m, 1H), 3.62-3.55 (m, 1H), 2.00-1.91 (m, 1H), 1.83-1.62 (m, 3H).

Example 113: (RS)-6-[3-(Difluoromethyl)-4-fluoro-phenyl]-1-(tetrahydrofuran-3-ylmethyl)pyrazolo[4,3-b]pyridine

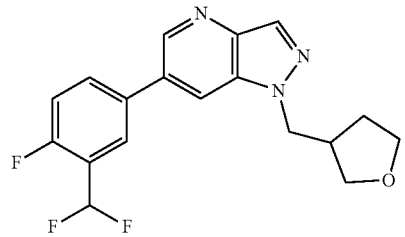 [SMILES: Fc1ccc(-c2cnc3cnn(CC4CCOC4)c3c2)cc1C(F)F]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 3-(bromomethyl)tetrahydrofuran instead of (chloromethyl)(ethyl)sulfane. Purified by prep HPLC (METHOD D). MS (ESI): mass calcd. for $C_{18}H_{16}F_3N_3O$, 347.1; m/z found, 348.1 [M+H]$^+$. $^1$H NMR (500 MHz, CDCl$_3$) δ 8.78 (d, J=1.9 Hz, 1H), 8.29 (d, J=1.0 Hz, 1H), 7.93-7.81 (m, 2H), 7.81-7.70 (m, 1H), 7.30 (ddt, J=9.7, 8.5, 1.1 Hz, 1H), 6.99 (t, J=54.8 Hz, 1H), 4.41 (d, J=7.7 Hz, 2H), 3.99 (td, J=8.3, 5.4 Hz, 1H), 3.84-3.73 (m, 2H), 3.65 (dd, J=9.0, 4.7 Hz, 1H), 3.01 (ddt, J=11.6, 7.9, 3.9 Hz, 1H), 2.07 (dtd, J=13.3, 8.1, 5.4 Hz, 1H), 1.82-1.68 (m, 1H).

Example 114: (RS)-5-((6-(3-(Difluoromethoxy)-4-fluorophenyl)-1H-pyrazolo[4,3-b]pyridin-1-yl)methyl)-1-methylpyrrolidin-2-one

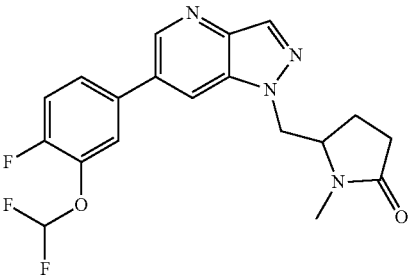 [SMILES: CN1C(=O)CCC1Cn1ncc2ncc(-c3ccc(F)c(OC(F)F)c3)cc21]

The title compound was prepared in a manner analogous to Intermediate 16, Step A, using 6-(3-(difluoromethoxy)-4-fluorophenyl)-1H-pyrazolo[4,3-b]pyridine (Intermediate 4) instead of 6-bromo-1H-pyrazolo[4,3-b]pyridine, and 5-(bromomethyl)-1-methylpyrrolidin-2-one instead of (chloromethyl)(ethyl)sulfane. MS (ESI): mass calcd. for $C_{19}H_{17}F_3N_4O_2$, 390.1; m/z found, 391.1 [M+H]$^+$. $^1$H NMR (500 MHz, DMSO-d$_6$) δ 8.89 (d, J=1.9 Hz, 1H), 8.60-8.50 (m, 1H), 8.44-8.33 (m, 1H), 7.91-7.83 (m, 1H), 7.82-7.75 (m, 1H), 7.65-7.57 (m, 1H), 7.38 (t, J=73.2 Hz, 1H), 4.75 (dd, J=14.6, 4.6 Hz, 1H), 4.68 (dd, J=14.6, 5.2 Hz, 1H), 4.14-4.02 (m, 1H), 2.71 (s, 3H), 2.08-1.92 (m, 2H), 1.83-1.67 (m, 2H).

Example 115: (RS)-5-[[6-[3-(Difluoromethyl)-4-fluoro-phenyl]pyrazolo[4,3-b]pyridin-1-yl]methyl]-1-methyl-pyrrolidin-2-one

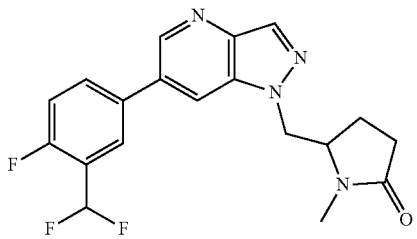 [SMILES: CN1C(=O)CCC1Cn1ncc2ncc(-c3ccc(F)c(C(F)F)c3)cc21]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 5-(bromomethyl)-1-methylpyrrolidin-2-one instead of (chloromethyl)(ethyl)sulfane. MS (ESI): mass calcd. for $C_{19}H_{17}F_3N_4O$, 374.1; m/z found, 375.1 $[M+H]^+$. $^1H$ NMR (500 MHz, MeOD) δ 8.80 (d, J=1.8 Hz, 1H), 8.39 (dd, J=1.9, 1.0 Hz, 1H), 8.27 (d, J=1.0 Hz, 1H), 8.00 (ddd, J=7.5, 2.2, 1.1 Hz, 1H), 7.95 (dddd, J=8.3, 3.4, 2.2, 0.9 Hz, 1H), 7.41 (dd, J=9.9, 8.7 Hz, 1H), 7.08 (t, J=54.6 Hz, 1H), 4.83-4.66 (m, 2H), 4.35-4.07 (m, 1H), 2.85 (s, 3H), 2.34-2.05 (m, 2H), 1.95 (ddt, J=12.1, 8.9, 2.9 Hz, 1H), 1.86-1.68 (m, 1H).

Example 116: (RS)-3-[[6-[3-(Difluoromethyl)-4-fluoro-phenyl]pyrazolo[4,3-b]pyridin-1-yl]methyl]-1-methyl-pyrrolidin-2-one

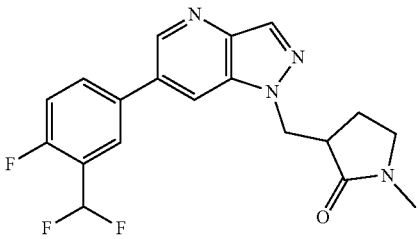 [SMILES: CN1CCC(Cn2ncc3ncc(-c4ccc(F)c(C(F)F)c4)cc32)C1=O]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 3-(bromomethyl)-1-methylpyrrolidin-2-one instead of (chloromethyl)(ethyl)sulfane. MS (ESI): mass calcd. for $C_{19}H_{17}F_3N_4O$, 374.1; m/z found, 375.1 $[M+H]^+$. $^1H$ NMR (500 MHz, MeOD) δ 8.81 (d, J=1.9 Hz, 1H), 8.44 (dd, J=1.9, 1.0 Hz, 1H), 8.26 (d, J=1.0 Hz, 1H), 8.07-7.94 (m, 2H), 7.50-7.40 (m, 1H), 7.11 (t, J=54.6 Hz, 1H), 4.82-4.76 (m, 2H), 3.39-3.28 (m, 1H), 3.20-3.04 (m, 1H), 2.75 (d, J=0.8 Hz, 3H), 2.20 (dddd, J=13.2, 9.3, 8.2, 4.0 Hz, 1H), 2.02 (dddd, J=13.1, 8.9, 7.9, 7.0 Hz, 1H).

Example 117: (S)-3-[[6-[3-(Difluoromethyl)-4-fluoro-phenyl]pyrazolo[4,3-b]pyridin-1-yl]methyl]-1-methyl-pyrrolidin-2-one

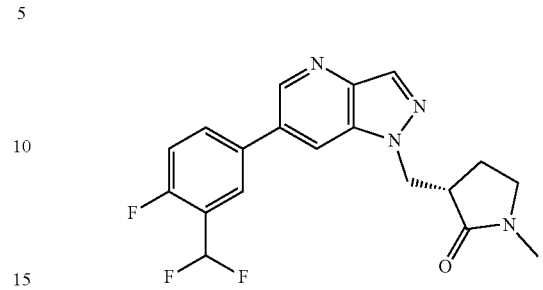

The title compound was prepared by the separation of Example 116 using chiral SFC (Stationary phase: Chiralpak IC, 5 um 250×21 mm, Mobile phase: 30% methanol, 70% $CO_2$). MS (ESI): mass calcd. for $C_{19}H_{17}F_3N_4O$, 374.1; m/z found, 375.1 $[M+H]^+$.

Example 118: (R)-3-[[6-[3-(Difluoromethyl)-4-fluoro-phenyl]pyrazolo[4,3-b]pyridin-1-yl]methyl]-1-methyl-pyrrolidin-2-one

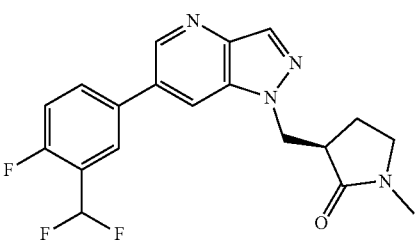 [SMILES: CN1CC[C@H](Cn2ncc3ncc(-c4ccc(F)c(C(F)F)c4)cc32)C1=O]

The title compound was prepared by the separation of Example 116 using chiral SFC (Stationary phase: Chiralpak IC, 5 M 250×21 mm, Mobile phase: 30% methanol, 70% $CO_2$). MS (ESI): mass calcd. for $C_{19}H_{17}F_3N_4O$, 374.1; m/z found, 375.1 $[M+H]^+$.

Example 119: (RS) 3-((6-(3-(Difluoromethoxy)-4-fluorophenyl)-1H-pyrazolo[4,3-b]pyridin-1-yl)methyl)-1-methylpyrrolidin-2-one

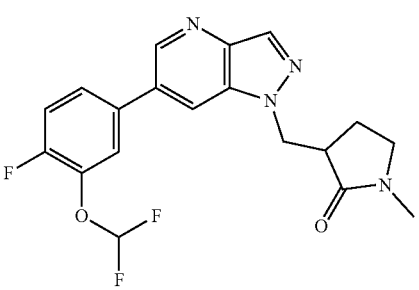 [SMILES: CN1CCC(Cn2ncc3ncc(-c4ccc(F)c(OC(F)F)c4)cc32)C1=O]

The title compound was prepared in a manner analogous to Example 19 using 3-(bromomethyl)-1-methylpyrrolidin-2-one instead of 4-(chloromethyl)-1-methyl-pyrrolidin-2-one. MS (ESI): mass calcd. for $C_{19}H_{17}F_3N_4O_2$, 390.4; m/z found, 391.1 $[M+H]^+$. $^1H$ NMR (500 MHz, DMSO-$d_6$) δ

8.87 (d, J=2.0 Hz, 1H), 8.52-8.49 (m, 1H), 8.35 (d, J=1.0 Hz, 1H), 7.86 (dd, J=7.6, 2.3 Hz, 1H), 7.82-7.75 (m, 1H), 7.60 (dd, J=10.5, 8.6 Hz, 1H), 7.38 (t, J=73.2 Hz, 1H), 4.74-4.65 (m, 2H), 3.23-3.16 (m, 1H), 3.07-2.99 (m, 2H), 2.66 (s, 3H), 1.98-1.90 (m, 1H), 1.81-1.71 (m, 1H).

Example 120: (RS)-4-[[6-[3-(Difluoromethyl)-4-fluoro-phenyl]pyrazolo[4,3-b]pyridin-1-yl]methyl]-1-methyl-pyrrolidin-2-one

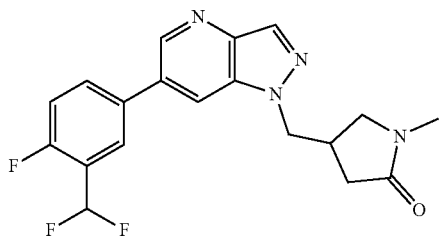 [SMILES: CN1CC(Cn2ncc3ncc(-c4ccc(F)c(C(F)F)c4)cc32)CC1=O]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 4-(bromomethyl)-1-methyl-2-pyrrolidinone instead of (chloromethyl)(ethyl)sulfane. MS (ESI): mass calcd. for $C_{19}H_{17}F_3N_4O$, 374.1; m/z found, 375.1 [M+H]$^+$. $^1$H NMR (500 MHz, MeOD) δ 8.81 (d, J=1.9 Hz, 1H), 8.44 (dd, J=1.8, 1.0 Hz, 1H), 8.25 (d, J=1.0 Hz, 1H), 8.08-7.93 (m, 2H), 7.42 (tt, J=9.7, 1.0 Hz, 1H), 7.08 (t, J=54.6 Hz, 1H), 4.68-4.51 (m, 2H), 3.52 (dd, J=10.3, 8.1 Hz, 1H), 3.38 (dd, J=10.3, 5.4 Hz, 1H), 3.19-3.06 (m, 1H), 2.84-2.73 (m, 3H), 2.53 (dd, J=17.0, 8.9 Hz, 1H), 2.31 (dd, J=17.0, 6.3 Hz, 1H).

Example 121: (S)-4-[[6-[3-(Difluoromethyl)-4-fluoro-phenyl]pyrazolo[4,3-b]pyridin-1-yl]methyl]-1-methyl-pyrrolidin-2-one

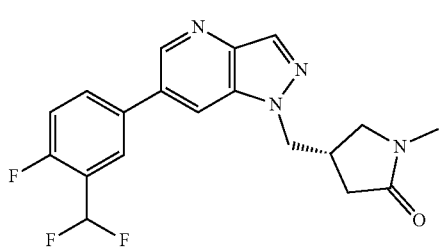 [SMILES: CN1C[C@@H](Cn2ncc3ncc(-c4ccc(F)c(C(F)F)c4)cc32)CC1=O]

The title compound was prepared by the separation of Example 120 using chiral SFC (Stationary phase: CHIRALPAK AD-H 5 µm 250*30 mm, Mobile phase: 75% $CO_2$, 25% MeOH). MS (ESI): mass calcd. for $C_{19}H_{17}F_3N_4O$, 374.1; m/z found, 375.0 [M+H]$^+$.

Example 122: (R)-4-[[6-[3-(Difluoromethyl)-4-fluoro-phenyl]pyrazolo[4,3-b]pyridin-1-yl]methyl]-1-methyl-pyrrolidin-2-one

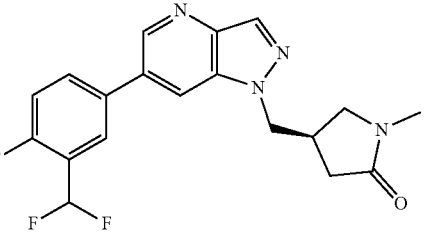

The title compound was prepared by the separation of Example 120 using chiral SFC (Stationary phase: CHIRALPAK AD-H 5 µm 250*30 mm, Mobile phase: 75% $CO_2$, 25% MeOH). MS (ESI): mass calcd. for $C_{19}H_{17}F_3N_4O$, 374.1; m/z found, 375.0 [M+H]$^+$.

Example 123: (R,S)-4-((6-(3-(difluoromethoxy)-4-fluorophenyl)-1H-pyrazolo[4,3-b]pyridin-1-yl)methyl)-3-methyloxazolidin-2-one

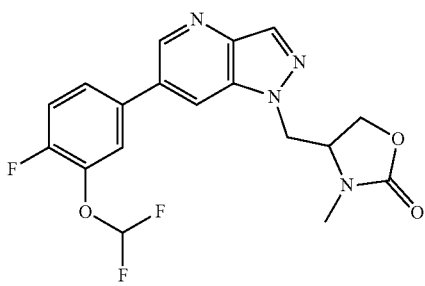 [SMILES: CN1C(=O)OCC1Cn1ncc2ncc(-c3ccc(F)c(OC(F)F)c3)cc21]

The title compound was prepared in a manner analogous to Example 18 using 6-(3-(difluoromethoxy)-4-fluorophenyl)-1H-pyrazolo[4,3-b]pyridine (Intermediate 4) instead of 6-[3-(difluoromethyl)-4-fluoro-phenyl]-1H-pyrazolo[4,3-b]pyridine, and (RS)-4-(chloromethyl)-3-methyloxazolidin-2-one (Intermediate 20) instead of 2-(chloromethyl)oxolane. MS (ESI): mass calcd. for $C_{18}H_{15}F_3N_4O_3$, 392.1; m/z found, 393.1 [M+H]$^+$. $^1$H NMR (500 MHz, DMSO-d$_6$) δ 8.90 (d, J=1.9 Hz, 1H), 8.62-8.58 (m, 1H), 8.42-8.39 (m, 1H), 7.87 (dd, J=7.6, 2.3 Hz, 1H), 7.82-7.77 (m, 1H), 7.61 (dd, J=10.5, 8.6 Hz, 1H), 7.38 (t, J=73.2 Hz, 1H), 4.83 (dd, J=14.8, 4.1 Hz, 1H), 4.73 (dd, J=14.7, 4.6 Hz, 1H), 4.39-4.28 (m, 2H), 4.13 (dd, J=8.0, 4.0 Hz, 1H), 2.75 (s, 3H).

Example 124: (RS)-4-[[6-[3-(Difluoromethyl)-4-fluoro-phenyl]pyrazolo[4,3-b]pyridin-1-yl]methyl]-3-methyl-oxazolidin-2-one

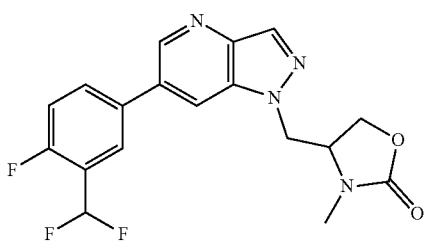 [SMILES: CN1C(=O)OCC1Cn1ncc2ncc(-c3ccc(F)c(C(F)F)c3)cc21]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and (RS)-4-(chloromethyl)-3-methyloxazolidin-2-one (Intermediate 20) instead of (chloromethyl)(ethyl)sulfane. MS (ESI): mass calcd. for $C_{18}H_{15}F_3N_4O_2$, 376.1; m/z found, 377.1 [M+H]$^+$. $^1$H NMR (500 MHz, MeOD) δ 8.82 (d, J=1.9 Hz, 1H), 8.44 (dd, J=1.9, 1.0 Hz, 1H), 8.28 (d, J=1.0 Hz, 1H), 8.07-7.99 (m, 1H), 7.99-7.93 (m, 1H), 7.42 (dd, J=9.9, 8.7 Hz, 1H), 7.08 (t, J=54.6 Hz, 1H), 4.86-4.80 (m, 1H), 4.77-4.69 (m, 1H), 4.47-4.33 (m, 2H), 4.33-4.23 (m, 1H), 2.87 (s, 3H).

Example 125: (RS)-5-[[6-[3-(Difluoromethoxy)-4-fluoro-phenyl]pyrazolo[4,3-b]pyridin-1-yl]methyl]oxazolidin-2-one

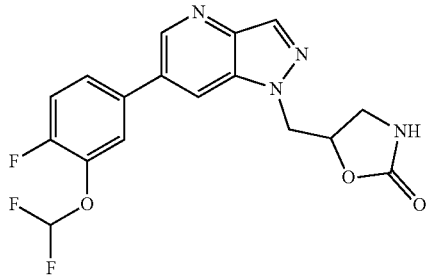 [SMILES: O=C1NCC(Cn2ncc3ncc(-c4ccc(F)c(OC(F)F)c4)cc32)O1]

The title compound was prepared in a manner analogous to Example 20, using 6-(3-(difluoromethoxy)-4-fluorophenyl)-1H-pyrazolo[4,3-b]pyridine (Intermediate 4) instead of 6-(3-(difluoromethyl)-4-fluorophenyl)-1H-pyrazolo[4,3-b]pyridine. MS (ESI): mass calcd. for $C_{17}H_{13}F_3N_4O_3$, 378.1; m/z found, 379.1 [M+H]$^+$. $^1$H NMR (500 MHz, DMSO-d$_6$) δ 8.88 (d, J=1.9 Hz, 1H), 8.52-8.48 (m, 1H), 8.39 (d, J=0.9 Hz, 1H), 7.85 (dd, J=7.6, 2.3 Hz, 1H), 7.80-7.75 (m, 1H), 7.61 (dd, J=10.5, 8.6 Hz, 1H), 7.52-7.48 (m, 1H), 7.38 (t, J=73.2 Hz, 1H), 5.08-5.00 (m, 1H), 4.83 (dd, J=15.0, 6.2 Hz, 1H), 4.77 (dd, J=14.9, 4.6 Hz, 1H), 3.66-3.60 (m, 1H), 3.38-3.33 (m, 1H).

Example 126: (RS)-5-[[6-[4-Chloro-3-(difluoromethoxy)phenyl]pyrazolo[4,3-b]pyridin-1-yl]methyl]oxazolidin-2-one

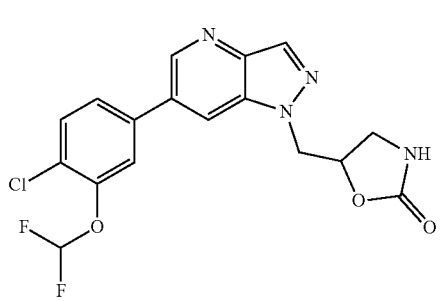 [SMILES: O=C1NCC(Cn2ncc3ncc(-c4ccc(Cl)c(OC(F)F)c4)cc32)O1]

The title compound was prepared in a manner analogous to Example 20, using 6-(4-chloro-3-(difluoromethoxy)phenyl)-1H-pyrazolo[4,3-b]pyridine (Intermediate 5) instead of 6-(3-(difluoromethyl)-4-fluorophenyl)-1H-pyrazolo[4,3-b]pyridine. MS (ESI): mass calcd. for $C_{17}H_{13}ClF_2N_4O_3$, 394.1; m/z found, 395.1 [M+H]$^+$. $^1$H NMR (300 MHz, DMSO-d$_6$) δ 8.91 (d, J=1.9 Hz, 1H), 8.58-8.49 (m, 1H), 8.43-8.36 (m, 1H), 7.87-7.72 (m, 3H), 7.55-7.47 (m, 1H), 7.44 (t, J=73.2 Hz, 1H), 5.12-4.97 (m, 1H), 4.90-4.73 (m, 2H), 3.63 (t, J=9.0 Hz, 1H), 3.42-3.30 (m, 1H).

Example 127: (RS)-5-[[6-[3-(1,1-Difluoroethyl)-4-fluoro-phenyl]pyrazolo[4,3-b]pyridin-1-yl]methyl]oxazolidin-2-one

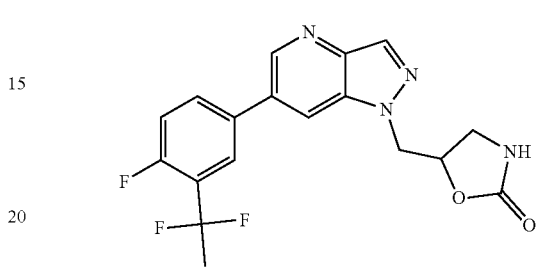

The title compound was prepared in a manner analogous to Example 20, using 6-(3-(1,1-difluoroethyl)-4-fluorophenyl)-1H-pyrazolo[4,3-b]pyridine (Intermediate 6) instead of 6-(3-(difluoromethyl)-4-fluorophenyl)-1H-pyrazolo[4,3-b]pyridine. MS (ESI): mass calcd. for $C_{18}H_{15}F_3N_4O_2$, 376.1; m/z found, 377.1 [M+H]$^+$. $^1$H NMR (500 MHz, DMSO-d$_6$) δ 8.88 (d, J=1.9 Hz, 1H), 8.53-8.50 (m, 1H), 8.39 (d, J=1.0 Hz, 1H), 8.05-7.99 (m, 1H), 7.99-7.95 (m, 1H), 7.56 (dd, J=11.0, 8.6 Hz, 1H), 7.52-7.47 (m, 1H), 5.08-5.00 (m, 1H), 4.84 (dd, J=14.9, 6.2 Hz, 1H), 4.79 (dd, J=14.9, 4.4 Hz, 1H), 3.66-3.60 (m, 1H), 3.38-3.33 (m, 1H), 2.10 (t, J=19.1 Hz, 3H).

Example 128: (RS)-5-((6-(3-(Difluoromethoxy)-4-fluorophenyl)-1H-pyrazolo[4,3-b]pyridin-1-yl)methyl)-3-methyloxazolidin-2-one

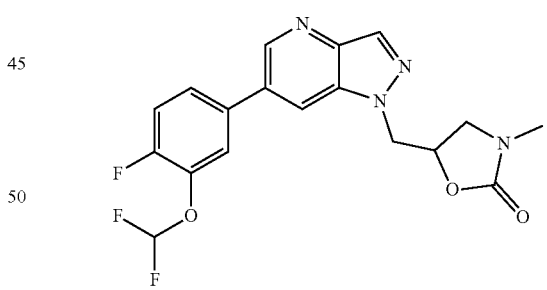

The title compound was prepared in a manner analogous to Intermediate 16, Step A, using 6-(3-(difluoromethoxy)-4-fluorophenyl)-1H-pyrazolo[4,3-b]pyridine (Intermediate 4) instead of 6-bromo-1H-pyrazolo[4,3-B]pyridine, and 5-(chloromethyl)-3-methyloxazolidin-2-one instead of (chloromethyl)(ethyl)sulfane. MS (ESI): mass calcd. for $C_{18}H_{15}F_3N_4O_3$, 392.1; m/z found, 393.1 [M+H]$^+$. $^1$H NMR (300 MHz, DMSO-d$_6$) δ 8.89 (d, J=1.9 Hz, 1H), 8.55-8.46 (m, 1H), 8.43-8.35 (m, 1H), 7.90-7.82 (m, 1H), 7.81-7.72 (m, 1H), 7.61 (dd, J=10.4, 8.7 Hz, 1H), 7.37 (t, J=73.1 Hz, 1H), 5.03-4.92 (m, 1H), 4.90-4.73 (m, 2H), 3.76-3.65 (m, 1H), 3.43 (dd, J=9.0, 5.9 Hz, 1H), 2.67 (s, 3H).

Example 129: (5R)-5-[[6-[3-(Difluoromethyl)-4-fluoro-phenyl]pyrazolo[4,3-b]pyridin-1-yl]methyl]-3-methyl-oxazolidin-2-one

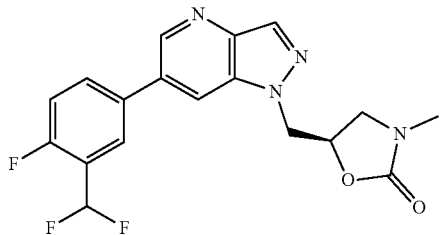 [SMILES: CN1C[C@H](Cn2ncc3ncc(-c4ccc(F)c(C(F)F)c4)cc32)OC1=O]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and (R)-5-(chloromethyl)-3-methyloxazolidin-2-one (Intermediate 18) instead of (chloromethyl)(ethyl)sulfane. MS (ESI): mass calcd. for $C_{18}H_{15}F_3N_4O_2$, 376.1; m/z found, 377.1 $[M+H]^+$. $^1H$ NMR (500 MHz, MeOD) δ 8.79 (d, J=1.9 Hz, 1H), 8.38 (dd, J=1.9, 1.0 Hz, 1H), 8.27 (d, J=1.0 Hz, 1H), 8.06-7.93 (m, 2H), 7.41 (dd, J=9.9, 8.7 Hz, 1H), 7.07 (t, J=54.6 Hz, 1H), 5.04 (dtd, J=9.1, 5.6, 3.4 Hz, 1H), 4.92-4.75 (m, 2H), 3.78 (t, J=9.1 Hz, 1H), 3.61 (dd, J=9.2, 5.6 Hz, 1H), 2.70 (s, 3H).

Example 130: (5S)-5-[[6-[3-(Difluoromethyl)-4-fluoro-phenyl]pyrazolo[4,3-b]pyridin-1-yl]methyl]-3-methyl-oxazolidin-2-one

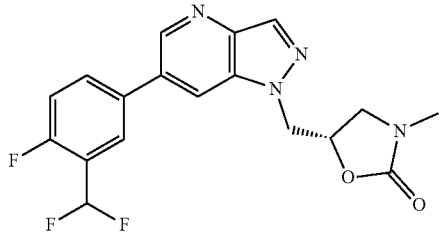 [SMILES: CN1C[C@@H](Cn2ncc3ncc(-c4ccc(F)c(C(F)F)c4)cc32)OC1=O]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and (S)-5-(chloromethyl)-3-methyloxazolidin-2-one (Intermediate 19) instead of (chloromethyl)(ethyl)sulfane. MS (ESI): mass calcd. for $C_{18}H_{15}F_3N_4O_2$, 376.1; m/z found, 377.1 $[M+H]^+$. $^1H$ NMR (500 MHz, MeOD) δ 8.76 (dd, J=1.7, 0.9 Hz, 1H), 8.35 (dt, J=1.8, 0.8 Hz, 1H), 8.29-8.22 (m, 1H), 7.97 (dd, J=7.0, 2.1 Hz, 1H), 7.92 (d, J=6.3 Hz, 1H), 7.37 (t, J=9.5 Hz, 1H), 7.06 (t, J=54.6 Hz, 1H), 5.02 (dtd, J=9.2, 5.7, 3.5 Hz, 1H), 4.87-4.74 (m, 2H), 3.77 (t, J=9.1 Hz, 1H), 3.59 (dd, J=9.2, 5.7 Hz, 1H), 2.70 (s, 3H).

Example 131: (RS)-5-[[6-[3-(Difluoromethyl)-4-fluoro-phenyl]pyrazolo[4,3-b]pyridin-1-yl]methyl]-3-ethyl-oxazolidin-2-one

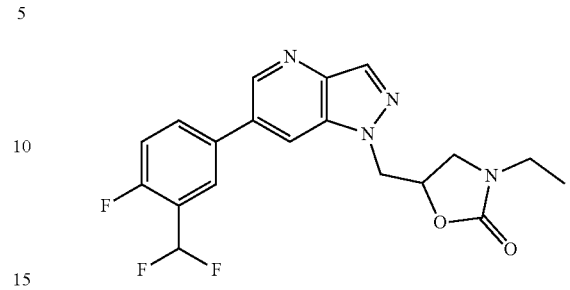

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 5-(bromomethyl)-3-ethyl-1,3-oxazolidin-2-one instead of (chloromethyl)(ethyl)sulfane. MS (ESI): mass calcd. for $C_{19}H_{17}F_3N_4O_2$, 390.1; m/z found, 391.2 $[M+H]^+$. $^1H$ NMR (500 MHz, MeOD) δ 8.79 (d, J=1.9 Hz, 1H), 8.38 (dd, J=1.9, 1.0 Hz, 1H), 8.27 (d, J=1.0 Hz, 1H), 8.05-7.93 (m, 2H), 7.41 (dd, J=10.0, 8.7 Hz, 1H), 7.07 (t, J=54.6 Hz, 1H), 5.06 (dtd, J=9.0, 5.2, 3.1 Hz, 1H), 4.94-4.87 (m, 1H), 4.82-4.74 (m, 1H), 3.77 (t, J=9.2 Hz, 1H), 3.63 (dd, J=9.2, 5.3 Hz, 1H), 3.17-3.00 (m, 2H), 0.90 (t, J=7.3 Hz, 3H).

Example 132: (S)-5-[[6-[3-(Difluoromethyl)-4-fluoro-phenyl]pyrazolo[4,3-b]pyridin-1-yl]methyl]-3-ethyl-oxazolidin-2-one

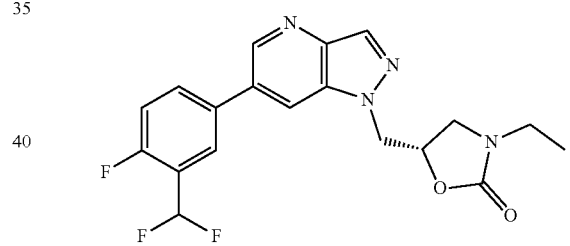

The title compound was prepared by the separation of Example 131 using chiral SFC (Stationary phase: Chiralpak IA, Sum 250×21 mm, Mobile phase: 35% methanol with 0.2% triethylamine, 65% $CO_2$). MS (ESI): mass calcd. for $C_{19}H_{17}F_3N_4O_2$, 390.1; m/z found, 391.2 $[M+H]^+$.

Example 133: (R)-5-[[6-[3-(Difluoromethyl)-4-fluoro-phenyl]pyrazolo[4,3-b]pyridin-1-yl]methyl]-3-ethyl-oxazolidin-2-one

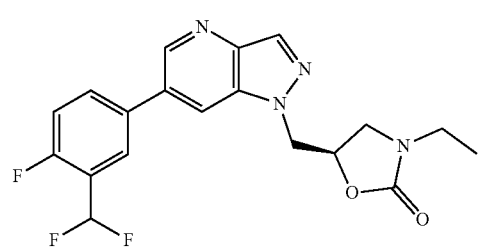 [SMILES: CCN1C[C@H](Cn2ncc3ncc(-c4ccc(F)c(C(F)F)c4)cc32)OC1=O]

The title compound was prepared by the separation of Example 131 using chiral SFC (Stationary phase: Chiralpak IA, 5um 250×21 mm, Mobile phase: 35% methanol with 0.2% triethylamine, 65% CO$_2$). MS (ESI): mass calcd. for C$_{19}$H$_{17}$F$_3$N$_4$O$_2$, 390.1; m/z found, 391.2 [M+H]$^+$.

Example 134: (RS)-3-Cyclopropyl-5-[[6-[3-(difluoromethyl)-4-fluoro-phenyl]pyrazolo[4,3-b]pyridin-1-yl]methyl]oxazolidin-2-one

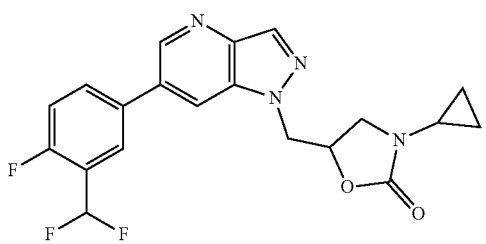 [SMILES: O=C1OC(Cn2ncc3ncc(-c4ccc(F)c(C(F)F)c4)cc32)CN1C1CC1]

The title compound was prepared in a manner analogous to Intermediate 16, Step A, using 6-(3-(difluoromethyl)-4-fluorophenyl)-1H-pyrazolo[4,3-b]pyridine (Intermediate 3) instead of 6-bromo-1H-pyrazolo[4,3-b]pyridine, and 5-(bromomethyl)-3-cyclopropyl-1,3-oxazolidin-2-one instead of (chloromethyl)(ethyl)sulfane. MS (ESI): mass calcd. for C$_2$H$_{17}$F$_3$N$_4$O$_2$, 402.1; m/z found, 403.2 [M+H]$^+$. $^1$H NMR (500 MHz, MeOD) δ 8.79 (d, J=1.9 Hz, 1H), 8.35 (dd, J=1.9, 1.0 Hz, 1H), 8.27 (d, J=1.0 Hz, 1H), 8.05-7.94 (m, 2H), 7.45-7.37 (m, 1H), 7.07 (t, J=54.6 Hz, 1H), 5.01 (dtd, J=9.2, 4.7, 3.0 Hz, 1H), 4.93-4.86 (m, 1H), 4.80-4.63 (m, 1H), 3.78 (t, J=9.1 Hz, 1H), 3.58 (dd, J=9.2, 4.7 Hz, 1H), 2.29 (tt, J=7.0, 3.6 Hz, 1H), 0.66-0.51 (m, 2H), 0.35 (dtd, J=11.1, 3.7, 2.1 Hz, 1H), 0.16 (dtd, J=10.2, 3.6, 2.0 Hz, 1H).

Example 135: (S)-3-Cyclopropyl-5-[[6-[3-(difluoromethyl)-4-fluoro-phenyl]pyrazolo[4,3-b]pyridin-1-yl]methyl]oxazolidin-2-one

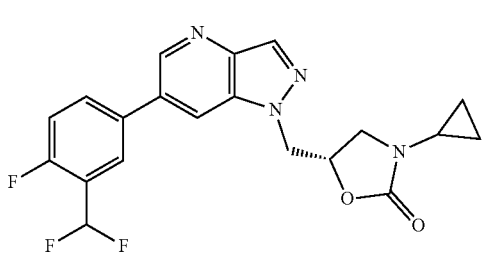 [SMILES: O=C1O[C@H](Cn2ncc3ncc(-c4ccc(F)c(C(F)F)c4)cc32)CN1C1CC1]

The title compound was prepared by the separation of Example 134 using chiral SFC (Stationary phase: Chiralpak AS, 5um 250×21 mm, Mobile phase: 15% methanol:isopropanol (1:1) with 0.2% isopropylamine, 85% CO$_2$). MS (ESI): mass calcd. for C$_2$H$_{17}$F$_3$N$_4$O$_2$, 402.1; m/z found, 403.2 [M+H]$^+$.

Example 136: (R)-3-Cyclopropyl-5-[[6-[3-(difluoromethyl)-4-fluoro-phenyl]pyrazolo[4,3-b]pyridin-1-yl]methyl]oxazolidin-2-one

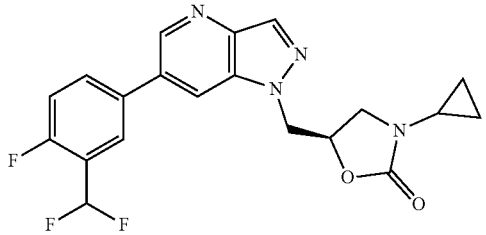 [SMILES: O=C1O[C@@H](Cn2ncc3ncc(-c4ccc(F)c(C(F)F)c4)cc32)CN1C1CC1]

The title compound was prepared by the separation of Example 134 using chiral SFC (Stationary phase: Chiralpak AS, 5 um 250×21 mm, Mobile phase: 15% methanol:isopropanol (1:1) with 0.2% isopropylamine, 85% CO$_2$). MS (ESI): mass calcd. for C$_2$H$_{17}$F$_3$N$_4$O$_2$, 402.1; m/z found, 403.2 [M+H]$^+$.

Example 137: 2-[6-[3-(Difluoromethyl)-4-fluoro-phenyl]pyrazolo[4,3-b]pyridin-1-yl]-1-(2-thienyl)ethanone

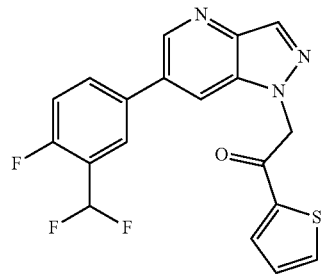 [SMILES: O=C(Cn1ncc2ncc(-c3ccc(F)c(C(F)F)c3)cc21)c1cccs1]

The title compound was prepared in a manner analogous to Intermediate 16, Step A, using 2-chloro-1-(thiophen-2-yl)ethan-1-one instead of (chloromethyl)(ethyl)sulfane, and 6-(3-(difluoromethyl)-4-fluorophenyl)-1H-pyrazolo[4,3-b]pyridine (Intermediate 3) instead of 6-bromo-1H-pyrazolo[4,3-b]pyridine. MS (ESI): mass calcd. for C$_{19}$H$_{12}$F$_3$N$_3$OS, 387.1; m/z found, 388.1 [M+H]$^+$. $^1$H NMR (300 MHz, DMSO-d$_6$) δ 8.92 (d, J=1.9 Hz, 1H), 8.59-8.52 (m, 1H), 8.46-8.37 (m, 1H), 8.30-8.22 (m, 1H), 8.18-8.12 (m, 1H), 8.10-8.01 (m, 2H), 7.61-7.50 (m, 1H), 7.41-7.35 (m, 1H), 7.28 (t, J=54.2 Hz, 1H), 6.20 (s, 2H).

Example 138: 2-[6-[3-(Difluoromethyl)-4-fluoro-phenyl]pyrazolo[4,3-b]pyridin-1-yl]-1-(3-thienyl)ethanone

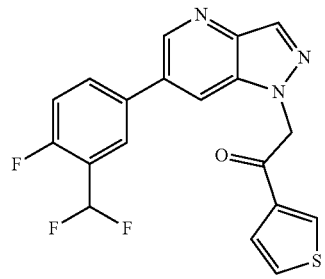 [SMILES: O=C(Cn1ncc2ncc(-c3ccc(F)c(C(F)F)c3)cc21)c1ccsc1]

The title compound was prepared in a manner analogous to Intermediate 16, Step A, using 2-chloro-1-(thiophen-3-yl)ethan-1-one instead of (chloromethyl)(ethyl)sulfane, and 6-(3-(difluoromethyl)-4-fluorophenyl)-1H-pyrazolo[4,3-b]pyridine (Intermediate 3) instead of 6-bromo-1H-pyrazolo[4,3-b]pyridine. MS (ESI): mass calcd. for $C_{19}H_{12}F_3N_3OS$, 387.1; m/z found, 388.0 [M+H]$^+$. $^1$H NMR (500 MHz, DMSO-d$_6$) δ 8.91 (d, J=1.9 Hz, 1H), 8.76 (dd, J=2.9, 1.3 Hz, 1H), 8.56-8.52 (m, 1H), 8.41 (d, J=1.0 Hz, 1H), 8.09-8.01 (m, 2H), 7.74 (dd, J=5.0, 2.8 Hz, 1H), 7.60 (dd, J=5.1, 1.3 Hz, 1H), 7.58-7.51 (m, 1H), 7.28 (t, J=54.1 Hz, 1H), 6.15 (s, 2H).

Example 139: 2-[6-[3-(Difluoromethyl)-4-fluorophenyl]pyrazolo[4,3-b]pyridin-1-yl]-1-(4-pyridyl)ethanone

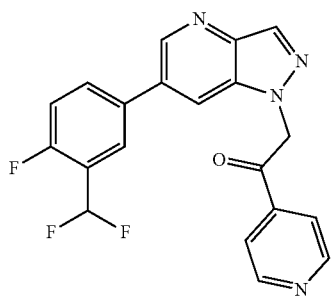 [SMILES: O=C(Cn1ncc2ncc(-c3ccc(F)c(C(F)F)c3)cc21)c1ccncc1]

The title compound was prepared in a manner analogous to Example 14 using 2-bromo-1-(pyridin-4-yl)ethan-1-one (Intermediate 22) instead of 2-bromo-1-(2-pyridyl)ethanone hydrobromide. MS (ESI): mass calcd. for $C_{20}H_{13}F_3N_4O$, 382.1; m/z found, 383.1 [M+H]$^+$. $^1$H NMR (500 MHz, DMSO-d$_6$) δ 8.97-8.85 (m, 3H), 8.57-8.51 (m, 1H), 8.46-8.40 (m, 1H), 8.09-8.00 (m, 2H), 7.99-7.94 (m, 2H), 7.59-7.51 (m, 1H), 7.28 (t, J=54.1 Hz, 1H), 6.32 (s, 2H).

Example 140: 2-(6-(3-(Difluoromethyl)-4-fluorophenyl)-1H-pyrazolo[4,3-b]pyridin-1-yl)-1-(3-fluoropyridin-2-yl)ethan-1-one

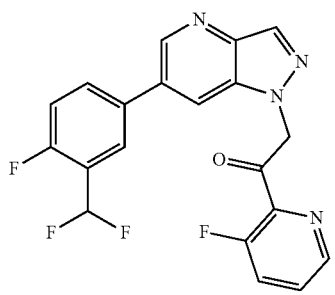 [SMILES: O=C(Cn1ncc2ncc(-c3ccc(F)c(C(F)F)c3)cc21)c1ncccc1F]

The title compound was prepared in a manner analogous to Example 15 using 2-bromo-1-(3-fluoropyridin-2-yl)ethan-1-one (Intermediate 24) instead of 2-bromo-1-(5-fluoropyridin-2-yl)ethan-1-one. MS (ESI): mass calcd. for $C_{20}H_{12}F_4N_4O$, 400.1; m/z found, 401.1 [M+H]$^+$. $^1$H NMR (500 MHz, DMSO-d$_6$) δ 8.99-8.86 (m, 1H), 8.74-8.65 (m, 1H), 8.61-8.53 (m, 1H), 8.46-8.38 (m, 1H), 8.05 (d, J=6.2 Hz, 2H), 8.02-7.94 (m, 1H), 7.92-7.83 (m, 1H), 7.60-7.49 (m, 1H), 7.28 (t, J=54.1 Hz, 1H), 6.25 (s, 2H).

Example 141: 2-(6-(3-(Difluoromethyl)-4-fluorophenyl)-1H-pyrazolo[4,3-b]pyridin-1-yl)-1-(3,5-difluoropyridin-2-yl)ethan-1-one

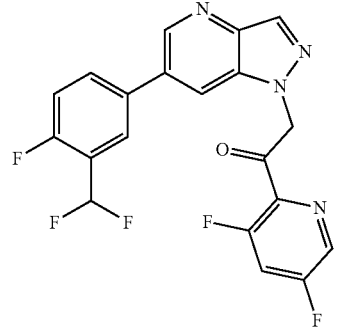 [SMILES: O=C(Cn1ncc2ncc(-c3ccc(F)c(C(F)F)c3)cc21)c1ncc(F)cc1F]

The title compound was prepared in a manner analogous to Example 15 using 2-bromo-1-(3,5-difluoropyridin-2-yl)ethan-1-one (Intermediate 23) instead of 2-bromo-1-(5-fluoropyridin-2-yl)ethan-1-one. MS (ESI): mass calcd. for $C_{20}H_{11}F_5N_4O$, 418.1; m/z found, 419.1 [M+H]$^+$. $^1$H NMR (500 MHz, DMSO-d$_6$) δ 8.91 (d, J=2.0 Hz, 1H), 8.80 (d, J=2.3 Hz, 1H), 8.56-8.51 (m, 1H), 8.43-8.41 (m, 1H), 8.24-8.18 (m, 1H), 8.08-8.02 (m, 2H), 7.60-7.52 (m, 1H), 7.28 (t, J=54.2 Hz, 1H), 6.22 (s, 2H).

Example 142: 2-(6-(3-(Difluoromethyl)-4-fluorophenyl)-1H-pyrazolo[4,3-b]pyridin-1-yl)-1-(pyrazin-2-yl)ethan-1-one

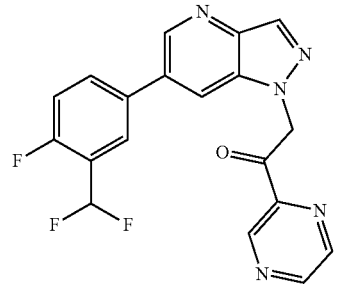 [SMILES: O=C(Cn1ncc2ncc(-c3ccc(F)c(C(F)F)c3)cc21)c1cnccn1]

The title compound was prepared in a manner analogous to Example 15 using 2-bromo-1-(pyrazin-2-yl)ethan-1-one (Intermediate 25) instead of 2-bromo-1-(5-fluoropyridin-2-yl)ethan-1-one. MS (ESI): mass calcd. for $C_{20}H_{11}F_5N_4O$, 383.1; m/z found, 384.1 [M+H]$^+$. $^1$H NMR (500 MHz, Methanol-d4) δ 9.20 (d, J=1.5 Hz, 1H), 8.91-8.89 (m, 1H), 8.85 (d, J=1.9 Hz, 1H), 8.84-8.82 (m, 1H), 8.38-8.36 (m, 1H), 8.34-8.31 (m, 1H), 7.97-7.91 (m, 2H), 7.42-7.37 (m, 1H), 7.06 (t, J=54.6 Hz, 1H), 6.31 (s, 2H). NMR in MeOH results in mixture of ketone and methanol hemiacetal

BIOLOGICAL ASSAYS

Effects of Test Articles on Cloned Human NR1/GluN2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular $Ca^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM $CaCl_2$, 0.5 mM $MgCl_2$ (standard assay) or 1.5 mM $MgCl_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM $CaC_2$, 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~$EC_{40}$ (standard assay) or $EC_{40}$ (HTS assay) is used to maximize the assay's signal window and ability to detect NMDA receptor antagonists and negative allosteric modulators. A saturating concentration (10 µM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 3

| Ex # | Compound Name | GluN2B Standard Assay $IC_{50}$ (µM) |
|---|---|---|
| 1 | 1-[6-(3,5-Difluorophenyl)pyrazolo[4,3-b]pyridin-1-yl]butan-2-one; | 0.019 |
| 2 | 3-Methyl-1-[6-[3-(trifluoromethyl)phenyl]pyrazolo[4,3-b]pyridin-1-yl]butan-2-one; | 0.061 |
| 3 | (RS)-3-Methyl-1-[6-[3-(trifluoromethyl)phenyl]pyrazolo[4,3-b]pyridin-1-yl]butan-2-ol; | 0.567 |
| 4 | 1-[6-[3-(Difluoromethyl)-4-fluoro-phenyl]pyrazolo[4,3-b]pyridin-1-yl]butan-2-one; | 0.010 |
| 5 | (RS)-1-[6-[3-(Difluoromethyl)-4-fluoro-phenyl]pyrazolo[4,3-b]pyridin-1-yl]butan-2-ol; | 0.048 |
| 6 | (E/Z)-3-Methyl-1-[6-[3-(trifluoromethyl)phenyl]pyrazolo[4,3-b]pyridin-1-yl]butan-2-one oxime; | 2.480 |
| 7 | 1-[6-(4-Fluoro-3-methyl-phenyl)pyrazolo[4,3-b]pyridin-1-yl]-3-methyl-butan-2-one; | 0.021 |
| 8 | (RS)-1-[6-(4-Fluoro-3-methyl-phenyl)pyrazolo[4,3-b]pyridin-1-yl]-3-methyl-butan-2-ol; | 0.222 |
| 9 | 1-Cyclopropyl-2-[6-(3,4,5-trifluorophenyl)pyrazolo[4,3-b]pyridin-1-yl]ethanone; | 0.030 |
| 10 | (RS)-1-Cyclopropyl-2-[6-(3,4,5-trifluorophenyl)pyrazolo[4,3-b]pyridin-1-yl]ethanol; | 0.696 |
| 11 | (RS)-1-(2-Cyclopropyl-2-methoxy-ethyl)-6-(3,4,5-trifluorophenyl)pyrazolo[4,3-b]pyridine; | 1.780 |
| 12 | (RS)-6-[3-(Difluoromethoxy)-4-fluoro-phenyl]-1-(ethylsulfinylmethyl)pyrazolo[4,3-b]pyridine; | 0.146 |
| 13 | 6-[3-(Difluoromethoxy)-4-fluoro-phenyl]-1-(ethylsulfonylmethyl)pyrazolo[4,3-b]pyridine; | 1.800 |
| 14 | 2-[6-[3-(Difluoromethyl)-4-fluoro-phenyl]pyrazolo[4,3-b]pyridin-1-yl]-1-(2-pyridyl)ethanone; | 0.112 |
| 15 | 2-(6-(3-(Difluoromethyl)-4-fluorophenyl)-1H-pyrazolo[4,3-b]pyridin-1-yl)-1-(5-fluoropyridin-2-yl)ethan-1-one; | 0.160 |
| 16 | 2-(6-(3-(Difluoromethyl)-4-fluorophenyl)-1H-pyrazolo[4,3-b]pyridin-1-yl)-1-(pyridin-3-yl)ethan-1-one; | 0.090 |
| 17 | (RS)-1-(Oxetan-2-ylmethyl)-6-[3-(trifluoromethyl)phenyl]pyrazolo[4,3-b]pyridine; | 0.085 |
| 18 | (RS)-6-[3-(Difluoromethyl)-4-fluoro-phenyl]-1-(tetrahydrofuran-2-ylmethyl)pyrazolo[4,3-b]pyridine; | 0.035 |
| 19 | (RS)-4-[[6-[3-(Difluoromethoxy)-4-fluoro-phenyl]pyrazolo[4,3-b]pyridin-1-yl]methyl]-1-methyl-pyrrolidin-2-one; | 0.992 |
| 20 | (RS)-5[[6-[3-(Difluoromethyl)-4-fluoro-phenyl]pyrazolo[4,3-b]pyridin-1-yl]methyl]oxazolidin-2-one; | 0.197 |
| 21 | (S)-5-[[6-[3-(Difluoromethyl)-4-fluoro-phenyl]pyrazolo[4,3-b]pyridin-1-yl]methyl]oxazolidin-2-one; | 1.840 |
| 22 | (R)-5-[[6-[3-(Difluoromethyl)-4-fluoro-phenyl]pyrazolo[4,3-b]pyridin-1-yl]methyl]oxazolidin-2-one; | 0.187 |

TABLE 3-continued

| Ex # | Compound Name | GluN2B Standard Assay IC$_{50}$ (μM) |
|---|---|---|
| 23 | 1-[6-[3-(Difluoromethyl)-4-fluoro-phenyl]pyrazolo[4,3-b]pyridin-1-yl]propan-2-one; | 0.014 |
| 24 | 1-[6-(4-Fluoro-3-methyl-phenyl)pyrazolo[4,3-b]pyridin-1-yl]propan-2-one; | 0.015 |
| 25 | 1-[6-[3-(Difluoromethoxy)-4-fluoro-phenyl]pyrazolo[4,3-b]pyridin-1-yl]propan-2-one; | 0.034 |
| 26 | 1-[6-[4-Chloro-3-(difluoromethoxy)phenyl]pyrazolo[4,3-b]pyridin-1-yl]propan-2-one; | 0.036 |
| 27 | 1-[6-(5-Chloro-2-thienyl)pyrazolo[4,3-b]pyridin-1-yl]butan-2-one; | 0.013 |
| 28 | 1-[6-(4-Fluorophenyl)pyrazolo[4,3-b]pyridin-1-yl]butan-2-one; | 0.032 |
| 29 | 1-[6-(3-Fluorophenyl)pyrazolo[4,3-b]pyridin-1-yl]butan-2-one; | 0.028 |
| 30 | 1-[6-[3-(Difluoromethyl)phenyl]pyrazolo[4,3-b]pyridin-1-yl]butan-2-one; | 0.027 |
| 31 | 1-[6-[3-(1,1-Difluoroethyl)phenyl]pyrazolo[4,3-b]pyridin-1-yl]butan-2-one; | 0.035 |
| 32 | 1-[6-(4-Fluoro-3-methyl-phenyl)pyrazolo[4,3-b]pyridin-1-yl]butan-2-one; | 0.012 |
| 33 | 1-[6-(2,3-Difluorophenyl)pyrazolo[4,3-b]pyridin-1-yl]butan-2-one; | 0.046 |
| 34 | 1-[6-(3,4-Difluorophenyl)pyrazolo[4,3-b]pyridin-1-yl]butan-2-one; | 0.017 |
| 35 | 1-[6-(3,4-Difluorophenyl)-3-fluoro-pyrazolo[4,3-b]pyridin-1-yl]butan-2-one; | 0.005 |
| 36 | 1-(6-(3-(Difluoromethyl)-4-fluorophenyl)-3-methyl-1H-pyrazolo[4,3-b]pyridin-1-yl)butan-2-one; | 0.027 |
| 37 | 1-[6-[3-(1,1-Difluoroethyl)-4-fluoro-phenyl]pyrazolo[4,3-b]pyridin-1-yl]butan-2-one; | 0.041 |
| 38 | 1-[6-[2-Fluoro-3-(trifluoromethyl)phenyl]pyrazolo[4,3-b]pyridin-1-yl]butan-2-one; | 0.030 |
| 39 | 1-[6-[4-Fluoro-3-(trifluoromethyl)phenyl]pyrazolo[4,3-b]pyridin-1-yl]butan-2-one; | 0.075 |
| 40 | 1-[6-[3-(Difluoromethoxy)-4-fluoro-phenyl]pyrazolo[4,3-b]pyridin-1-yl]butan-2-one; | 0.011 |
| 41 | 1-[6-[4-Chloro-3-(difluoromethoxy)phenyl]pyrazolo[4,3-b]pyridin-1-yl]butan-2-one; | 0.021 |
| 42 | 1-[6-(3,4,5-Trifluorophenyl)pyrazolo[4,3-b]pyridin-1-yl]butan-2-one; | 0.027 |
| 43 | 1-[6-(2,3,4-Trifluorophenyl)pyrazolo[4,3-b]pyridin-1-yl]butan-2-one; | 0.028 |
| 44 | 3-Methyl-1-(6-phenylpyrazolo[4,3-b]pyridin-1-yl)butan-2-one; | 0.089 |
| 45 | 1-[6-(4-Fluorophenyl)pyrazolo[4,3-b]pyridin-1-yl]-3-methyl-butan-2-one; | 0.036 |
| 46 | 1-[6-(3-Fluorophenyl)pyrazolo[4,3-b]pyridin-1-yl]-3-methyl-butan-2-one; | 0.030 |
| 47 | 1-[6-[3-(Difluoromethyl)phenyl]pyrazolo[4,3-b]pyridin-1-yl]-3-methyl-butan-2-one; | 0.023 |
| 48 | 1-[6-(2,3-Difluorophenyl)pyrazolo[4,3-b]pyridin-1-yl]-3-methyl-butan-2-one; | 0.172 |
| 49 | 1-[6-(3,4-Difluorophenyl)pyrazolo[4,3-b]pyridin-1-yl]-3-methyl-butan-2-one; | 0.025 |
| 50 | 1-[6-[2-Fluoro-3-(trifluoromethyl)phenyl]pyrazolo[4,3-b]pyridin-1-yl]-3-methyl-butan-2-one; | 0.076 |
| 51 | 1-[6-[4-Fluoro-3-(trifluoromethyl)phenyl]pyrazolo[4,3-b]pyridin-1-yl]-3-methyl-butan-2-one; | 0.296 |
| 52 | 1-[6-(4-Fluoro-2-methyl-phenyl)pyrazolo[4,3-b]pyridin-1-yl]-3-methyl-butan-2-one; | 0.090 |
| 53 | 3-Methyl-1-[6-(3,4,5-trifluorophenyl)pyrazolo[4,3-b]pyridin-1-yl]butan-2-one; | 0.041 |
| 54 | 3-Methyl-1-[6-(2,3,4-trifluorophenyl)pyrazolo[4,3-b]pyridin-1-yl]butan-2-one; | 0.205 |
| 55 | 2-[6-(5-Chloro-2-thienyl)pyrazolo[4,3-b]pyridin-1-yl]-1-cyclopropyl-ethanone; | 0.008 |
| 56 | 1-Cyclopropyl-2-[6-(5-methyl-2-thienyl)pyrazolo[4,3-b]pyridin-1-yl]ethanone; | 0.015 |
| 57 | 1-Cyclopropyl-2-[6-(3-fluorophenyl)pyrazolo[4,3-b]pyridin-1-yl]ethanone; | 0.026 |
| 58 | 1-Cyclopropyl-2-[6-(2-fluorophenyl)pyrazolo[4,3-b]pyridin-1-yl]ethanone; | 0.148 |
| 59 | 1-Cyclopropyl-2-[6-(4-fluorophenyl)pyrazolo[4,3-b]pyridin-1-yl]ethanone; | 0.013 |
| 60 | 1-Cyclopropyl-2-[6-(m-tolyl)pyrazolo[4,3-b]pyridin-1-yl]ethanone; | 0.008 |

TABLE 3-continued

| Ex # | Compound Name | GluN2B Standard Assay IC$_{50}$ (μM) |
|---|---|---|
| 61 | 1-Cyclopropyl-2-[6-[3-(difluoromethyl)phenyl]pyrazolo[4,3-b]pyridin-1-yl]ethanone; | 0.012 |
| 62 | 1-Cyclopropyl-2-[6-[3-(trifluoromethyl)phenyl]pyrazolo[4,3-b]pyridin-1-yl]ethanone; | 0.046 |
| 63 | 1-Cyclopropyl-2-[6-[3-(trifluoromethoxy)phenyl]pyrazolo[4,3-b]pyridin-1-yl]ethanone; | 0.031 |
| 64 | 1-Cyclopropyl-2-[6-(2,3-difluorophenyl)pyrazolo[4,3-b]pyridin-1-yl]ethanone; | 0.037 |
| 65 | 1-Cyclopropyl-2-[6-(3,4-difluorophenyl)pyrazolo[4,3-b]pyridin-1-yl]ethanone; | 0.013 |
| 66 | 1-Cyclopropyl-2-[6-(3,5-difluorophenyl)pyrazolo[4,3-b]pyridin-1-yl]ethanone; | 0.019 |
| 67 | 2-[6-(3-Chloro-2-fluoro-phenyl)pyrazolo[4,3-b]pyridin-1-yl]-1-cyclopropyl-ethanone; | 0.016 |
| 68 | 2-[6-(3-Chloro-4-fluoro-phenyl)pyrazolo[4,3-b]pyridin-1-yl]-1-cyclopropyl-ethanone; | 0.007 |
| 69 | 1-Cyclopropyl-2-[6-(4-fluoro-3-methyl-phenyl)pyrazolo[4,3-b]pyridin-1-yl]ethanone; | 0.019 |
| 70 | 1-Cyclobutyl-246-(4-fluoro-3-methyl-phenyl)pyrazolo[4,3-b]pyridin-1-yl]ethanone; | 0.063 |
| 71 | 1-Cyclopropyl-2-[6-(2-fluoro-3-methyl-phenyl)pyrazolo[4,3-b]pyridin-1-yl]ethanone; | 0.007 |
| 72 | 1-Cyclopropyl-2-[6-(4-fluoro-2-methyl-phenyl)pyrazolo[4,3-b]pyridin-1-yl]ethanone; | 0.199 |
| 73 | 1-Cyclopropyl-2-[6-[2-fluoro-3-(trifluoromethyl)phenyl]pyrazolo[4,3-b]pyridin-1-yl]ethanone; | 0.043 |
| 74 | 1-Cyclopropyl-2-[6-[4-fluoro-3-(trifluoromethyl)phenyl]pyrazolo[4,3-b]pyridin-1-yl]ethanone; | 0.036 |
| 75 | 2-[6-[4-Chloro-3-(trifluoromethyl)phenyl]pyrazolo[4,3-b]pyridin-1-yl]-1-cyclopropyl-ethanone; | 0.076 |
| 76 | 1-Cyclopropyl-2-[6-[3-(difluoromethyl)-4-fluoro-phenyl]pyrazolo[4,3-b]pyridin-1-yl]ethanone; | 0.018 |
| 77 | 1-Cyclopropyl-2-[6-[3-(difluoromethoxy)-4-fluoro-phenyl]pyrazolo[4,3-b]pyridin-1-yl]ethanone; | 0.014 |
| 78 | 1-Cyclopropyl-2-[6-(4-fluoro-2,3-dimethyl-phenyl)pyrazolo[4,3-b]pyridin-1-yl]ethanone; | 0.085 |
| 79 | 1-Cyclopropyl-2-[6-(2,3,4-trifluorophenyl)pyrazolo[4,3-b]pyridin-1-yl]ethanone; | 0.030 |
| 80 | (RS)-1-(Ethylsulfinylmethyl)-6-(3-fluorophenyl)pyrazolo[4,3-b]pyridine; | 0.823 |
| 81 | (RS)-1-(Ethylsulfinylmethyl)-6-[3-(trifluoromethyl)phenyl]pyrazolo[4,3-b]pyridine; | 0.128 |
| 82 | (RS) 6-(3,4-Difluorophenyl)-1-(ethylsulfinylmethyl)pyrazolo[4,3-b]pyridine; | 0.893 |
| 83 | (RS)-6-(3-(Difluoromethyl)-4-fluorophenyl)-1-((ethylsulfinyl)methyl)-1H-pyrazolo[4,3-b]pyridine; | 0.034 |
| 84 | (S*)-6-(3-(Difluoromethyl)-4-fluorophenyl)-1-((ethylsulfinyl)methyl)-1H-pyrazolo[4,3-b]pyridine; | 0.029 |
| 85 | (R*)-6-(3-(Difluoromethyl)-4-fluorophenyl)-1-((ethylsulfinyl)methyl)-1H-pyrazolo[4,3-b]pyridine; | 0.066 |
| 86 | (RS)-1-(Ethylsulfinylmethyl)-6-[2-fluoro-3-(trifluoromethyl)phenyl]pyrazolo[4,3-b]pyridine; | 0.080 |
| 87 | (RS)-6-[4-Chloro-3-(difluoromethoxy)phenyl]-1-(ethylsulfinylmethyl)pyrazolo[4,3-b]pyridine; | 0.109 |
| 88 | (RS)-1-(Ethylsulfinylmethyl)-6-(3,4,5-trifluorophenyl)pyrazolo[4,3-b]pyridine; | 0.736 |
| 89 | 6-(4-Fluoro-3-methyl-phenyl)-1-(2-methoxyethyl)pyrazolo[4,3-b]pyridine; | 0.754 |
| 90 | (RS)-4-Methoxy-1-[6-[3-(trifluoromethyl)phenyl]pyrazolo[4,3-b]pyridin-1-yl]butan-2-ol; | 1.420 |
| 91 | (RS)-1-[6-(3,4-Difluorophenyl)pyrazolo[4,3-b]pyridin-1-yl]butan-2-ol; | 0.526 |
| 92 | (RS)-1-[6-[3-(difluoromethoxy)-4-fluoro-phenyl]pyrazolo[4,3-b]pyridin-1-yl]butan-2-ol; | 0.282 |
| 93 | (RS)-1-[6-[4-Chloro-3-(difluoromethoxy)phenyl]pyrazolo[4,3-b]pyridin-1-yl]butan-2-ol; | 0.415 |
| 94 | (RS)-1-[6-(3,4-Difluorophenyl)-3-fluoro-pyrazolo[4,3-b]pyridin-1-yl]butan-2-ol; | 0.965 |
| 95 | (RS)-1-[6-[3-(1,1-Difluoroethyl)phenyl]pyrazolo[4,3-b]pyridin-1-yl]butan-2-ol; | 0.272 |

TABLE 3-continued

| Ex # | Compound Name | GluN2B Standard Assay IC$_{50}$ (μM) |
|---|---|---|
| 96 | (RS)-3-Methyl-1-(6-phenylpyrazolo[4,3-b]pyridin-1-yl)butan-2-ol; | 1.530 |
| 97 | (RS)-3-Methyl-1-[6-(3,4,5-trifluorophenyl)pyrazolo[4,3-b]pyridin-1-yl]butan-2-ol; | 0.591 |
| 98 | 1-(2,2-Difluorobutyl)-6-[3-(difluoromethyl)-4-fluoro-phenyl]pyrazolo[4,3-b]pyridine; | 0.089 |
| 99 | 1-(2,2-Difluorobutyl)-6-[3-(difluoromethoxy)-4-fluoro-phenyl]pyrazolo[4,3-b]pyridine; | 0.213 |
| 100 | (RS)-1-Cyclopropyl-2-[6-[3-(trifluoromethyl)phenyl]pyrazolo[4,3-b]pyridin-1-yl]ethanol; | 0.290 |
| 101 | (RS)-1-Cyclopropyl-2-[6-(4-fluoro-3-methyl-phenyl)pyrazolo[4,3-b]pyridin-1-yl]ethanol; | 0.167 |
| 102 | (R)-1-Cyclopropyl-2-[6-(4-fluoro-3-methyl-phenyl)pyrazolo[4,3-b]pyridin-1-yl]ethanol; | 0.109 |
| 103 | (S)-1-Cyclopropyl-2-[6-(4-fluoro-3-methyl-phenyl)pyrazolo[4,3-b]pyridin-1-yl]ethanol; | 0.272 |
| 104 | (RS)-1-Cyclopropyl-2-(6-(3-(difluoromethyl)-4-fluorophenyl)-1H-pyrazolo[4,3-b]pyridin-1-yl)ethan-1-ol; | 0.165 |
| 105 | (E/Z)-N-Methoxy-3-methyl-1-[6-[3-(trifluoromethyl)phenyl]pyrazolo[4,3-b]pyridin-1-yl]butan-2-imine; | 5.250 |
| 106 | (E/Z)-1-Cyclopropyl-2-[6-[3-(trifluoromethyl)phenyl]pyrazolo[4,3-b]pyridin-1-yl]ethanone oxime; | 1.490 |
| 107 | (E/Z)-1-Cyclopropyl-2-[6-[3-(difluoromethyl)-4-fluoro-phenyl]pyrazolo[4,3-b]pyridin-1-yl]ethanone oxime; | 0.065 |
| 108 | 1-(2-Cyclopropyl-2,2-difluoro-ethyl)-6-[3-(difluoromethyl)-4-fluoro-phenyl]pyrazolo[4,3-b]pyridine; | 0.045 |
| 109 | 1-(2-Cyclopropyl-2,2-difluoro-ethyl)-6-[3-(difluoromethoxy)-4-fluoro-phenyl]pyrazolo[4,3-b]pyridine; | 0.069 |
| 110 | 6-[3-(Difluoromethyl)-4-fluoro-phenyl]-1-[(3-methyloxetan-3-yl)methyl]pyrazolo[4,3-b]pyridine; | 2.060 |
| 111 | (RS)-1-(Tetrahydrofuran-2-ylmethyl)-6-[3-(trifluoromethyl)phenyl]pyrazolo[4,3-b]pyridine; | 0.093 |
| 112 | (RS)-6-[3-(Difluoromethoxy)-4-fluoro-phenyl]-1-(tetrahydrofuran-2-ylmethyl)pyrazolo[4,3-b]pyridine; | 0.113 |
| 113 | (RS)-6-[3-(Difluoromethoxy)-4-fluoro-phenyl]-1-(tetrahydrofuran-3-ylmethyl)pyrazolo[4,3-b]pyridine; | 0.023 |
| 114 | (RS)-5-((6-(3-(Difluoromethoxy)-4-fluorophenyl)-1H-pyrazolo[4,3-b]pyridin-1-yl)methyl)-1-methylpyrrolidin-2-one; | >2.99985 |
| 115 | (RS)-5-[[6-(Difluoromethyl)-4-fluoro-phenyl]pyrazolo[4,3-b]pyridin-1-yl]methyl]-1-methyl-pyrrolidin-2-one; | >2.99985 |
| 116 | (RS)-3-[[6-[3-(Difluoromethyl)-4-fluoro-phenyl]pyrazolo[4,3-b]pyridin-1-yl]methyl]-1-methyl-pyrrolidin-2-one; | 0.303 |
| 117 | (S)-3-[[6-[3-(Difluoromethyl)-4-fluoro-phenyl]pyrazolo[4,3-b]pyridin-1-yl]methyl]-1-methyl-pyrrolidin-2-one; | 1.210 |
| 118 | (R)-3-[[6-[3-(Difluoromethyl)-4-fluoro-phenyl]pyrazolo[4,3-b]pyridin-1-yl]methyl]-1-methyl-pyrrolidin-2-one; | 0.125 |
| 119 | (RS)-3-((6-(3-(Difluoromethoxy)-4-fluorophenyl)-1H-pyrazolo[4,3-b]pyridin-1-yl)methyl)-1-methylpyrrolidin-2-one; | 0.352 |
| 120 | (RS)-4-[[6-[3-(Difluoromethyl)-4-fluoro-phenyl]pyrazolo[4,3-b]pyridin-1-yl]methyl]-1-methyl-pyrrolidin-2-one; | 0.089 |
| 121 | (S)-4-[[6-[3-(Difluoromethyl)-4-fluoro-phenyl]pyrazolo[4,3-b]pyridin-1-yl]methyl]-1-methyl-pyrrolidin-2-one; | 0.685 |
| 122 | (R)-4-[[6-[3-(Difluoromethyl)-4-fluoro-phenyl]pyrazolo[4,3-b]pyridin-1-yl]methyl]-1-methyl-pyrrolidin-2-one; | 0.120 |
| 123 | (RS)-4-((6-(3-(difluoromethoxy)-4-fluorophenyl)-1H-pyrazolo[4,3-b]pyridin-1-yl)methyl)-3-methyloxazolidin-2-one; | 2.830 |
| 124 | (RS)-4[[6-[3-(Difluoromethyl)-4-fluoro-phenyl]pyrazolo[4,3-b]pyridin-1-yl]methyl]-3-methyl-oxazolidin-2-one; | 1.890 |
| 125 | (RS)-5-[[6-[3-(Difluoromethoxy)-4-fluoro-phenyl]pyrazolo[4,3-b]pyridin-1-yl]methyl]oxazolidin-2-one; | 0.498 |
| 126 | (RS)-5-[[6-[4-Chloro-3-(difluoromethoxy)phenyl]pyrazolo[4,3-b]pyridin-1-yl]methyl]oxazolidin-2-one; | 0.306 |
| 127 | (RS)-5-[[6-[3-(1,1-Difluoroethyl)-4-fluoro-phenyl]pyrazolo[4,3-b]pyridin-1-yl]methyl]oxazolidin-2-one; | 0.973 |

TABLE 3-continued

| Ex # | Compound Name | GluN2B Standard Assay IC$_{50}$ (µM) |
|---|---|---|
| 128 | (RS)-5-((6-(3-(Difluoromethoxy)-4-fluorophenyl)-1H-pyrazolo[4,3-b]pyridin-1-yl)methyl)-3-methyloxazolidin-2-one; | 0.165 |
| 129 | (5R)-54[643-(Difluoromethyl)-4-fluoro-phenyl]pyrazolo[4,3-b]pyridin-1-yl]methyl]-3-methyl-oxazolidin-2-one; | 0.030 |
| 130 | (5S)-5-[[6-[3-(Difluoromethyl)-4-fluoro-phenyl]pyrazolo[4,3-b]pyridin-1-yl]methyl]-3-methyl-oxazolidin-2-one; | 0.478 |
| 131 | (RS)-54[6-[3-(Difluoromethyl)-4-fluoro-phenyl]pyrazolo[4,3-b]pyridin-1-yl]methyl]-3-ethyl-oxazolidin-2-one; | 0.193 |
| 132 | (S)-5-[[6-[3-(Difluoromethyl)-4-fluoro-phenyl]pyrazolo[4,3-b]pyridin-1-yl]methyl]-3-ethyl-oxazolidin-2-one; | 1.430 |
| 133 | (R)-5-[[643-(Difluoromethyl)-4-fluoro-phenyl]pyrazolo[4,3-b]pyridin-1-yl]methyl]-3-ethyl-oxazolidin-2-one; | 0.204 |
| 134 | (RS)-3-Cyclopropyl-5-[[6-[3-(difluoromethyl)-4-fluoro-phenyl]pyrazolo[4,3-b]pyridin-1-yl]methyl]oxazolidin-2-one; | 1.630 |
| 135 | (S)-3-Cyclopropyl-5-[[6-[3-(difluoromethyl)-4-fluoro-phenyl]pyrazolo[4,3-b]pyridin-1-yl]methyl]oxazolidin-2-one; | >2.99985 |
| 136 | (R)-3-Cyclopropyl-5-[[6-[3-(difluoromethyl)-4-fluoro-phenyl]pyrazolo[4,3-b]pyridin-1-yl]methyl]oxazolidin-2-one; | 0.997 |
| 137 | 2-[6-[3-(Difluoromethyl)-4-fluoro-phenyl]pyrazolo[4,3-b]pyridin-1-yl]-1-(2-thienyl)ethanone; | 0.036 |
| 138 | 2-[6-[3-(Difluoromethyl)-4-fluoro-phenyl]pyrazolo[4,3-b]pyridin-1-yl]-1-(3-thienyl)ethanone; | 0.100 |
| 139 | 2-[6-[3-(Difluoromethyl)-4-fluoro-phenyl]pyrazolo[4,3-b]pyridin-1-yl]-1-(4-pyridyl)ethanone; | 0.118 |
| 140 | 2-(6-(3-(Difluoromethyl)-4-fluorophenyl)-1H-pyrazolo[4,3-b]pyridin-1-yl)-1-(3-fluoropyridin-2-yl)ethan-1-one; | 0.191 |
| 141 | 2-(6-(3-(Difluoromethyl)-4-fluorophenyl)-1H-pyrazolo[4,3-b]pyridin-1-yl)-1-(3,5-difluoropyridin-2-yl)ethan-1-one; and | 0.409 |
| 142 | 2-(6-(3-(Difluoromethyl)-4-fluorophenyl)-1H-pyrazolo[4,3-b]pyridin-1-yl)-1-(pyrazin-2-yl)ethan-1-one. | 0.074 |

Protocol for Liver Microsomal Stability (Extraction Ratio)

Liver Microsomal Stability.

Microsomal stability studies (Chrovian et al, "1H-Pyrrolo[3,2-b]pyridine GluN2B-Selective Negative Allosteric Modulators". ACS Med Chem Lett. 2019 Jan. 10; 10(3): 261-266) were conducted on a Biomek® FX Robotic Liquid Handling Workstation (Beckman Coulter, Brea, Calif.), which consists of a 96-channel pipette head, a 12-position workstation deck, and a plate incubator. Test compounds (1 µm) were spiked in a reaction mix consisting of 100 mM potassium phosphate buffer (pH 7.4), 3 mM MgCl$_2$, and 0.5 mg/mL liver microsomes from mouse, rat, and human (BD Gentest). The reaction was brought to 37° C. and initiated by adding NADPH to a final concentration of 1 mM. After mixing on the plate deck, 50 µL aliquots were excised from the reaction plate at 0, 5, 10, 20, 40, and 60 min and quenched with four volumes of acetonitrile spiked with 500 µg/nL of the internal standard phenytoin. Quenched plates were centrifuged at 5700 rpm for 10 min at 4° C., and supernatant was diluted 1:3 in water before LC/MS/MS analysis. The compound half-lives were derived from plots of the ln of percent remaining compound over time to determine the intrinsic clearance. The predicted hepatic clearance was derived from the intrinsic clearance value using equations from the well-stirred model (Current Drug Metabolism, 2008, 9, 940-951), where no correction was made plasma protein binding and the blood to plasma concentration ratio was assumed to be one. The extraction ratio (ER) was calculated by dividing the predicted hepatic clearance by species blood flow (Q), where Q is 90, 55, and 21.7 mL/min/kg for mouse, rat and human, respectively.

Results of the assay performed on the compounds of Examples are shown in Table 4.

| Example # | Extraction Ratio @ 1 µM |
|---|---|
| 4 | 0.66 |
| 25 | 0.64 |
| 36 | 0.72 |
| 38 | 0.61 |
| 42 | 0.63 |
| 61 | 0.43 |
| 78 | 0.52 |
| 85 | 0.46 |
| 86 | 0.50 |
| 131 | 0.58 |

Specific Embodiments

The present disclosure is exemplified by specific embodiments 1 to 27 below.

1. A compound having the structure of Formula (I):

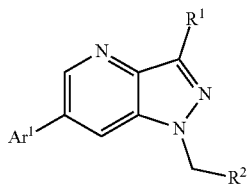

wherein
R$^1$ is H, halo, or CH$_3$;
Ar$^1$ is selected from the group consisting of:
   (a) phenyl;
   (b) phenyl substituted with one member selected from the group consisting of: halo, C$_{1-6}$alkyl, C$_{1-6}$perhaloalkyl, and OC$_{1-6}$perhaloalkyl;
   (c) phenyl substituted with two or three members each independently selected from the group consisting of: halo, C$_{1-6}$alkyl, C$_{1-6}$perhaloalkyl, and OC$_{1-6}$perhaloalkyl; and
   (d) thienyl substituted with one member selected from the group consisting of: halo, and C$_{1-6}$alkyl;
R$^2$ is selected from the group consisting of:
   (e)

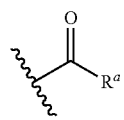

wherein R$^a$ is selected from the group consisting of: C$_{1-6}$alkyl; C$_{3-6}$cycloalkyl; thienyl; pyridyl; pyridyl substituted with one or two F members; pyrazinyl;

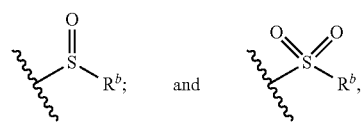

wherein R is C$_{1-6}$alkyl;
   (f) C$_{1-6}$alkyl substituted with one, two, or three members each independently selected from the group consisting of: OH, halo, OC$_{1-6}$alkyl, (=N—OH), (=N—OCH$_3$), and cyclopropyl; and
   (g) oxetanyl; oxetanyl substituted with C$_{1-6}$alkyl; tetrahydrofuranyl; oxazolidinone; oxazolidinone substituted with C$_{1-4}$alkyl, or cyclopropyl; and pyrrolidinone substituted with C$_{1-4}$alkyl;
   and pharmaceutically acceptable salts, solvates, stereoisomers, isotopic variants, or N-oxides thereof.
2. The compound of embodiment 1, wherein R$^1$ is H.
3. The compound of embodiment 1, wherein R$^1$ is F.
4. The compound of embodiment 1, wherein R$^1$ is CH$_3$.
5. The compound of embodiment 1, wherein Ar$^1$ is phenyl.
6. The compound of embodiment 1, wherein Ar$^1$ is phenyl substituted with one member selected from the group consisting of: F, CH$_3$, CF$_2$H, CF$_2$CH$_3$, CF$_3$, and OCF$_3$.
7. The compound of embodiment 1, wherein Ar$^1$ is selected from the group consisting of:

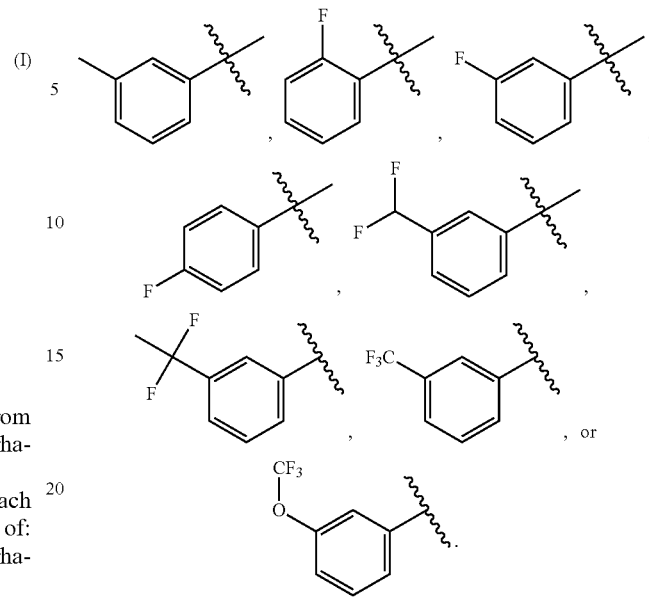

8. The compound of embodiment 1, wherein Ar$^1$ is phenyl substituted with two members each independently selected from the group consisting of: F, Cl, CH$_3$, CF$_2$H, CF$_3$, CF$_2$CH$_3$, and OCF$_2$H.
9. The compound of embodiment 1, wherein Ar$^1$ is selected from the group consisting of:

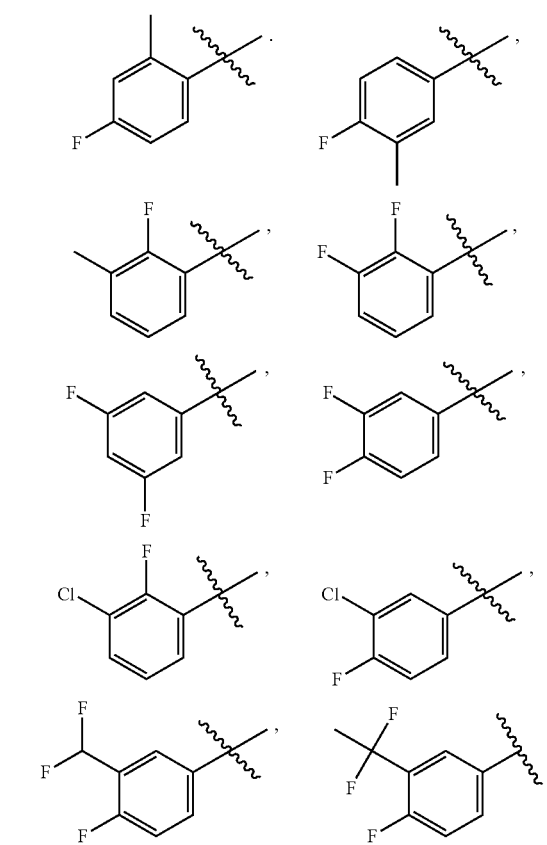

-continued

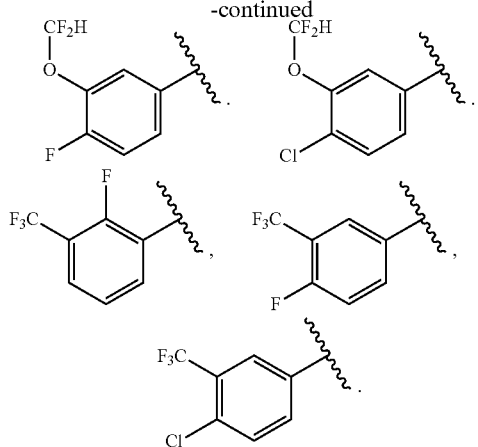

10. The compound of embodiment 1, wherein Ar¹ is phenyl substituted with three members each independently selected from the group consisting of: F and CH₃.

11. The compound of embodiment 1, wherein Ar¹ is

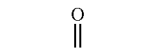

12. The compound of embodiment 1, wherein Ar¹ is thienyl is substituted with Cl or CH₃.

13. The compound of embodiment 1, wherein Ar¹ is or.

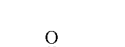

14. The compound of embodiment 1, wherein R² is

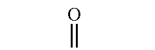

-continued

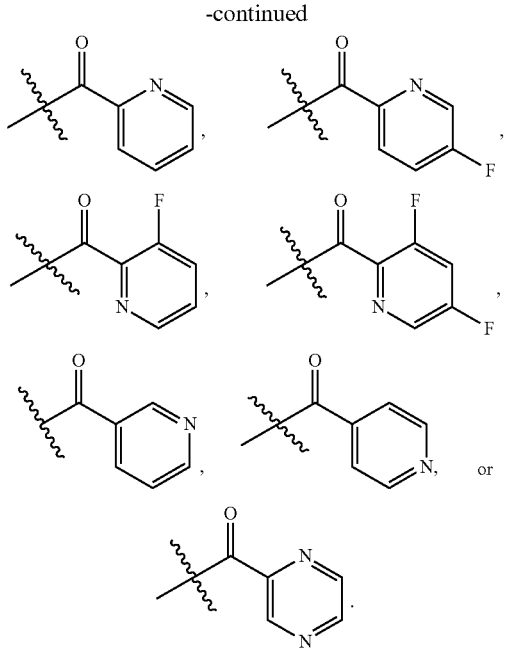

15. The compound of embodiment 1, wherein R² is

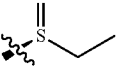

16. The compound of embodiment 1, wherein R² is

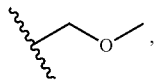

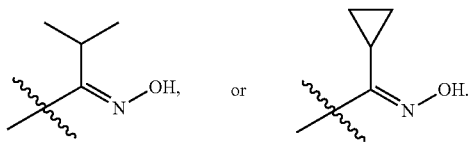

17. The compound of embodiment 1, wherein R² is

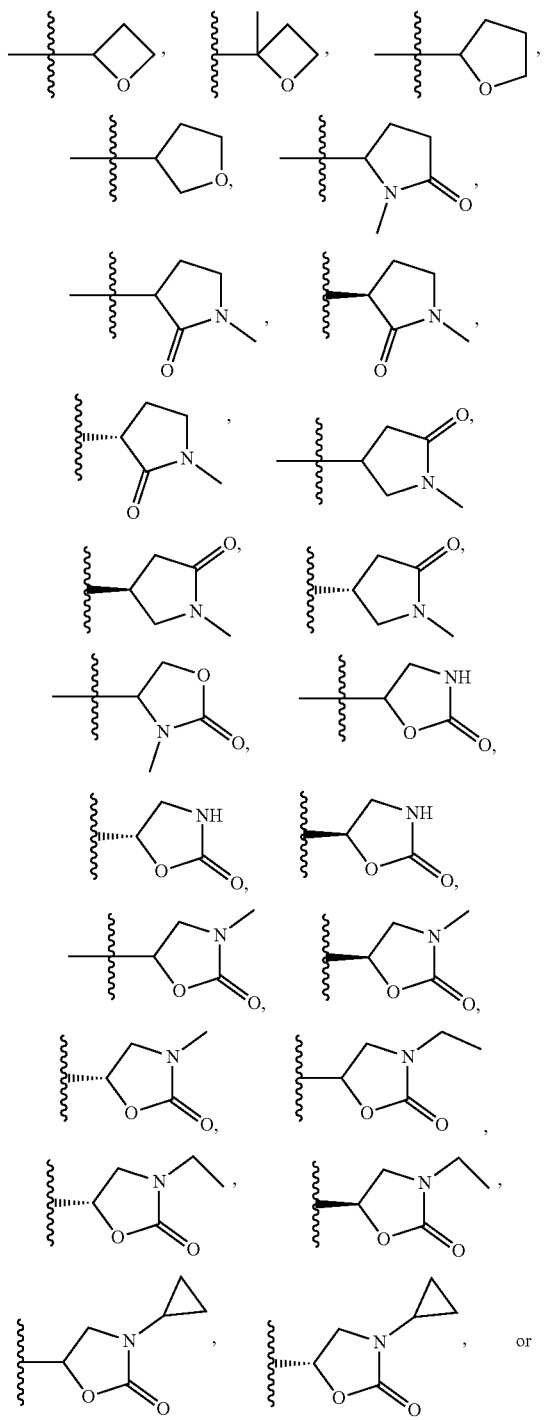

18. The compound of embodiment 1, having the structure of Formula (IA):

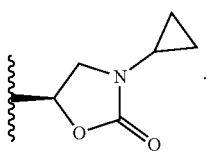 [SMILES: *[C@H]1CN(C2CC2)C(=O)O1]

(IA)

wherein

HAL is F or Cl;

R¹ is H, F, or CH₃;

R² is selected from the group consisting of:

(a) (S=O)CH₂CH₃; (SO₂)CH₂CH₃; or

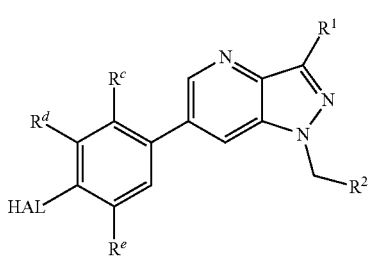

wherein $R^a$ is selected from the group consisting of: CH₃, CH₂CH₃, CH(CH₃)₂, cyclopropyl, cyclobutyl,

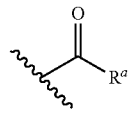

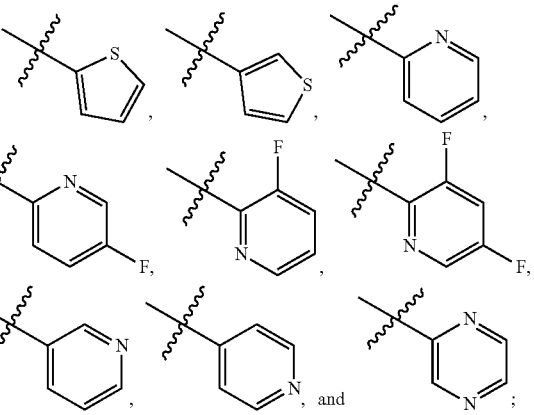

(b) CH₂OCH₃, CH(OH)(CH₂CH₃), CH(OH)CH(CH₃)₂, CF₂CH₂CH₃, CF₂(cyclopropyl), CH(OCH₃)(cyclopropyl), CH(OH)(cyclopropyl), or

135

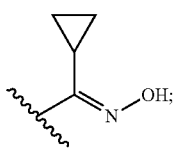 [SMILES: */C(=N/O)C1CC1]

and (c)

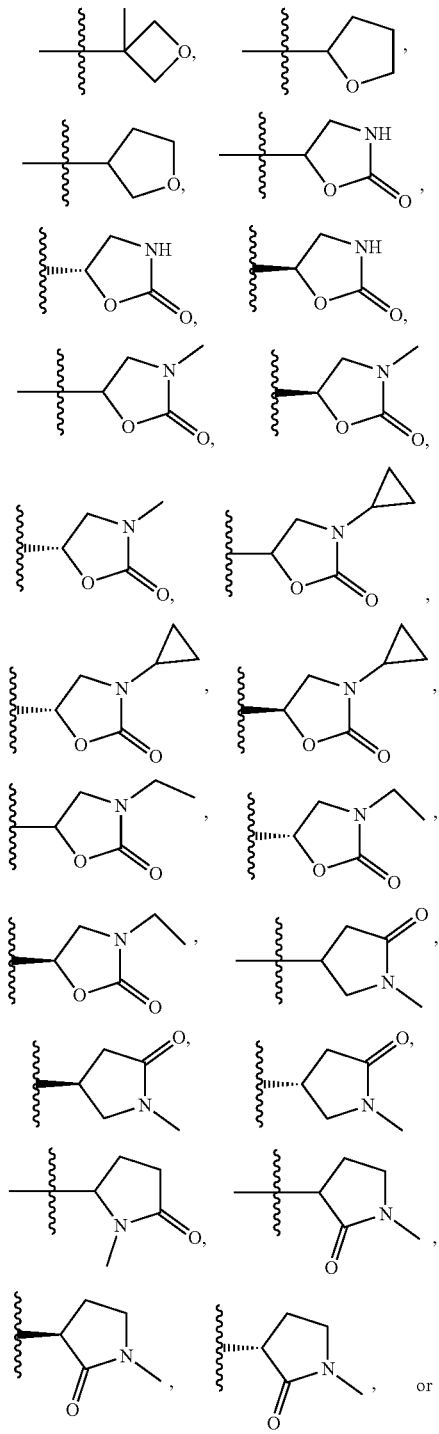

136

-continued

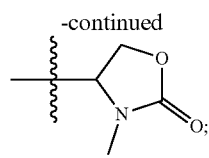

$R^c$ is H, F or $CH_3$;
$R^d$ is selected from the group consisting of: H, F, Cl, $CH_3$, $CF_2H$, $CF_2CH_3$, $CF_3$, and $OCF_2H$; and
$R^e$ is H or F; wherein when $R^e$ is F, $R^c$ is H;
and pharmaceutically acceptable salts, solvates, stereoisomers, isotopic variants, or N-oxides thereof.

19. The compound of embodiment 18, where HAL is F; R is H; $R^c$ is H; and $R^e$ is H.

20. The compound of embodiment 1, having the structure of Formula (IB):

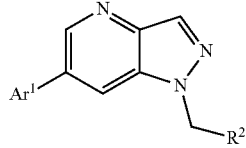

(IB)

wherein
Ar¹ is selected from the group consisting of:
(a) phenyl, 3-methylphenyl, 2-fluorophenyl, 3-fluorophenyl, 3-(difluoromethyl)phenyl, 3-(1,1-difluoroethyl)phenyl, 3-(trifluoromethyl)phenyl, 3-(trifluoromethoxy)phenyl, 5-methyl-2-thienyl, or 5-chloro-2-thienyl; and
(b) 2-fluoro-3-methyl-phenyl, 2,3-difluorophenyl, 3,5-difluorophenyl, 3-chloro-2-fluoro-phenyl, 2-fluoro-3-(trifluoromethyl)phenyl, 4-chloro-3-(difluoromethoxy)phenyl, or 4-chloro-3-(trifluoromethyl)phenyl; and
R² is selected from the group consisting of: (S=O)CH₂CH₃, (C=O)CH₂CH₃, (C=O)CH(CH₃)₂, and (C=O)cyclopropyl;
and pharmaceutically acceptable salts, solvates, stereoisomers, isotopic variants, or N-oxides thereof.

21. A compound selected from the group consisting of:
1-[6-(3,5-Difluorophenyl)pyrazolo[4,3-b]pyridin-1-yl]butan-2-one;
3-Methyl-1-[6-[3-(trifluoromethyl)phenyl]pyrazolo[4,3-b]pyridin-1-yl]butan-2-one;
(RS)-3-Methyl-1-[6-[3-(trifluoromethyl)phenyl]pyrazolo[4,3-b]pyridin-1-yl]butan-2-ol;
1-[6-[3-(Difluoromethyl)-4-fluoro-phenyl]pyrazolo[4,3-b]pyridin-1-yl]butan-2-one;
(RS)-1-[6-[3-(Difluoromethyl)-4-fluoro-phenyl]pyrazolo[4,3-b]pyridin-1-yl]butan-2-ol;
(E/Z)-3-Methyl-1-[6-[3-(trifluoromethyl)phenyl]pyrazolo[4,3-b]pyridin-1-yl]butan-2-one oxime;
1-[6-(4-Fluoro-3-methyl-phenyl)pyrazolo[4,3-b]pyridin-1-yl]-3-methyl-butan-2-one;
(RS)-1-[6-(4-Fluoro-3-methyl-phenyl)pyrazolo[4,3-b]pyridin-1-yl]-3-methyl-butan-2-ol;
1-Cyclopropyl-2-[6-(3,4,5-trifluorophenyl)pyrazolo[4,3-b]pyridin-1-yl]ethanone;
(RS)-1-Cyclopropyl-2-[6-(3,4,5-trifluorophenyl)pyrazolo[4,3-b]pyridin-1-yl]ethanol;

(RS)-1-(2-Cyclopropyl-2-methoxy-ethyl)-6-(3,4,5-trifluorophenyl)pyrazolo[4,3-b]pyridine;
(RS)-6-[3-(Difluoromethoxy)-4-fluoro-phenyl]-1-(ethylsulfinylmethyl)pyrazolo[4,3-b]pyridine;
6-[3-(Difluoromethoxy)-4-fluoro-phenyl]-1-(ethylsulfonylmethyl)pyrazolo[4,3-b]pyridine;
2-[6-[3-(Difluoromethyl)-4-fluoro-phenyl]pyrazolo[4,3-b]pyridin-1-yl]-1-(2-pyridyl)ethanone;
2-(6-(3-(Difluoromethyl)-4-fluorophenyl)-1H-pyrazolo[4,3-b]pyridin-1-yl)-1-(5-fluoropyridin-2-yl)ethan-1-one;
2-(6-(3-(Difluoromethyl)-4-fluorophenyl)-1H-pyrazolo[4,3-b]pyridin-1-yl)-1-(pyridin-3-yl)ethan-1-one;
(RS)-1-(Oxetan-2-ylmethyl)-6-[3-(trifluoromethyl)phenyl]pyrazolo[4,3-b]pyridine;
(RS)-6-[3-(Difluoromethyl)-4-fluoro-phenyl]-1-(tetrahydrofuran-2-ylmethyl)pyrazolo[4,3-b]pyridine;
(RS)-4-[[6-[3-(Difluoromethoxy)-4-fluoro-phenyl]pyrazolo[4,3-b]pyridin-1-yl]methyl]-1-methyl-pyrrolidin-2-one;
(RS)-5-[[6-[3-(Difluoromethyl)-4-fluoro-phenyl]pyrazolo[4,3-b]pyridin-1-yl]methyl]oxazolidin-2-one;
(S)-5-[[6-[3-(Difluoromethyl)-4-fluoro-phenyl]pyrazolo[4,3-b]pyridin-1-yl]methyl]oxazolidin-2-one;
(R)-5-[[6-[3-(Difluoromethyl)-4-fluoro-phenyl]pyrazolo[4,3-b]pyridin-1-yl]methyl]oxazolidin-2-one;
1-[6-[3-(Difluoromethyl)-4-fluoro-phenyl]pyrazolo[4,3-b]pyridin-1-yl]propan-2-one;
1-[6-(4-Fluoro-3-methyl-phenyl)pyrazolo[4,3-b]pyridin-1-yl]propan-2-one;
1-[6-[3-(Difluoromethoxy)-4-fluoro-phenyl]pyrazolo[4,3-b]pyridin-1-yl]propan-2-one;
1-[6-[4-Chloro-3-(difluoromethoxy)phenyl]pyrazolo[4,3-b]pyridin-1-yl]propan-2-one;
1-[6-(5-Chloro-2-thienyl)pyrazolo[4,3-b]pyridin-1-yl]butan-2-one;
1-[6-(4-Fluorophenyl)pyrazolo[4,3-b]pyridin-1-yl]butan-2-one;
1-[6-(3-Fluorophenyl)pyrazolo[4,3-b]pyridin-1-yl]butan-2-one;
1-[6-[3-(Difluoromethyl)phenyl]pyrazolo[4,3-b]pyridin-1-yl]butan-2-one;
1-[6-[3-(1,1-Difluoroethyl)phenyl]pyrazolo[4,3-b]pyridin-1-yl]butan-2-one;
1-[6-(4-Fluoro-3-methyl-phenyl)pyrazolo[4,3-b]pyridin-1-yl]butan-2-one;
1-[6-(2,3-Difluorophenyl)pyrazolo[4,3-b]pyridin-1-yl]butan-2-one;
1-[6-(3,4-Difluorophenyl)pyrazolo[4,3-b]pyridin-1-yl]butan-2-one;
1-[6-(3,4-Difluorophenyl)-3-fluoro-pyrazolo[4,3-b]pyridin-1-yl]butan-2-one;
1-(6-(3-(Difluoromethyl)-4-fluorophenyl)-3-methyl-1H-pyrazolo[4,3-b]pyridin-1-yl)butan-2-one;
1-[6-[3-(1,1-Difluoroethyl)-4-fluoro-phenyl]pyrazolo[4,3-b]pyridin-1-yl]butan-2-one;
1-[6-[2-Fluoro-3-(trifluoromethyl)phenyl]pyrazolo[4,3-b]pyridin-1-yl]butan-2-one;
1-[6-[4-Fluoro-3-(trifluoromethyl)phenyl]pyrazolo[4,3-b]pyridin-1-yl]butan-2-one;
1-[6-[3-(Difluoromethoxy)-4-fluoro-phenyl]pyrazolo[4,3-b]pyridin-1-yl]butan-2-one;
1-[6-[4-Chloro-3-(difluoromethoxy)phenyl]pyrazolo[4,3-b]pyridin-1-yl]butan-2-one;
1-[6-(3,4,5-Trifluorophenyl)pyrazolo[4,3-b]pyridin-1-yl]butan-2-one;
1-[6-(2,3,4-Trifluorophenyl)pyrazolo[4,3-b]pyridin-1-yl]butan-2-one;
3-Methyl-1-(6-phenylpyrazolo[4,3-b]pyridin-1-yl)butan-2-one;
1-[6-(4-Fluorophenyl)pyrazolo[4,3-b]pyridin-1-yl]-3-methyl-butan-2-one;
1-[6-(3-Fluorophenyl)pyrazolo[4,3-b]pyridin-1-yl]-3-methyl-butan-2-one;
1-[6-[3-(Difluoromethyl)phenyl]pyrazolo[4,3-b]pyridin-1-yl]-3-methyl-butan-2-one;
1-[6-(2,3-Difluorophenyl)pyrazolo[4,3-b]pyridin-1-yl]-3-methyl-butan-2-one;
1-[6-(3,4-Difluorophenyl)pyrazolo[4,3-b]pyridin-1-yl]-3-methyl-butan-2-one;
1-[6-[2-Fluoro-3-(trifluoromethyl)phenyl]pyrazolo[4,3-b]pyridin-1-yl]-3-methyl-butan-2-one;
1-[6-[4-Fluoro-3-(trifluoromethyl)phenyl]pyrazolo[4,3-b]pyridin-1-yl]-3-methyl-butan-2-one;
1-[6-(4-Fluoro-2-methyl-phenyl)pyrazolo[4,3-b]pyridin-1-yl]-3-methyl-butan-2-one;
3-Methyl-1-[6-(3,4,5-trifluorophenyl)pyrazolo[4,3-b]pyridin-1-yl]butan-2-one;
3-Methyl-1-[6-(2,3,4-trifluorophenyl)pyrazolo[4,3-b]pyridin-1-yl]butan-2-one;
2-[6-(5-Chloro-2-thienyl)pyrazolo[4,3-b]pyridin-1-yl]-1-cyclopropyl-ethanone;
1-Cyclopropyl-2-[6-(5-methyl-2-thienyl)pyrazolo[4,3-b]pyridin-1-yl]ethanone;
1-Cyclopropyl-2-[6-(3-fluorophenyl)pyrazolo[4,3-b]pyridin-1-yl]ethanone;
1-Cyclopropyl-2-[6-(2-fluorophenyl)pyrazolo[4,3-b]pyridin-1-yl]ethanone;
1-Cyclopropyl-2-[6-(4-fluorophenyl)pyrazolo[4,3-b]pyridin-1-yl]ethanone;
1-Cyclopropyl-2-[6-(m-tolyl)pyrazolo[4,3-b]pyridin-1-yl]ethanone;
1-Cyclopropyl-2-[6-[3-(difluoromethyl)phenyl]pyrazolo[4,3-b]pyridin-1-yl]ethanone;
1-Cyclopropyl-2-[6-[3-(trifluoromethyl)phenyl]pyrazolo[4,3-b]pyridin-1-yl]ethanone;
1-Cyclopropyl-2-[6-[3-(trifluoromethoxy)phenyl]pyrazolo[4,3-b]pyridin-1-yl]ethanone;
1-Cyclopropyl-2-[6-(2,3-difluorophenyl)pyrazolo[4,3-b]pyridin-1-yl]ethanone;
1-Cyclopropyl-2-[6-(3,4-difluorophenyl)pyrazolo[4,3-b]pyridin-1-yl]ethanone;
1-Cyclopropyl-2-[6-(3,5-difluorophenyl)pyrazolo[4,3-b]pyridin-1-yl]ethanone;
2-[6-(3-Chloro-2-fluoro-phenyl)pyrazolo[4,3-b]pyridin-1-yl]-1-cyclopropyl-ethanone;
2-[6-(3-Chloro-4-fluoro-phenyl)pyrazolo[4,3-b]pyridin-1-yl]-1-cyclopropyl-ethanone;
1-Cyclopropyl-2-[6-(4-fluoro-3-methyl-phenyl)pyrazolo[4,3-b]pyridin-1-yl]ethanone;
1-Cyclobutyl-2-[6-(4-fluoro-3-methyl-phenyl)pyrazolo[4,3-b]pyridin-1-yl]ethanone;
1-Cyclopropyl-2-[6-(2-fluoro-3-methyl-phenyl)pyrazolo[4,3-b]pyridin-1-yl]ethanone;
1-Cyclopropyl-2-[6-(4-fluoro-2-methyl-phenyl)pyrazolo[4,3-b]pyridin-1-yl]ethanone;
1-Cyclopropyl-2-[6-[2-fluoro-3-(trifluoromethyl)phenyl]pyrazolo[4,3-b]pyridin-1-yl]ethanone;
1-Cyclopropyl-2-[6-[4-fluoro-3-(trifluoromethyl)phenyl]pyrazolo[4,3-b]pyridin-1-yl]ethanone;
2-[6-[4-Chloro-3-(trifluoromethyl)phenyl]pyrazolo[4,3-b]pyridin-1-yl]-1-cyclopropyl-ethanone;
1-Cyclopropyl-2-[6-[3-(difluoromethyl)-4-fluoro-phenyl]pyrazolo[4,3-b]pyridin-1-yl]ethanone;

1-Cyclopropyl-2-[6-[3-(difluoromethoxy)-4-fluoro-phenyl]pyrazolo[4,3-b]pyridin-1-yl]ethanone;
1-Cyclopropyl-2-[6-(4-fluoro-2,3-dimethyl-phenyl)pyrazolo[4,3-b]pyridin-1-yl]ethanone;
1-Cyclopropyl-2-[6-(2,3,4-trifluorophenyl)pyrazolo[4,3-b]pyridin-1-yl]ethanone;
(RS)-1-(Ethylsulfinylmethyl)-6-(3-fluorophenyl)pyrazolo[4,3-b]pyridine;
(RS)-1-(Ethylsulfinylmethyl)-6-[3-(trifluoromethyl)phenyl]pyrazolo[4,3-b]pyridine;
(RS) 6-(3,4-Difluorophenyl)-1-(ethylsulfinylmethyl)pyrazolo[4,3-b]pyridine;
(RS)-6-(3-(Difluoromethyl)-4-fluorophenyl)-1-((ethylsulfinyl)methyl)-1H-pyrazolo[4,3-b]pyridine;
(S*)-6-(3-(Difluoromethyl)-4-fluorophenyl)-1-((ethylsulfinyl)methyl)-1H-pyrazolo[4,3-b]pyridine;
(R*)-6-(3-(Difluoromethyl)-4-fluorophenyl)-1-((ethylsulfinyl)methyl)-1H-pyrazolo[4,3-b]pyridine;
(RS)-1-(Ethylsulfinylmethyl)-6-[2-fluoro-3-(trifluoromethyl)phenyl]pyrazolo[4,3-b]pyridine;
(RS)-6-[4-Chloro-3-(difluoromethoxy)phenyl]-1-(ethylsulfinylmethyl)pyrazolo[4,3-b]pyridine;
(RS)-1-(Ethylsulfinylmethyl)-6-(3,4,5-trifluorophenyl)pyrazolo[4,3-b]pyridine;
6-(4-Fluoro-3-methyl-phenyl)-1-(2-methoxyethyl)pyrazolo[4,3-b]pyridine;
(RS)-4-Methoxy-1-[6-[3-(trifluoromethyl)phenyl]pyrazolo[4,3-b]pyridin-1-yl]butan-2-ol;
(RS)-1-[6-(3,4-Difluorophenyl)pyrazolo[4,3-b]pyridin-1-yl]butan-2-ol;
(RS)-1-[6-[3-(Difluoromethoxy)-4-fluoro-phenyl]pyrazolo[4,3-b]pyridin-1-yl]butan-2-ol;
(RS)-1-[6-[4-Chloro-3-(difluoromethoxy)phenyl]pyrazolo[4,3-b]pyridin-1-yl]butan-2-ol;
(RS)-1-[6-(3,4-Difluorophenyl)-3-fluoro-pyrazolo[4,3-b]pyridin-1-yl]butan-2-ol;
(RS)-1-[6-[3-(1,1-Difluoroethyl)phenyl]pyrazolo[4,3-b]pyridin-1-yl]butan-2-ol;
(RS)-3-Methyl-1-(6-phenylpyrazolo[4,3-b]pyridin-1-yl)butan-2-ol;
(RS)-3-Methyl-1-[6-(3,4,5-trifluorophenyl)pyrazolo[4,3-b]pyridin-1-yl]butan-2-ol;
1-(2,2-Difluorobutyl)-6-[3-(difluoromethyl)-4-fluoro-phenyl]pyrazolo[4,3-b]pyridine;
1-(2,2-Difluorobutyl)-6-[3-(difluoromethoxy)-4-fluoro-phenyl]pyrazolo[4,3-b]pyridine;
(RS)-1-Cyclopropyl-2-[6-[3-(trifluoromethyl)phenyl]pyrazolo[4,3-b]pyridin-1-yl]ethanol;
(RS)-1-Cyclopropyl-2-[6-(4-fluoro-3-methyl-phenyl)pyrazolo[4,3-b]pyridin-1-yl]ethanol;
(R)-1-Cyclopropyl-2-[6-(4-fluoro-3-methyl-phenyl)pyrazolo[4,3-b]pyridin-1-yl]ethanol;
(S)-1-Cyclopropyl-2-[6-(4-fluoro-3-methyl-phenyl)pyrazolo[4,3-b]pyridin-1-yl]ethanol;
(RS)-1-Cyclopropyl-2-(6-(3-(difluoromethyl)-4-fluorophenyl)-1H-pyrazolo[4,3-b]pyridin-1-yl)ethan-1-ol;
(E/Z)-N-Methoxy-3-methyl-1-[6-[3-(trifluoromethyl)phenyl]pyrazolo[4,3-b]pyridin-1-yl]butan-2-imine;
(E/Z)-1-Cyclopropyl-2-[6-[3-(trifluoromethyl)phenyl]pyrazolo[4,3-b]pyridin-1-yl]ethanone oxime;
(E/Z)-1-Cyclopropyl-2-[6-[3-(difluoromethyl)-4-fluoro-phenyl]pyrazolo[4,3-b]pyridin-1-yl]ethanone oxime;
1-(2-Cyclopropyl-2,2-difluoro-ethyl)-6-[3-(difluoromethyl)-4-fluoro-phenyl]pyrazolo[4,3-b]pyridine;
1-(2-Cyclopropyl-2,2-difluoro-ethyl)-6-[3-(difluoromethoxy)-4-fluoro-phenyl]pyrazolo[4,3-b]pyridine;
6-[3-(Difluoromethyl)-4-fluoro-phenyl]-1-[(3-methyloxetan-3-yl)methyl]pyrazolo[4,3-b]pyridine;
(RS)-1-(Tetrahydrofuran-2-ylmethyl)-6-[3-(trifluoromethyl)phenyl]pyrazolo[4,3-b]pyridine;
(RS)-6-[3-(Difluoromethoxy)-4-fluoro-phenyl]-1-(tetrahydrofuran-2-ylmethyl)pyrazolo[4,3-b]pyridine;
(RS)-6-[3-(Difluoromethyl)-4-fluoro-phenyl]-1-(tetrahydrofuran-3-ylmethyl)pyrazolo[4,3-b]pyridine;
(RS)-5-((6-(3-(Difluoromethoxy)-4-fluorophenyl)-1H-pyrazolo[4,3-b]pyridin-1-yl)methyl)-1-methylpyrrolidin-2-one;
(RS)-5-[[6-[3-(Difluoromethyl)-4-fluoro-phenyl]pyrazolo[4,3-b]pyridin-1-yl]methyl]-1-methyl-pyrrolidin-2-one;
(RS)-3-[[6-[3-(Difluoromethyl)-4-fluoro-phenyl]pyrazolo[4,3-b]pyridin-1-yl]methyl]-1-methyl-pyrrolidin-2-one;
(S)-3-[[6-[3-(Difluoromethyl)-4-fluoro-phenyl]pyrazolo[4,3-b]pyridin-1-yl]methyl]-1-methyl-pyrrolidin-2-one;
(R)-3-[[6-[3-(Difluoromethyl)-4-fluoro-phenyl]pyrazolo[4,3-b]pyridin-1-yl]methyl]-1-methyl-pyrrolidin-2-one;
(RS)-3-((6-(3-(Difluoromethoxy)-4-fluorophenyl)-1H-pyrazolo[4,3-b]pyridin-1-yl)methyl)-1-methylpyrrolidin-2-one;
(RS)-4-[[6-[3-(Difluoromethyl)-4-fluoro-phenyl]pyrazolo[4,3-b]pyridin-1-yl]methyl]-1-methyl-pyrrolidin-2-one;
(S)-4-[[6-[3-(Difluoromethyl)-4-fluoro-phenyl]pyrazolo[4,3-b]pyridin-1-yl]methyl]-1-methyl-pyrrolidin-2-one;
(R)-4-[[6-[3-(Difluoromethyl)-4-fluoro-phenyl]pyrazolo[4,3-b]pyridin-1-yl]methyl]-1-methyl-pyrrolidin-2-one;
(RS)-4-((6-(3-(difluoromethoxy)-4-fluorophenyl)-1H-pyrazolo[4,3-b]pyridin-1-yl)methyl)-3-methyloxazolidin-2-one;
(RS)-4-[[6-[3-(Difluoromethyl)-4-fluoro-phenyl]pyrazolo[4,3-b]pyridin-1-yl]methyl]-3-methyl-oxazolidin-2-one;
(RS)-5-[[6-[3-(Difluoromethoxy)-4-fluoro-phenyl]pyrazolo[4,3-b]pyridin-1-yl]methyl]oxazolidin-2-one;
(RS)-5-[[6-[4-Chloro-3-(difluoromethoxy)phenyl]pyrazolo[4,3-b]pyridin-1-yl]methyl]oxazolidin-2-one;
(RS)-5-[[6-[3-(1,1-Difluoroethyl)-4-fluoro-phenyl]pyrazolo[4,3-b]pyridin-1-yl]methyl]oxazolidin-2-one;
(RS)-5-((6-(3-(Difluoromethoxy)-4-fluorophenyl)-1H-pyrazolo[4,3-b]pyridin-1-yl)methyl)-3-methyloxazolidin-2-one;
(5R)-5-[[6-[3-(Difluoromethyl)-4-fluoro-phenyl]pyrazolo[4,3-b]pyridin-1-yl]methyl]-3-methyl-oxazolidin-2-one;
(5S)-5-[[6-[3-(Difluoromethyl)-4-fluoro-phenyl]pyrazolo[4,3-b]pyridin-1-yl]methyl]-3-methyl-oxazolidin-2-one;
(RS)-5-[[6-[3-(Difluoromethyl)-4-fluoro-phenyl]pyrazolo[4,3-b]pyridin-1-yl]methyl]-3-ethyl-oxazolidin-2-one;
(S)-5-[[6-[3-(Difluoromethyl)-4-fluoro-phenyl]pyrazolo[4,3-b]pyridin-1-yl]methyl]-3-ethyl-oxazolidin-2-one;
(R)-5-[[6-[3-(Difluoromethyl)-4-fluoro-phenyl]pyrazolo[4,3-b]pyridin-1-yl]methyl]-3-ethyl-oxazolidin-2-one;
(RS)-3-Cyclopropyl-5-[[6-[3-(difluoromethyl)-4-fluoro-phenyl]pyrazolo[4,3-b]pyridin-1-yl]methyl]oxazolidin-2-one;
(S)-3-Cyclopropyl-5-[[6-[3-(difluoromethyl)-4-fluoro-phenyl]pyrazolo[4,3-b]pyridin-1-yl]methyl]oxazolidin-2-one;
(R)-3-Cyclopropyl-5-[[6-[3-(difluoromethyl)-4-fluoro-phenyl]pyrazolo[4,3-b]pyridin-1-yl]methyl]oxazolidin-2-one;
2-[6-[3-(Difluoromethyl)-4-fluoro-phenyl]pyrazolo[4,3-b]pyridin-1-yl]-1-(2-thienyl)ethanone;
2-[6-[3-(Difluoromethyl)-4-fluoro-phenyl]pyrazolo[4,3-b]pyridin-1-yl]-1-(3-thienyl)ethanone;
2-[6-[3-(Difluoromethyl)-4-fluoro-phenyl]pyrazolo[4,3-b]pyridin-1-yl]-1-(4-pyridyl)ethanone;

2-(6-(3-(Difluoromethyl)-4-fluorophenyl)-1H-pyrazolo[4,3-b]pyridin-1-yl)-1-(3-fluoropyridin-2-yl)ethan-1-one;
2-(6-(3-(Difluoromethyl)-4-fluorophenyl)-1H-pyrazolo[4,3-b]pyridin-1-yl)-1-(3,5-difluoropyridin-2-yl)ethan-1-one;
2-(6-(3-(Difluoromethyl)-4-fluorophenyl)-1H-pyrazolo[4,3-b]pyridin-1-yl)-1-(pyrazin-2-yl)ethan-1-one;
and pharmaceutically acceptable salts, solvates, stereoisomers, isotopic variants, or N-oxides thereof.

22. A compound selected from the group consisting of:
1-[6-[3-(Difluoromethyl)-4-fluoro-phenyl]pyrazolo[4,3-b]pyridin-1-yl]butan-2-one;
1-[6-[3-(Difluoromethyl)-4-fluoro-phenyl]pyrazolo[4,3-b]pyridin-1-yl]propan-2-one;
1-[6-(3,4-Difluorophenyl)pyrazolo[4,3-b]pyridin-1-yl]butan-2-one;
1-(6-(3-(Difluoromethyl)-4-fluorophenyl)-3-methyl-1H-pyrazolo[4,3-b]pyridin-1-yl)butan-2-one;
1-[6-[3-(Difluoromethoxy)-4-fluoro-phenyl]pyrazolo[4,3-b]pyridin-1-yl]butan-2-one;
1-Cyclopropyl-2-[6-(4-fluorophenyl)pyrazolo[4,3-b]pyridin-1-yl]ethanone;
1-Cyclopropyl-2-[6-[3-(difluoromethyl)-4-fluoro-phenyl]pyrazolo[4,3-b]pyridin-1-yl]ethanone;
(RS)-6-(3-(Difluoromethyl)-4-fluorophenyl)-1-((ethylsulfinyl)methyl)-1H-pyrazolo[4,3-b]pyridine;
(S*)-6-(3-(Difluoromethyl)-4-fluorophenyl)-1-((ethylsulfinyl)methyl)-1H-pyrazolo[4,3-b]pyridine; and
(5R)-5-[[6-[3-(Difluoromethyl)-4-fluoro-phenyl]pyrazolo[4,3-b]pyridin-1-yl]methyl]-3-methyl-oxazolidin-2-one;
and pharmaceutically acceptable salts, solvates, stereoisomers, isotopic variants, or N-oxides thereof.

23. A pharmaceutical composition comprising: (A) an effective amount of at least one compound selected from compounds of Formula (I):

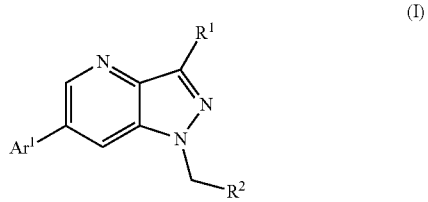

wherein
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo, and $C_{1-6}$alkyl;
$R^2$ is selected from the group consisting of:
(e)

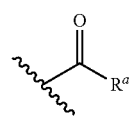

wherein R is selected from the group consisting of: $C_{1-6}$alkyl; $C_{3-6}$cycloalkyl; thienyl; pyridyl; pyridyl substituted with one or two F members; pyrazinyl;

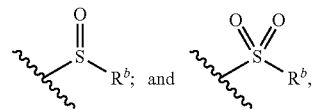

wherein $R^b$ is $C_{1-6}$alkyl;
(f) $C_{1-6}$alkyl substituted with one, two, or three members each independently selected from the group consisting of: OH, halo, $OC_{1-6}$alkyl, (=N—OH), (=N—OCH_3), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl;
and pharmaceutically acceptable salts, stereoisomers, isotopic variants, N-oxides, or solvates of compounds of Formula (I);
(B) at least one pharmaceutically acceptable excipient.

24. A pharmaceutical composition comprising an effective amount of at least one compound of embodiment 21 and at least one pharmaceutically acceptable excipient.

25. A method of treating a subject suffering from or diagnosed with a disease, disorder, or medical condition mediated by GluN2B receptor activity, comprising administering to a subject in need of such treatment an effective amount of at least one compound selected from compounds of Formula (I):

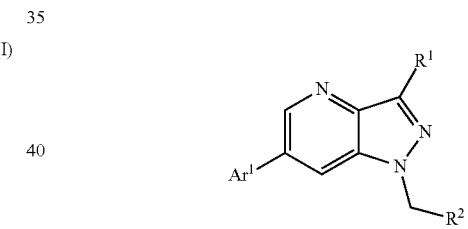

wherein
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo, and $C_{1-6}$alkyl;
$R^2$ is selected from the group consisting of:
(e)

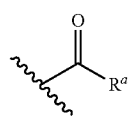

wherein $R^a$ is selected from the group consisting of: $C_{1-6}$alkyl; $C_{3-6}$cycloalkyl; thienyl; pyridyl; pyridyl substituted with one or two F members; pyrazinyl;

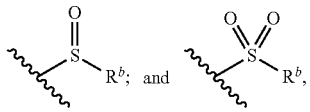

wherein $R^b$ is $C_{1-6}$alkyl;
(f) $C_{1-6}$alkyl substituted with one, two, or three members each independently selected from the group consisting of: OH, halo, $OC_{1-6}$alkyl, (=N—OH), (=N—OCH$_3$), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl;
and pharmaceutically acceptable salts, stereoisomers, isotopic variants, N-oxides, or solvates of compounds of Formula (I).

26. The method of embodiment 25, wherein the disorder, disease or condition mediated by the GluN2B receptor is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD) and addictive illnesses.

27. The method of embodiment 25 wherein the disorder, disease or condition is selected from the group consisting of treatment-resistant depression, major depressive disorder and bipolar disorder.

The present disclosure is further exemplified by specific embodiments 1 to 45 below.

1. A compound having the structure of Formula (I):

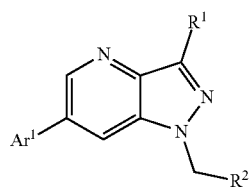

or a pharmaceutically acceptable salt, solvate, stereoisomer, isotopic variant, or N-oxide thereof,
wherein
$R^1$ is H, halo, or CH$_3$;
Ar$^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and (d) thienyl substituted with one member selected from the group consisting of: halo, and $C_{1-6}$alkyl;
$R^2$ is selected from the group consisting of:
(e)

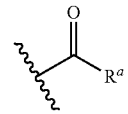

wherein $R^a$ is selected from the group consisting of: $C_{1-6}$alkyl; $C_{3-6}$cycloalkyl; thienyl; pyridyl; pyridyl substituted with one or two F members; pyrazinyl;

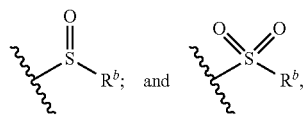

wherein $R^b$ is $C_{1-6}$alkyl;
(f) $C_{1-6}$alkyl substituted with one, two, or three members each independently selected from the group consisting of: OH, halo, $OC_{1-6}$alkyl, (=N—OH), (=N—OCH$_3$), and cyclopropyl; and
(g) oxetanyl; oxetanyl substituted with $C_{1-6}$alkyl; tetrahydrofuranyl; oxazolidinone; oxazolidinone substituted with $C_{1-4}$alkyl, or cyclopropyl; and pyrrolidinone substituted with $C_{1-4}$alkyl.

2. The compound of embodiment 1 or a pharmaceutically acceptable salt, solvate, stereoisomer, isotopic variant, or N-oxide thereof, wherein $R^1$ is H.

3. The compound of embodiment 1 or a pharmaceutically acceptable salt, solvate, stereoisomer, isotopic variant, or N-oxide thereof, wherein $R^1$ is F.

4. The compound of embodiment 1 or a pharmaceutically acceptable salt, solvate, stereoisomer, isotopic variant, or N-oxide thereof, wherein $R^1$ is CH$_3$.

5. The compound of any one of embodiments 1 to 4, or a pharmaceutically acceptable salt, solvate, stereoisomer, isotopic variant, or N-oxide thereof, wherein Ar$^1$ is phenyl.

6. The compound of any one of embodiments 1 to 4, or a pharmaceutically acceptable salt, solvate, stereoisomer, isotopic variant, or N-oxide thereof, wherein Ar$^1$ is phenyl substituted with one member selected from the group consisting of: F, CH$_3$, CF$_2$H, CF$_2$CH$_3$, CF$_3$, and OCF$_3$.

7. The compound of any one of embodiments 1 to 4, or a pharmaceutically acceptable salt, solvate, stereoisomer, isotopic variant, or N-oxide thereof, wherein Ar$^1$ is selected from the group consisting of:

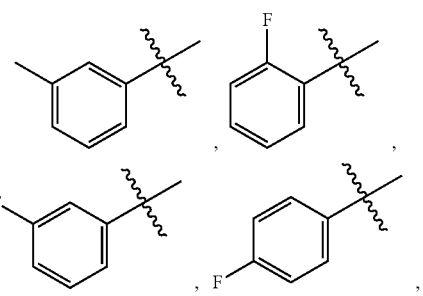

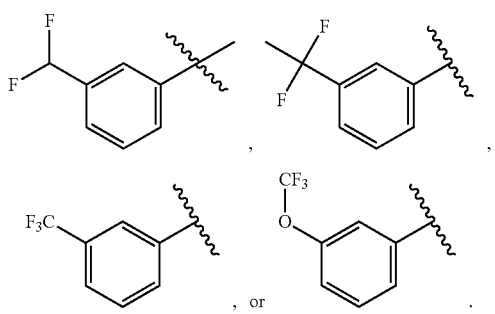

, or

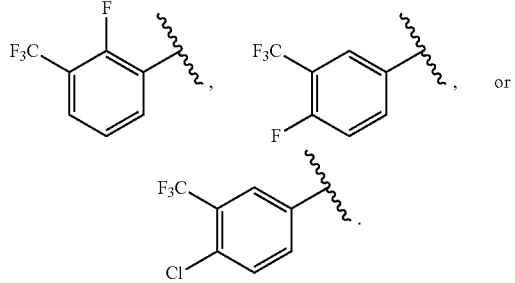

, or

8. The compound of any one of embodiments 1 to 4, or a pharmaceutically acceptable salt, solvate, stereoisomer, isotopic variant, or N-oxide thereof, wherein $Ar^1$ is phenyl substituted with two members each independently selected from the group consisting of: F, Cl, $CH_3$, $CF_2H$, $CF_3$, $CF_2CH_3$, and $OCF_2H$.

9. The compound of any one of embodiments 1 to 4, or a pharmaceutically acceptable salt, solvate, stereoisomer, isotopic variant, or N-oxide thereof, wherein $Ar^1$ is selected from the group consisting of:

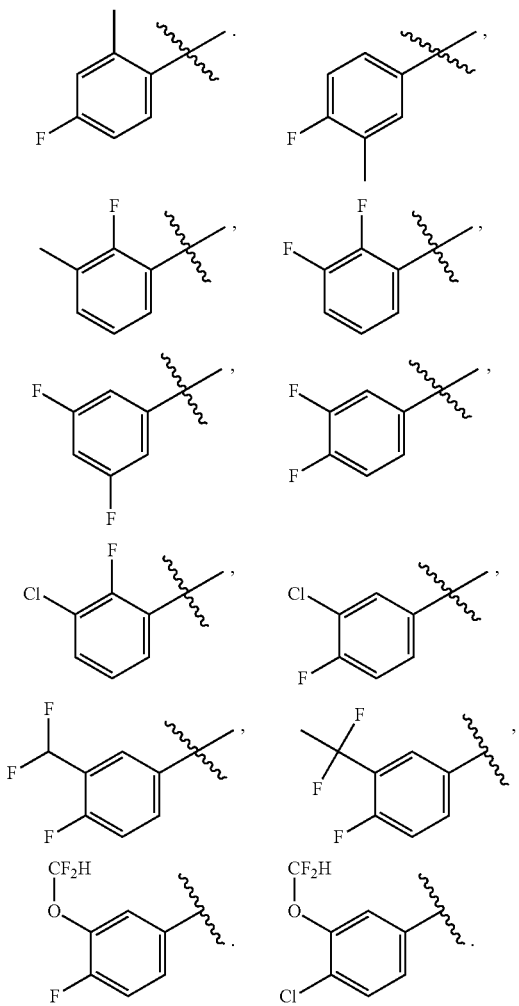

10. The compound of any one of embodiments 1 to 4, or a pharmaceutically acceptable salt, solvate, stereoisomer, isotopic variant, or N-oxide thereof, wherein $Ar^1$ is phenyl substituted with three members each independently selected from the group consisting of: F and $CH_3$.

11. The compound of any one of embodiments 1 to 4, or a pharmaceutically acceptable salt, solvate, stereoisomer, isotopic variant, or N-oxide thereof, wherein $Ar^1$ is

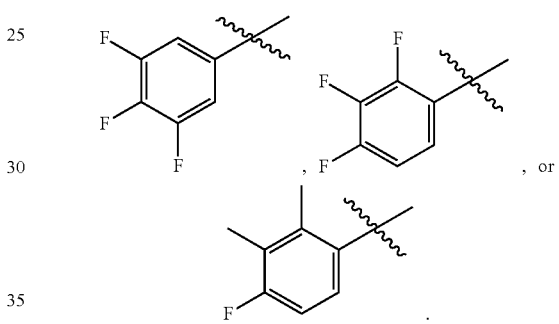

12. The compound of any one of embodiments 1 to 4, or a pharmaceutically acceptable salt, solvate, stereoisomer, isotopic variant, or N-oxide thereof, wherein $Ar^1$ is thienyl is substituted with Cl or $CH_3$.

13. The compound of any one of embodiments 1 to 4, or a pharmaceutically acceptable salt, solvate, stereoisomer, isotopic variant, or N-oxide thereof, wherein $Ar^1$ is

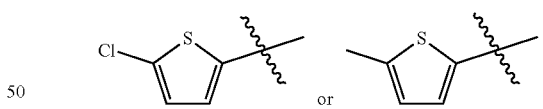

14. The compound of any one of embodiments 1 to 13, or a pharmaceutically acceptable salt, solvate, stereoisomer, isotopic variant, or N-oxide thereof, wherein $R^2$ is

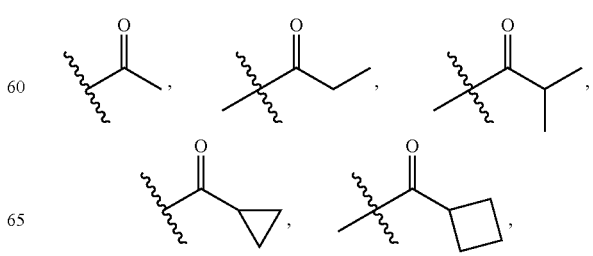

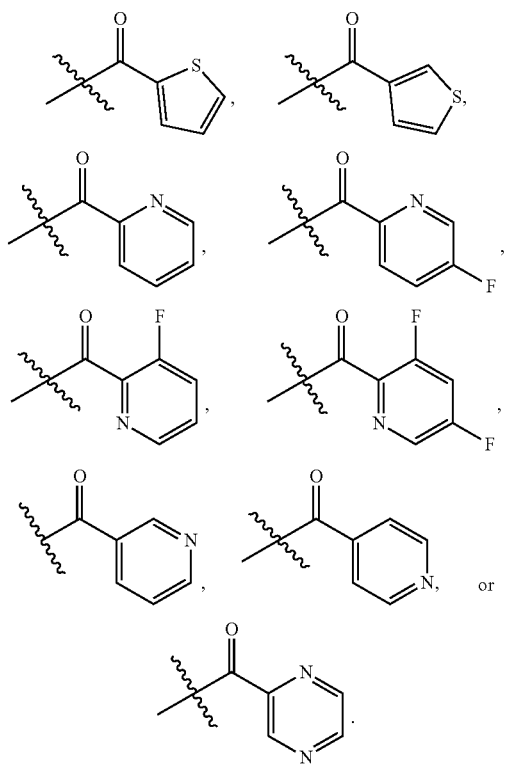

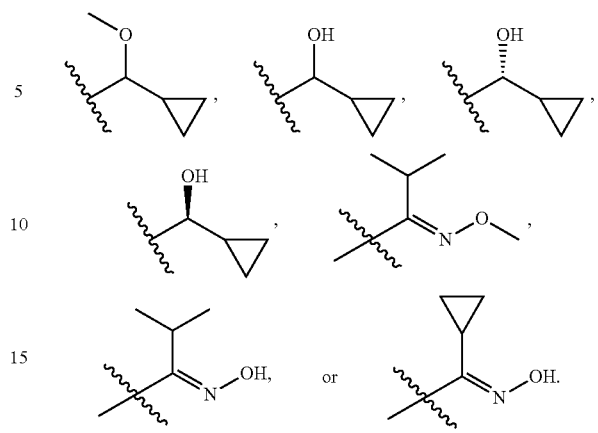

15. The compound of any one of embodiments 1 to 13, or a pharmaceutically acceptable salt, solvate, stereoisomer, isotopic variant, or N-oxide thereof, wherein R² is

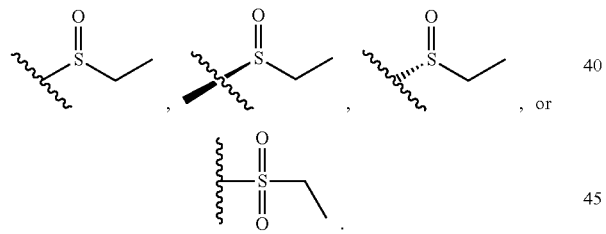

16. The compound of any one of embodiments 1 to 13, or a pharmaceutically acceptable salt, solvate, stereoisomer, isotopic variant, or N-oxide thereof, wherein R² is

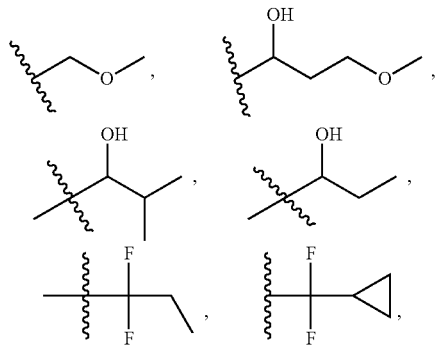

17. The compound of any one of embodiments 1 to 13, or a pharmaceutically acceptable salt, solvate, stereoisomer, isotopic variant, or N-oxide thereof, wherein R² is

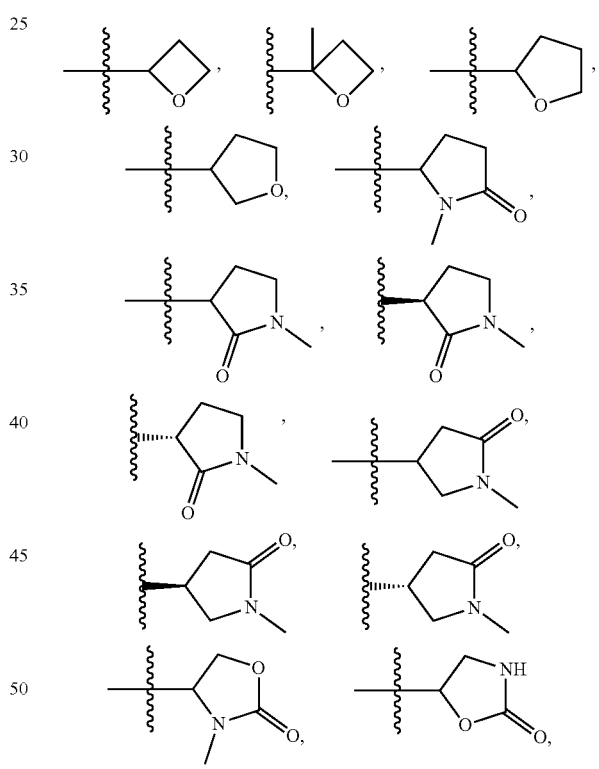

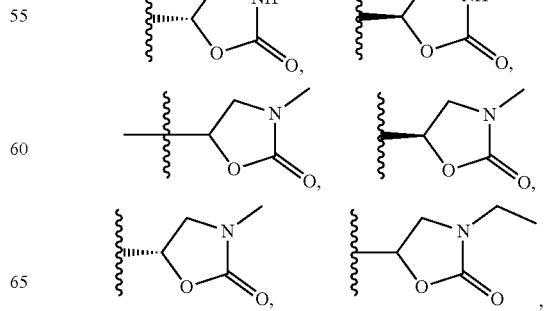

-continued

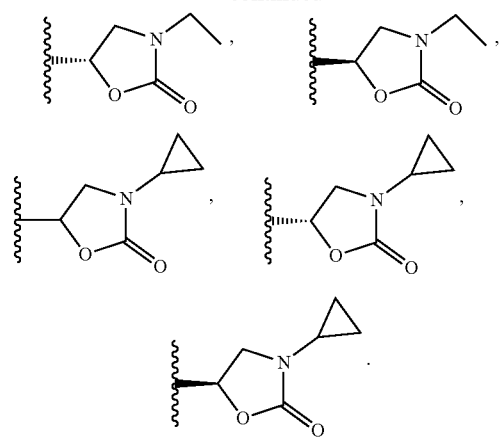

or

18. The compound of embodiment or a pharmaceutically acceptable salt, solvate, stereoisomer, isotopic variant, or N-oxide thereof, having the structure of Formula (IA):

(IA)

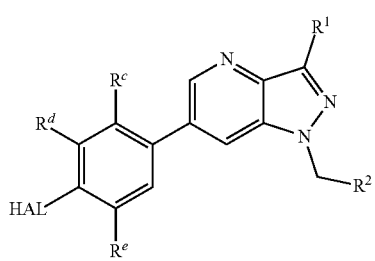

wherein
HAL is F or Cl;
$R^1$ is H, F, or $CH_3$;
$R^2$ is selected from the group consisting of:
(a) (S=O)$CH_2CH_3$; (SO$_2$)$CH_2CH_3$; or

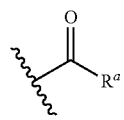

wherein $R^a$ is selected from the group consisting of: $CH_3$, $CH_2CH_3$, $CH(CH_3)_2$, cyclopropyl, cyclobutyl,

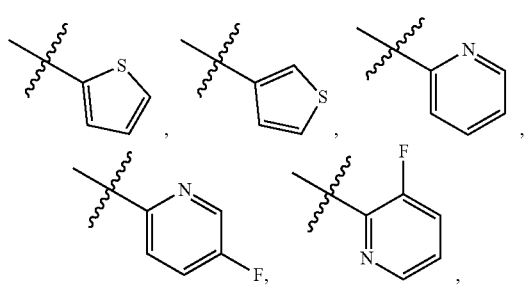

-continued

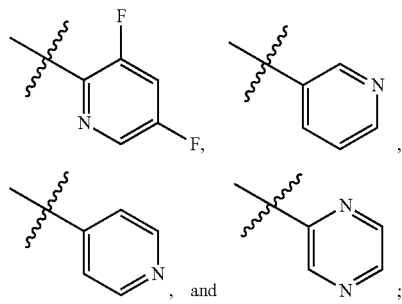
and (b) $CH_2OCH_3$, $CH(OH)(CH_2CH_3)$, $CH(OH)CH(CH_3)_2$, $CF_2CH_2CH_3$, $CF_2$(cyclopropyl), or

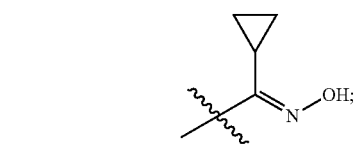

and (c)

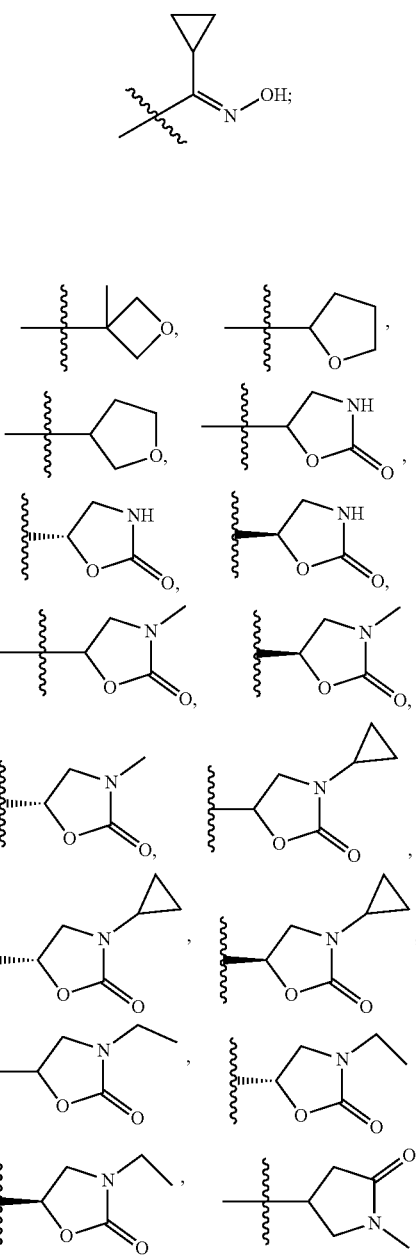

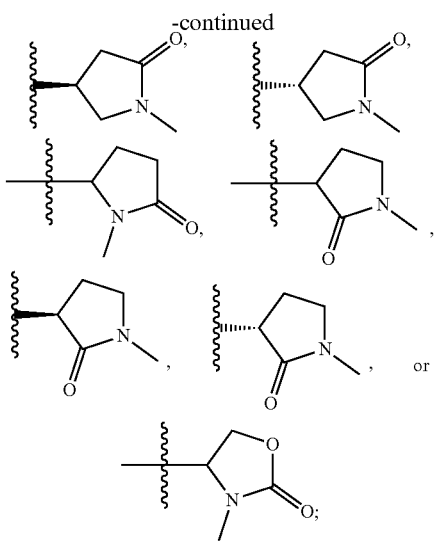

$R^c$ is H, F or $CH_3$;
$R^d$ is selected from the group consisting of: H, F, Cl, $CH_3$, $CF_2H$, $CF_2CH_3$, $CF_3$, and $OCF_2H$; and
$R^e$ is H or F; wherein when $R^e$ is F, $R^c$ is H.

19. The compound of embodiment 18 or a pharmaceutically acceptable salt, solvate, stereoisomer, isotopic variant, or N-oxide thereof, where HAL is F; $R^1$ is H; $R^c$ is H; and $R^e$ is H.

20. The compound of embodiment 1 or a pharmaceutically acceptable salt, solvate, stereoisomer, isotopic variant, or N-oxide thereof, having the structure of Formula (IB):

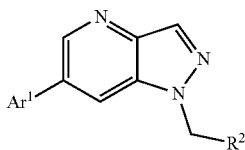

(IB)

wherein
$Ar^1$ is selected from the group consisting of:
(a) phenyl, 3-methylphenyl, 2-fluorophenyl, 3-fluorophenyl, 3-(difluoromethyl)phenyl, 3-(1,1-difluoroethyl)phenyl, 3-(trifluoromethyl)phenyl, 3-(trifluoromethoxy)phenyl, 5-methyl-2-thienyl, or 5-chloro-2-thienyl; and
(b) 2-fluoro-3-methyl-phenyl, 2,3-difluorophenyl, 3,5-difluorophenyl, 3-chloro-2-fluoro-phenyl, 2-fluoro-3-(trifluoromethyl)phenyl, 4-chloro-3-(difluoromethoxy)phenyl, or 4-chloro-3-(trifluoromethyl)phenyl; and
$R^2$ is selected from the group consisting of: (S=O)$CH_2CH_3$, (C=O)$CH_2CH_3$, (C=O)$CH(CH_3)_2$, and (C=O)cyclopropyl.

21. A compound selected from the compounds in Table 1 and pharmaceutically acceptable salts, solvates, stereoisomers, isotopic variants, and N-oxides thereof.

22. The compound of any one of embodiments 1 to 21, or a pharmaceutically acceptable salt or solvate thereof.

23. The compound of any one of embodiments 1 to 21, or a pharmaceutically acceptable salt or N-oxide thereof.

24. The compound of any one of embodiments 1 to 21, or a pharmaceutically acceptable salt thereof.

25. The compound of any one of embodiments 1 to 21.

26. A pharmaceutically acceptable salt of the compound of any one of embodiments 1 to 21.

27. A pharmaceutical composition comprising the compound of any one of embodiments 1 to 21, or a pharmaceutically acceptable salt, solvate, isotopic variant, or N-oxide thereof, and a pharmaceutically acceptable excipient.

28. A pharmaceutical composition comprising the compound of any one of embodiments 1 to 21, or a pharmaceutically acceptable salt or solvate thereof, and a pharmaceutically acceptable excipient.

29. A pharmaceutical composition comprising the compound of any one of embodiments 1 to 21, or a pharmaceutically acceptable salt or N-oxide thereof, and a pharmaceutically acceptable excipient.

30. A pharmaceutical composition comprising the compound of any one of embodiments 1 to 21, or a pharmaceutically acceptable salt thereof, and a pharmaceutically acceptable excipient.

31. A pharmaceutical composition comprising the compound of any one of embodiments 1 to 21 and a pharmaceutically acceptable excipient.

32. A pharmaceutical composition comprising a pharmaceutically acceptable salt of the compound of any one of embodiments 1 to 21, and a pharmaceutically acceptable excipient.

33. A unit dosage form comprising a therapeutically effective amount of the pharmaceutical composition of any one of embodiments 27 to 32.

34. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt, solvate, isotopic variant, or N-oxide thereof.

35. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt, or solvate thereof.

36. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt or N-oxide thereof.

37. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt thereof.

38. A method of treating a subject suffering from or diagnosed with a disease, disorder, or medical condition mediated by GluN2B receptor activity, comprising administering to the subject a therapeutically effective amount of the pharmaceutical composition of any one of embodiments 27 to 32 or the unit dosage form of embodiment 33.

39. The method of any one of embodiments 34 to 38, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

40. The method of embodiment 39, wherein the disease, disorder or medical condition mediated by GluN2B receptor activity comprises bipolar disorder, a mood disorder, treatment resistant depression, major depressive disorder, or epilepsy.

41. The method of embodiment 39, wherein the disease, disorder or medical condition mediated by GluN2B receptor activity comprises bipolar disorder.

42. The method of embodiment 39, wherein the disease, disorder or medical condition mediated by GluN2B receptor activity comprises a mood disorder.

43. The method of embodiment 39, wherein the disease, disorder or medical condition mediated by GluN2B receptor activity comprises treatment resistant depression.

44. The method of embodiment 39, wherein the disease, disorder or medical condition mediated by GluN2B receptor activity comprises major depressive disorder.

45. The method of embodiment 39, wherein the disease, disorder or medical condition mediated by GluN2B receptor activity comprises epilepsy.

What is claimed is:

1. A compound having the structure of Formula (I):

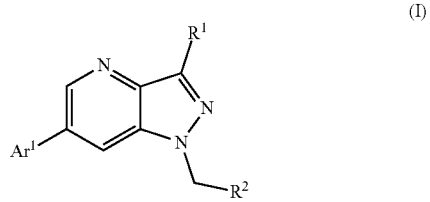

(I)

or a pharmaceutically acceptable salt or stereoisomer thereof, wherein:

$R^1$ is H, halo, or $CH_3$;

$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo and $C_{1-6}$alkyl;

$R^2$ is selected from the group consisting of:
(a)

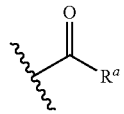

wherein $R^a$ is selected from the group consisting of:
$C_{1-6}$alkyl;
$C_{3-6}$cycloalkyl; thienyl; pyridyl; pyridyl substituted with one or two F members;
pyrazinyl;

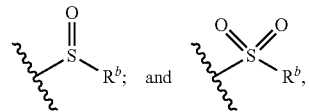

wherein $R^b$ is $C_{1-6}$alkyl;
(b) $C_{1-6}$alkyl substituted with one, two, or three members each independently selected from the group consisting of: OH, halo, $OC_{1-6}$alkyl, (=N—OH), (=N—OCH$_3$), and cyclopropyl; and
(c) oxetanyl; oxetanyl substituted with $C_{1-6}$alkyl; tetrahydrofuranyl; oxazolidinone; oxazolidinone substituted with $C_{1-4}$alkyl or cyclopropyl; and pyrrolidinone substituted with $C_{1-4}$alkyl.

2. The compound of claim 1 or a pharmaceutically acceptable salt, solvate, stereoisomer thereof, wherein $R^1$ is H.

3. The compound of claim 1 or a pharmaceutically acceptable salt or stereoisomer thereof, wherein $R^1$ is F.

4. The compound of claim 1 or a pharmaceutically acceptable salt or stereoisomer thereof, wherein $R^1$ is $CH_3$.

5. The compound of claim 1 or a pharmaceutically acceptable salt or stereoisomer thereof, wherein $Ar^1$ is phenyl.

6. The compound of claim 1 or a pharmaceutically acceptable salt or stereoisomer thereof, wherein $Ar^1$ is phenyl substituted with one member selected from the group consisting of: F, $CH_3$, $CF_2H$, $CF_2CH_3$, $CF_3$, and $OCF_3$.

7. The compound of claim 1 or a pharmaceutically acceptable salt or stereoisomer thereof, wherein $Ar^1$ is:

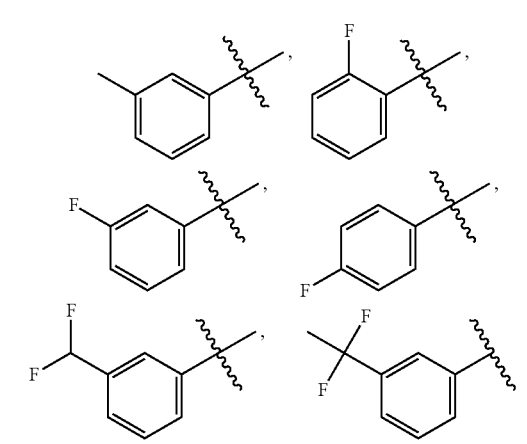

-continued

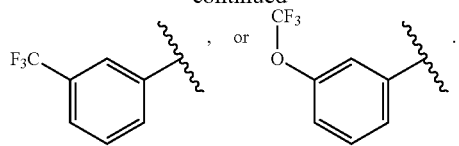

8. The compound of claim 1 or a pharmaceutically acceptable salt or stereoisomer thereof, wherein $Ar^1$ is phenyl substituted with two members each independently selected from the group consisting of: F, Cl, $CH_3$, $CF_2H$, $CF_3$, $CF_2CH_3$, and $OCF_2H$.

9. The compound of claim 1 or a pharmaceutically acceptable salt or stereoisomer thereof, wherein $Ar^1$ is:

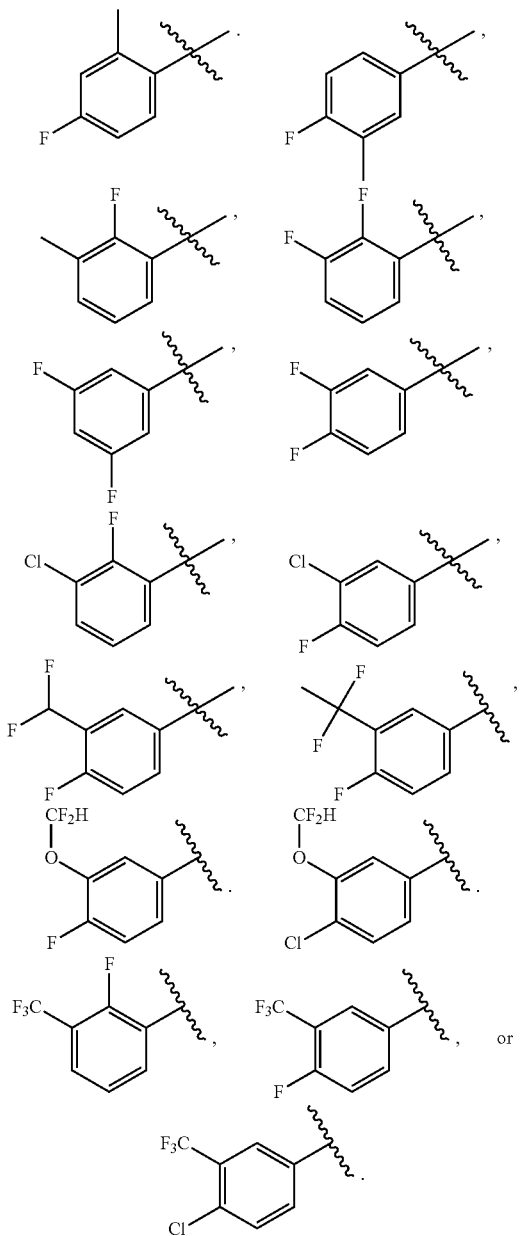

10. The compound of claim 1 or a pharmaceutically acceptable salt or stereoisomer thereof, wherein $Ar^1$ is phenyl substituted with three members each independently selected from the group consisting of: F and $CH_3$.

11. The compound of claim 1 or a pharmaceutically acceptable salt or stereoisomer thereof, wherein $Ar^1$ is

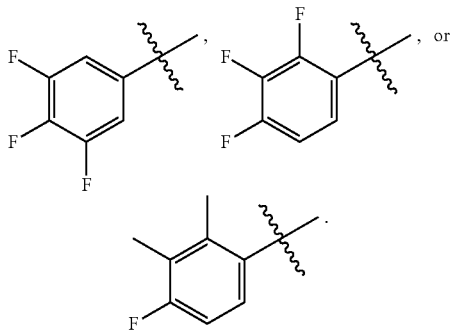

12. The compound of claim 1 or a pharmaceutically acceptable salt or stereoisomer thereof, wherein $Ar^1$ is thienyl substituted with Cl or $CH_3$.

13. The compound of claim 1 or a pharmaceutically acceptable salt or stereoisomer thereof, wherein $Ar^1$ is

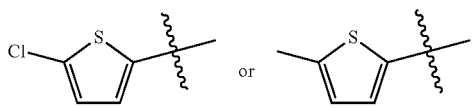

14. The compound of claim 1 or a pharmaceutically acceptable salt or stereoisomer thereof, wherein $R^2$ is

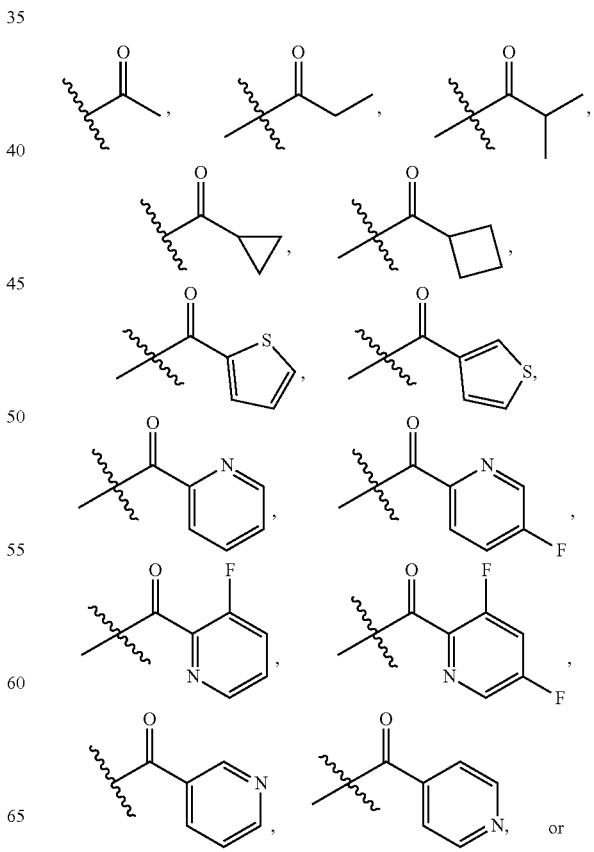

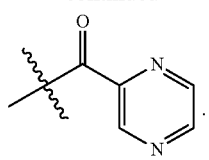

15. The compound of claim 1 or a pharmaceutically acceptable salt or stereoisomer thereof, wherein $R^2$ is

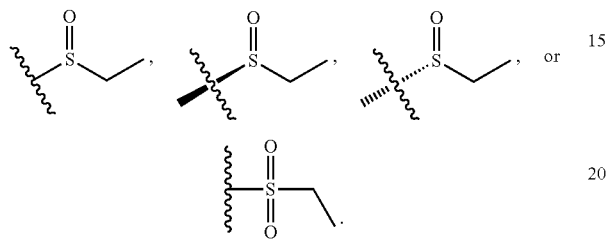

16. The compound of claim 1 or a pharmaceutically acceptable salt or stereoisomer thereof, wherein $R^2$ is

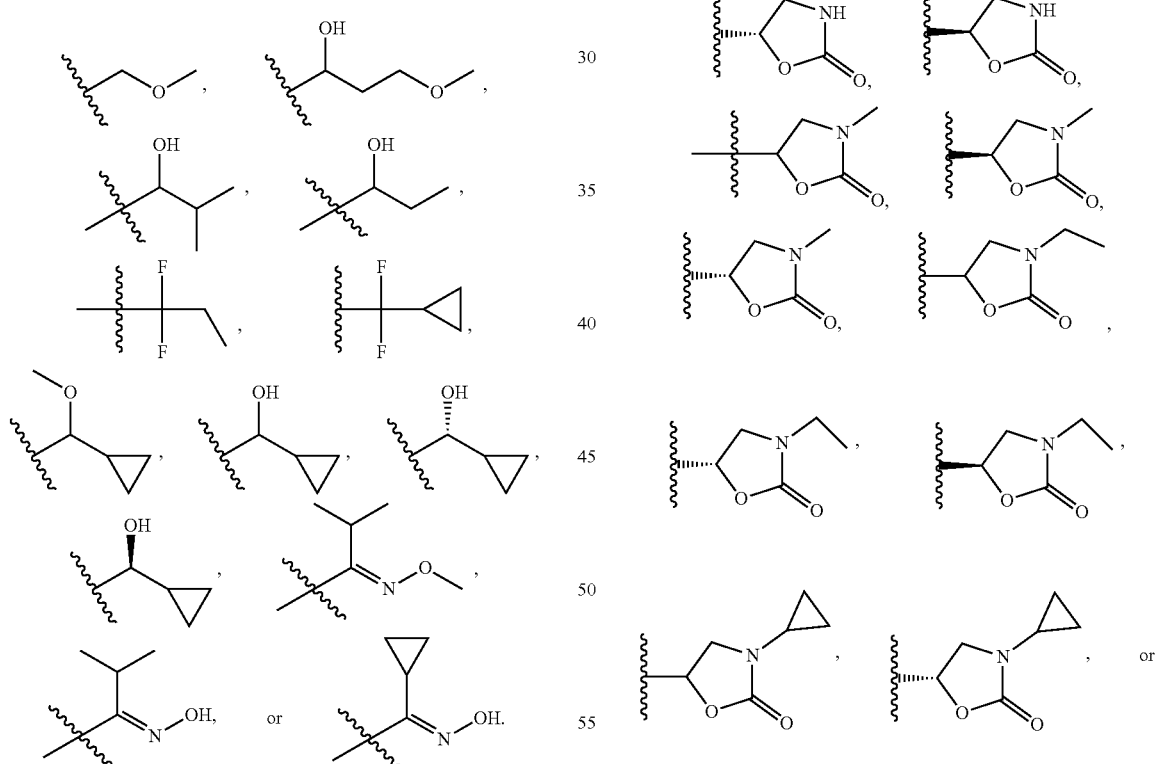

17. The compound of claim 1 or a pharmaceutically acceptable salt or stereoisomer thereof, wherein $R^2$ is

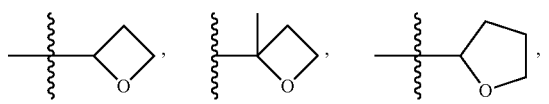

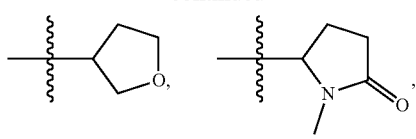
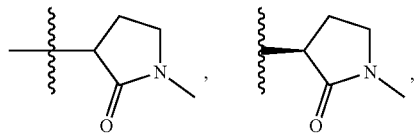
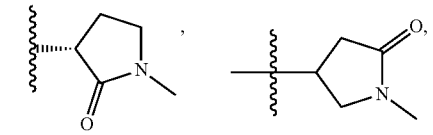
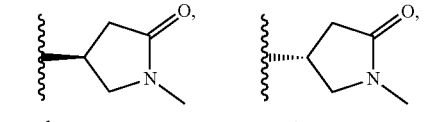
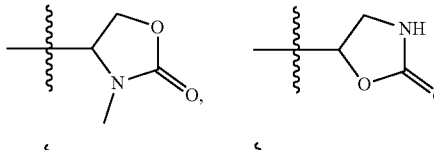
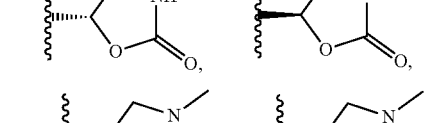
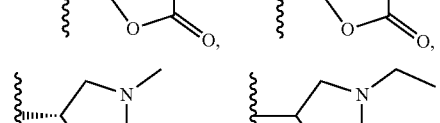
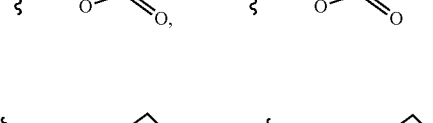
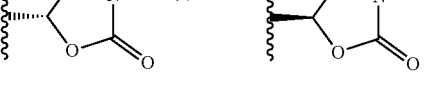
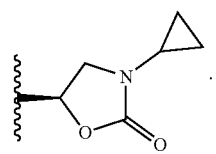 [SMILES: *[C@H]1CN(C2CC2)C(=O)O1]

18. The compound of claim 1 having the structure of Formula (IA):

(IA)

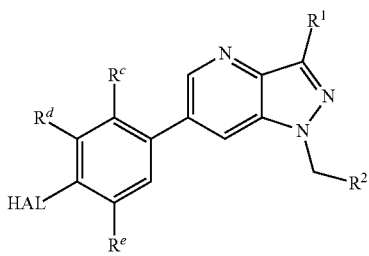

or a pharmaceutically acceptable salt or stereoisomer thereof, wherein:

HAL is F or Cl;

$R^1$ is H, F, or $CH_3$;

$R^2$ is selected from the group consisting of:

(a) (S=O)$CH_2CH_3$; ($SO_2$)$CH_2CH_3$; and

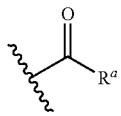

wherein $R^a$ is selected from the group consisting of: $CH_3$, $CH_2CH_3$, $CH(CH_3)_2$, cyclopropyl, cyclobutyl,

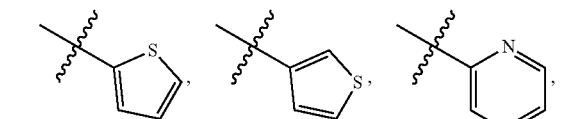

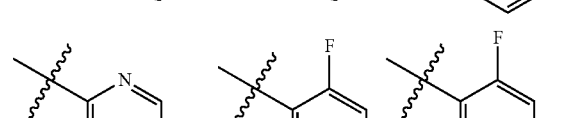

, and

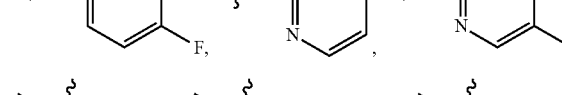

;

(b) $CH_2OCH_3$; CH(OH)($CH_2CH_3$); CH(OH)CH($CH_3$)$_2$; $CF_2CH_2CH_3$; $CF_2$(cyclopropyl); CH(O$CH_3$)(cyclopropyl); CH(OH)(cyclopropyl); and

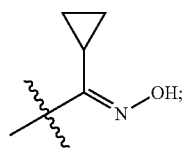 [SMILES: */C(=N/O)C1CC1]

and (c)

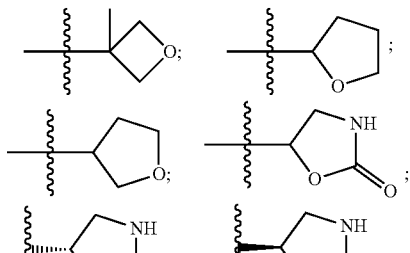

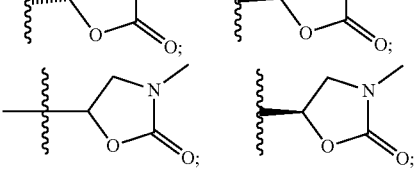

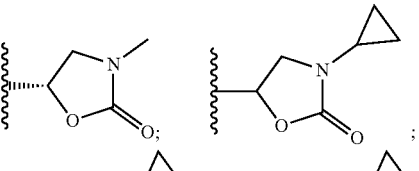

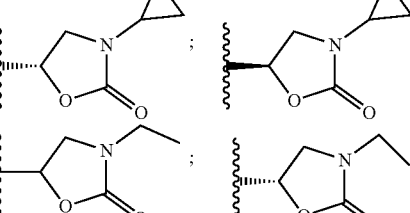

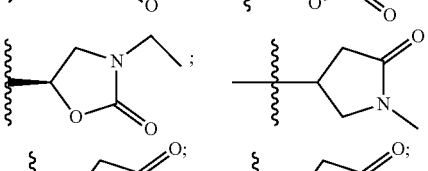

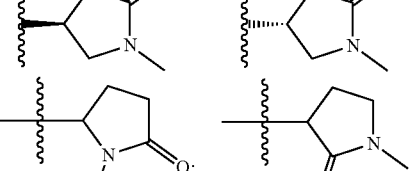

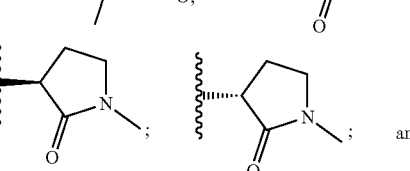

; and

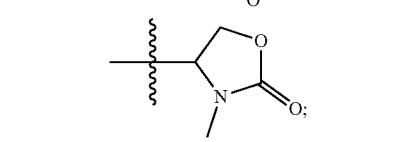

$R^c$ is H, F or $CH_3$;

$R^d$ is selected from the group consisting of: H, F, Cl, $CH_3$, $CF_2H$, $CF_2CH_3$, $CF_3$, and $OCF_2H$; and $R^e$ is H or F; wherein when $R^c$ is F, $R^e$ is H.

19. The compound of claim 18 or a pharmaceutically acceptable salt or stereoisomer thereof, where HAL is F; $R^1$ is H; $R^c$ is H; and $R^e$ is H.

20. The compound of claim 1 having the structure of Formula (IB):

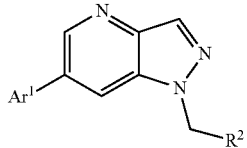

or a Pharmaceutically acceptable salt or stereoisomer thereof,
wherein:
Ar¹ is selected from the group consisting of:
(a) phenyl, 3-methylphenyl, 2-fluorophenyl, 3-fluorophenyl, 3-(difluoromethyl)phenyl, 3-(1,1-difluoroethyl)phenyl, 3-(trifluoromethyl)phenyl, 3-(trifluoromethoxy)phenyl, 5-methyl-2-thienyl, and; 5-chloro-2-thienyl; and
(b) 2-fluoro-3-methyl-phenyl, 2,3-difluorophenyl, 3,5-difluorophenyl, 3-chloro-2-fluoro-phenyl, 2-fluoro-3-(trifluoromethyl)phenyl, 4-chloro-3-(difluoromethoxy)phenyl, and; 4-chloro-3-(trifluoromethyl)phenyl; and
R² is selected from the group consisting of: (S=O)CH₂CH₃, (C=O)CH₂CH₃, (C=O)CH(CH₃)₂, and (C=O)cyclopropyl.

21. A compound selected from the group consisting of:
1-[6-(3,5-Difluorophenyl)pyrazolo[4,3-b]pyridin-1-yl]butan-2-one;
3-Methyl-1-[6-[3-(trifluoromethyl)phenyl]pyrazolo[4,3-b]pyridin-1-yl]butan-2-one;
(RS)-3-Methyl-1-[6-[3-(trifluoromethyl)phenyl]pyrazolo[4,3-b]pyridin-1-yl]butan-2-ol;
1-[6-[3-(Difluoromethyl)-4-fluoro-phenyl]pyrazolo[4,3-b]pyridin-1-yl]butan-2-one;
(RS)-1-[6-[3-(Difluoromethyl)-4-fluoro-phenyl]pyrazolo[4,3-b]pyridin-1-yl]butan-2-ol;
(E/Z)-3-Methyl-1-[6-[3-(trifluoromethyl)phenyl]pyrazolo[4,3-b]pyridin-1-yl]butan-2-one oxime;
1-[6-(4-Fluoro-3-methyl-phenyl)pyrazolo[4,3-b]pyridin-1-yl]-3-methyl-butan-2-one;
(RS)-1-[6-(4-Fluoro-3-methyl-phenyl)pyrazolo[4,3-b]pyridin-1-yl]-3-methyl-butan-2-ol;
1-Cyclopropyl-2-[6-(3,4,5-trifluorophenyl)pyrazolo[4,3-b]pyridin-1-yl]ethanone;
(RS)-1-Cyclopropyl-2-[6-(3,4,5-trifluorophenyl)pyrazolo[4,3-b]pyridin-1-yl]ethanol;
(RS)-1-(2-Cyclopropyl-2-methoxy-ethyl)-6-(3,4,5-trifluorophenyl)pyrazolo[4,3-b]pyridine;
(RS)-6-[3-(Difluoromethoxy)-4-fluoro-phenyl]-1-(ethylsulfinylmethyl)pyrazolo[4,3-b]pyridine;
6-[3-(Difluoromethoxy)-4-fluoro-phenyl]-1-(ethylsulfonylmethyl)pyrazolo[4,3-b]pyridine;
2-[6-[3-(Difluoromethyl)-4-fluoro-phenyl]pyrazolo[4,3-b]pyridin-1-yl]-1-(2-pyridyl)ethanone;
2-(6-(3-(Difluoromethyl)-4-fluorophenyl)-1H-pyrazolo[4,3-b]pyridin-1-yl)-1-(5-fluoropyridin-2-yl)ethan-1-one;
2-(6-(3-(Difluoromethyl)-4-fluorophenyl)-1H-pyrazolo[4,3-b]pyridin-1-yl)-1-(pyridin-3-yl)ethan-1-one;
(RS)-1-(Oxetan-2-ylmethyl)-6-[3-(trifluoromethyl)phenyl]pyrazolo[4,3-b]pyridine;
(RS)-6-[3-(Difluoromethyl)-4-fluoro-phenyl]-1-(tetrahydrofuran-2-ylmethyl)pyrazolo[4,3-b]pyridine;
(RS)-4-[[6-[3-(Difluoromethoxy)-4-fluoro-phenyl]pyrazolo[4,3-b]pyridin-1-yl]methyl]-1-methyl-pyrrolidin-2-one;
(RS)-5-[[6-[3-(Difluoromethyl)-4-fluoro-phenyl]pyrazolo[4,3-b]pyridin-1-yl]methyl]oxazolidin-2-one;
(S)-5-[[6-[3-(Difluoromethyl)-4-fluoro-phenyl]pyrazolo[4,3-b]pyridin-1-yl]methyl]oxazolidin-2-one;
(R)-5-[[6-[3-(Difluoromethyl)-4-fluoro-phenyl]pyrazolo[4,3-b]pyridin-1-yl]methyl]oxazolidin-2-one;
1-[6-[3-(Difluoromethyl)-4-fluoro-phenyl]pyrazolo[4,3-b]pyridin-1-yl]propan-2-one;
1-[6-(4-Fluoro-3-methyl-phenyl)pyrazolo[4,3-b]pyridin-1-yl]propan-2-one;
1-[6-[3-(Difluoromethoxy)-4-fluoro-phenyl]pyrazolo[4,3-b]pyridin-1-yl]propan-2-one;
1-[6-[4-Chloro-3-(difluoromethoxy)phenyl]pyrazolo[4,3-b]pyridin-1-yl]propan-2-one;
1-[6-(5-Chloro-2-thienyl)pyrazolo[4,3-b]pyridin-1-yl]butan-2-one;
1-[6-(4-Fluorophenyl)pyrazolo[4,3-b]pyridin-1-yl]butan-2-one;
1-[6-(3-Fluorophenyl)pyrazolo[4,3-b]pyridin-1-yl]butan-2-one;
1-[6-[3-(Difluoromethyl)phenyl]pyrazolo[4,3-b]pyridin-1-yl]butan-2-one;
1-[6-[3-(1,1-Difluoroethyl)phenyl]pyrazolo[4,3-b]pyridin-1-yl]butan-2-one;
1-[6-(4-Fluoro-3-methyl-phenyl)pyrazolo[4,3-b]pyridin-1-yl]butan-2-one;
1-[6-(2,3-Difluorophenyl)pyrazolo[4,3-b]pyridin-1-yl]butan-2-one;
1-[6-(3,4-Difluorophenyl)pyrazolo[4,3-b]pyridin-1-yl]butan-2-one;
1-[6-(3,4-Difluorophenyl)-3-fluoro-pyrazolo[4,3-b]pyridin-1-yl]butan-2-one;
1-(6-(3-(Difluoromethyl)-4-fluorophenyl)-3-methyl-1H-pyrazolo[4,3-b]pyridin-1-yl)butan-2-one;
1-[6-[3-(1,1-Difluoroethyl)-4-fluoro-phenyl]pyrazolo[4,3-b]pyridin-1-yl]butan-2-one;
1-[6-[2-Fluoro-3-(trifluoromethyl)phenyl]pyrazolo[4,3-b]pyridin-1-yl]butan-2-one;
1-[6-[4-Fluoro-3-(trifluoromethyl)phenyl]pyrazolo[4,3-b]pyridin-1-yl]butan-2-one;
1-[6-[3-(Difluoromethoxy)-4-fluoro-phenyl]pyrazolo[4,3-b]pyridin-1-yl]butan-2-one;
1-[6-[4-Chloro-3-(difluoromethoxy)phenyl]pyrazolo[4,3-b]pyridin-1-yl]butan-2-one;
1-[6-(3,4,5-Trifluorophenyl)pyrazolo[4,3-b]pyridin-1-yl]butan-2-one;
1-[6-(2,3,4-Trifluorophenyl)pyrazolo[4,3-b]pyridin-1-yl]butan-2-one;
3-Methyl-1-(6-phenylpyrazolo[4,3-b]pyridin-1-yl)butan-2-one;
1-[6-(4-Fluorophenyl)pyrazolo[4,3-b]pyridin-1-yl]-3-methyl-butan-2-one;
1-[6-(3-Fluorophenyl)pyrazolo[4,3-b]pyridin-1-yl]-3-methyl-butan-2-one;
1-[6-[3-(Difluoromethyl)phenyl]pyrazolo[4,3-b]pyridin-1-yl]-3-methyl-butan-2-one;
1-[6-(2,3-Difluorophenyl)pyrazolo[4,3-b]pyridin-1-yl]-3-methyl-butan-2-one;
1-[6-(3,4-Difluorophenyl)pyrazolo[4,3-b]pyridin-1-yl]-3-methyl-butan-2-one;
1-[6-[2-Fluoro-3-(trifluoromethyl)phenyl]pyrazolo[4,3-b]pyridin-1-yl]-3-methyl-butan-2-one;
1-[6-[4-Fluoro-3-(trifluoromethyl)phenyl]pyrazolo[4,3-b]pyridin-1-yl]-3-methyl-butan-2-one;

1-[6-(4-Fluoro-2-methyl-phenyl)pyrazolo[4,3-b]pyridin-1-yl]-3-methyl-butan-2-one;
3-Methyl-1-[6-(3,4,5-trifluorophenyl)pyrazolo[4,3-b]pyridin-1-yl]butan-2-one;
3-Methyl-1-[6-(2,3,4-trifluorophenyl)pyrazolo[4,3-b]pyridin-1-yl]butan-2-one;
2-[6-(5-Chloro-2-thienyl)pyrazolo[4,3-b]pyridin-1-yl]-1-cyclopropyl-ethanone;
1-Cyclopropyl-2-[6-(5-methyl-2-thienyl)pyrazolo[4,3-b]pyridin-1-yl]ethanone;
1-Cyclopropyl-2-[6-(3-fluorophenyl)pyrazolo[4,3-b]pyridin-1-yl]ethanone;
1-Cyclopropyl-2-[6-(2-fluorophenyl)pyrazolo[4,3-b]pyridin-1-yl]ethanone;
1-Cyclopropyl-2-[6-(4-fluorophenyl)pyrazolo[4,3-b]pyridin-1-yl]ethanone;
1-Cyclopropyl-2-[6-(m-tolyl)pyrazolo[4,3-b]pyridin-1-yl]ethanone;
1-Cyclopropyl-2-[6-[3-(difluoromethyl)phenyl]pyrazolo[4,3-b]pyridin-1-yl]ethanone;
1-Cyclopropyl-2-[6-[3-(trifluoromethyl)phenyl]pyrazolo[4,3-b]pyridin-1-yl]ethanone;
1-Cyclopropyl-2-[6-[3-(trifluoromethoxy)phenyl]pyrazolo[4,3-b]pyridin-1-yl]ethanone;
1-Cyclopropyl-2-[6-(2,3-difluorophenyl)pyrazolo[4,3-b]pyridin-1-yl]ethanone;
1-Cyclopropyl-2-[6-(3,4-difluorophenyl)pyrazolo[4,3-b]pyridin-1-yl]ethanone;
1-Cyclopropyl-2-[6-(3,5-difluorophenyl)pyrazolo[4,3-b]pyridin-1-yl]ethanone;
2-[6-(3-Chloro-2-fluoro-phenyl)pyrazolo[4,3-b]pyridin-1-yl]-1-cyclopropyl-ethanone;
2-[6-(3-Chloro-4-fluoro-phenyl)pyrazolo[4,3-b]pyridin-1-yl]-1-cyclopropyl-ethanone;
1-Cyclopropyl-2-[6-(4-fluoro-3-methyl-phenyl)pyrazolo[4,3-b]pyridin-1-yl]ethanone;
1-Cyclobutyl-2-[6-(4-fluoro-3-methyl-phenyl)pyrazolo[4,3-b]pyridin-1-yl]ethanone;
1-Cyclopropyl-2-[6-(2-fluoro-3-methyl-phenyl)pyrazolo[4,3-b]pyridin-1-yl]ethanone;
1-Cyclopropyl-2-[6-(4-fluoro-2-methyl-phenyl)pyrazolo[4,3-b]pyridin-1-yl]ethanone;
1-Cyclopropyl-2-[6-[2-fluoro-3-(trifluoromethyl)phenyl]pyrazolo[4,3-b]pyridin-1-yl]ethanone;
1-Cyclopropyl-2-[6-[4-fluoro-3-(trifluoromethyl)phenyl]pyrazolo[4,3-b]pyridin-1-yl]ethanone;
2-[6-[4-Chloro-3-(trifluoromethyl)phenyl]pyrazolo[4,3-b]pyridin-1-yl]-1-cyclopropyl-ethanone;
1-Cyclopropyl-2-[6-[3-(difluoromethyl)-4-fluoro-phenyl]pyrazolo[4,3-b]pyridin-1-yl]ethanone;
1-Cyclopropyl-2-[6-[3-(difluoromethoxy)-4-fluoro-phenyl]pyrazolo[4,3-b]pyridin-1-yl]ethanone;
1-Cyclopropyl-2-[6-(4-fluoro-2,3-dimethyl-phenyl)pyrazolo[4,3-b]pyridin-1-yl]ethanone;
1-Cyclopropyl-2-[6-(2,3,4-trifluorophenyl)pyrazolo[4,3-b]pyridin-1-yl]ethanone;
(RS)-1-(Ethylsulfinylmethyl)-6-(3-fluorophenyl)pyrazolo[4,3-b]pyridine;
(RS)-1-(Ethylsulfinylmethyl)-6-[3-(trifluoromethyl)phenyl]pyrazolo[4,3-b]pyridine;
(RS) 6-(3,4-Difluorophenyl)-1-(ethylsulfinylmethyl)pyrazolo[4,3-b]pyridine;
(RS)-6-(3-(Difluoromethyl)-4-fluorophenyl)-1-((ethylsulfinyl)methyl)-1H-pyrazolo[4,3-b]pyridine;
(S*)-6-(3-(Difluoromethyl)-4-fluorophenyl)-1-((ethylsulfinyl)methyl)-1H-pyrazolo[4,3-b]pyridine;
(R*)-6-(3-(Difluoromethyl)-4-fluorophenyl)-1-((ethylsulfinyl)methyl)-1H-pyrazolo[4,3-b]pyridine;
(RS)-1-(Ethylsulfinylmethyl)-6-[2-fluoro-3-(trifluoromethyl)phenyl]pyrazolo[4,3-b]pyridine;
(RS)-6-[4-Chloro-3-(difluoromethoxy)phenyl]-1-(ethylsulfinylmethyl)pyrazolo[4,3-b]pyridine;
(RS)-1-(Ethylsulfinylmethyl)-6-(3,4,5-trifluorophenyl)pyrazolo[4,3-b]pyridine;
6-(4-Fluoro-3-methyl-phenyl)-1-(2-methoxyethyl)pyrazolo[4,3-b]pyridine;
(RS)-4-Methoxy-1-[6-[3-(trifluoromethyl)phenyl]pyrazolo[4,3-b]pyridin-1-yl]butan-2-ol;
(RS)-1-[6-(3,4-Difluorophenyl)pyrazolo[4,3-b]pyridin-1-yl]butan-2-ol;
(RS)-1-[6-[3-(Difluoromethoxy)-4-fluoro-phenyl]pyrazolo[4,3-b]pyridin-1-yl]butan-2-ol;
(RS)-1-[6-[4-Chloro-3-(difluoromethoxy)phenyl]pyrazolo[4,3-b]pyridin-1-yl]butan-2-ol;
(RS)-1-[6-(3,4-Difluorophenyl)-3-fluoro-pyrazolo[4,3-b]pyridin-1-yl]butan-2-ol;
(RS)-1-[6-[3-(1,1-Difluoroethyl)phenyl]pyrazolo[4,3-b]pyridin-1-yl]butan-2-ol;
(RS)-3-Methyl-1-(6-phenylpyrazolo[4,3-b]pyridin-1-yl)butan-2-ol;
(RS)-3-Methyl-1-[6-(3,4,5-trifluorophenyl)pyrazolo[4,3-b]pyridin-1-yl]butan-2-ol;
1-(2,2-Difluorobutyl)-6-[3-(difluoromethyl)-4-fluoro-phenyl]pyrazolo[4,3-b]pyridine;
1-(2,2-Difluorobutyl)-6-[3-(difluoromethoxy)-4-fluoro-phenyl]pyrazolo[4,3-b]pyridine;
(RS)-1-Cyclopropyl-2-[6-[3-(trifluoromethyl)phenyl]pyrazolo[4,3-b]pyridin-1-yl]ethanol;
(RS)-1-Cyclopropyl-2-[6-(4-fluoro-3-methyl-phenyl)pyrazolo[4,3-b]pyridin-1-yl]ethanol;
(R)-1-Cyclopropyl-2-[6-(4-fluoro-3-methyl-phenyl)pyrazolo[4,3-b]pyridin-1-yl]ethanol;
(S)-1-Cyclopropyl-2-[6-(4-fluoro-3-methyl-phenyl)pyrazolo[4,3-b]pyridin-1-yl]ethanol;
(RS)-1-Cyclopropyl-2-(6-(3-(difluoromethyl)-4-fluorophenyl)-1H-pyrazolo[4,3-b]pyridin-1-yl)ethan-1-ol;
(E/Z)-N-Methoxy-3-methyl-1-[6-[3-(trifluoromethyl)phenyl]pyrazolo[4,3-b]pyridin-1-yl]butan-2-imine;
(E/Z)-1-Cyclopropyl-2-[6-[3-(trifluoromethyl)phenyl]pyrazolo[4,3-b]pyridin-1-yl]ethanone oxime;
(E/Z)-1-Cyclopropyl-2-[6-[3-(difluoromethyl)-4-fluoro-phenyl]pyrazolo[4,3-b]pyridin-1-yl]ethanone oxime;
1-(2-Cyclopropyl-2,2-difluoro-ethyl)-6-[3-(difluoromethyl)-4-fluoro-phenyl]pyrazolo[4,3-b]pyridine;
1-(2-Cyclopropyl-2,2-difluoro-ethyl)-6-[3-(difluoromethoxy)-4-fluoro-phenyl]pyrazolo[4,3-b]pyridine;
6-[3-(Difluoromethyl)-4-fluoro-phenyl]-1-[(3-methyloxetan-3-yl)methyl]pyrazolo[4,3-b]pyridine;
(RS)-1-(Tetrahydrofuran-2-ylmethyl)-6-[3-(trifluoromethyl)phenyl]pyrazolo[4,3-b]pyridine;
(RS)-6-[3-(Difluoromethoxy)-4-fluoro-phenyl]-1-(tetrahydrofuran-2-ylmethyl)pyrazolo[4,3-b]pyridine;
(RS)-6-[3-(Difluoromethyl)-4-fluoro-phenyl]-1-(tetrahydrofuran-3-ylmethyl)pyrazolo[4,3-b]pyridine;
(RS)-5-((6-(3-(Difluoromethoxy)-4-fluorophenyl)-1H-pyrazolo[4,3-b]pyridin-1-yl)methyl)-1-methylpyrrolidin-2-one;
(RS)-5-[[6-[3-(Difluoromethyl)-4-fluoro-phenyl]pyrazolo[4,3-b]pyridin-1-yl]methyl]-1-methyl-pyrrolidin-2-one;
(RS)-3-[[6-[3-(Difluoromethyl)-4-fluoro-phenyl]pyrazolo[4,3-b]pyridin-1-yl]methyl]-1-methyl-pyrrolidin-2-one;

(S)-3-[[6-[3-(Difluoromethyl)-4-fluoro-phenyl]pyrazolo[4,3-b]pyridin-1-yl]methyl]-1-methyl-pyrrolidin-2-one;
(R)-3-[[6-[3-(Difluoromethyl)-4-fluoro-phenyl]pyrazolo[4,3-b]pyridin-1-yl]methyl]-1-methyl-pyrrolidin-2-one;
(RS)-3-((6-(3-(Difluoromethoxy)-4-fluorophenyl)-1H-pyrazolo[4,3-b]pyridin-1-yl)methyl)-1-methylpyrrolidin-2-one;
(RS)-4-[[6-[3-(Difluoromethyl)-4-fluoro-phenyl]pyrazolo[4,3-b]pyridin-1-yl]methyl]-1-methyl-pyrrolidin-2-one;
(S)-4-[[6-[3-(Difluoromethyl)-4-fluoro-phenyl]pyrazolo[4,3-b]pyridin-1-yl]methyl]-1-methyl-pyrrolidin-2-one;
(R)-4-[[6-[3-(Difluoromethyl)-4-fluoro-phenyl]pyrazolo[4,3-b]pyridin-1-yl]methyl]-1-methyl-pyrrolidin-2-one;
(RS)-4-((6-(3-(difluoromethoxy)-4-fluorophenyl)-1H-pyrazolo[4,3-b]pyridin-1-yl)methyl)-3-methyloxazolidin-2-one;
(RS)-4-[[6-[3-(Difluoromethyl)-4-fluoro-phenyl]pyrazolo[4,3-b]pyridin-1-yl]methyl]-3-methyl-oxazolidin-2-one;
(RS)-5-[[6-[3-(Difluoromethoxy)-4-fluoro-phenyl]pyrazolo[4,3-b]pyridin-1-yl]methyl]oxazolidin-2-one;
(RS)-5-[[6-[4-Chloro-3-(difluoromethoxy)phenyl]pyrazolo[4,3-b]pyridin-1-yl]methyl]oxazolidin-2-one;
(RS)-5-[[6-[3-(1,1-Difluoroethyl)-4-fluoro-phenyl]pyrazolo[4,3-b]pyridin-1-yl]methyl]oxazolidin-2-one;
(RS)-5-((6-(3-(Difluoromethoxy)-4-fluorophenyl)-1H-pyrazolo[4,3-b]pyridin-1-yl)methyl)-3-methyloxazolidin-2-one;
(5R)-5-[[6-[3-(Difluoromethyl)-4-fluoro-phenyl]pyrazolo[4,3-b]pyridin-1-yl]methyl]-3-methyl-oxazolidin-2-one;
(5S)-5-[[6-[3-(Difluoromethyl)-4-fluoro-phenyl]pyrazolo[4,3-b]pyridin-1-yl]methyl]-3-methyl-oxazolidin-2-one;
(RS)-5-[[6-[3-(Difluoromethyl)-4-fluoro-phenyl]pyrazolo[4,3-b]pyridin-1-yl]methyl]-3-ethyl-oxazolidin-2-one;
(S)-5-[[6-[3-(Difluoromethyl)-4-fluoro-phenyl]pyrazolo[4,3-b]pyridin-1-yl]methyl]-3-ethyl-oxazolidin-2-one;
(R)-5-[[6-[3-(Difluoromethyl)-4-fluoro-phenyl]pyrazolo[4,3-b]pyridin-1-yl]methyl]-3-ethyl-oxazolidin-2-one;
(RS)-3-Cyclopropyl-5-[[6-[3-(difluoromethyl)-4-fluoro-phenyl]pyrazolo[4,3-b]pyridin-1-yl]methyl]oxazolidin-2-one;
(S)-3-Cyclopropyl-5-[[6-[3-(difluoromethyl)-4-fluoro-phenyl]pyrazolo[4,3-b]pyridin-1-yl]methyl]oxazolidin-2-one;
(R)-3-Cyclopropyl-5-[[6-[3-(difluoromethyl)-4-fluoro-phenyl]pyrazolo[4,3-b]pyridin-1-yl]methyl]oxazolidin-2-one;
2-[6-[3-(Difluoromethyl)-4-fluoro-phenyl]pyrazolo[4,3-b]pyridin-1-yl]-1-(2-thienyl)ethanone;
2-[6-[3-(Difluoromethyl)-4-fluoro-phenyl]pyrazolo[4,3-b]pyridin-1-yl]-1-(3-thienyl)ethanone;
2-[6-[3-(Difluoromethyl)-4-fluoro-phenyl]pyrazolo[4,3-b]pyridin-1-yl]-1-(4-pyridyl)ethanone;
2-(6-(3-(Difluoromethyl)-4-fluorophenyl)-1H-pyrazolo[4,3-b]pyridin-1-yl)-1-(3-fluoropyridin-2-yl)ethan-1-one;
2-(6-(3-(Difluoromethyl)-4-fluorophenyl)-1H-pyrazolo[4,3-b]pyridin-1-yl)-1-(3,5-difluoropyridin-2-yl)ethan-1-one;
2-(6-(3-(Difluoromethyl)-4-fluorophenyl)-1H-pyrazolo[4,3-b]pyridin-1-yl)-1-(pyrazin-2-yl)ethan-1-one;
and pharmaceutically acceptable salts and stereoisomers thereof.

22. A compound selected from the group consisting of:
1-[6-[3-(Difluoromethyl)-4-fluoro-phenyl]pyrazolo[4,3-b]pyridin-1-yl]butan-2-one;
1-[6-[3-(Difluoromethyl)-4-fluoro-phenyl]pyrazolo[4,3-b]pyridin-1-yl]propan-2-one;
1-[6-(3,4-Difluorophenyl)pyrazolo[4,3-b]pyridin-1-yl]butan-2-one;
1-(6-(3-(Difluoromethyl)-4-fluorophenyl)-3-methyl-1H-pyrazolo[4,3-b]pyridin-1-yl)butan-2-one;
1-[6-[3-(Difluoromethoxy)-4-fluoro-phenyl]pyrazolo[4,3-b]pyridin-1-yl]butan-2-one;
1-Cyclopropyl-2-[6-(4-fluorophenyl)pyrazolo[4,3-b]pyridin-1-yl]ethanone;
1-Cyclopropyl-2-[6-[3-(difluoromethyl)-4-fluoro-phenyl]pyrazolo[4,3-b]pyridin-1-yl]ethanone;
(RS)-6-(3-(Difluoromethyl)-4-fluorophenyl)-1-((ethylsulfinyl)methyl)-1H-pyrazolo[4,3-b]pyridine;
(S*)-6-(3-(Difluoromethyl)-4-fluorophenyl)-1-((ethylsulfinyl)methyl)-1H-pyrazolo[4,3-b]pyridine;
(5R)-5-[[6-[3-(Difluoromethyl)-4-fluoro-phenyl]pyrazolo[4,3-b]pyridin-1-yl]methyl]-3-methyl-oxazolidin-2-one;
and pharmaceutically acceptable salts and stereoisomers thereof.

23. A pharmaceutical composition comprising: (A) at least one compound selected from compounds of Formula (I):

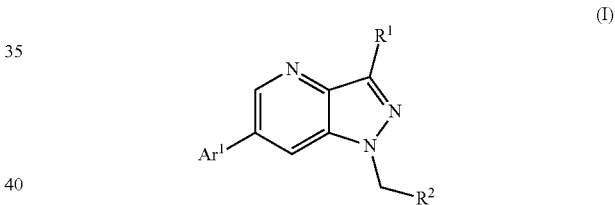

and pharmaceutically acceptable salts and stereoisomers of compounds of Formula (I),
wherein:
$R^1$ is H, halo, or $CH_3$;
$Ar^1$ is selected from the group consisting of:
(a) phenyl;
(b) phenyl substituted with one member selected from the group consisting of: halo, $C_{1-6}$alkyl, $C_{1-6}$perhaloalkyl, and $OC_{1-6}$perhaloalkyl;
(c) phenyl substituted with two or three members each independently selected from the group consisting of: halo, $C_{1-6}$alkyl, $C_{1-6}$perhaloalkyl, and $OC_{1-6}$perhaloalkyl; and
(d) thienyl substituted with one member selected from the group consisting of: halo and $C_{1-6}$alkyl;
$R^2$ is selected from the group consisting of:
(a)

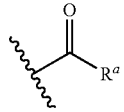

wherein $R^a$ is selected from the group consisting of:
$C_{1-6}$alkyl;
$C_{3-6}$cycloalkyl; thienyl; pyridyl; pyridyl substituted with one or two F members;
pyrazinyl;

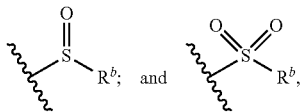

wherein $R^b$ is $C_{1-6}$alkyl;
(b) $C_{1-6}$alkyl substituted with one, two, or three members each independently selected from the group consisting of: OH, halo, $OC_{1-6}$alkyl, (=N—OH), (=N—OCH$_3$), and cyclopropyl; and
(c) oxetanyl; oxetanyl substituted with $C_{1-6}$alkyl; tetrahydrofuranyl; oxazolidinone; oxazolidinone substituted with $C_{1-4}$alkyl or cyclopropyl; and pyrrolidinone substituted with $C_{1-4}$alkyl; and
(B) at least one pharmaceutically acceptable excipient.

24. A pharmaceutical composition comprising at least one compound of claim 21 or a pharmaceutically acceptable salt or stereoisomer thereof, and at least one pharmaceutically acceptable excipient.

25. A method of treating a subject suffering from or diagnosed with treatment-resistant depression, comprising administering to the subject an effective amount of a compound of claim 1 or a pharmaceutically acceptable salt or stereoisomer thereof.

26. A method of treating a subject suffering from or diagnosed with major depressive disorder, comprising administering to the subject an effective amount of a compound of claim 1 or a pharmaceutically acceptable salt or stereoisomer thereof.

* * * * *